United States Patent
Wetzel et al.

(10) Patent No.: US 12,043,782 B2
(45) Date of Patent: Jul. 23, 2024

(54) LIQUID CRYSTALLINE MEDIUM

(71) Applicant: Merck Patent GmbH, Darmstadt (DE)

(72) Inventors: Christoph Wetzel, Darmstadt (DE); Peer Kirsch, Seeheim-Jugenheim (DE); Susann Gunst, Darmstadt (DE); Andreas Ruhl, Rossdorf (DE); Andrea Ritter, Egelsbach (DE); Rene Lutz, Brensbach (DE); Michael Junge, Pfungstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 7 days.

(21) Appl. No.: 17/253,654

(22) PCT Filed: Jun. 17, 2019

(86) PCT No.: PCT/EP2019/065800
§ 371 (c)(1),
(2) Date: Dec. 18, 2020

(87) PCT Pub. No.: WO2019/243216
PCT Pub. Date: Dec. 26, 2019

(65) Prior Publication Data
US 2022/0275277 A1 Sep. 1, 2022

(30) Foreign Application Priority Data
Jun. 20, 2018 (EP) .................... 18178768

(51) Int. Cl.
*G02F 1/1333* (2006.01)
*C09K 19/32* (2006.01)
*C09K 19/34* (2006.01)

(52) U.S. Cl.
CPC .......... *C09K 19/32* (2013.01); *C09K 19/3402* (2013.01); *C09K 2019/3422* (2013.01); *C09K 19/3497* (2013.01)

(58) Field of Classification Search
CPC .............. C09K 19/32; C09K 19/3402; C09K 19/3497; C09K 19/3405; C09K 2019/3422
See application file for complete search history.

(56) References Cited

U.S. PATENT DOCUMENTS

| | | | |
|---|---|---|---|
| 9,865,821 B2 | 1/2018 | Tamayo et al. | |
| 9,978,954 B2 | 5/2018 | Tokito et al. | |
| 10,344,217 B2 | 7/2019 | Kirsch et al. | |
| 11,168,257 B2 * | 11/2021 | Kirsch | C09K 19/3001 |
| 2016/0108317 A1 | 4/2016 | Kirsch et al. | |
| 2018/0114930 A1 | 4/2018 | Wood et al. | |
| 2018/0142153 A1 | 5/2018 | Kirsch et al. | |
| 2018/0159052 A1 | 6/2018 | Tamayo et al. | |
| 2019/0153320 A1 | 5/2019 | Kirsch et al. | |
| 2019/0300791 A1 | 10/2019 | Kirsch et al. | |
| 2022/0275277 A1 * | 9/2022 | Wetzel | C09K 19/3402 |

FOREIGN PATENT DOCUMENTS

| | | |
|---|---|---|
| EP | 3048107 B1 | 1/2021 |
| JP | 2016522442 A | 7/2016 |
| WO | 13123047 A1 | 8/2013 |
| WO | 13123508 A2 | 8/2013 |
| WO | 2015041026 A1 | 3/2015 |
| WO | 16154624 A1 | 9/2016 |
| WO | 16177449 A1 | 11/2016 |
| WO | 18015320 A1 | 1/2018 |
| WO | 18104285 A2 | 6/2018 |

OTHER PUBLICATIONS

Abdelsamie et al., "Toward Additive-Free Small-Molecule Organic Solar Cells: Roles of the Donor Crystallization Pathway and Dynamics", Advanced Material, 2015, vol. 27, Issue 45, pp. 7285-7292. (Year: 2015).*
International Search Report PCT/EP2019/065800 dated Sep. 18, 2019 (pp. 1-3).
R. Sen et al., " Strategical Designing of Donar-Acceptor -Donor based Organic Molecules for tuning Their Linear Optical Properties" J. Phys. Chem. A, 2018, 122, 492-504.
English translation of Office Action in corresponding JP application 2020570803 dated Jun. 20, 2023 (pp. 1-3).
Kitamura C et al: "Synthesis and properties of a new ethyne-linked donor/acceptor pentamer", Tetrahedron Letters, Else Vier, Amsterdam, NL, vol. 43, No. 18, Apr. 29, 2002 (Apr. 29, 2002), pp. 3373-3376, XP004349388, ISSN: 0040-4039, DOI: 10.1 016/S0040-4039(02)00478-1.
Search report in corresponding EP application 1 9 730 3 64.7 dated Mar. 1, 2023 (pp. 1-5).

* cited by examiner

*Primary Examiner* — Geraldina Visconti
(74) *Attorney, Agent, or Firm* — MILLEN, WHITE, ZELANO & BRANIGAN, P.C.; Csaba Henter

(57) ABSTRACT

The present invention relates to a liquid crystalline medium comprising dichroitic dyes made of benzothiadiazoles and related extended heterocyclic derivatives, the use of said medium for optical, electro-optical and electronic purposes, in particular in devices for regulating the passage of radiation energy from an outside space into an inside space, for example in windows. The invention further relates to devices containing the liquid crystalline medium according to the invention. Some new dichroitic dyes are disclosed.

20 Claims, No Drawings

LIQUID CRYSTALLINE MEDIUM

The present invention relates to a liquid crystalline medium comprising dichroitic dyes made of benzothiadiazoles and related extended heterocyclic derivatives, the use of said medium for optical, electro-optical and electronic purposes, in particular in devices for regulating the passage of radiation energy from an outside space into an inside space, for example in windows. The invention further relates to devices containing the liquid crystalline medium according to the invention. Some new dichroitic dyes are disclosed.

Liquid crystals are used in particular as dielectrics in display devices, since the optical properties of such substances can be influenced by an applied voltage. Electro-optical devices based on liquid crystals are extremely well known to the person skilled in the art and can be based on various effects. Devices of this type are, for example, cells having dynamic scattering, DAP (deformation of aligned phases) cells, TN cells having a twisted nematic structure, STN ("supertwisted nematic") cells, SBE ("superbirefringence effect") cells, OMI ("optical mode interference") cells and guest-host cells.

The last-mentioned devices based on the guest-host effect were described for the first time by Heilmeier and Zanoni (G. H. Heilmeier et al., Appl. Phys. Lett., 1968, 13, 91f) and have since then found widespread use, principally in LC display elements. In a guest-host system, the LC medium comprises one or more dichroic dyes in addition to the liquid crystal. Owing to the directional dependence of the absorption by the dye molecules, the transparency of the liquid crystal to light can be modulated if the dyes change their alignment together with the liquid crystal.

Besides use in LC displays, devices of this type are known as switching elements for regulating the passage of light or energy, for example from WO 2009/141295 and WO 2010/118422; a device for regulating the passage of energy is in the present application taken to mean a device which regulates the passage of energy through an area which is arranged within a structure of relatively lower energy transmissivity. For example, the area of relatively high energy transmissivity can be a glass area or an open area, and the structure of lower energy transmissivity which contains the area of higher energy transmissivity can be a wall.

The device preferably regulates the passage of energy from insolation, either directly or indirectly.

The regulated passage of energy takes place from an outside space, preferably the environment exposed directly to insolation, into an inside space, for example a building or a vehicle, or another unit which is substantially sealed off from the environment.

For the purposes of the present invention, the term energy is taken to mean, in particular, energy by electromagnetic radiation in the UV-A, VIS and NIR region. In particular, it is taken to mean energy by radiation which is not absorbed or is only absorbed to a negligible extent by the materials usually used in windows (for example glass). According to the definitions usually used, the UV-A region is taken to mean a wavelength of 320 to 380 nm, the VIS region is taken to mean a wavelength of 380 nm to 780 nm and the NIR region is taken to mean a wavelength of 780 nm to 2000 nm. Correspondingly, the term light is generally taken to mean electromagnetic radiation having wavelengths between 320 and 2000 nm.

For the purposes of the present invention, a dichroic dye is taken to mean a light-absorbing compound in which the absorption properties are dependent on the alignment of the compound with the direction of polarisation of the light. A dichroic dye compound in accordance with the present invention typically has an elongate shape, i.e. the compound is significantly longer in one spatial direction (longitudinal axis) than in the other two spatial directions.

In the area of devices for regulating the passage of energy from an outside space into an inside space, a number of different technical solutions have been proposed in past years.

An advantageous solution is the use of switching layers comprising a liquid-crystalline medium in combination with one or more dichroic dyes. By application of a voltage, a change in the spatial alignment of the molecules of the dichroic compound can be achieved in these switching layers, causing a change in the transmission of the switching layer owing to their direction-dependent absorption. A corresponding device is described, for example, in WO 2009/141295.

Alternatively, such a change in transmission can also be achieved without electrical voltage by a temperature-induced transition from an isotropic state of the liquid-crystalline medium to a liquid-crystalline state, as described, for example, in US 2010/0259698.

The prior art discloses liquid-crystal media for display elements of the guest-host type which comprise cyanobiphenyl derivatives and one or more dichroic dyes (WO 2009/141295 and WO 2010/118422). For the same application, U.S. Pat. Nos. 6,033,598 and 5,762,824 describe LC media which, besides one or more dichroic dyes, comprise one or more compounds each consisting of three ring elements which are substituted by one or more fluorine atoms.

Rylene dyes have been described for use in the above-mentioned devices, for example in WO 2009/141295, WO 2013/004677 and WO2014/090373. However, rylene dyes generally have some disadvantages, in particular they often have low solubility in LC media, resulting in low low-temperature stability of the liquid-crystal mixture. They often exhibit low colour purity, which, in particular, makes use in windows more difficult, where, for architectonic reasons, the aesthetic impression is important and the purest colours possible are desired.

Furthermore known are naphthothiadiazole derivatives for various applications as for example for the use as organic semiconductor, as disclosed in WO 2015/041026, exemplified by the following structure:

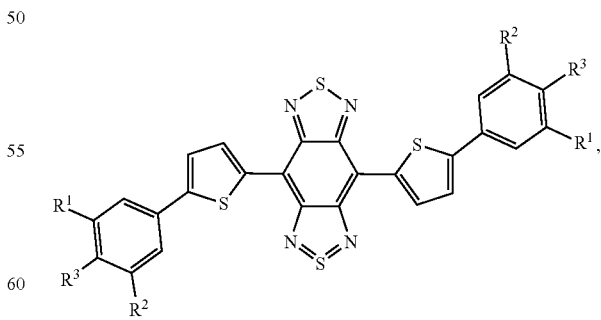

wherein, inter alia, $R^1$ denotes straight chain or branched alkyl and $R^2$ and $R^3$ denote H.

A similar compound with an oxadiazolothiadiazolobenzene central ring of the following structure

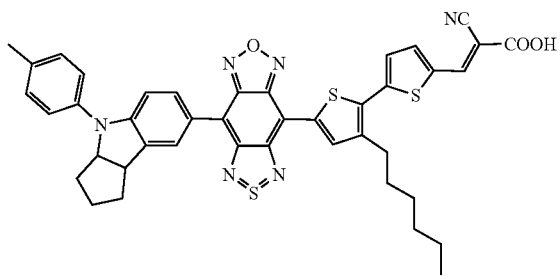 [SMILES: CCCCCCc1cc(-c2c3c(c(-c4ccc5c(c4)C4CCCC4N5c4ccc(C)cc4)c4nonc24)N=S=N3)sc1-c1ccc(/C=C(\C#N)C(=O)O)s1]

is described in M. Li et al., J. Phys. Chem. C 2015, 119, 9782-9790.

In the documents cited above, the use of these compounds as dichroitic dye in liquid crystal mixtures is neither disclosed nor suggested.

The invention is based on the object of providing novel dichroic dyes for use in liquid crystal mixtures which do not exhibit the above-mentioned disadvantages, or only do so to a small extent, and in addition have at least one, preferably several of the following desired properties: good solubility of the dyes in the liquid-crystalline medium, good light and temperature stability and high anisotropy of the absorption, i.e. a high capacity of the dye to align with the liquid crystal. In addition, the dyes should have strong light absorption in the VIS and/or NIR region of light. Furthermore, the invention is based on the object of providing compounds which not only have a favourable combination of the application-technical parameters, but also, in addition, are distinguished by particularly high colour purity.

Usually, mixtures of dyes are used in liquid crystal media for the application according to the present invention because of the limited solubility of a single dye material in the liquid crystal medium and especially when it is desired to achieve black, i.e. when the whole range of the VIS and NIR part of the electromagnetic spectrum has to be covered and dyes of different colours are mixed. Therefore, there is generally a strong need for novel dichroic dyes to be able to choose from for the development of tailor-made liquid crystal media.

Surprisingly, it has been found that one or more of the requirements mentioned above are satisfied by compounds of the formula I as described below.

The invention relates to an LC medium comprising a dye component A) comprising one or more compounds of the formula I and optionally further dichroic dyes, and a liquid-crystalline component B), also referred to below as "LC host mixture", comprising one or more, preferably two or more mesogenic compounds, where formula I is defined as

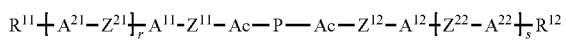 I in which the variables are defined as

Ac independently of each other, denotes a group selected from

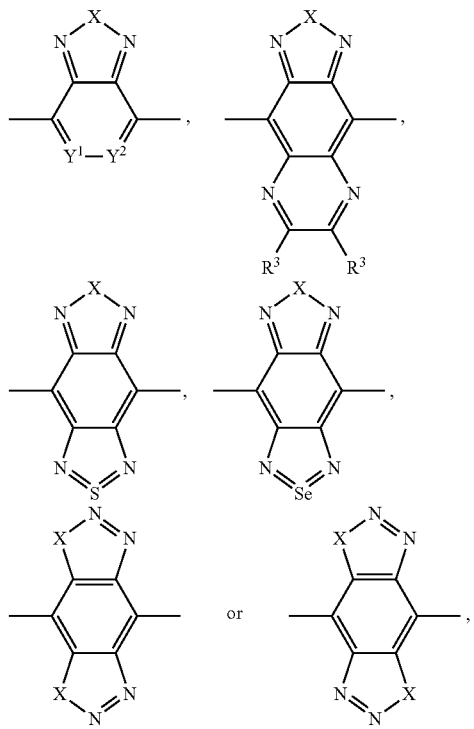

X independently is O, S, Se, $NR^2$ or Te, $Y^1$, $Y^2$ independently is $CR^3$ or N, $R^2$ independently is H, alkyl having 1 to 25 C atoms or aryl, $R^3$ independently is H, F, Cl, CN, alkyl having 1 to 25 C atoms, alkoxy having 1 to 25 C atoms or aryl, $R^{11}$, $R^{12}$ independently denote H, F, Cl, —CN, straight-chain or branched alkyl having 1 to 25 C atoms, in which, in addition, one or more non-adjacent $CH_2$ groups may each be replaced, independently of one another, by —C($R^z$)=C($R^z$)—, —C≡C—, —N($R^z$)—, —O—, —S—, —CO—, —CO—O—, —O—CO— or —O—CO—O— in such a way that O and/or S addition, one or more H atoms may be replaced by F, Cl, Br, I or CN, $R^z$ on each occurrence, identically or differently, denotes H, halogen, straight-chain, branched or cyclic alkyl having 1 to 25 C atoms, in which, in addition, one or more non-adjacent $CH_2$ groups may be replaced by —O—, —S—, —CO—, —CO—O—, —O—CO— or —O—CO—O— in such a way that O and/or S atoms are not linked directly to one another, and in which, in addition, one or more H atoms may be replaced by F or Cl, $A^{11}$, $A^{12}$ each, independently of one another, denote an aryl or heteroaryl group, which may be substituted by one or more groups L, $A^{21}$, $A^{22}$ are each, independently of one another, defined like $A^{11}$ or denote a cyclic alkyl group having 3 to 10 C atoms, in which one or more non-adjacent $CH_2$ groups may be replaced by 0 in such a way that no two O atoms are adjacent, L on each occurrence, identically or differently, denotes OH, $CH_2OH$, F, Cl, Br, I, —CN, —$NO_2$, $SF_5$, —NCO, —NCS, —OCN, —SCN, —C(=O)N($R^z$)$_2$, —C(=O)$R^z$, —N($R^z$)$_2$, optionally substituted silyl, optionally substituted aryl having 6 to 20 C atoms, or straight-chain or branched alkyl, alkoxy, alkylcarbonyl, alkoxycarbonyl, alkylcarbonyloxy or alkoxycarbonyloxy having 1 to 25 C atoms, in which, in addition, one or more H atoms may be replaced by F or Cl, an aryl or heteroaryl group, which may be substituted by one or more F, Cl, $C_1$-$C_6$ alkyl or alkoxy, and alternatively two adjacent groups L together also denote a straight-chain or branched alkylene group having 2 to 10 C atoms, in which one, several or all H atoms may be replaced by F and in which one or more —$CH_2CH_2$— groups can be replaced by —CH=CH—, $Z^{11}$, $Z^{12}$ on each occurrence, identically or differently, denote a single bond, —$CR^{x1}$=$CR^{x2}$—, —C≡C— or —$NR^1$—, $R^1$ is H, F, alkyl having 1-12 C atoms or aryl, $Z^{21}$, $Z^{22}$ are, on each occurrence identically or differently, defined like $Z^{11}$ or denote —O—, —S—, —$CR^{y1}R^{y2}$—, —$CF_2O$—, —$OCF_2$—, —C(O)—O—, —O—C(O)—, —O—C(O)—O—, —$OCH_2$—, —$CH_2O$—, —$SCH_2$—, —$CH_2S$—, —$CF_2S$—, —$SCF_2$—, —$(CH_2)_{n1}$—, —$CF_2CH_2$—, —$CH_2CF_2$—, —$(CF_2)_{n1}$—, —CH=CH—C(O)O— or —OC(O)—CH=CH—, $R^{x1}$, $R^{x2}$, independently of one another, denote H, F, Cl, CN or alkyl having 1-12 C atoms, $R^{y1}$, $R^{y2}$ each, independently of one another, denote H or alkyl having 1-12 C atoms, r, s, independently of one another, denote 0, 1, 2 or 3, n1 denotes 1, 2, 3 or 4, P denotes a single bond, —$(CH_2)_n$—, —$O(CH_2)_mO$—, —C=C—, —NH—, —$NR^1$—, —O(CO)O—, —O—, —S— or a group selected from the following partial groups:

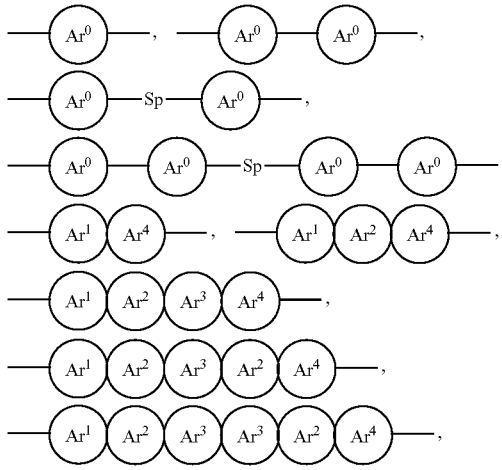

wherein the ring elements $Ar^0$, $Ar^1$, $Ar^2$, $Ar^3$ and $Ar^4$ are defined independently from the corresponding definitions:

$Ar^0$ is independently selected from the following formulae

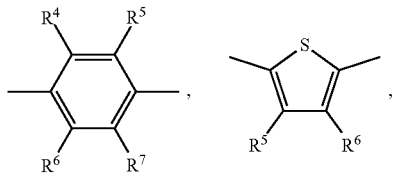

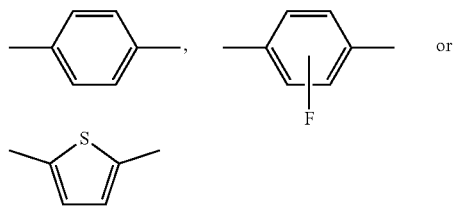

preferably $R^{4-7}$ H, F, Cl, CN, or straight-chain, branched or cyclic alkyl with 1 to 30, preferably 1 to 20, C atoms, in which one or more $CH_2$ groups are optionally replaced by —O—, —S—, —C(=O)—, —C(=S)—, —C(=O)—O—, —O—C(=O)—, —$NR^0$—, —$SiR^0R^{00}$—, —$CF_2$—, —$CR^{x1}$=$CR^{x2}$— or —C≡C— in such a manner that O and/or S atoms are not linked directly to one another, and in which one or more H atoms are optionally replaced by F, Cl, Br, I or CN, $R^0$, $R^{00}$ H or straight-chain or branched alkyl with 1 to 20, preferably 1 to 12, C atoms that is optionally fluorinated, $Ar^1$ is independently selected from the following formulae

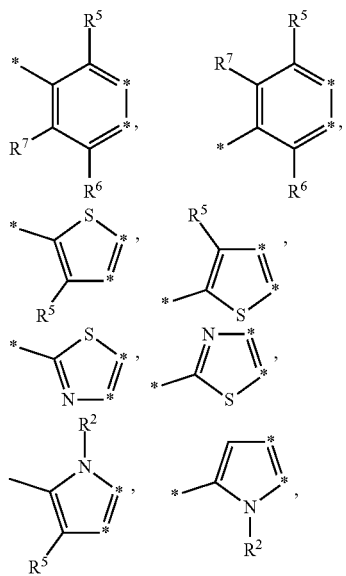

$Ar^4$ is independently selected from the following formulae

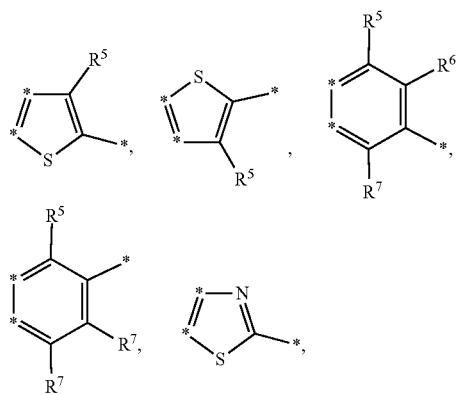

-continued

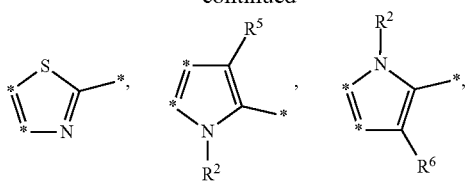

Ar², Ar³ are independently selected from the following formulae

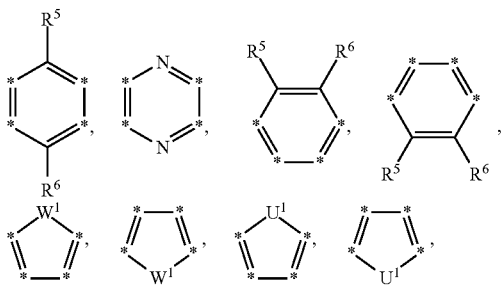

W¹ is S, O or Se,
U¹ is $CR^aR^b$, $SiR^aR^b$, $GeR^aR^b$, $PR^2$ or $NR^2$, wherein $R^a$ and $R^b$ are independently defined as $R^4$,

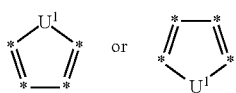

wherein a group is preferably not adjacent to another group

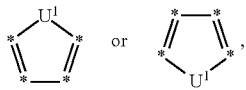

Sp a spacer group, preferably —O(CH₂)ₘO—, —(CH₂)ₙ—, —NH— or —NR¹—,
m is 2 to 18, and
and
n is 1 to 18.
Preferred definitions of the group P are

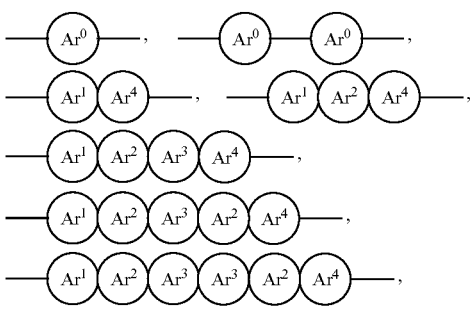

more preferably selected from the following part structures:

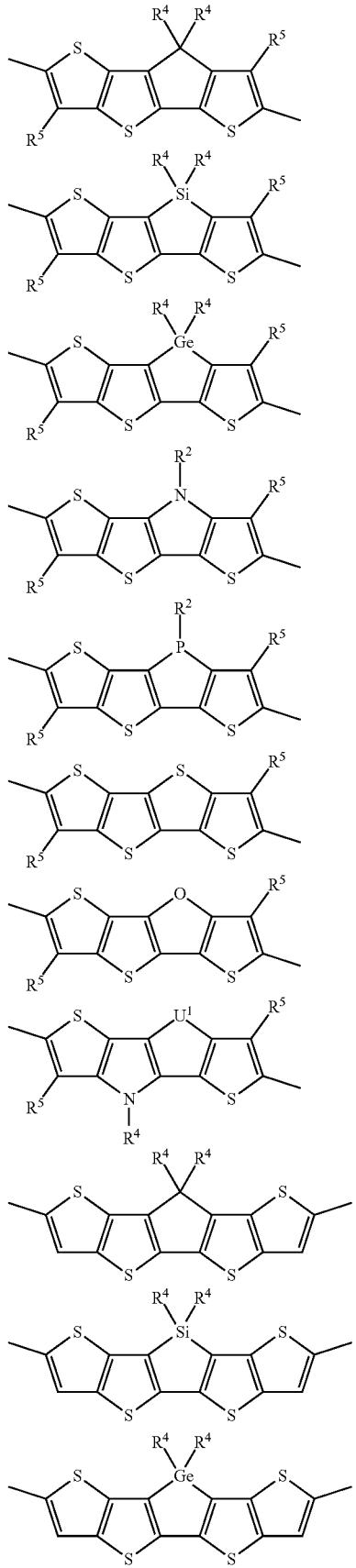

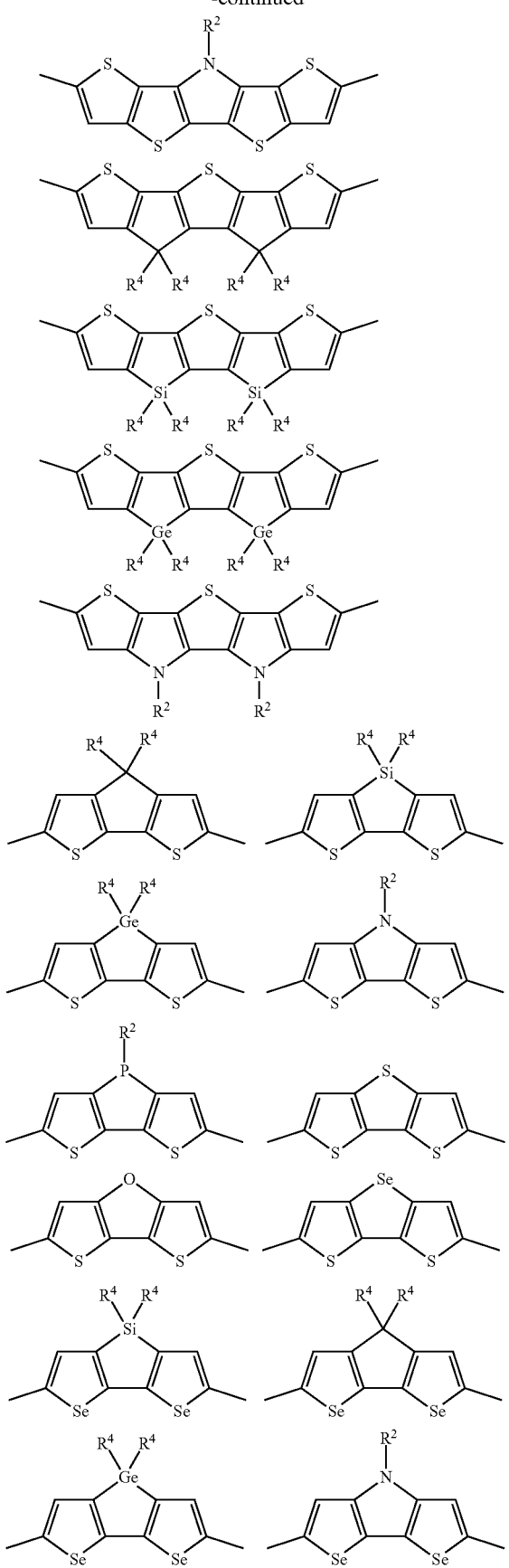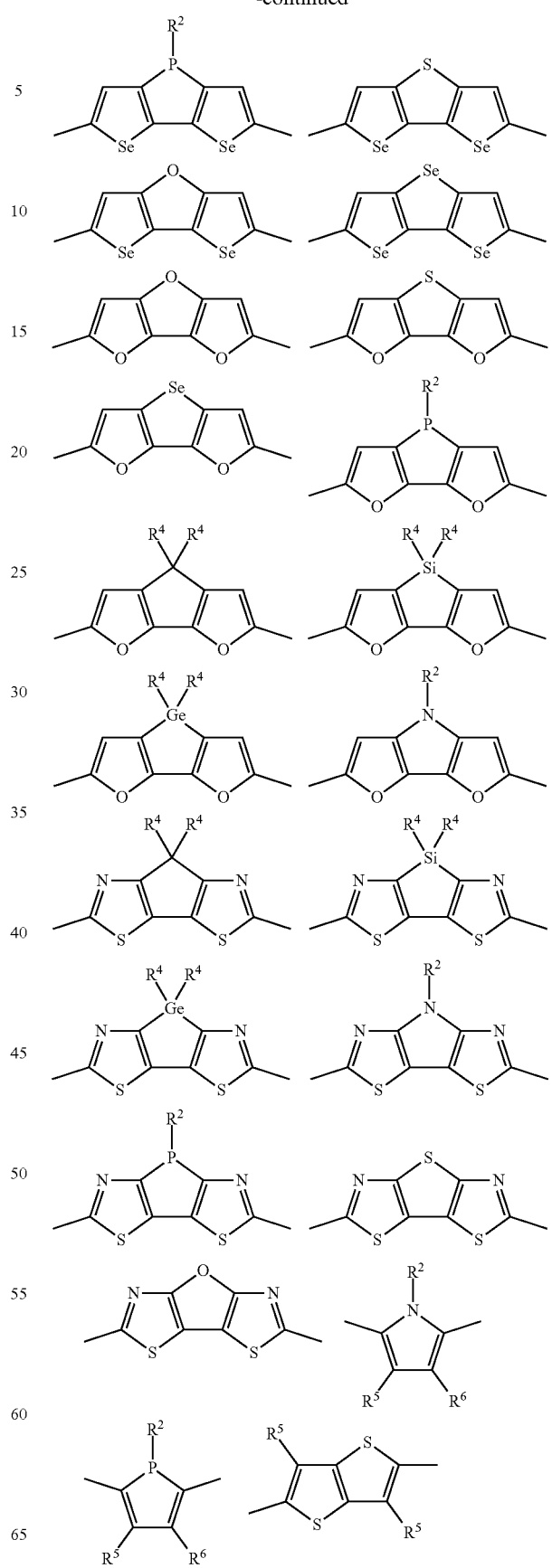

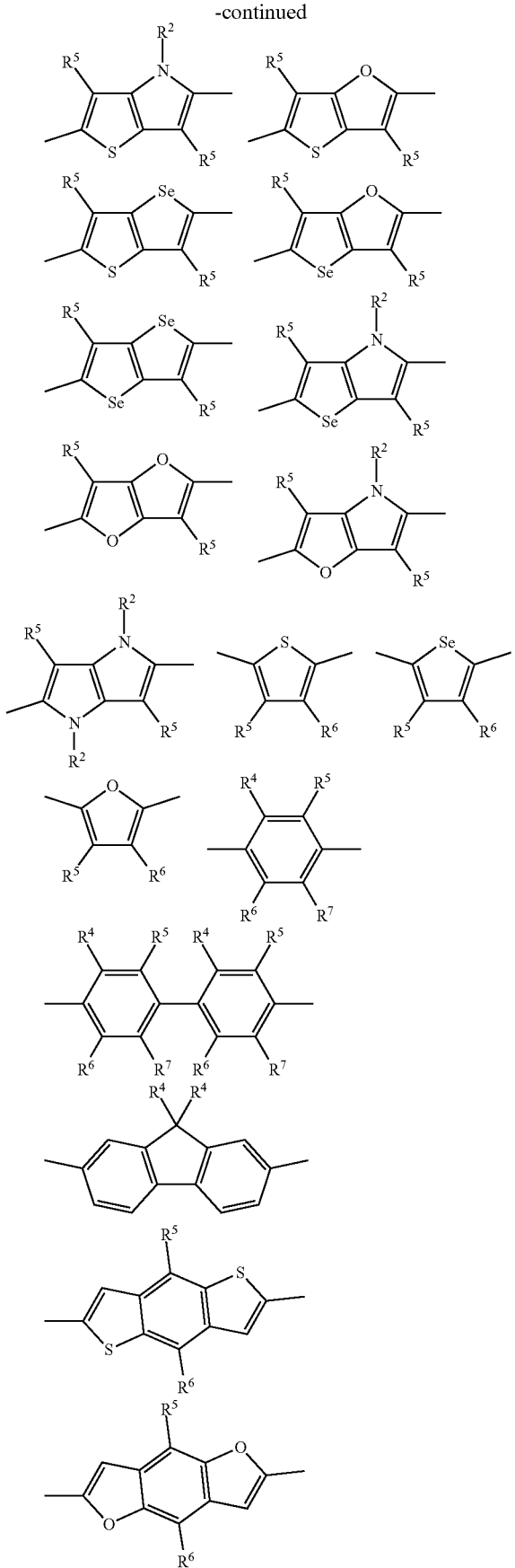
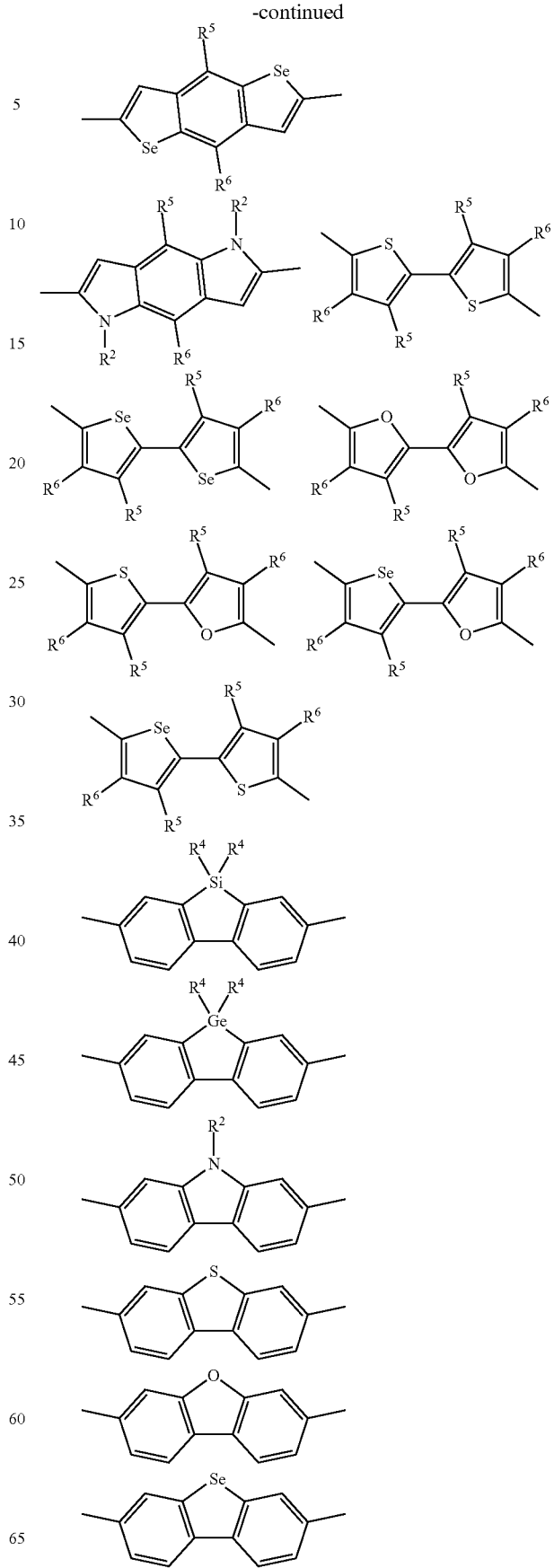

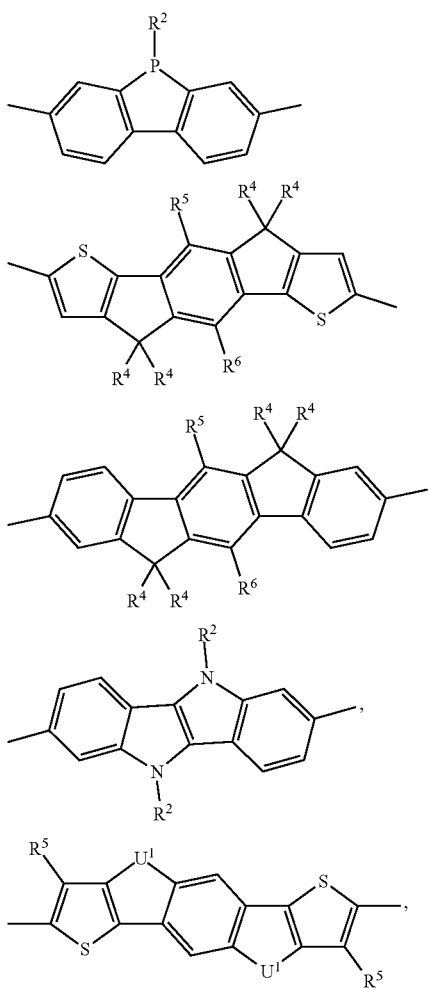
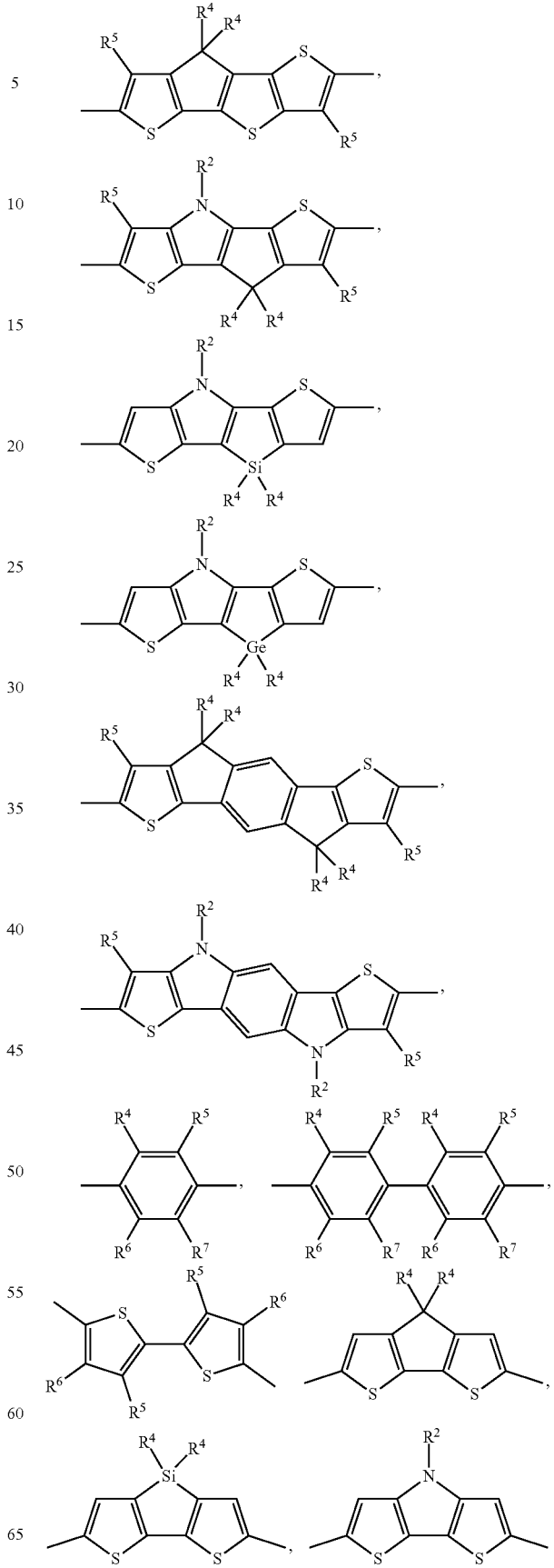
in which $U^1$, $R^4$, $R^5$ and $R^6$ are each independently defined as for formula I. $R^5$ preferably is H or alkyl with 1-20 C atoms, more preferably H.
More preferably,
P is selected from the part structures:
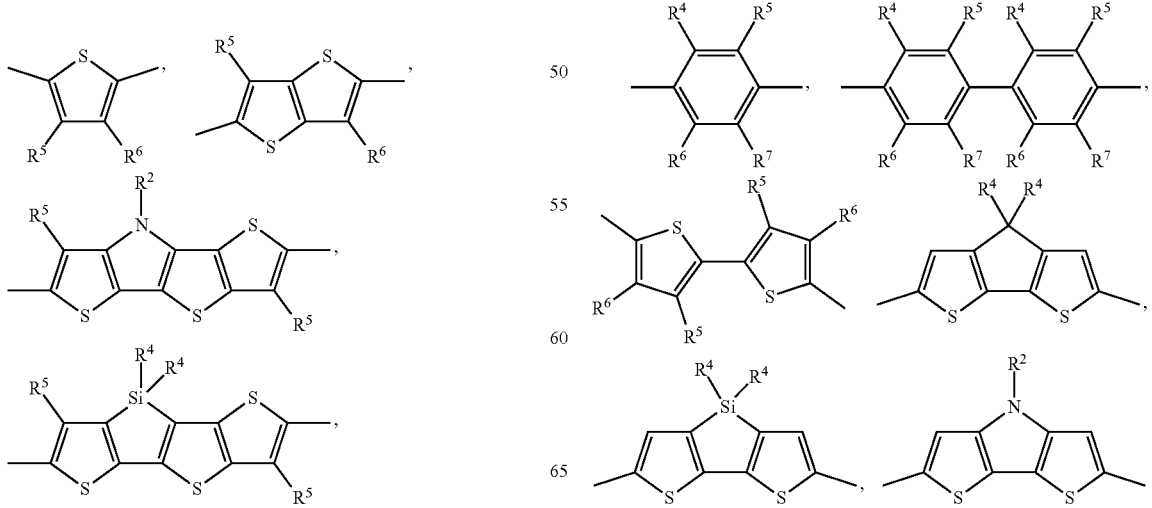

-continued
and

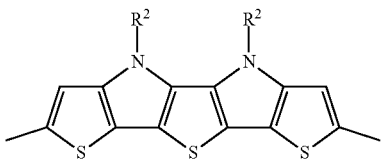

wherein the groups are defined as above and below.

Preference is given to LC media in which component B) is an LC compound or an LC mixture which has a nematic liquid-crystal phase.

The invention furthermore relates to the use of LC media comprising one or more dichroic dyes of the formula I as described above and below for optical, electro-optical and electronic purposes, in particular in devices for regulating the passage of energy from an outside space into an inside space.

The invention furthermore relates to devices for regulating the passage of energy from an outside space into an inside space.

The invention further relates to new compounds of formula I shown below.

The invention relates to compounds of formula I defined above, wherein the group P denotes

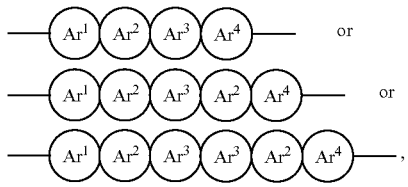

wherein $Ar^{1-4}$ are defined as above,
more preferably

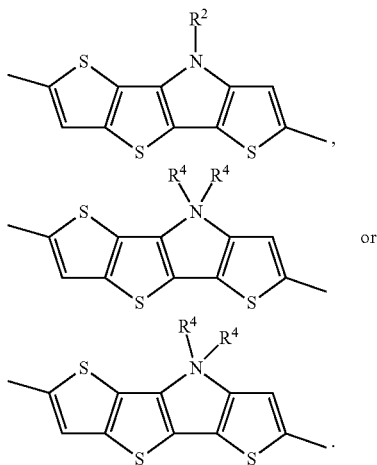

The invention further relates to compounds of formula I wherein $R^{11}$ and $R^{12}$, independently of one another, denote a branched alkyl group having 3 to 25 C atoms, in which one or more H atoms can be replaced by F, one or more $CH_2$ groups can be replaced by O and/or NH and one or more CH groups can be replaced by N.

Above and below, the following meanings apply:

The term "organic group" denotes a carbon or hydrocarbon group.

The term "carbon group" denotes a mono- or polyvalent organic group containing at least one carbon atom, where this either contains no further atoms (such as, for example, —C≡C—) or optionally contains one or more further atoms, such as, for example, N, O, S, P, Si, Se, As, Te or Ge (for example carbonyl, etc.). The term "hydrocarbon group" denotes a carbon group which additionally contains one or more H atoms and optionally one or more heteroatoms, such as, for example, N, O, S, P, Si, Se, As, Te or Ge.

"Halogen" denotes F, Cl, Br or I.

A carbon or hydrocarbon group can be a saturated or unsaturated group. Unsaturated groups are, for example, aryl, alkenyl or alkynyl groups. A carbon or hydrocarbon radical having 3 or more atoms can be straight-chain, branched and/or cyclic and may also contain spiro links or condensed rings.

The terms "alkyl", "aryl", "heteroaryl", etc., also encompass polyvalent groups, for example alkylene, arylene, heteroarylene, etc.

The term "aryl" denotes an aromatic carbon group or a group derived therefrom. The term "heteroaryl" denotes "aryl" as defined above, containing one or more heteroatoms.

Preferred carbon and hydrocarbon groups are optionally substituted alkyl, alkenyl, alkynyl, alkoxy, alkylcarbonyl, alkoxycarbonyl, alkylcarbonyloxy and alkoxycarbonyloxy having 1 to 40, preferably 1 to 25, particularly preferably 1 to 18, C atoms, optionally substituted aryl or aryloxy having 6 to 40, preferably 6 to 25, C atoms, or optionally substituted alkylaryl, arylalkyl, alkylaryloxy, arylalkyloxy, arylcarbonyl, aryloxycarbonyl, arylcarbonyloxy and aryloxycarbonyloxy having 6 to 40, preferably 6 to 25, C atoms.

Further preferred carbon and hydrocarbon groups are $C_1$-$C_{40}$ alkyl, $C_2$-$C_{40}$ alkenyl, $C_2$-$C_{40}$ alkynyl, $C_3$-$C_{40}$ allyl, $C_4$-$C_{40}$ alkyldienyl, $C_4$-$C_{40}$ polyenyl, $C_6$-$C_{40}$ aryl, $C_6$-$C_{40}$ alkylaryl, $C_6$-$C_{40}$ arylalkyl, $C_6$-$C_{40}$ alkylaryloxy, $C_6$-$C_{40}$ arylalkyloxy, $C_2$-$C_{40}$ heteroaryl, $C_4$-$C_{40}$ cycloalkyl, $C_4$-$C_{40}$ cycloalkenyl, etc. Particular preference is given to $C_1$-$C_{22}$ alkyl, $C_2$-$C_{22}$ alkenyl, $C_2$-$C_{22}$ alkynyl, $C_3$-$C_{22}$ allyl, $C_4$-$C_{22}$ alkyldienyl, $C_6$-$C_{12}$ aryl, $C_6$-$C_{20}$ arylalkyl and $C_2$-$C_{20}$ heteroaryl.

Further preferred carbon and hydrocarbon groups are straight-chain, branched or cyclic alkyl radicals having 1 to 40, preferably 1 to 25, C atoms, which are unsubstituted or mono- or polysubstituted by F, Cl, Br, I or CN and in which one more non-adjacent $CH_2$ groups may each be replaced, independently of one another, by —C($R^z$)=C($R^z$)—, —C≡C—, —N($R^z$)—, —O—, —S—, —CO—, —CO—O—, —O—CO—, —O—CO—O— in such a way that O and/or S atoms are not linked directly to one another.

$R^z$ preferably denotes H, halogen, a straight-chain, branched or cyclic alkyl chain having 1 to 25 C atoms, in which, in addition, one or more non-adjacent C atoms may be replaced by —O—, —S—, —CO—, —CO—O—, —O—CO— or —O—CO—O— and in which one or more H atoms may be replaced by fluorine, an optionally substituted aryl or aryloxy group having 6 to 40 C atoms, or an optionally substituted heteroaryl or heteroaryloxy group having 2 to 40 C atoms.

Preferred alkyl groups are, for example, methyl, ethyl, n-propyl, iso-propyl, n-butyl, isobutyl, s-butyl, t-butyl, 2-methylbutyl, n-pentyl, s-pentyl, cyclopentyl, n-hexyl, cyclohexyl, 2-ethylhexyl, n-heptyl, cycloheptyl, n-octyl, cyclooctyl, n-nonyl, n-decyl, n-undecyl, n-dodecyl, trifluoromethyl, perfluoro-n-butyl, 2,2,2-trifluoroethyl, perfluorooctyl and perfluorohexyl.

Preferred alkenyl groups are, for example, ethenyl, propenyl, butenyl, pentenyl, cyclopentenyl, hexenyl, cyclohexenyl, heptenyl, cycloheptenyl, octenyl and cyclooctenyl.

Preferred alkynyl groups are, for example, ethynyl, propynyl, butynyl, pentynyl, hexynyl and octynyl.

Preferred alkoxy groups are, for example, methoxy, ethoxy, 2-methoxyethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, n-decoxy, n-undecoxy and n-dodecoxy.

Preferred amino groups are, for example, dimethylamino, methylamino, methylphenylamino and phenylamino.

Aryl and heteroaryl groups can be monocyclic or polycyclic, i.e. they can contain one ring (such as, for example, phenyl) or two or more rings, which may also be fused (such as, for example, naphthyl) or covalently bonded (such as, for example, biphenyl), or contain a combination of fused and linked rings. Heteroaryl groups contain one or more heteroatoms, preferably selected from O, N, S and Se. A ring system of this type may also contain individual non-conjugated units, as is the case, for example, in the fluorene basic structure.

Particular preference is given to mono-, bi- or tricyclic aryl groups having 6 to 25 C atoms and mono-, bi- or tricyclic heteroaryl groups having 2 to 25 C atoms, which optionally contain fused rings and are optionally substituted.

Preference is furthermore given to 5-, 6- or 7-membered aryl and heteroaryl groups.

Preferred aryl groups are derived, for example, from the parent structures benzene, biphenyl, terphenyl, [1,1':3',1"]terphenyl, naphthalene, anthracene, binaphthyl, phenanthrene, pyrene, dihydropyrene, chrysene, perylene, tetracene, pentacene, benzopyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, dihydrothieno [3,4-b]-1,4-dioxin, isobenzothiophene, dibenzothiophene, benzothiadiazothiophene, or combinations of these groups. The heteroaryl groups may also be substituted by alkyl, alkoxy, thioalkyl, fluorine, fluoroalkyl or one further aryl or heteroaryl group.

The (non-aromatic) alicyclic and heterocyclic groups encompass both saturated rings, i.e. those containing exclusively single bonds, and also partially unsaturated rings, i.e. those which may also contain multiple bonds. Heterocyclic rings contain one or more heteroatoms, preferably selected from Si, O, N, S and Se.

The (non-aromatic) alicyclic and heterocyclic groups can be monocyclic, i.e. contain only one ring (such as, for example, cyclohexane), or polycyclic, i.e. contain a plurality of rings (such as, for example, decahydronaphthalene or bicyclooctane). Particular preference is given to saturated groups. Preference is furthermore given to mono-, bi- or tricyclic groups having 3 to 25 C atoms, which optionally contain fused rings and are optionally substituted. Preference is furthermore given to 5-, 6-, 7- or 8-membered carbocyclic groups, in which, in addition, one or more C atoms may be replaced by Si and/or one or more CH groups may be replaced by N and/or one or more non-adjacent $CH_2$ groups may be replaced by —O— and/or —S—.

Preferred alicyclic and heterocyclic groups are, for example, 5-membered groups, such as cyclopentane, tetrahydrofuran, tetrahydrothiofuran, pyrrolidine, 6-membered groups, such as cyclohexane, silinane, cyclohexene, tetrahydropyran, tetrahydrothiopyran, 1,3-dioxane, 1,3-dithiane, piperidine, 7-membered groups, such as cycloheptane, and fused groups, such as tetrahydronaphthalene, decahydronaphthalene, indane, bicyclo[1.1.1]-pentane-1,3-diyl, bicyclo[2.2.2]octane-1,4-diyl, spiro[3.3]heptane-2,6-diyl, octahydro-4,7-methanoindane-2,5-diyl.

The aryl, heteroaryl, carbon and hydrocarbon radicals optionally have one or more substituents, which are preferably selected from the group comprising silyl, sulfo, sulfonyl, formyl, amine, imine, nitrile, mercapto, nitro, halogen, $C_{1-12}$ alkyl, $C_{6-12}$ aryl, $C_{1-12}$ alkoxy, hydroxy, or combinations of these groups.

Preferred substituents are, for example, solubility-promoting groups, such as alkyl or alkoxy, electron-withdrawing groups, such as fluorine, nitro or nitrile, or substituents for increasing the glass transition temperature (Tg) in the polymer, in particular bulky groups, such as, for example, t-butyl or optionally substituted aryl groups.

Preferred substituents, also referred to as "L" below, are F, Cl, Br, I, —ON, —$NO_2$, —NCO, —NOS, —OCN, —SON, —C(=O)N($R^z$)$_2$, —C(=O)$Y^1$, —C(=O)$R^z$, —N($R^z$)$_2$, in which $R^z$ has the meaning indicated above, and $Y^1$ denotes halogen, optionally substituted silyl or aryl having 6 to 40, preferably 6 to 20, C atoms, and straight-chain or branched alkyl, alkoxy, alkylcarbonyl, alkoxycarbonyl, alkylcarbonyloxy or alkoxycarbonyloxy having 1 to 25 C atoms, in which one or more H atoms may optionally be replaced by F or Cl.

More preferred substituents L are, for example, F, Cl, ON, $NO_2$, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$, furthermore phenyl.

"Substituted silyl or aryl" preferably means silyl or aryl substituted by halogen, —ON, $RY^1$, —OW, —CO—$RY^1$, —OC—O—$RY^1$, —O—CO—$RY^1$ or —O—OC—O—$RY^1$, in which $RY^1$ has the meaning indicated above.

In a preferred embodiment, W in formula I denotes —S— or —O—, preferably —S—.

$Z^{11}$ and $Z^{12}$ preferably stand, independently of one another, for a single bond, —CH=CH—, —CF=CF— or —C≡O—, very particularly preferably for a single bond.

$Z^{21}$ and $Z^{22}$ preferably denote, independently of one another, a single bond, —$CH_2CH_2$—, —$CF_2CF_2$—, —CH=CH—, —CF=CF—, —C≡O—, —$OCH_2$—, —$CH_2O$—, —$OCF_2$— or —$CF_2O$—, particularly preferably —$OCF_2$—, —$CF_2O$— or a single bond, and very particularly preferably a single bond.

$A^{11}, A^{12}, A^{21}, A^{22}$ preferably on each occurrence, identically or differently, represent an aryl group having 6 to 15 C atoms or a heteroaryl group having 2 to 15 C atoms, which may be substituted by one or more radicals L.

$A^{11}, A^{12}, A^{21}, A^{22}$ are particularly preferably selected on each occurrence, identically or differently, from groups, optionally substituted by radicals L, derived from the parent substances benzene, fluorene, naphthalene, pyridine, pyrimidine, thiophene, thiadiazole, dihydrothienodioxin, benzothiophene, dibenzothiophene, benzodithiophene, cyclopentadithiophene, thienothiophene, indenothiophene, furan, benzofuran, dibenzofuran and quinoline, very particularly preferably thiophene, thienothiophene, naphthalene, thiadiazole, and benzene, most preferably thiophene or thienothiophene.

In a preferred embodiment the rings $A^{11}$ and $A^{12}$ both are selected from a thiophene containing ring, including thiophene-2,5-diyl or thienothiophene-2,5-diyl, and the groups $Z^{11}$ and $Z^{12}$ are single bonds.

The groups $R^{11}$ and $R^{12}$ preferably, independently of one another, denote a linear or branched alkyl group having 3 to 25 C atoms, in which one or more H atoms can be replaced by F, one or more $CH_2$ groups can be replaced by O and/or NH and one or more CH groups can be replaced by N.

The groups $R^{11}$ and $R^{12}$ very particularly preferably, independently of one another, denote a branched alkyl group with 3 to 20 C atoms, preferably comprising a methyl, ethyl, n-propyl, n-butyl, or n-pentyl group bonded to a non-terminal C-atom of a radical selected from ethyl, n-propyl, n-hexyl, n-heptyl, n-octyl, n-nonyl or n-decyl group, for example and preferably 2-ethylhexyl, 2-ethylheptyl, 2-ethyloctyl, 2-ethylnonyl, 2-ethyldecyl, 3-ethylhexyl, 3-ethylheptyl, 3-ethyloctyl, 3-ethylnonyl, 3-ethyldecyl, and the like.

In another preferred embodiment, the groups $R^{11}$ and $R^{12}$, independently of one another, denote a straight chain or branched alkyl or dialkylamino group having 1 to 25 C atoms per alkyl group.

The groups $R^{x1}$ and $R^{x2}$ are preferably on each occurrence, identically or differently, H, F or an alkyl group having 1 to 6 C atoms. $R^{x1}$ and $R^{x2}$ are particularly preferably on each occurrence, identically or differently, H or F, very particularly preferably H.

The indices r and s are preferably, independently of one another, equal to 1, 2 or 3, particularly preferably equal to 1 or 2, very particularly preferably equal to 1.

$R^2$ preferably is alkyl having 1 to 10 C atoms.

The compounds of formula I are preferably selected from the group of compounds of the sub-formulae IA to IC

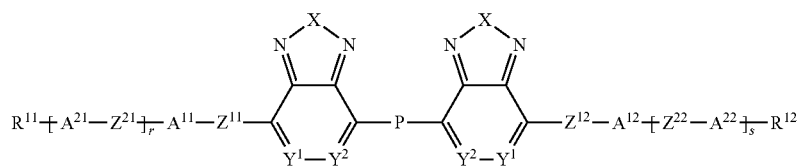

IA

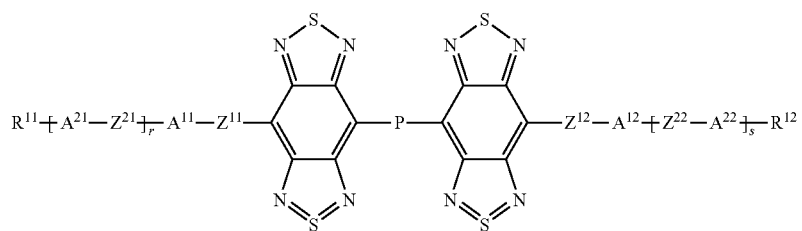

IB

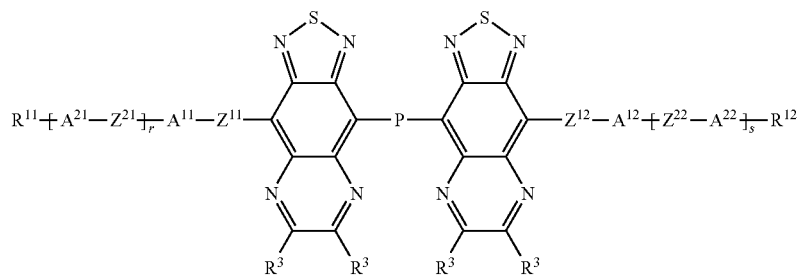

IC wherein the occurring groups have the meaning indicated for formula I above.

The compounds of formula I are preferably chosen from compounds of sub-formula IA.

Preferred embodiments comprise the following formulae:

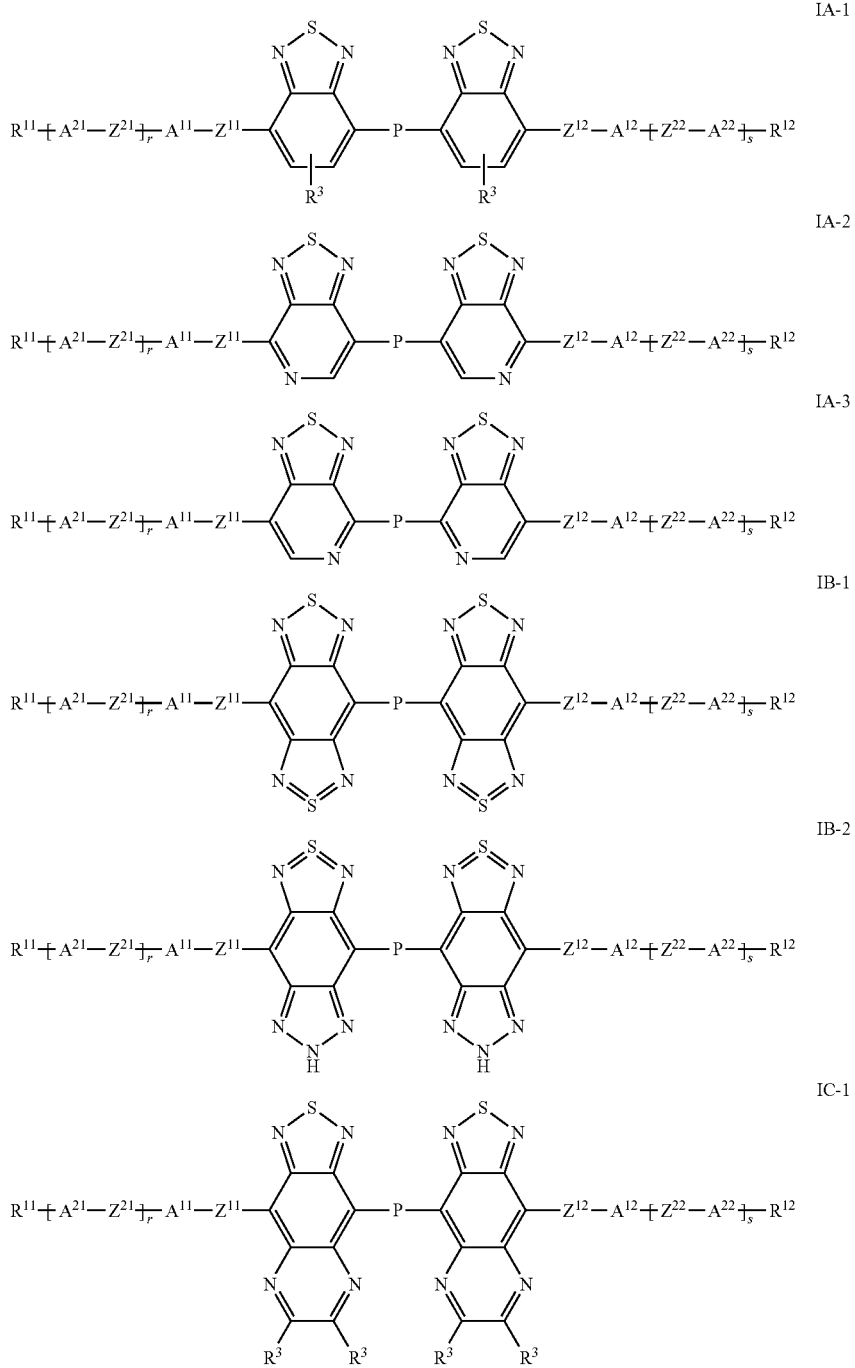

where the groups occurring have the meanings:
P is defined as above, particularly the preferred definitions,
$Z^{11}$, $Z^{12}$ on each occurrence, identically or differently, denote a single bond, —CH=CH—, —CF=CF— or —C≡C—, preferably a single bond,
$Z^{21}$, $Z^{22}$ on each occurrence, identically or differently, denote a single bond, —$CR^{x1}$=$CR^{x2}$—, —C≡C— or —C(O)—, preferably a single bond,
$R^{11}$, $R^{12}$, are independently defined as for formula I,
$A^{11}$, $A^{12}$ are independently defined as for formula I,
$A^{21}$, $A^{22}$ are independently defined as for formula I,
$R^3$ is H, F, Cl, CN, alkyl having 1-25 C-atoms, alkoxy having 1-25 C-atoms or aryl, and
r, s are independently defined as for formula I.

For the compounds of formula I and its dependent formulae (e.g. IA to IC, IA-1 to IC-1 etc.), it is preferred that at least one A[11] or A[12] is bonded directly to the ring relating to Ac (e.g. benzo-bis(thiadiazole)) and is selected from 1,4-phenylene, 1,4-naphthylene, 2,6-naphthylene, thiazole-2,5-diyl, thiophene-2,5-diyl, or thienothiophene-2,5-diyl, preferably from thiophene-2,5-diyl, or thienothiophene-2,5-diyl. The groups may be substituted by one or more radicals L defined above. Particularly preferred substituents L are F, Cl, CN, $CH_3$, $C_2H_5$, $OCH_3$, $CF_3$, $OCF_3$, $OCHF_2$, $OC_2F_5$, furthermore phenyl.

Particularly preferred subformulae of formula IA-1 to IA-3 are the following:

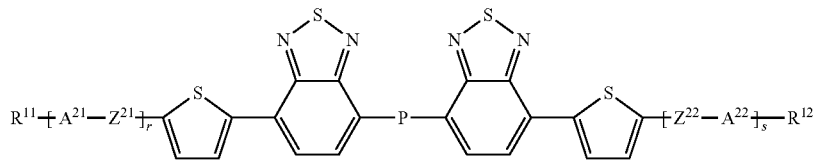

IA-1-1

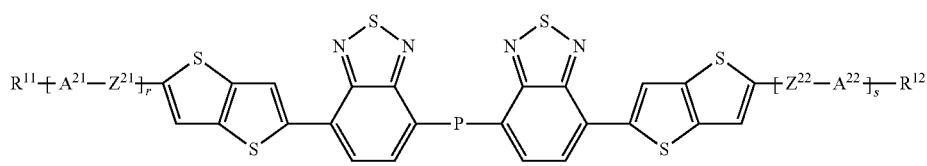

IA-1-2

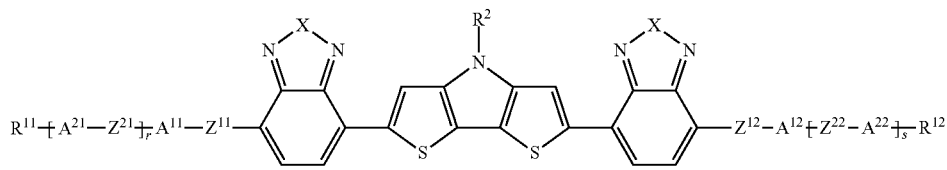

IA-1-3

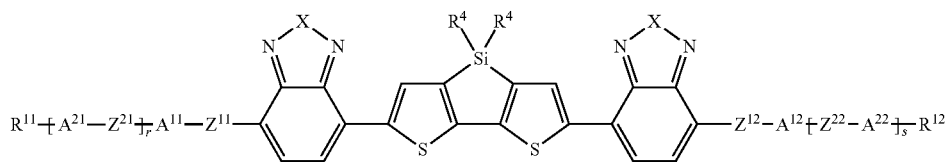

IA-1-4

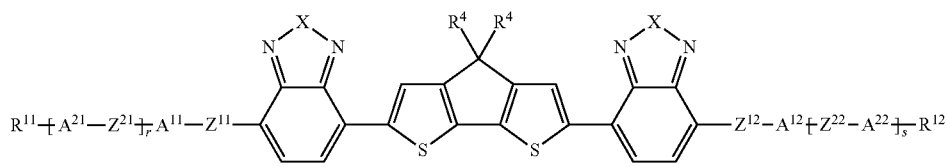

IA-1-5

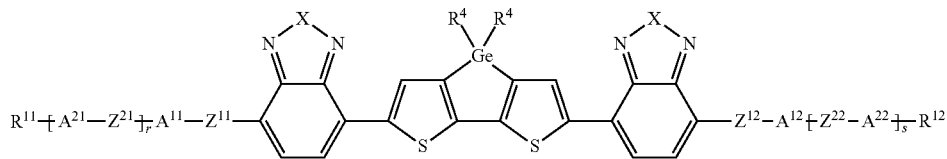

IA-1-6

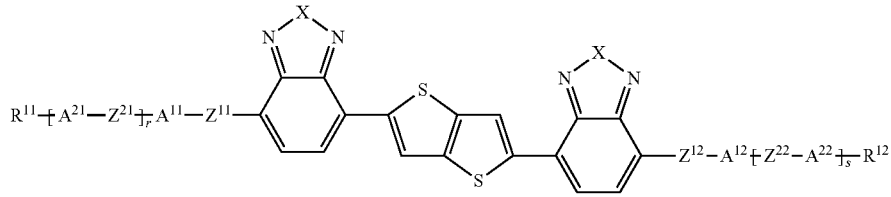

IA-1-7

-continued
IA-1-8
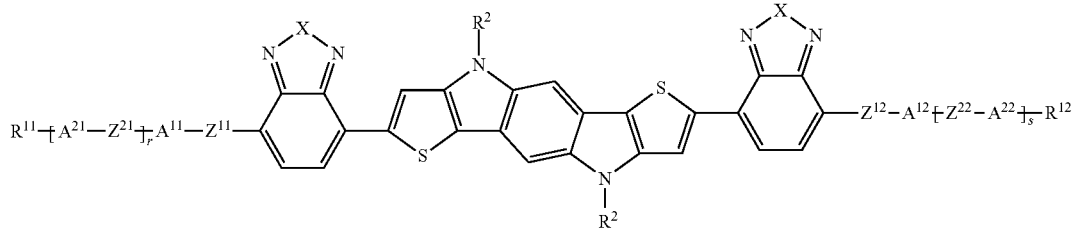
IA-1-9
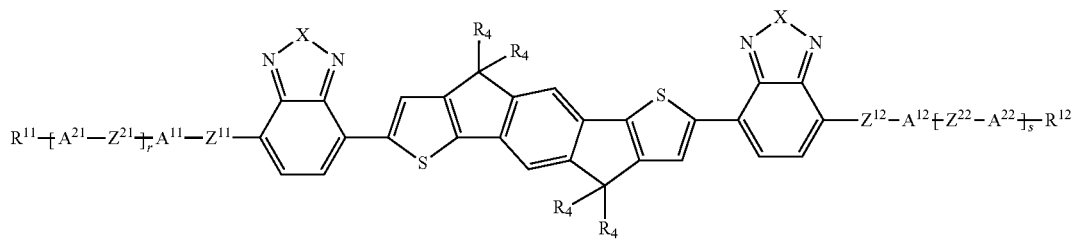
IA-1-10
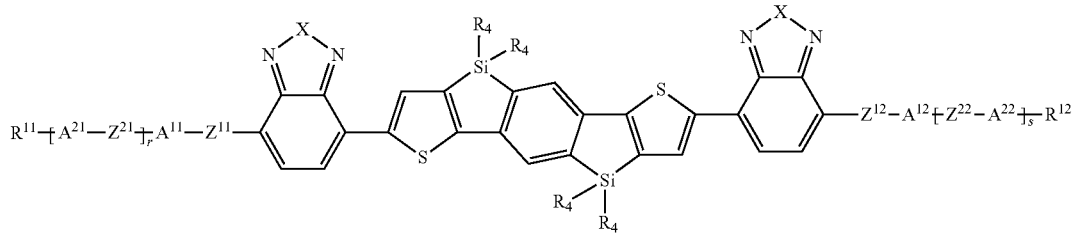
IA-1-11
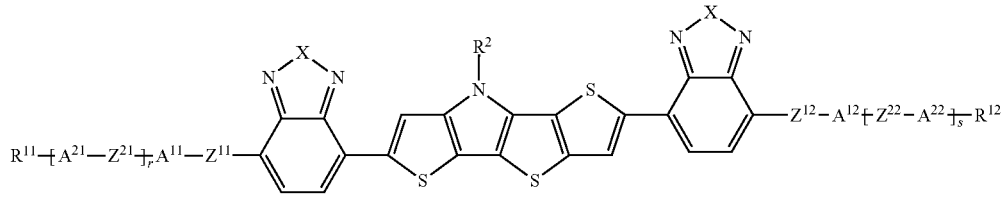
IA-1-12
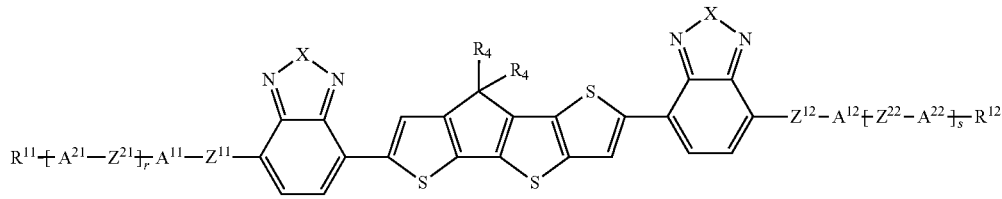
IA-1-13
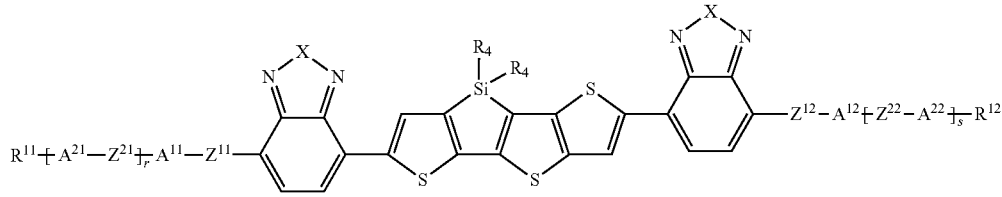
IA-1-14
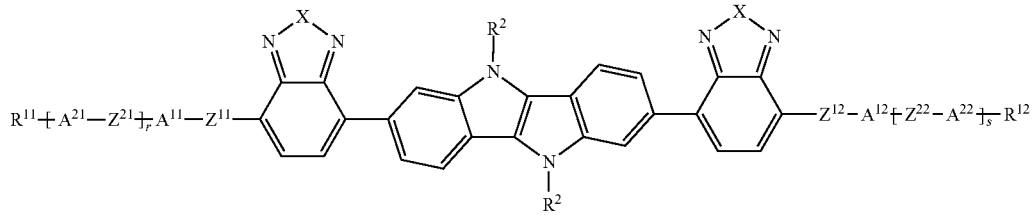

-continued
IA-2-1
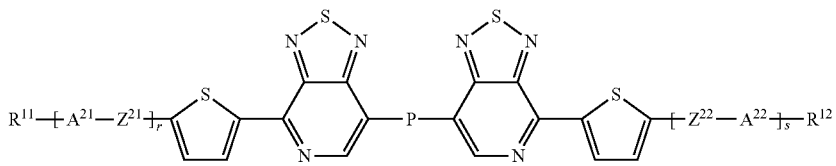
IA-2-2
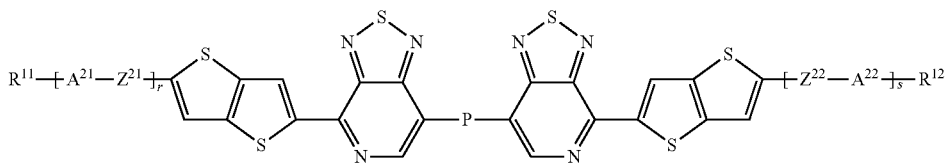
IA-2-3
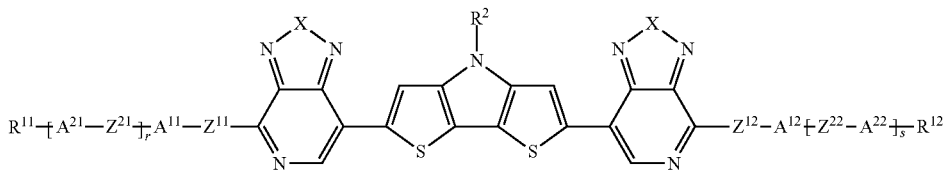
IA-2-4
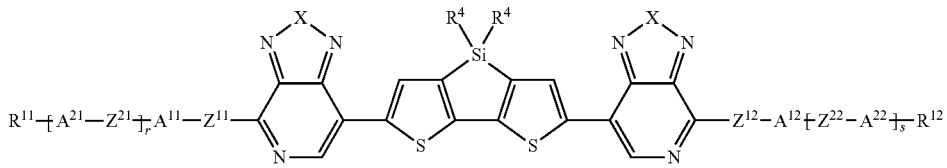
IA-2-5
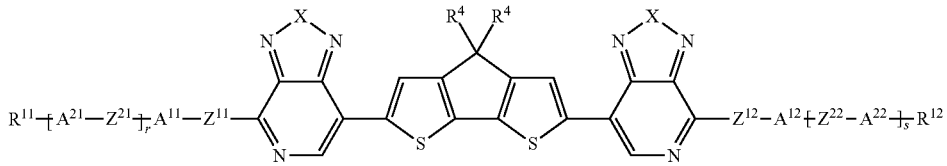
IA-2-6
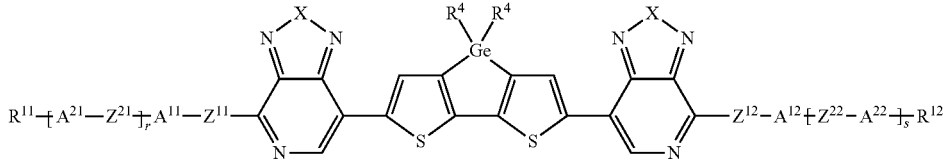
IA-2-7
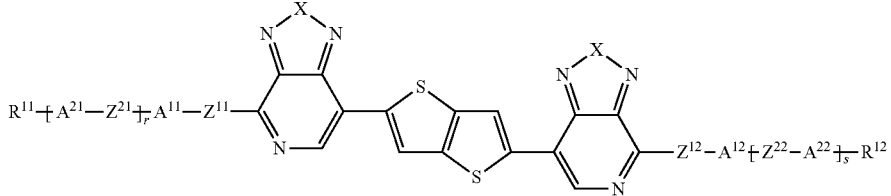
IA-2-8
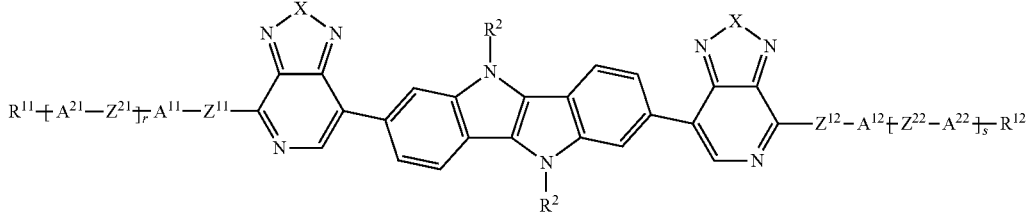

-continued
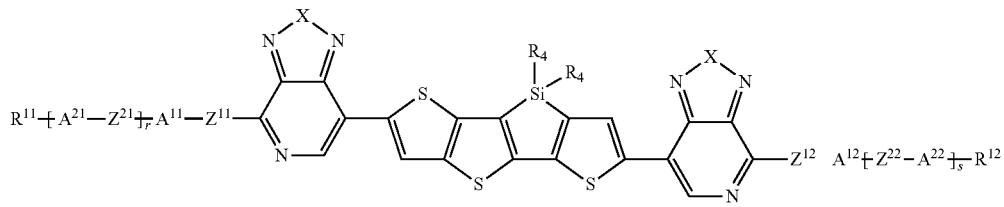
IA-2-9
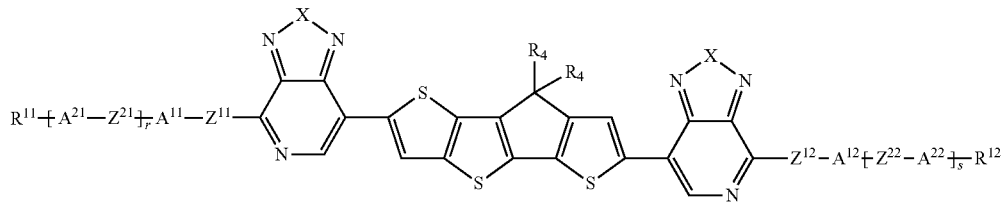
IA-2-10
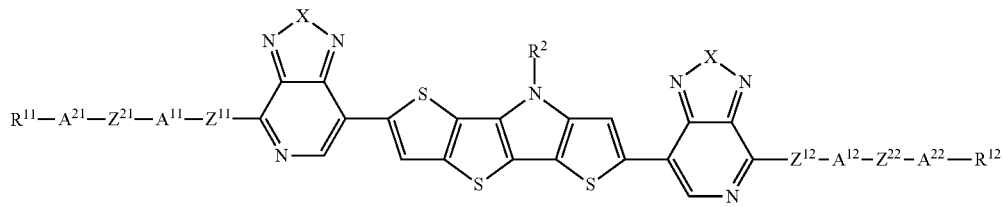
IA-2-11
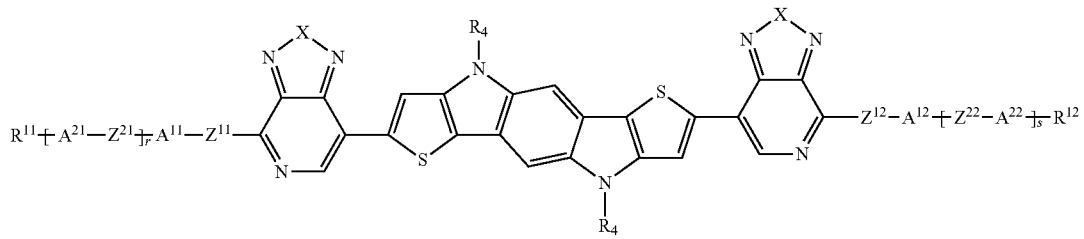
IA-2-12
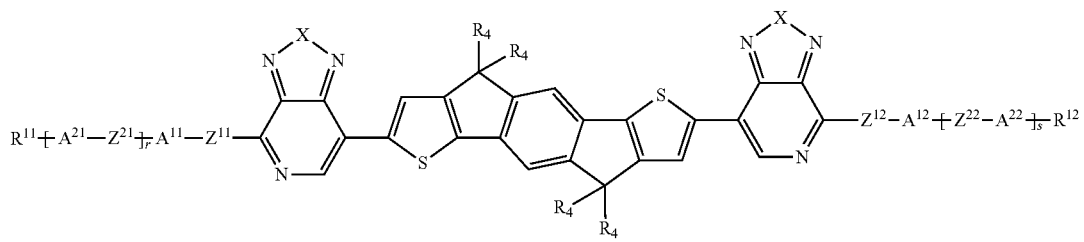
IA-2-13
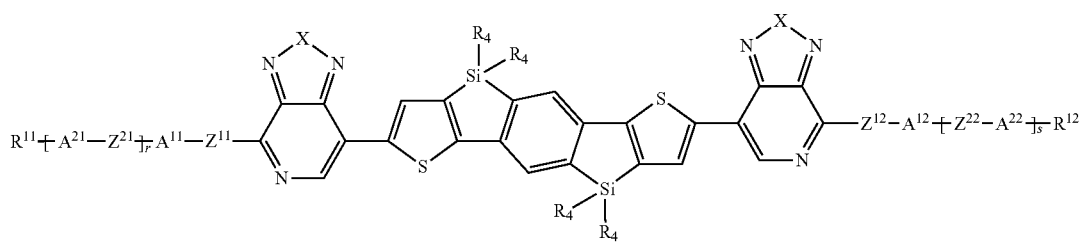
IA-2-14
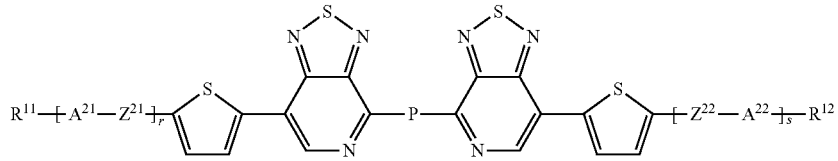
IA-3-1

-continued
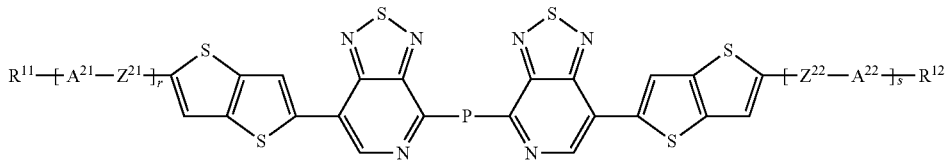
IA-3-2
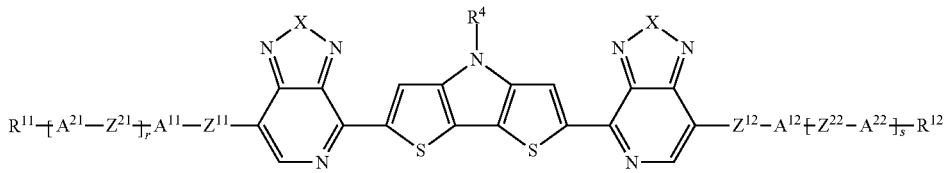
IA-3-3
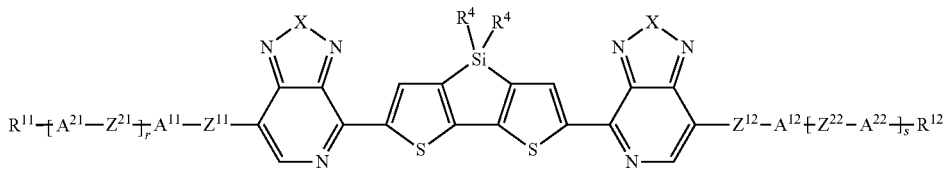
IA-3-4
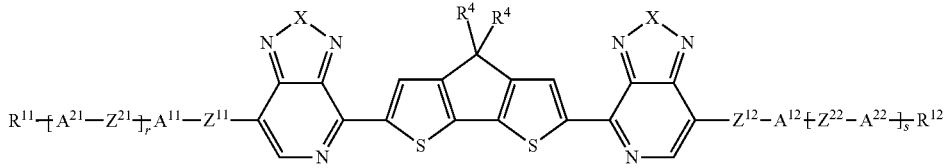
IA-3-5
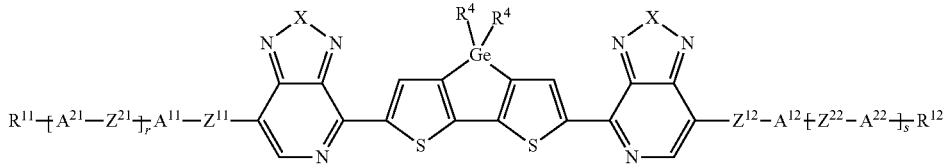
IA-3-6
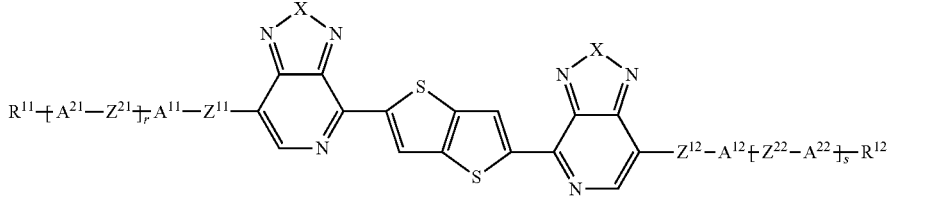
IA-3-7
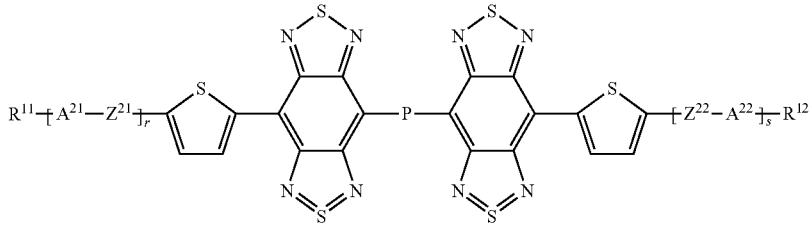
IB-1-1
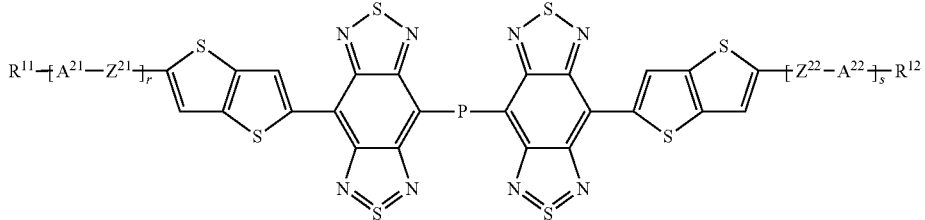
IB-1-2

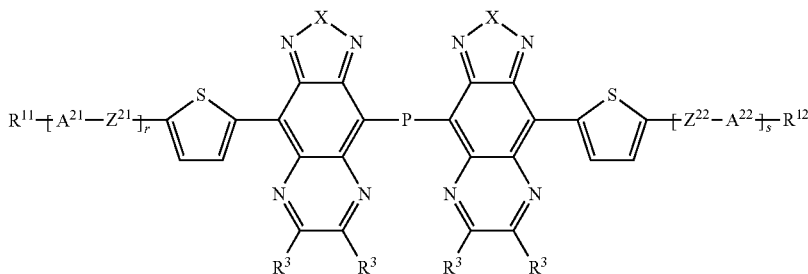

IC-1-1

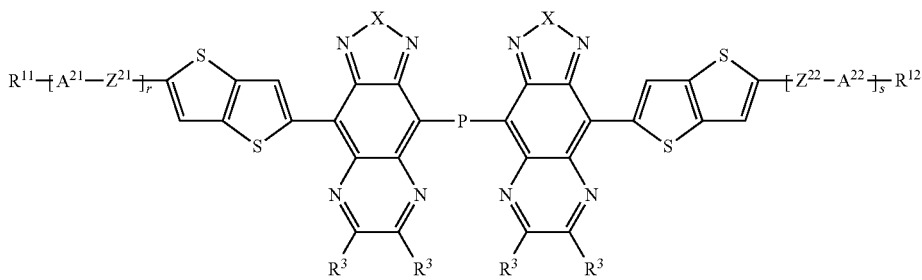

IC-1-2 where the groups $R^{11}$, $R^{12}$, $A^{11}$, $A^{12}$, $A^{21}$, $A^{22}$, $Z^{21}$, $Z^{22}$, X, $R^2$, $R^3$, $R^4$ and L and r, s are defined as for formula I and its subformulae, and preferably $A^{11}$, $A^{12}$, $A^{21}$, $A^{22}$ independently from one another, denote 1,4-phenylene, 1,4-naphthylene, 2,6-naphthylene, thiazole-2,5-diyl, thiophene-2,5-diyl, or thienothiophene-2,5-diyl, which may be substituted by one or more radicals L, L independently denotes F, Cl, ON, $CH_3$, $C_2H_5$, $OCH_3$, $CF_3$, $OCF_3$, $OCHF_2$.

$Z^{11}$, $Z^{12}$ on each occurrence, identically or differently, denote a single bond, —CH═CH—, —CF═CF— or —C≡O—, preferably a single bond, and $Z^{21}$, $Z^{22}$ on each occurrence, identically or differently, denote a single bond, —$CR^{x1}$═$CR^{x2}$—, —C≡O— or —C(O)—, preferably a single bond.

The compounds of the formula I can be prepared analogously to processes known to the person skilled in the art and described in standard works of organic chemistry, such as, for example, Houben-Weyl, Methoden der organischen Chemie [Methods of Organic Chemistry], Thieme Verlag, Stuttgart. For specific processes for the preparation of compounds of the formula I, reference is furthermore made to the known literature and to the working examples.

In consideration of reactivity and regioselectivity of each chemical building block one or more of the following synthetic strategies can be applied for making the desired dyes (Schemes 1 to 4). Each reaction in the Schemes 1 to 4 can be accomplished by a suitable coupling reaction selected from C—H activation, Stille, Suzuki, Negishi, Sonogashira, Buchwald-Hartwig or Ullmann type.

Scheme 1. General synthetic scheme.

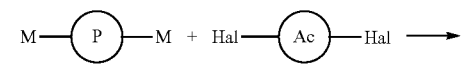

M = H, SnR$_3$, B(OR)$_2$, ZnHal

Hal = H, Br, I, Cl

Scheme 2. General synthetic scheme.

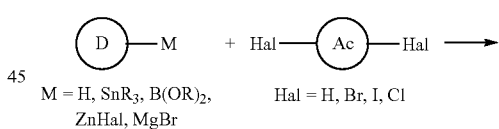

M = H, SnR$_3$, B(OR)$_2$, ZnHal, MgBr

Hal = H, Br, I, Cl

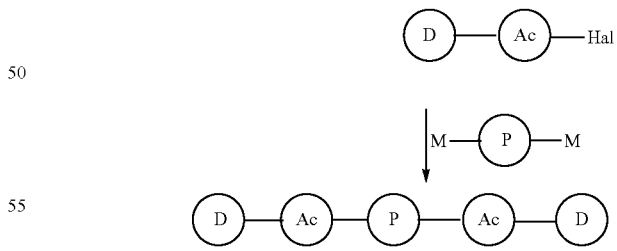

Scheme 3. General synthetic scheme.

M = H, SnR$_3$, B(OR)$_2$, ZnHal, MgBr

Hal = H, Br, I, Cl

-continued

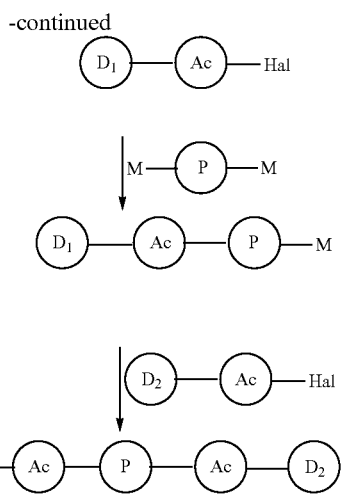

Scheme 4. General synthetic scheme.

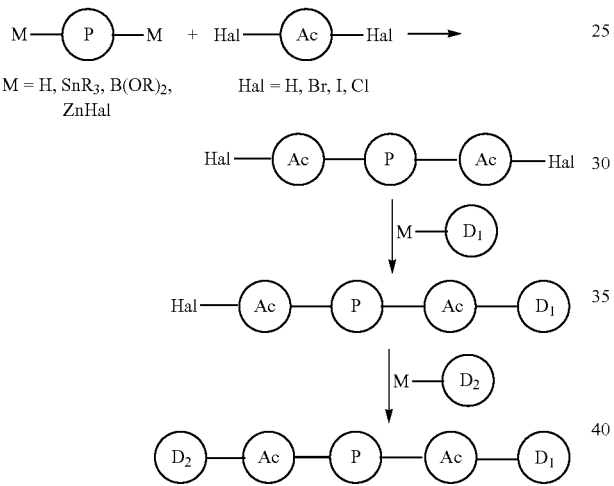

M = H, SnR$_3$, B(OR)$_2$, ZnHal
Hal = H, Br, I, Cl

The compound of the formula I is preferably a positively dichroic dye, i.e. a dye which has a positive degree of anisotropy R. The degree of anisotropy R is determined, from the value for the extinction coefficient of the LC mixture comprising the dye in the case of alignment of the molecules parallel to the direction of polarisation of the light and the value for the extinction coefficient in the case of perpendicular alignment of the molecules to the direction of polarisation of the light.

The degree of anisotropy R is particularly preferably greater than 0.4, very particularly preferably greater than 0.6 and most preferably greater than 0.7.

The absorption preferably reaches a maximum when the polarisation direction of the light is parallel to the direction of the longest elongation of the molecule of the formula I, and it reaches a minimum when the polarisation direction of the light is perpendicular to the direction of the longest elongation of the molecule of the formula I.

In principle, a suitable host mixture is any dielectrically negative or positive LC mixture which is suitable for use in conventional VA, TN, IPS or FFS displays.

Suitable LC mixtures are known to the person skilled in the art and are described in the literature. LC media for VA displays having negative dielectric anisotropy are described in for example EP 1 378 557 A$^1$.

Suitable LC mixtures having positive dielectric anisotropy which are suitable for LCDs and especially for IPS displays are known, for example, from JP 07-181 439 (A), EP 0 667 555, EP 0 673 986, DE 195 09 410, DE 195 28 106, DE 195 28 107, WO 96/23 851, WO 96/28 521 and WO2012/079676.

Preferred embodiments of the liquid-crystalline medium having negative or positive dielectric anisotropy according to the invention are indicated below.

The LC host mixture is preferably a nematic LC mixture, and preferably does not have a chiral LC phase.

In a preferred embodiment of the present invention the LC medium contains an LC host mixture with negative dielectric anisotropy. Preferred embodiments of such an LC medium, and the corresponding LC host mixture, are those of sections a)-w) below:

a) LC medium which comprises one or more compounds selected from the group of compounds of the formulae CY, PY and AC:

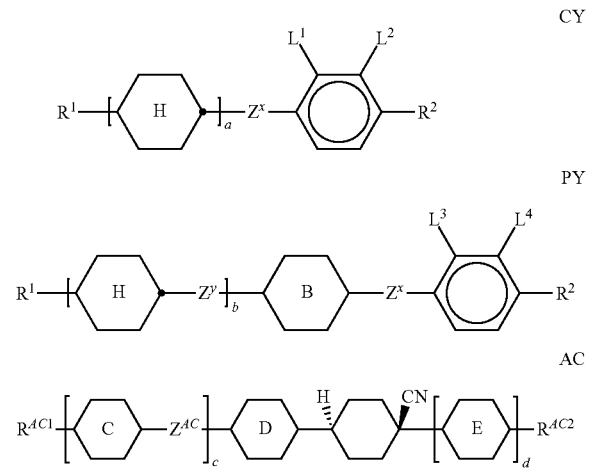

wherein
a denotes 1 or 2,
b denotes 0 or 1,
c is 0, 1 or 2,
d is 0 or 1,

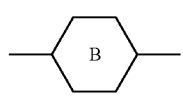

denotes

or

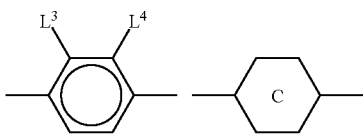

and

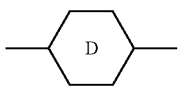

denote

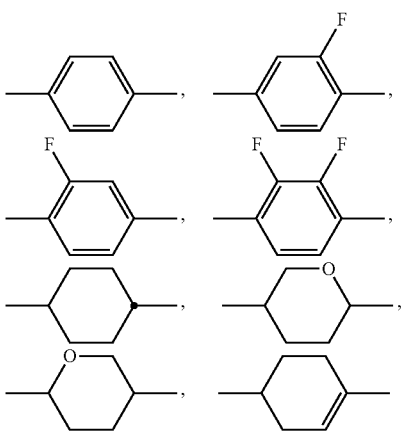

or

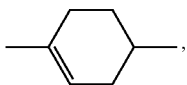

and

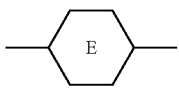

denotes

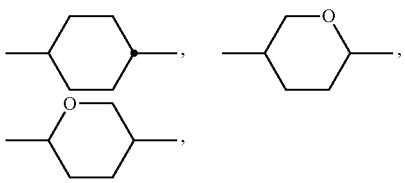

$R^1$ and $R^2$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, preferably alkyl or alkoxy having 1 to 6 C atoms, $R^{AC1}$ and $R^{AC2}$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that 0 atoms are not linked directly to one another, preferably alkyl or alkoxy having 1 to 6 C atoms, $Z^x$ and $Z^y$ each, independently of one another, denote —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond, $L^{1-4}$ each, independently of one another, denote F, Cl, CN, OCF$_3$, CF$_3$, CH$_3$, CH$_2$F, CHF$_2$, and $Z^{AC}$ denotes —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond.

Preferably, both $L^1$ and $L^2$ denote F or one of $L^1$ and $L^2$ denotes F and the other denotes Cl, or both $L^3$ and $L^4$ denote F or one of $L^3$ and $L^4$ denotes F and the other denotes Cl.

The compounds of the formula CY are preferably selected from the group consisting of the following sub-formulae:

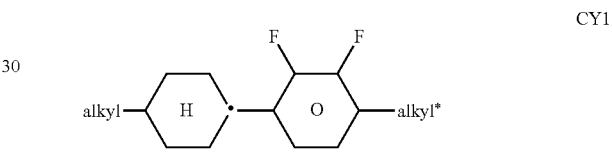

CY1

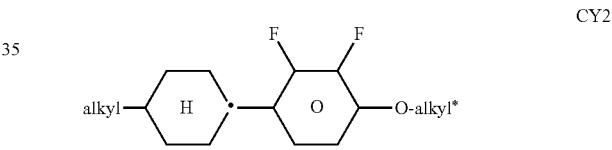

CY2

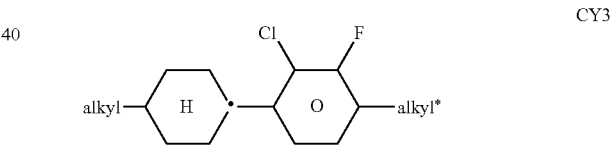

CY3

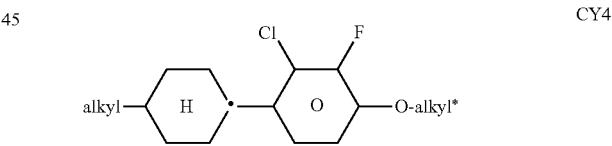

CY4

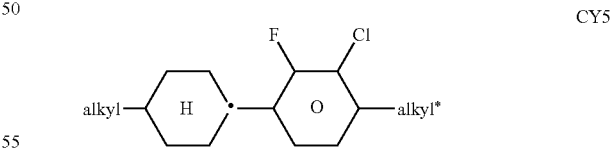

CY5

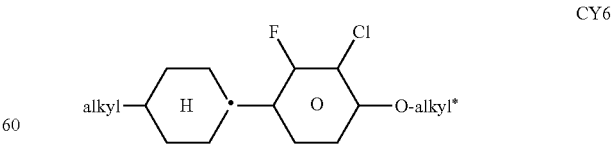

CY6

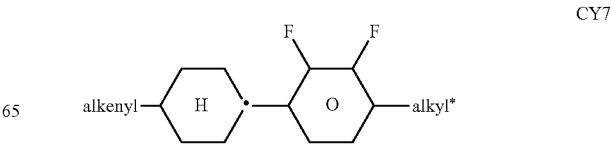

CY7

CY8 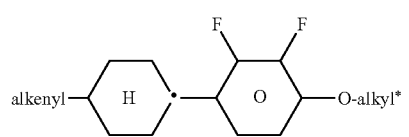
CY9 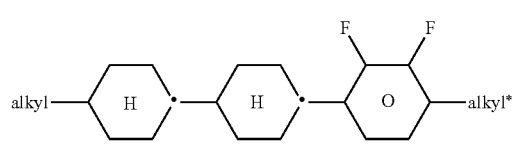
CY10 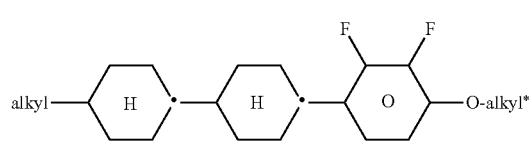
CY11 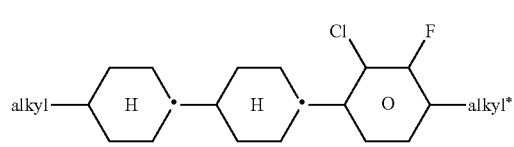
CY12 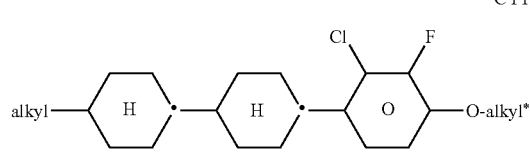
CY13 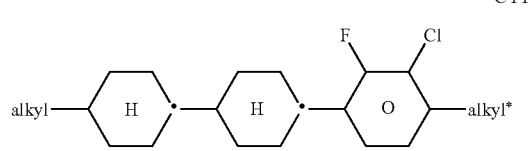
CY14 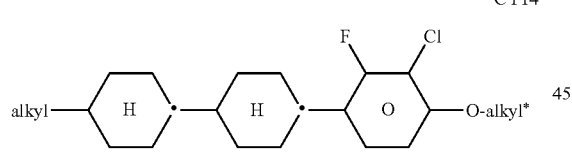
CY15 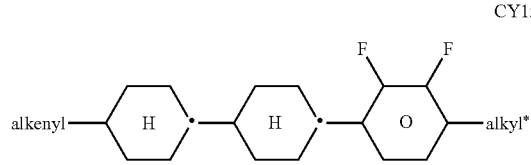
CY16 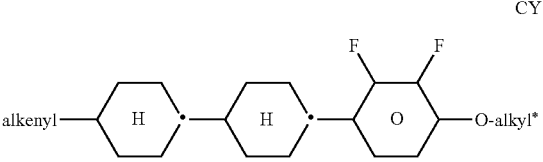
CY17 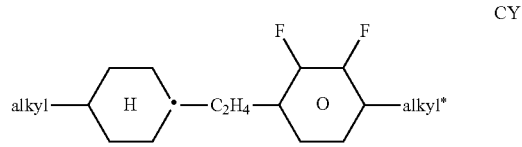
CY18 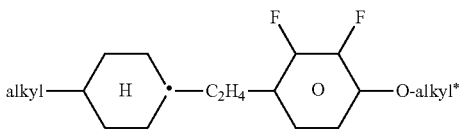
CY19 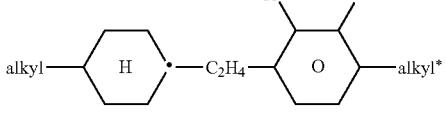
CY20 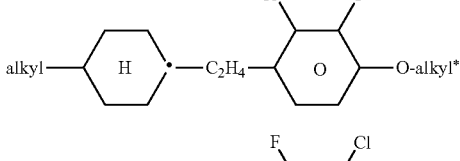
CY21 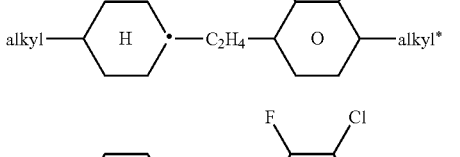
CY22 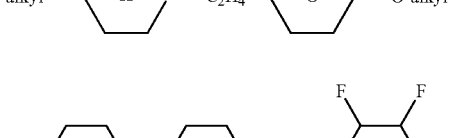
CY23 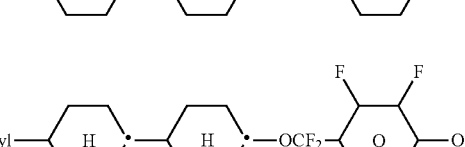
CY24 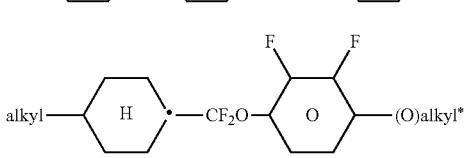
CY25 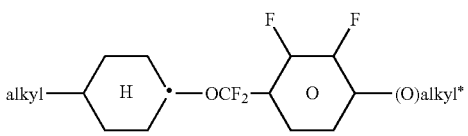
CY26 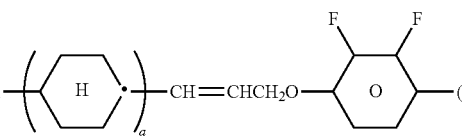
CY27 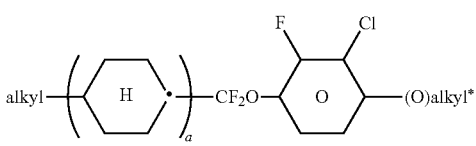
CY28

-continued

CY29
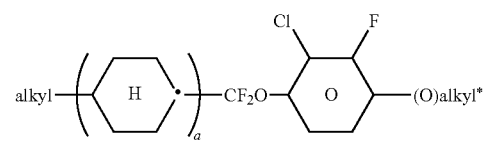

CY30
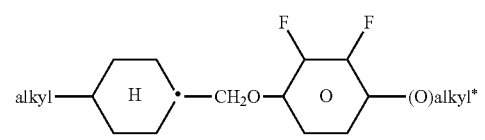

CY31
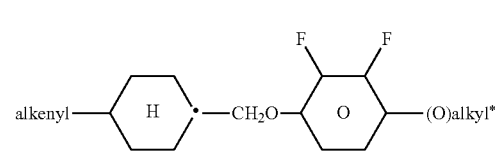

CY32
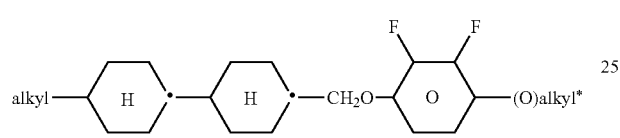

CY33
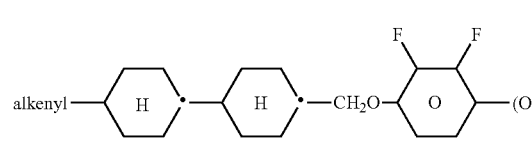

wherein a denotes 1 or 2, alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes CH$_2$=CH—, CH$_2$=CH—CH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

The compounds of the formula PY are preferably selected from the group consisting of the following sub-formulae:

PY1
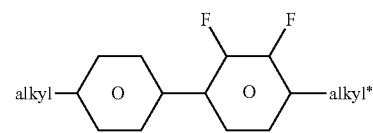

PY2
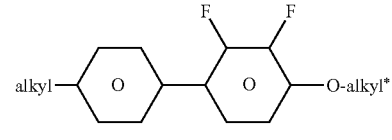

PY3
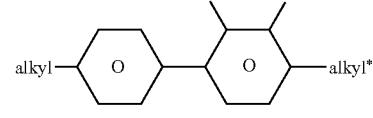

PY4
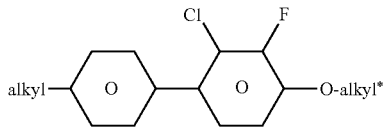

PY5
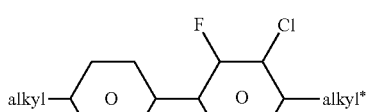

PY6
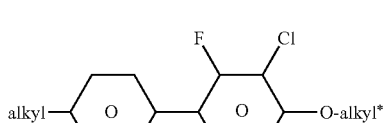

PY7
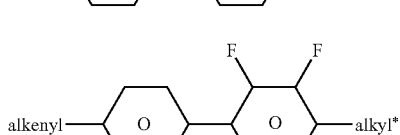

PY8
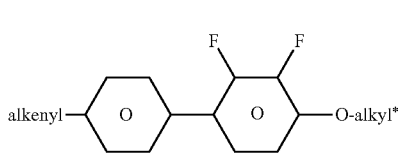

PY9
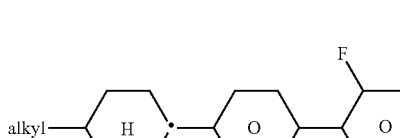

PY10
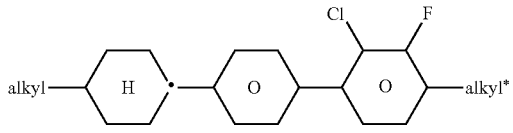

PY11
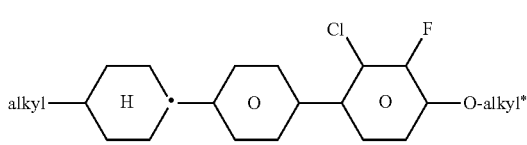

PY12
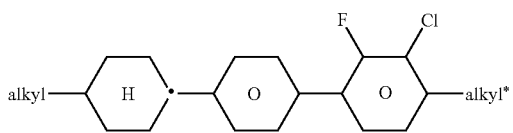

PY13

-continued

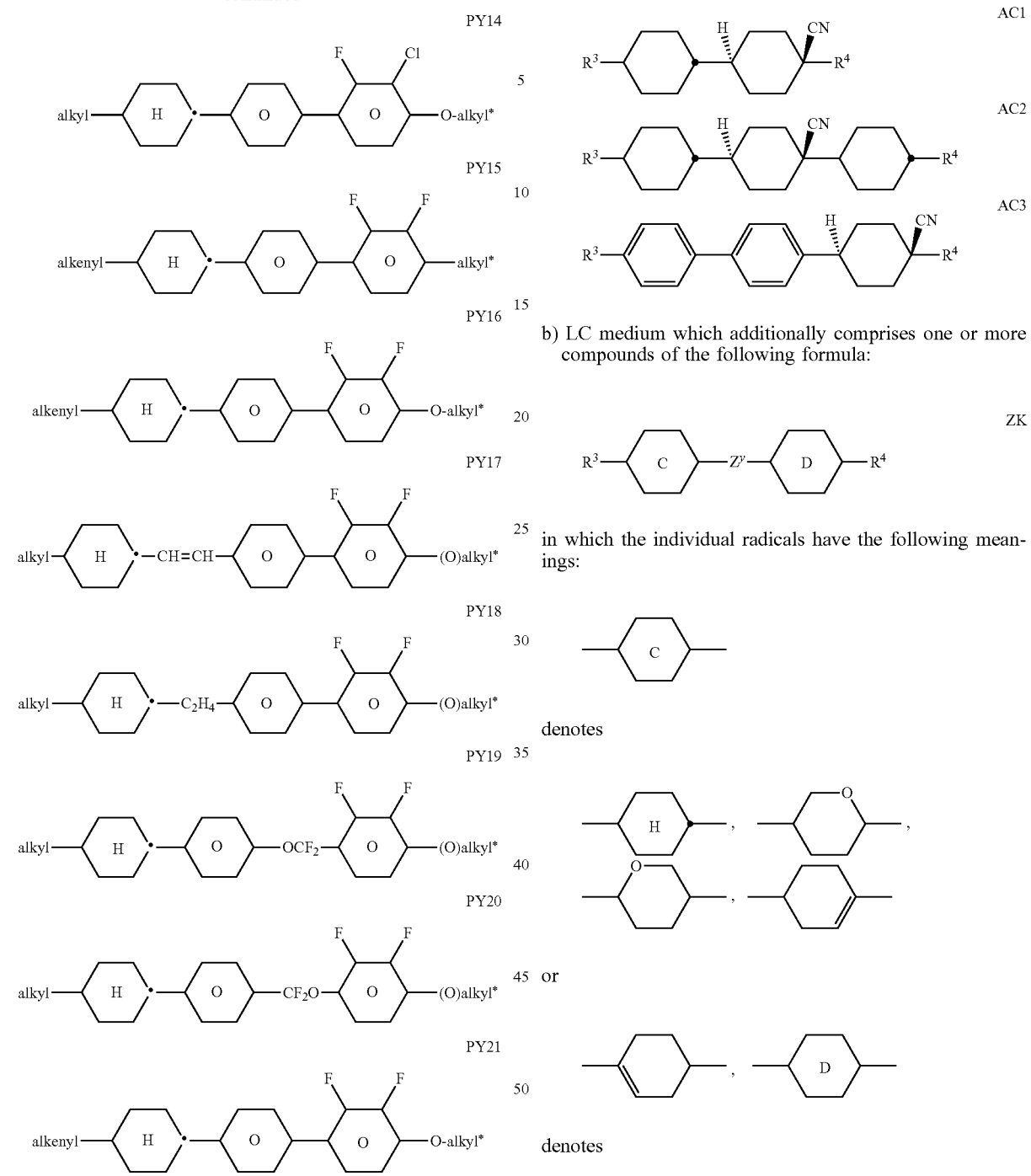

wherein alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The compounds of the formula AC are preferably selected from the group of compounds of the following sub-formulae:

b) LC medium which additionally comprises one or more compounds of the following formula:

in which the individual radicals have the following meanings:

denotes or denotes or

R³ and R⁴ each, independently of one another, denote alkyl having 1 to 12 C atoms, in which, in addition, one or two non-adjacent CH₂ groups may be replaced by —O—, —CH=CH—, —CO—, —O—CO— or —OC—O— in such a way that O atoms are not linked directly to one another, $Z^y$ denotes —CH₂CH₂—, —CH=CH—, —CF₂O—, —OCF₂—, —CH₂O—, —OCH₂—, —CO—O—, —O—CO—, —C₂F₄—, —CF=CF—, —CH=CH—CH₂O— or a single bond, preferably a single bond.

The compounds of the formula ZK are preferably selected from the group consisting of the following sub-formulae:

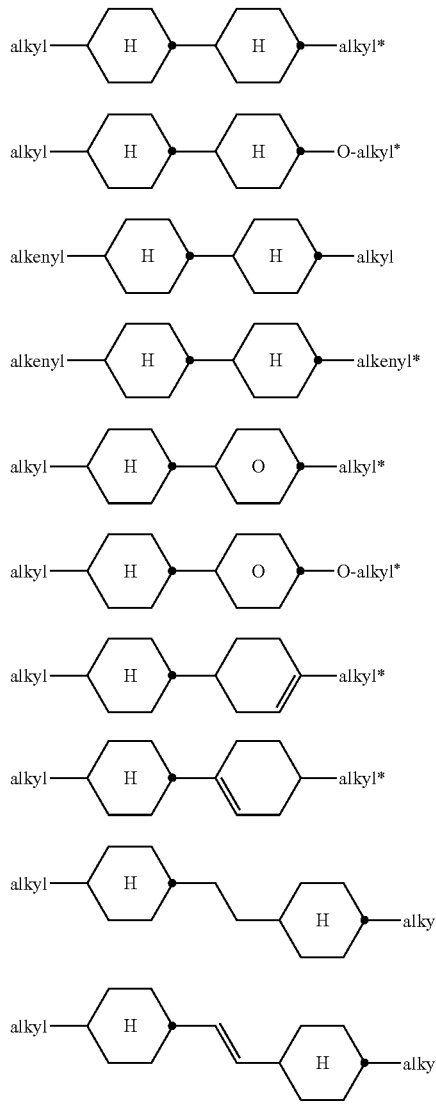

in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes CH₂=CH—, CH₂=CHCH₂CH₂—, CH₃—CH=CH—, CH₃—CH₂—CH=CH—, CH₃—(CH₂)₂—CH=CH—, CH₃—(CH₂)₃—CH=CH— or CH₃—CH=CH—(CH₂)₂—.

Especially preferred are compounds of formula ZK1 and ZK3.

Particularly preferred compounds of formula ZK are selected from the following sub-formulae:

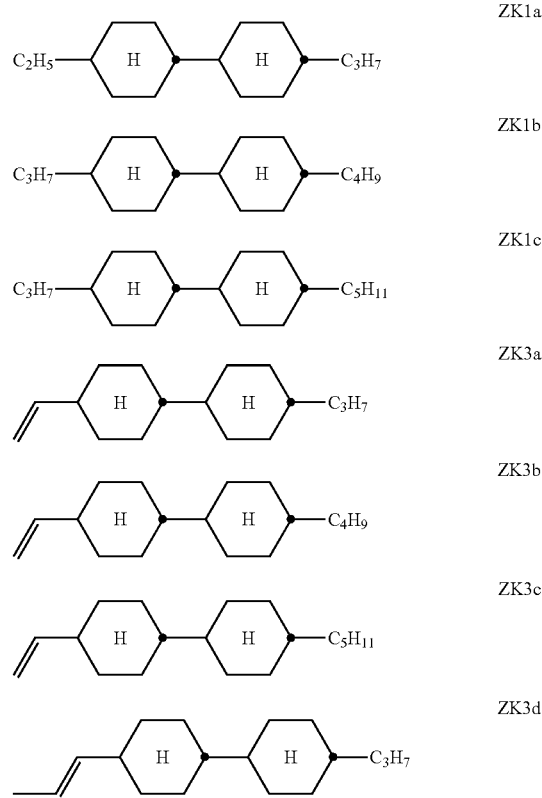

wherein the propyl, butyl and pentyl groups are straight-chain groups.

Most preferred are compounds of formula ZK1a and ZK3a.

c) LC medium which additionally comprises one or more compounds of the following formula:

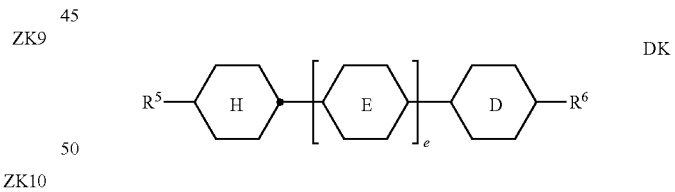

in which the individual radicals on each occurrence, identically or differently, have the following meanings:

R⁵ and R⁶ each, independently of one another, denote alkyl having 1 to 12 C atoms, where, in addition, one or two non-adjacent CH₂ groups may be replaced by —O—, —CH=CH—, —CO—, —OCO— or —COO— in such a way that O atoms are not linked directly to one another, preferably alkyl or alkoxy having 1 to 6 C atoms,

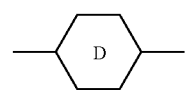

denotes

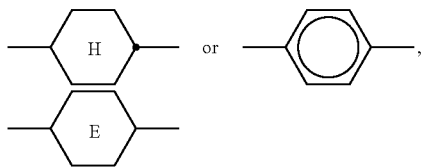

denotes

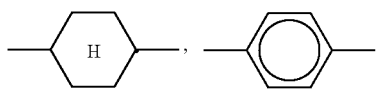

or

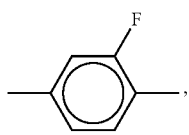

and e denotes 1 or 2.

Preferably the compounds of formula DK comprise at least one ring which denotes

or

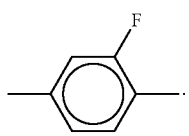

The compounds of the formula DK are preferably selected from the group consisting of the following sub-formulae:

DK1
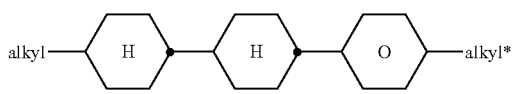

DK2
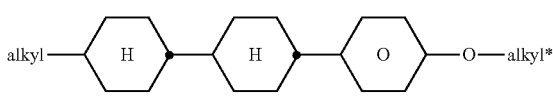

DK3
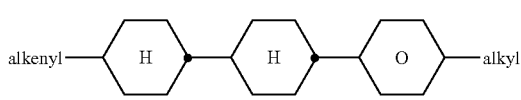

DK4
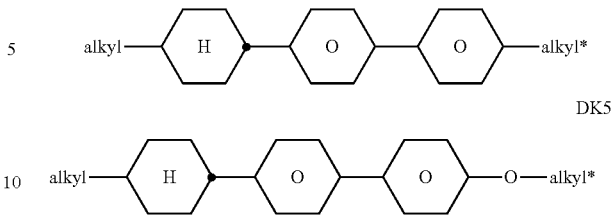

DK5
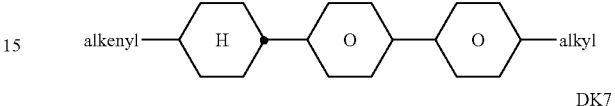

DK6
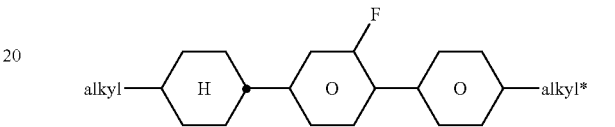

DK7

DK8

DK9

DK10
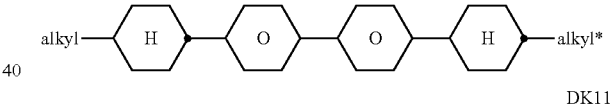

DK11

DK12 in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Preference is give to compounds of the formulae DK1, DK4, DK7, DK 9, DK10 and DK11.

d) LC medium which additionally comprises one or more compounds of the following formula:

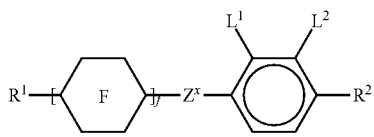

in which the individual radicals have the following meanings:

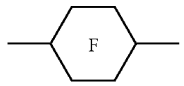

denotes

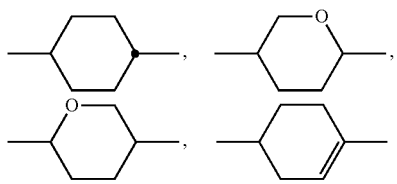

or

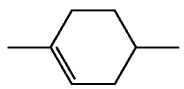

with at least one ring F being different from cyclohexylene,
f denotes 1 or 2,
R$^1$ and R$^2$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another,
Z$^x$ denotes —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond,
L$^1$ and L$^2$ each, independently of one another, denote F, Cl, OCF$_3$, CF$_3$, CHs, CH$_2$F, CHF$_2$.

Preferably, both radicals L$^1$ and L$^2$ denote F or one of the radicals L$^1$ and L$^2$ denotes F and the other denotes Cl.

The compounds of the formula LY are preferably selected from the group consisting of the following sub-formulae:

LY1
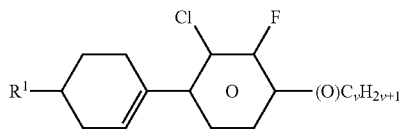

LY2
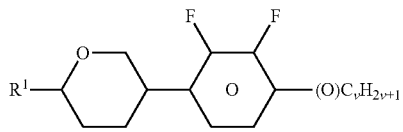

LY3
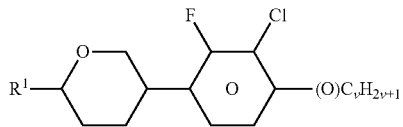

LY4
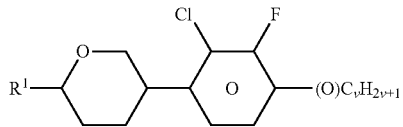

LY5
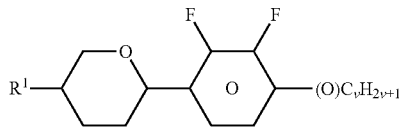

LY6
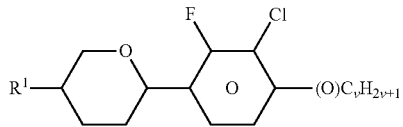

LY7
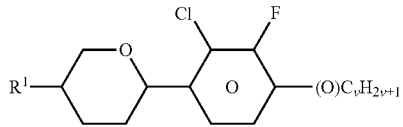

LY8
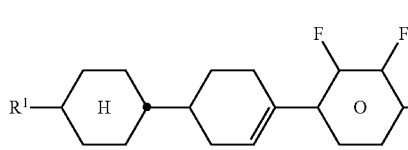

LY9
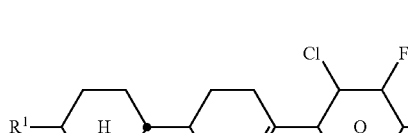

LY10
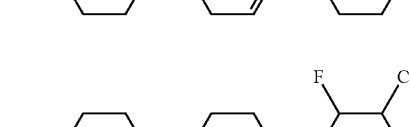

LY11
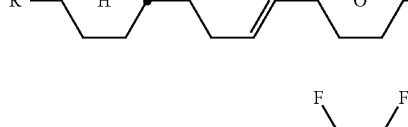

LY12
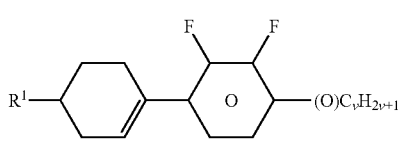

LY13
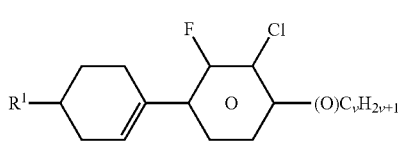

LY14
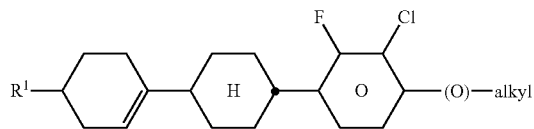

LY15
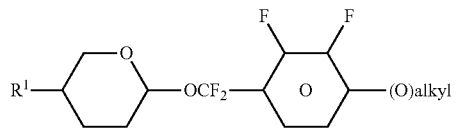

LY16
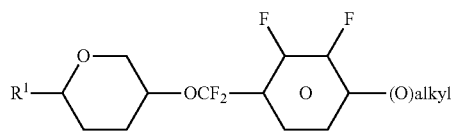

LY17
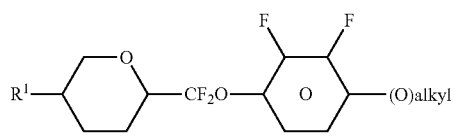

LY18
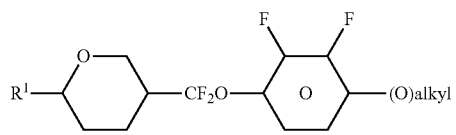

LY19
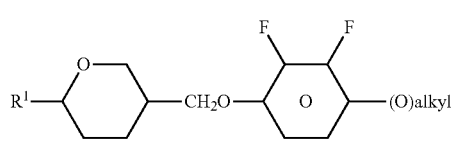

LY20
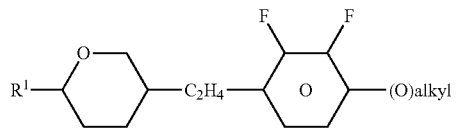

LY21
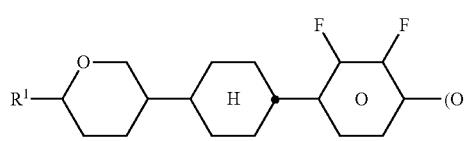

LY22
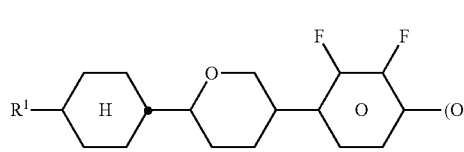

LY23
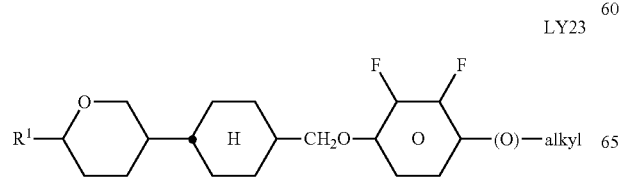

LY24
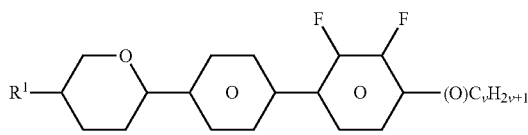

in which $R^1$ has the meaning indicated above, alkyl denotes a straight-chain alkyl radical having 1-6 C atoms, (O) denotes an oxygen atom or a single bond, and v denotes an integer from 1 to 6. $R^1$ preferably denotes straight-chain alkyl having 1 to 6 C atoms or straight-chain alkenyl having 2 to 6 C atoms, in particular $CH_3$, $C_2H_5$, n-$C_3H_7$, n-$C_4H_9$, n-$C_5H_{11}$, $CH_2$=CH—, $CH_2$=$CHCH_2CH_2$—, $CH_3$—CH=CH—, $CH_3$—$CH_2$—CH=CH—, $CH_3$—$(CH_2)_2$—CH=CH—, $CH_3$—$(CH_2)_3$—CH=CH— or $CH_3$—CH=CH—$(CH_2)_2$—.

e) LC medium which additionally comprises one or more compounds selected from the group consisting of the following formulae:

G1
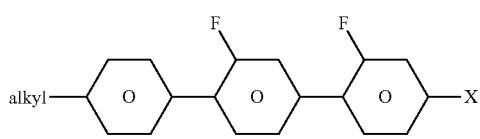

G2
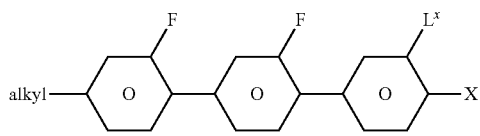

G3
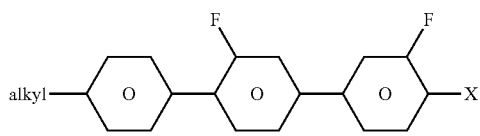

G4
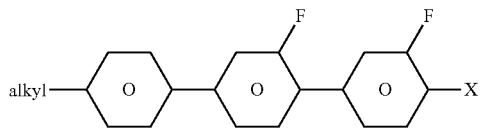

in which alkyl denotes $C_{1-6}$-alkyl, Lx denotes H or F, and X denotes F, Cl, $OCF_3$, $OCHF_2$ or OCH=$CF_2$. Particular preference is given to compounds of the formula G1 in which X denotes F.

f) LC medium which additionally comprises one or more compounds selected from the group consisting of the following formulae:

Y1
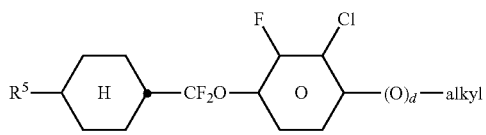

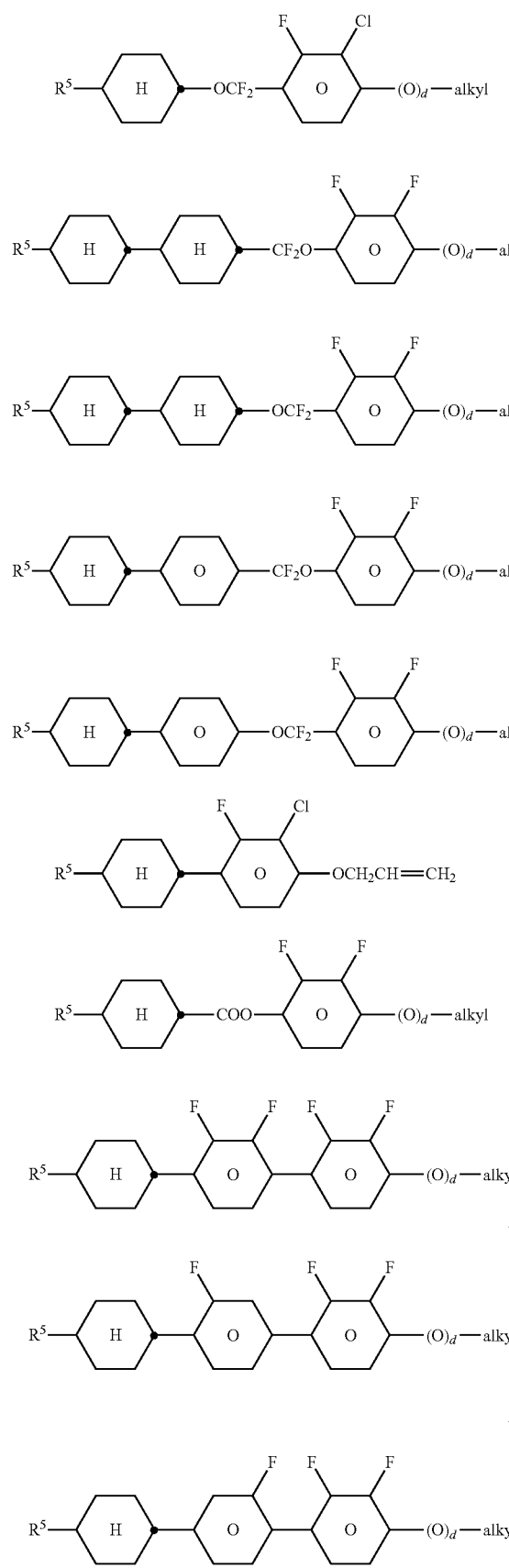

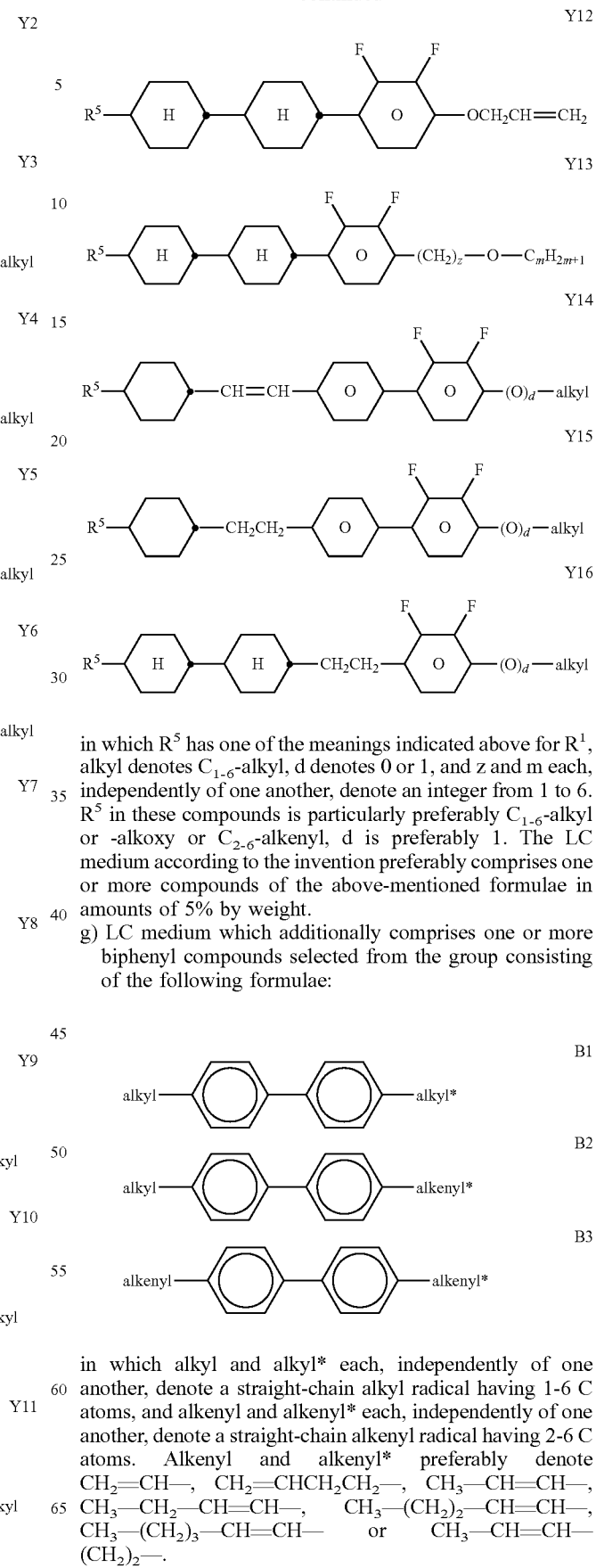

in which $R^5$ has one of the meanings indicated above for $R^1$, alkyl denotes $C_{1-6}$-alkyl, d denotes 0 or 1, and z and m each, independently of one another, denote an integer from 1 to 6. $R^5$ in these compounds is particularly preferably $C_{1-6}$-alkyl or -alkoxy or $C_{2-6}$-alkenyl, d is preferably 1. The LC medium according to the invention preferably comprises one or more compounds of the above-mentioned formulae in amounts of 5% by weight.

g) LC medium which additionally comprises one or more biphenyl compounds selected from the group consisting of the following formulae:

in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote $CH_2$=CH—, $CH_2$=CHCH$_2$CH$_2$—, $CH_3$—CH=CH—, $CH_3$—CH$_2$—CH=CH—, $CH_3$—(CH$_2$)$_2$—CH=CH—, $CH_3$—(CH$_2$)$_3$—CH=CH— or $CH_3$—CH=CH—(CH$_2$)$_2$—.

The proportion of the biphenyls of the formulae B1 to B3 in the LC mixture is preferably at least 3% by weight, in particular 5% by weight.

The compounds of the formula B2 are particularly preferred.

The compounds of the formulae B1 to B3 are preferably selected from the group consisting of the following sub-formulae:

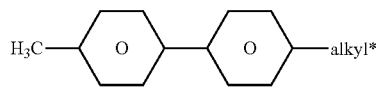
B1a

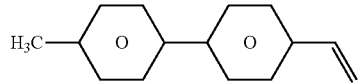
B2a

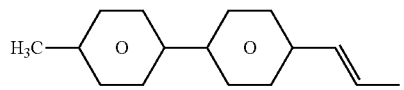
B2b

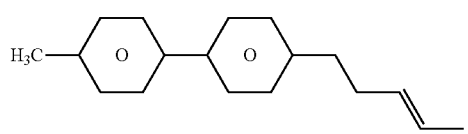
B2c in which alkyl* denotes an alkyl radical having 1-6 C atoms. The medium according to the invention particularly preferably comprises one or more compounds of the formulae B1a and/or B2c.

h) LC medium which additionally comprises one or more terphenyl compounds of the following formula:

T in which $R^5$ and $R^6$ each, independently of one another, have one of the meanings indicated above, and

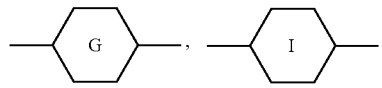

and

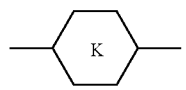

each, independently of one another, denote

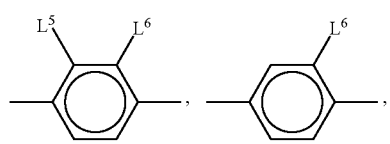

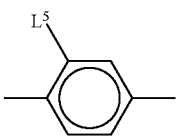

or

in which $L^5$ denotes F or Cl, preferably F, and $L^6$ denotes F, Cl, $OCF_3$, $CF_3$, $CH_3$, $CH_2F$ or $CHF_2$, preferably F.

The compounds of the formula T are preferably selected from the group consisting of the following sub-formulae:

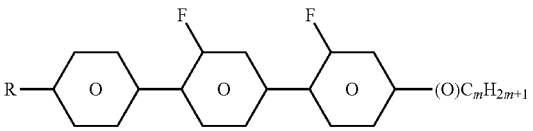
T1

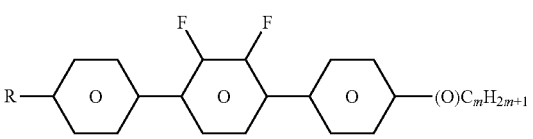
T2

T3

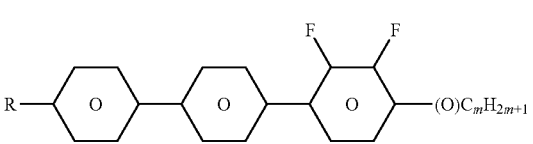
T4

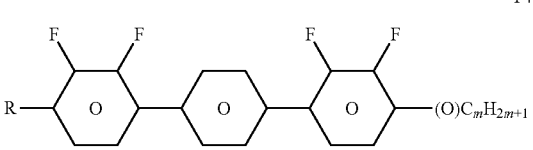
T5

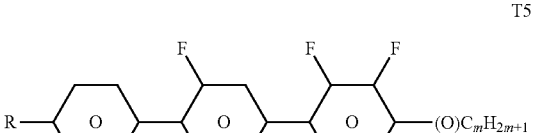
T6

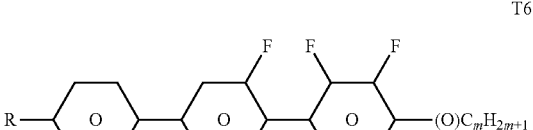
T7

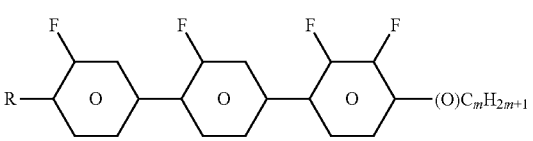

T8
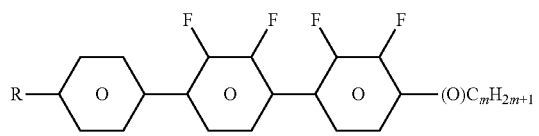
T9
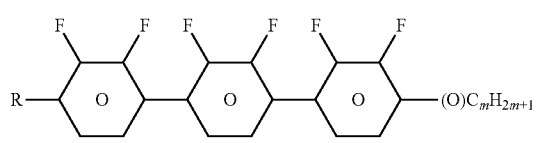
T10
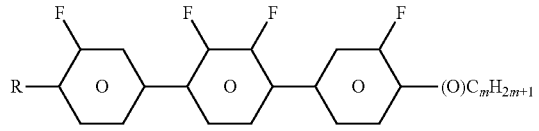
T11
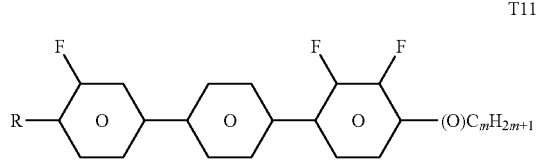
T12
T13
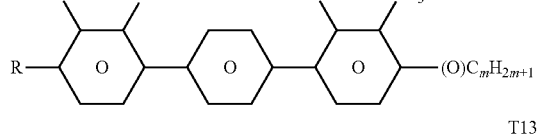
T14
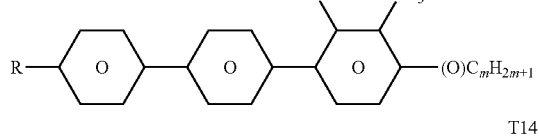
T15
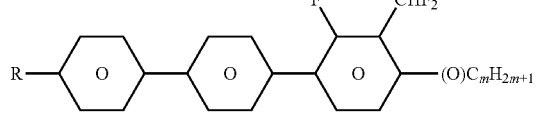
T16
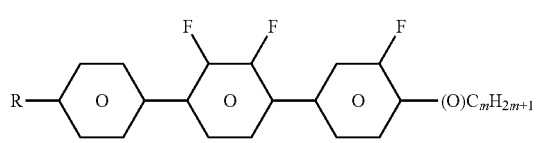
T17
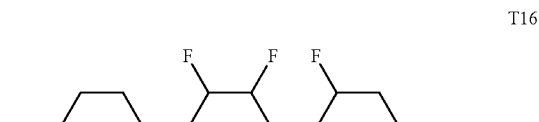
T18
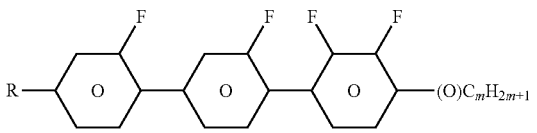
T19
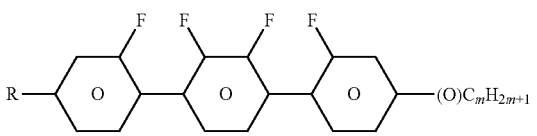
T20
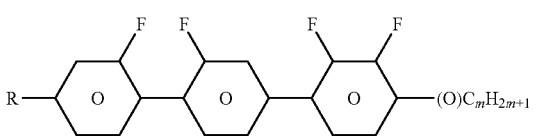
T21
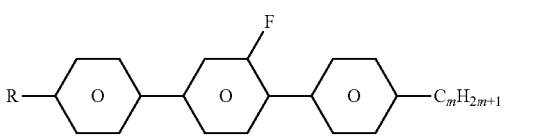
T22
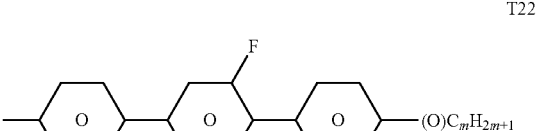
T23
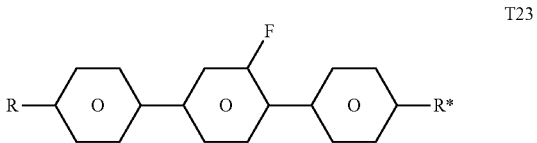
T24
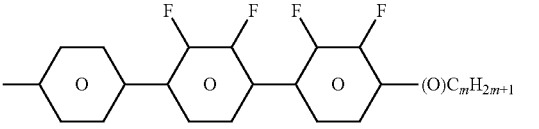
T25
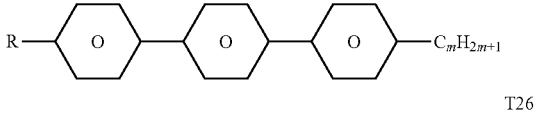
T26
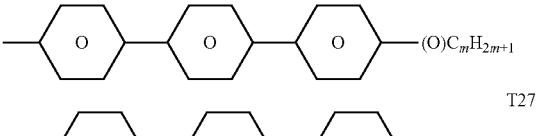
T27
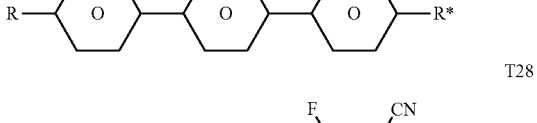
T28
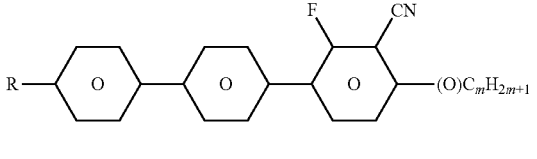

in which R denotes a straight-chain alkyl or alkoxy radical having 1-7 C atoms, R* denotes a straight-chain alkenyl radical having 2-7 C atoms, (O) denotes an oxygen atom or a single bond, and m denotes an integer from 1 to 6. R* preferably denotes CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

R preferably denotes methyl, ethyl, propyl, butyl, pentyl, hexyl, methoxy, ethoxy, propoxy, butoxy or pentoxy.

i) LC medium which additionally comprises one or more compounds of the following formula O:

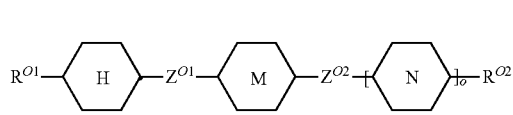

wherein

denotes

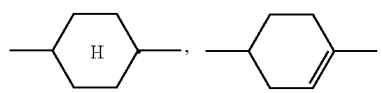

or

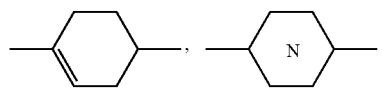

denotes

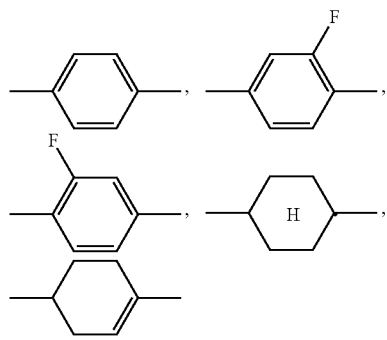

or

$R^{O1}$, $R^{O2}$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, $Z^{O1}$ denotes —CH$_2$CH$_2$—, —CF$_2$CF$_2$—, —C≡C— or a single bond, $Z^{O2}$ denotes CH$_2$O, —C(O)O—, —CH$_2$CH$_2$—, —CF$_2$CF$_2$—, or a single bond, o is 1 or 2.

The compounds of the formula O are preferably selected from the group consisting of the following sub-formulae:

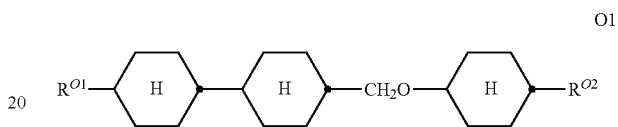

O1

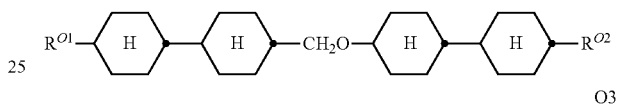

O2

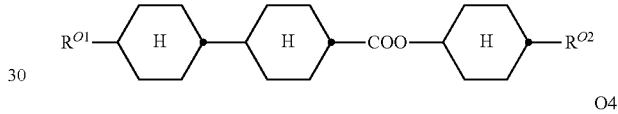

O3

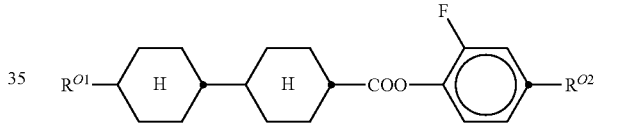

O4

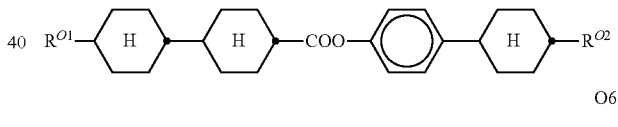

O5

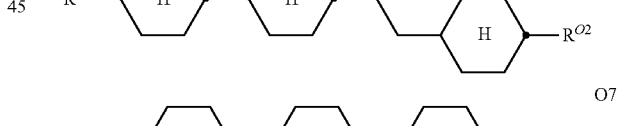

O6

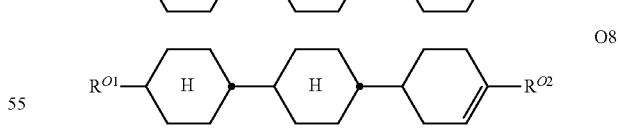

O7

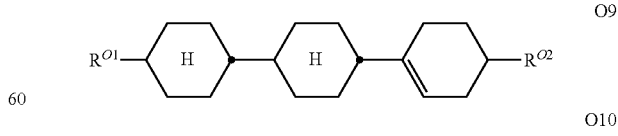

O8

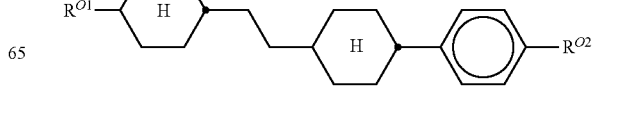

O9

O10

-continued

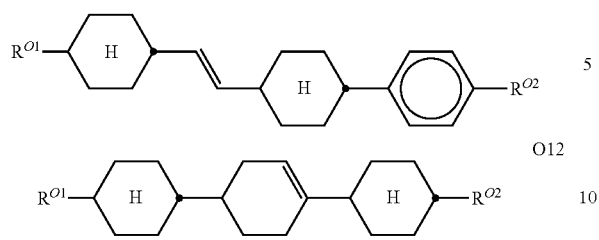

in which $R^{O1}$ and $R^{O2}$ have the meanings indicated above and preferably each, independently of one another, denote straight-chain alkyl having 1 to 6 C atoms or straight-chain alkenyl having 2 to 6 C atoms.

Preferred media comprise one or more compounds selected from the formulae O3, O4 and O5.

k) LC medium which additionally comprises one or more compounds of the following formula:

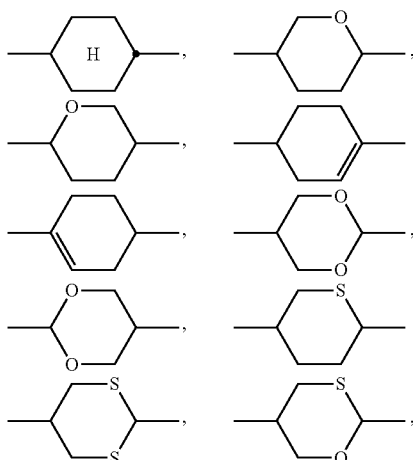

in which

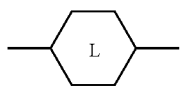

denotes

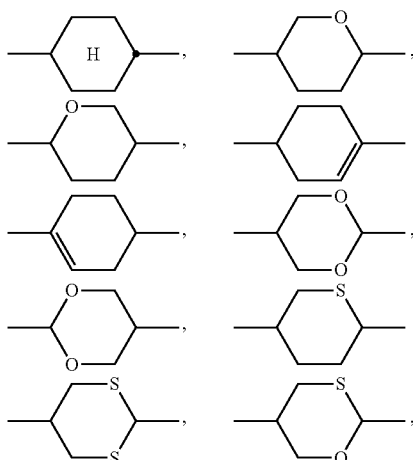

$R^9$ denotes H, $CH_3$, $C_2H_5$ or n-$C_3H_7$, (F) denotes an optional fluorine substituent, and q denotes 1, 2 or 3, and $R^7$ has one of the meanings indicated for $R^1$, preferably in amounts of >3% by weight, in particular ≥5% by weight and very particularly preferably 5-30% by weight.

Particularly preferred compounds of the formula FI are selected from the group consisting of the following sub-formulae:

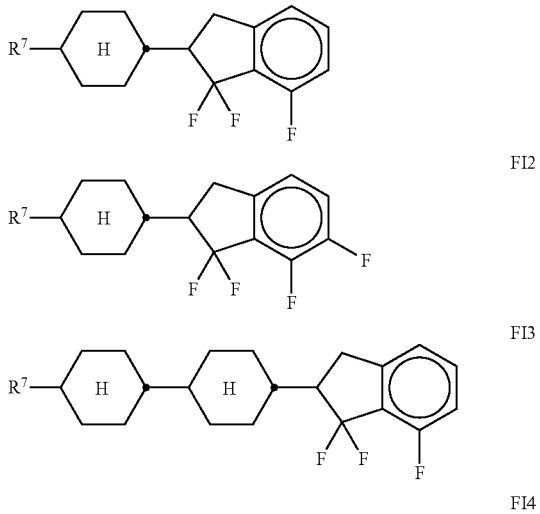

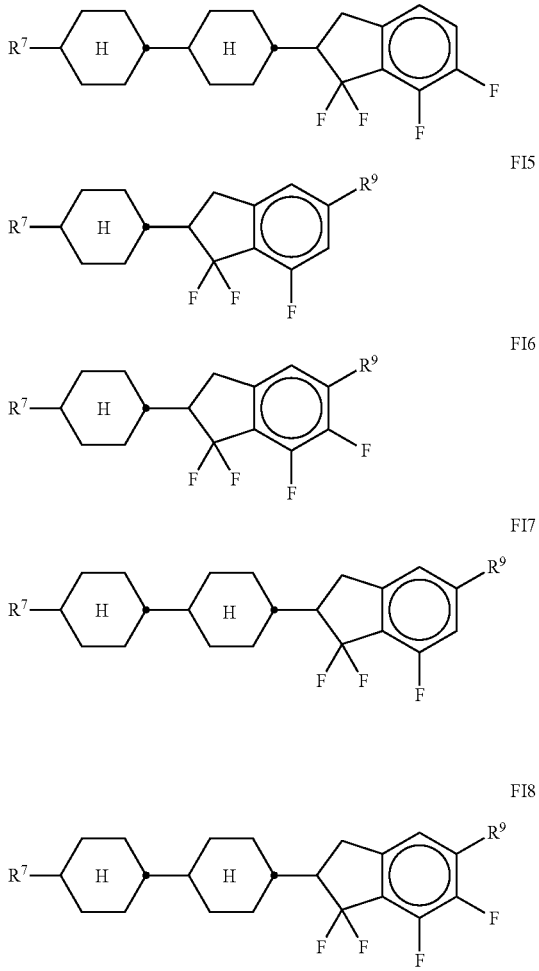

in which $R^7$ preferably denotes straight-chain alkyl, and $R^9$ denotes $CH_3$, $C_2H_5$ or n-$C_3H_7$. Particular preference is given to the compounds of the formulae FI1, FI2 and FI3.

l) LC medium which additionally comprises one or more compounds selected from the group consisting of the following formulae:

VK1
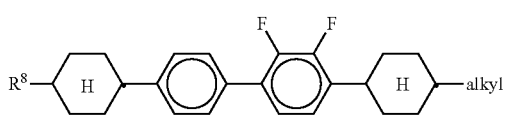

VK2
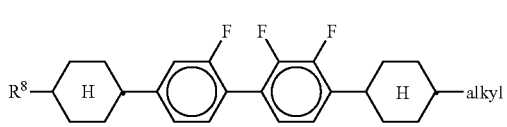

VK3
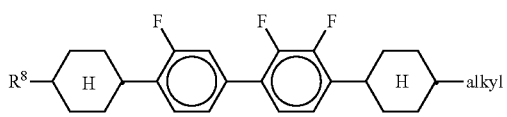

VK4
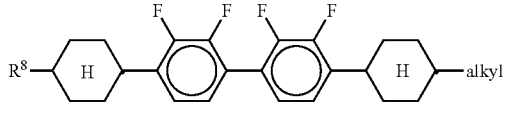

in which R⁹ has the meaning indicated for R¹, and alkyl denotes a straight-chain alkyl radical having 1-6 C atoms.

m) LC medium which additionally comprises one or more compounds which contain a tetrahydronaphthyl or naphthyl unit, such as, for example, the compounds selected from the group consisting of the following formulae:

N1
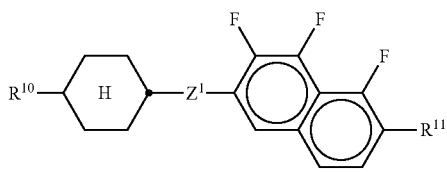

N2
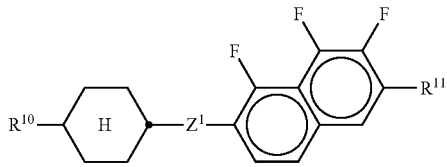

N3
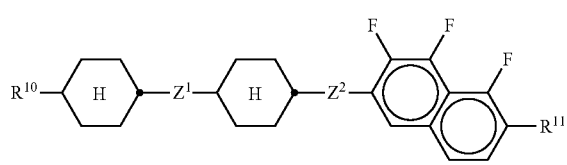

N4
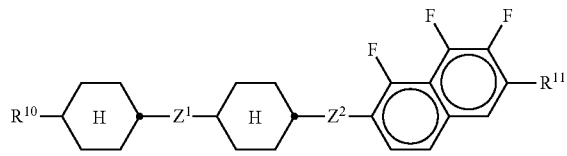

N5
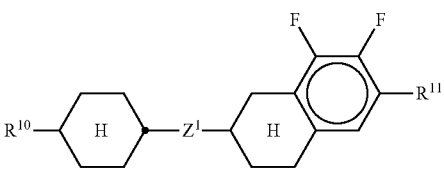

N6
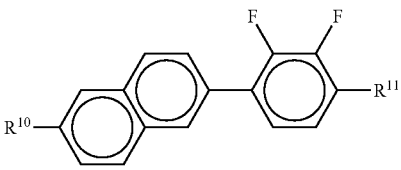

N7
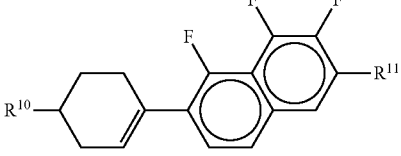

N8
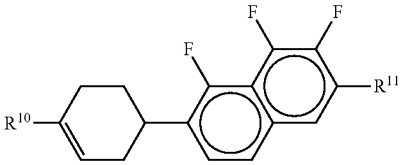

N9
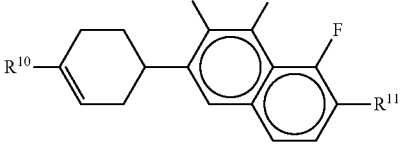

N10 in which $R^{10}$ and $R^{11}$ each, independently of one another, denote alkyl having 1 to 12 C atoms, where, in addition, one or two non-adjacent CH₂ groups may be replaced by —O—, —CH=CH—, —CO—, —OCO— or —COO— in such a way that O atoms are not linked directly to one another, preferably alkyl or alkoxy having 1 to 6 C atoms, and $R^{10}$ and $R^{11}$ preferably denote straight-chain alkyl or alkoxy having 1 to 6 C atoms or straight-chain alkenyl having 2 to 6 C atoms, and $Z^1$ and $Z^2$ each, independently of one another, denote —C₂H₄—, —CH=CH—, —(CH₂)₄—, —(CH₂)₃O—, —O(CH₂)₃—, —CH=CH—CH₂CH₂—, —CH₂CH₂CH=CH—, —CH₂O—, —OCH₂—, —CO—O—, —O—CO—, —C₂F₄—, —CF=CF—, —CF=CH—, —CH=CF—, —CH₂— or a single bond.

n) LC medium which additionally comprises one or more difluorobenzochromans and/or difluorochromans of the following formulae:

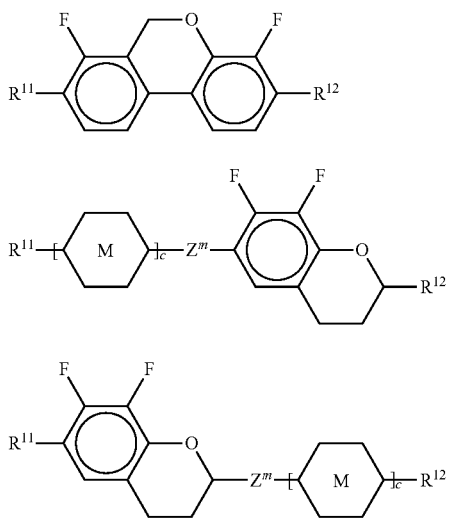

in which $R^{11}$ and $R^{12}$ each, independently of one another, have one of the meanings indicated above for $R^{11}$, ring M is trans-1,4-cyclohexylene or 1,4-phenylene, $Z^m$ —$C_2H_4$—, —$CH_2O$—, —$OCH_2$—, —CO—O— or —O—CO—, c is 0, 1 or 2, preferably in amounts of 3 to 20% by weight, in particular in amounts of 3 to 15% by weight.

Particularly preferred compounds of the formulae BC, CR and RC are selected from the group consisting of the following sub-formulae:

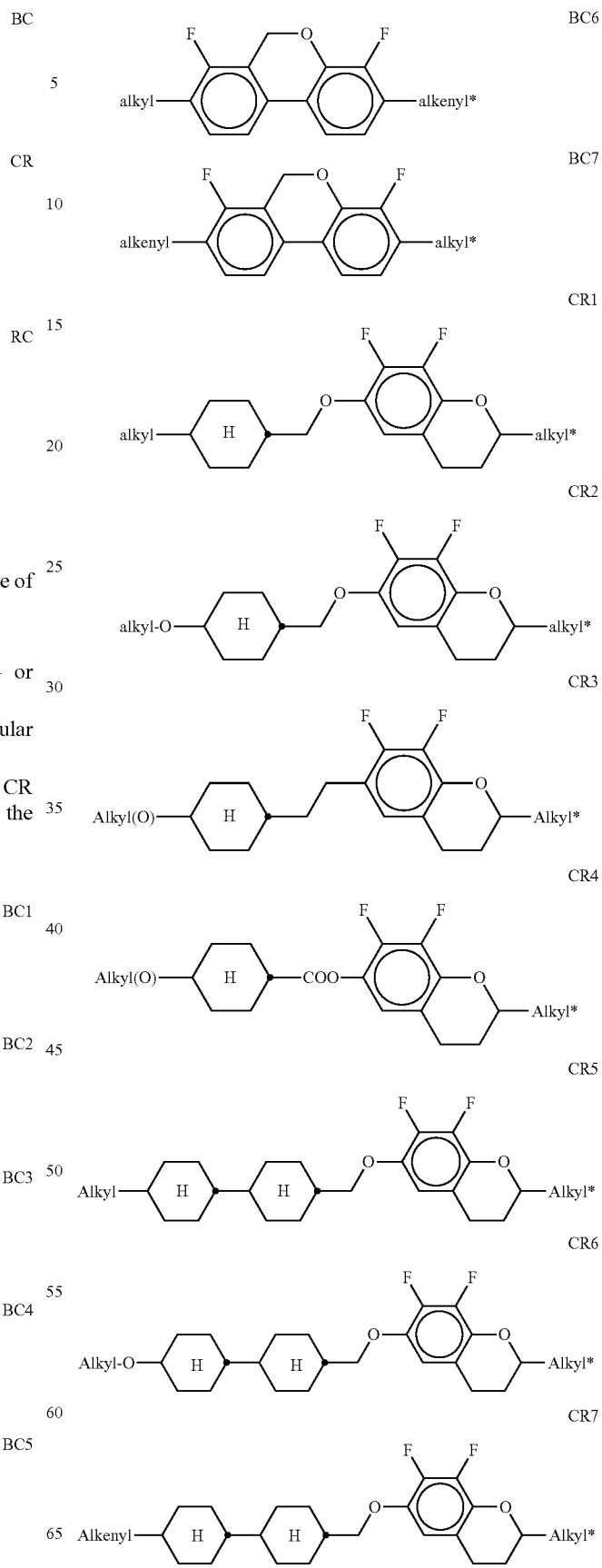

-continued

CR8
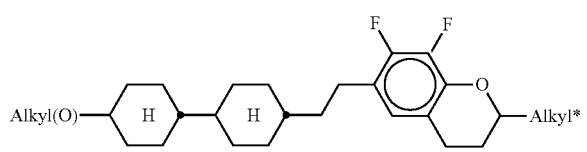

CR9
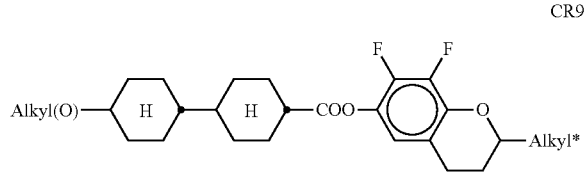

RC1
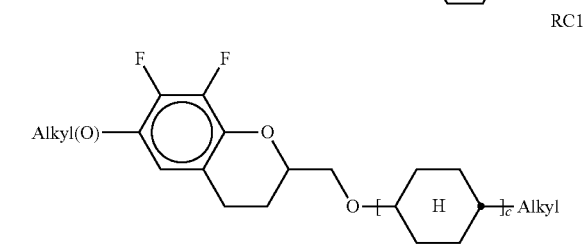

RC2
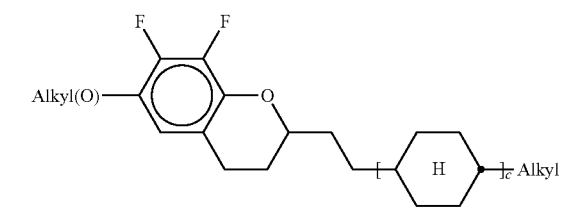

RC3
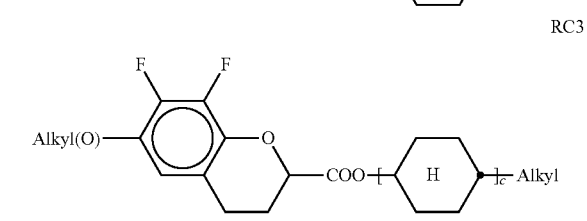

in which alkyl and alkyl* each, independently of one another, denote a straight-chain alkyl radical having 1-6 C atoms, (O) denotes an oxygen atom or a single bond, c is 1 or 2, and alkenyl and alkenyl* each, independently of one another, denote a straight-chain alkenyl radical having 2-6 C atoms. Alkenyl and alkenyl* preferably denote $CH_2=CH—$, $CH_2=CHCH_2CH_2—$, $CH_3—CH=CH—$, $CH_3—CH_2—CH=CH—$, $CH_3—(CH_2)_2—CH=CH—$, $CH_3—(CH_2)_3—CH=CH—$ or $CH_3—CH=CH—(CH_2)_2—$.

Very particular preference is given to mixtures comprising one, two or three compounds of the formula BC-2.

o) LC medium which additionally comprises one or more fluorinated phenanthrenes, dibenzofurans and/or dibenzothiophenes of the following formulae:

PH
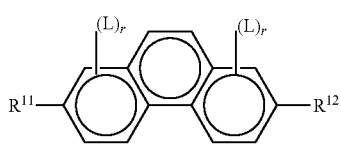

-continued

BF
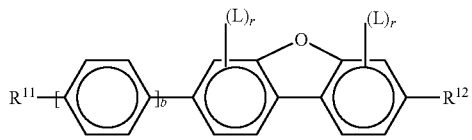

BSF
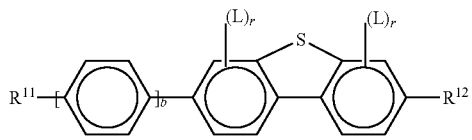

in which $R^{11}$ and $R^{12}$ each, independently of one another, have one of the meanings indicated above for $R^{11}$, b denotes 0 or 1, L denotes F, and r denotes 1, 2 or 3.

Particularly preferred compounds of the formulae PH and BF are selected from the group consisting of the following sub-formulae:

PH1
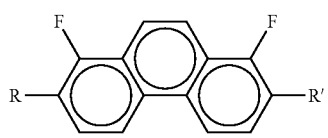

PH2
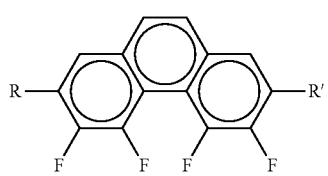

BF1
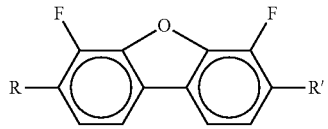

BF2
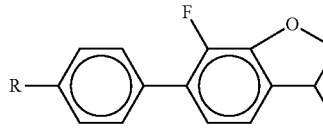

BSF1
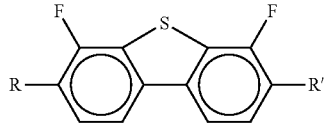

BSF2
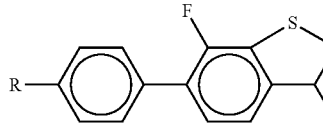

in which R and R' each, independently of one another, denote a straight-chain alkyl or alkoxy radical having 1-7 C atoms.

p) LC medium which additionally comprises one or more monocyclic compounds of the following formula

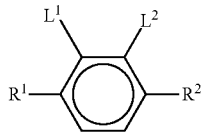

wherein
R¹ and R² each, independently of one another, denote alkyl having 1 to 12 C atoms, where, in addition, one or two non-adjacent CH₂ groups may be replaced by —O—, —CH=CH—, —CO—, —OCO— or —COO— in such a way that O atoms are not linked directly to one another, preferably alkyl or alkoxy having 1 to 6 C atoms, L¹ and L² each, independently of one another, denote F, Cl, OCF₃, CF₃, CHs, CH₂F, CHF₂.

Preferably, both L¹ and L² denote F or one of L¹ and L² denotes F and the other denotes Cl, The compounds of the formula Y are preferably selected from the group consisting of the following sub-formulae:

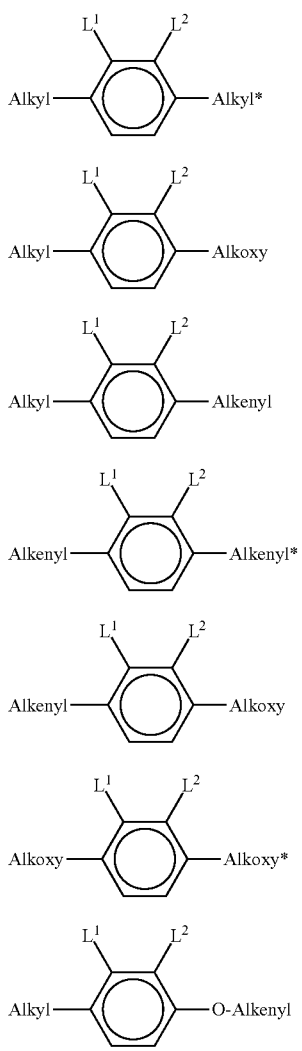

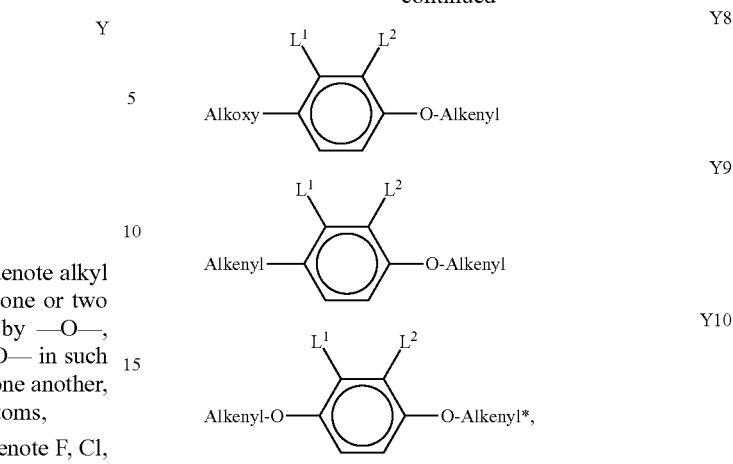

in which, Alkyl and Alkyl* each, independently of one another, denote a straight-chain alkyl radical having 1-6 C atoms, Alkoxy denotes a straight-chain alkoxy radical having 1-6 C atoms, Alkenyl and Alkenyl* each, independently of one another, denote a straight-chain alkenyl radical having 2-6 C atoms, and O denotes an oxygen atom or a single bond. Alkenyl and Alkenyl* preferably denote CH₂=CH—, CH₂=CHCH₂CH₂—, CH₃—CH=CH—, CH₃—CH₂—CH=CH—, CH₃—(CH₂)₂—CH=CH—, CH₃—(CH₂)₃—CH=CH— or CH₃—CH=CH—(CH₂)₂—.

Particularly preferred compounds of the formula Y are selected from the group consisting of the following sub-formulae:

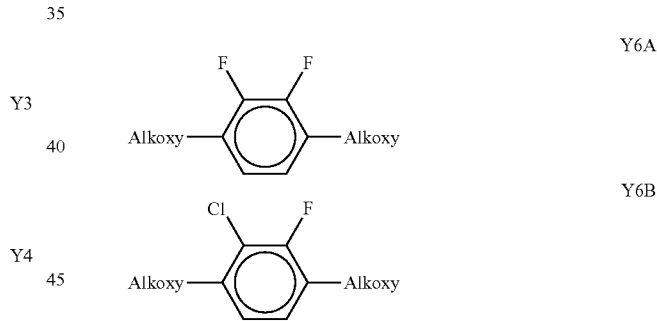

wherein Alkoxy preferably denotes straight-chain alkoxy with 3, 4, or 5 C atoms.

q) LC medium which comprises 1 to 15, preferably 3 to 12, compounds of the formulae CY1, CY2, PY1, PY2, AC1, AC2 and/or AC3. The proportion of these compounds in the mixture as a whole is preferably 20 to 99%, more preferably 30 to 95%, particularly preferably 40 to 90%. The content of these individual compounds is preferably in each case 2 to 20%.

r) LC medium which comprises 1 to 10, preferably 1 to 8, compounds of the formula ZK, in particular compounds of the formulae ZK1, ZK2 and/or ZK6. The proportion of these compounds in the mixture as a whole is preferably 3 to 25%, particularly preferably 5 to 45%. The content of these individual compounds is preferably in each case 2 to 20%.

s) LC medium in which the proportion of compounds of the formulae CY, PY and ZK in the mixture as a whole is greater than 70%, preferably greater than 80%.

t) LC medium which contains one or more, preferably 1 to 5, compounds selected of formula PY1-PY8, very preferably of formula PY2. The proportion of these compounds in the mixture as a whole is preferably 1 to 30%, particularly preferably 2 to 20%. The content of these individual compounds is preferably in each case 1 to 20%.

u) LC medium which contains one or more, preferably 1, 2 or 3, compounds of formula T2. The content of these compounds in the mixture as a whole is preferably 1 to 20%.

The LC medium according to the invention preferably comprises the terphenyls of the formula T and the preferred sub-formulae thereof in an amount of 0.5-30% by weight, in particular 1-20% by weight. Particular preference is given to compounds of the formulae T1, T2, T3 and T21. In these compounds, R preferably denotes alkyl, furthermore alkoxy, each having 1-5 C atoms.

The terphenyls are preferably employed in mixtures according to the invention if the Δn value of the mixture is to be 0.1. Preferred mixtures comprise 2-20% by weight of one or more terphenyl compounds of the formula T, preferably selected from the group of compounds T1 to T22.

v) LC medium which contains one or more, preferably 1, 2 or 3, compounds of formula BF1 and/or BSF1. The total content of these compounds in the mixture as a whole is preferably 1 to 15%, preferably 2 to 10% particularly preferably 4 to 8%.

v) Preferred media comprise one or more compounds of formula O, preferably selected from the formulae O3, O4 and O5 in a total concentration of 2 to 25%, preferably 3 to 20%, particularly preferably 5 to 15%.

w) Preferred media comprise one or more compounds of formula DK, preferably selected from the formulae DK1, DK4, DK7, DK 9, DK10 and DK11. The total concentration of compounds of formulae DK9, DK10 and DK11 is preferably 2 to 25%, more preferably 3 to 20%, particularly preferably 5 to 15%.

In another preferred embodiment of the present invention the LC medium contains an LC host mixture with positive dielectric anisotropy. Preferred embodiments of such an LC medium, and the corresponding LC host mixture, are those of sections aa)-zz) below:

aa) LC-medium comprising one or more compounds selected from the following formulae:

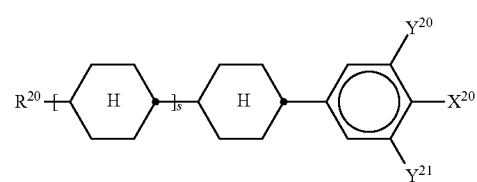
IV

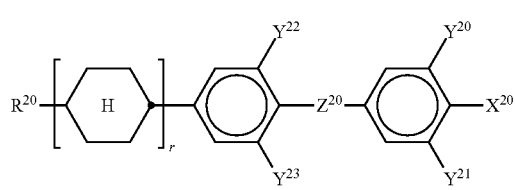
V

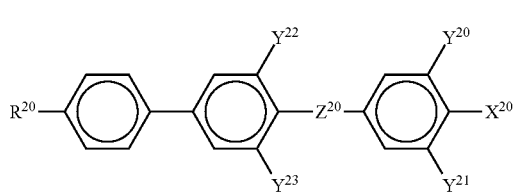
VI

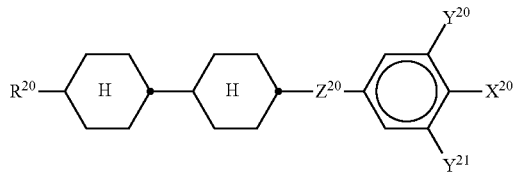
VII

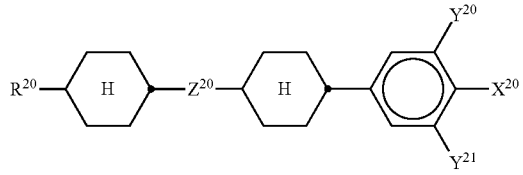
VIII wherein $R^{20}$ each, identically or differently, denote a halogenated or unsubstituted alkyl or alkoxy radical having 1 to 15 C atoms, where, in addition, one or more $CH_2$ groups in these radicals may each be replaced, independently of one another, by —C≡C—, —$CF_2$O—, —CH═CH—,

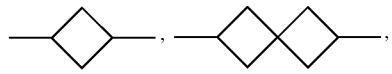

—O—, —CO—O— or —O—CO— in such a way that O atoms are not linked directly to one another, $X^{20}$ each, identically or differently, denote F, Cl, CN, $SF_5$, SCN, NCS, a halogenated alkyl radical, a halogenated alkenyl radical, a halogenated alkoxy radical or a halogenated alkenyloxy radical, each having up to 6 C atoms, and $Y^{20-23}$ each, identically or differently, denote H or F;

$Z^{20}$ denotes —$C_2H_4$—, —$(CH_2)_4$—, —CH═CH—, —CF═CF—, —$C_2F_4$—, —$CH_2CF_2$—, —$CF_2CH_2$—, —$CH_2$O—, —O$CH_2$—, —COO— or —O$CF_2$—, in formulae V and VI also a single bond, in formulae V and VIII also —$CF_2$O—, r denotes 0 or 1, and s denotes 0 or 1;

The compounds of the formula IV are preferably selected from the following formulae:

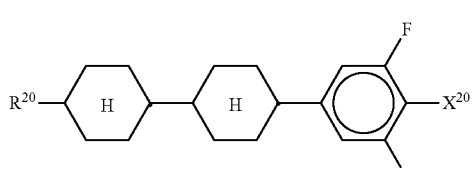
IVa

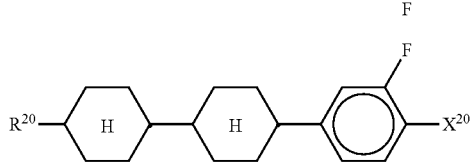
IVb

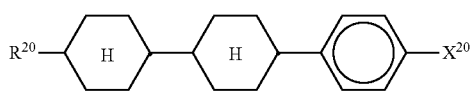
IVc

IVd

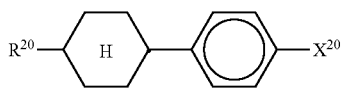

wherein $R^{20}$ and $X^{20}$ have the meanings indicated above.

$R^{20}$ preferably denotes alkyl having 1 to 6 C atoms. $X^{20}$ preferably denotes F, CN or $OCF_3$, furthermore $OCF=CF_2$ or Cl;

The compounds of the formula V are preferably selected from the following formulae:

Va

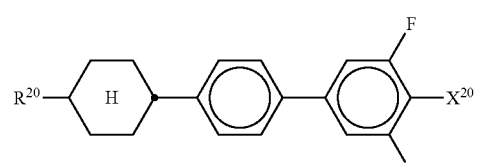

Vb

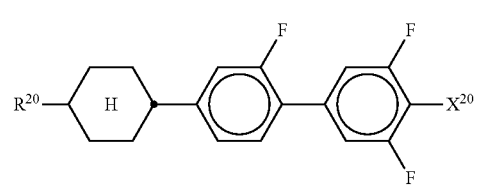

Vc

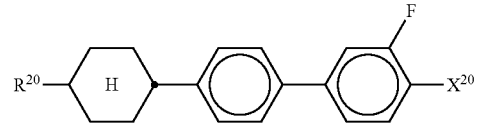

Vd

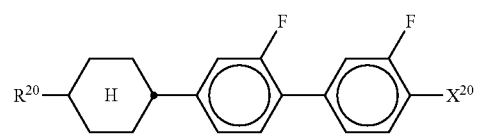

Ve

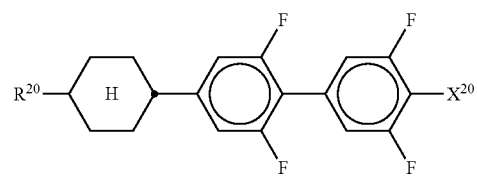

Vf

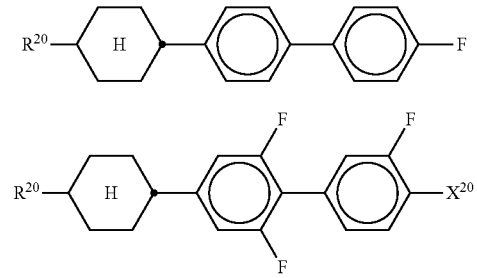

Vg

Vh

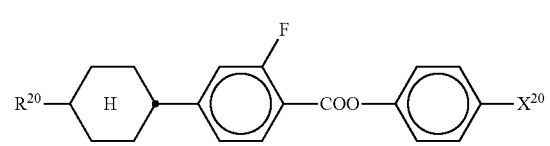

-continued

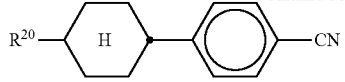

wherein $R^{20}$ and $X^{20}$ have the meanings indicated above.

$R^{20}$ preferably denotes alkyl having 1 to 6 C atoms. $X^{20}$ preferably denotes F and $OCF_3$, furthermore $OCHF_2$, $CF_3$, $OCF=CF_2$ and $OCH=CF_2$;

The compounds of the formula VI are preferably selected from the following formulae:

VIa

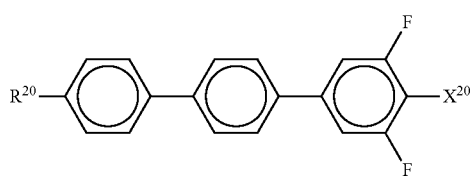

VIb

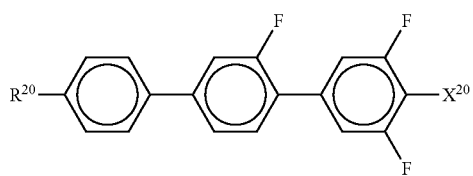

VIc

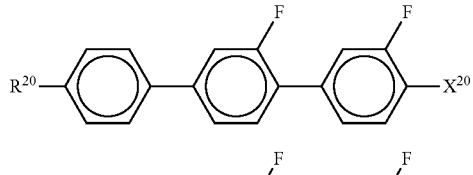

VId

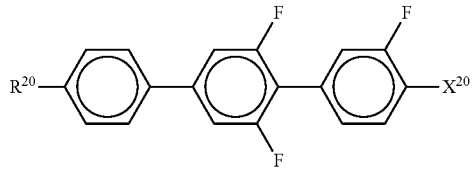

wherein $R^{20}$ and $X^{20}$ have the meanings indicated above.

$R^{20}$ preferably denotes alkyl having 1 to 6 C atoms. $X^{20}$ preferably denotes F, furthermore $OCF_3$, $CF_3$, $CF=CF_2$, $OCHF_2$ and $OCH=CF_2$;

The compounds of the formula VII are preferably selected from the following formulae:

VIIa

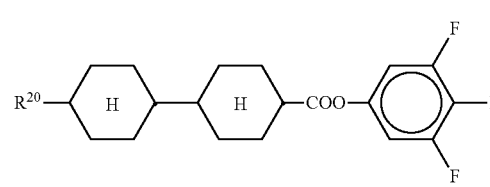

VIIb

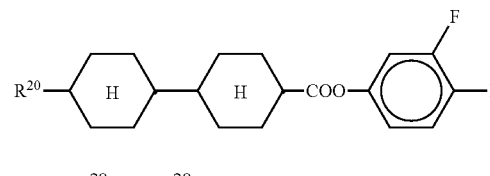

wherein $R^{20}$ and $X^{20}$ have the meanings indicated above.

$R^{20}$ preferably denotes alkyl having 1 to 6 C atoms. $X^{20}$ preferably denotes F, furthermore $OCF_3$, $OCHF_2$ and $OCH{=}CF_2$.

bb) LC-medium, characterised in that it additionally comprises one or more compounds selected from the group of compounds of the formulae II and III

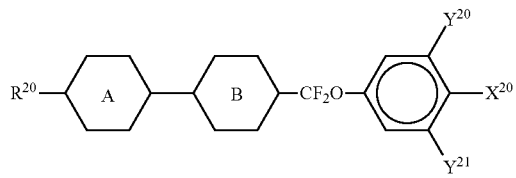
II

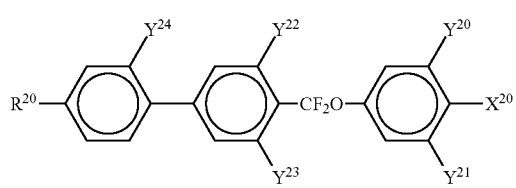
III wherein $R^{20}$ each, identically or differently, denote a halogenated or unsubstituted alkyl or alkoxy radical having 1 to 15 C atoms, where, in addition, one or more $CH_2$ groups in these radicals may each be replaced, independently of one another, by —C≡C—, —$CF_2$O—, —CH=CH—,

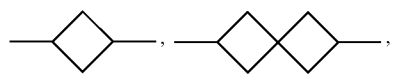

—O—, —CO—O— or —O—CO— in such a way that O atoms are not linked directly to one another, $X^{20}$ each, identically or differently, denote F, Cl, CN, $SF_5$, SCN, NCS, a halogenated alkyl radical, a halogenated alkenyl radical, a halogenated alkoxy radical or a halogenated alkenyloxy radical, each having up to 6 C atoms, and $Y^{20-24}$ each, identically or differently, denote H or F;

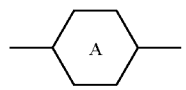

and

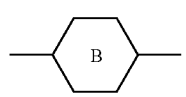

each, independently of one another, denote

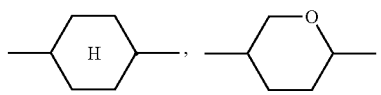

or

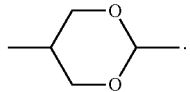

The compounds of the formula II are preferably selected from the following formulae:

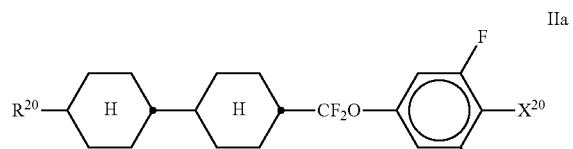
IIa

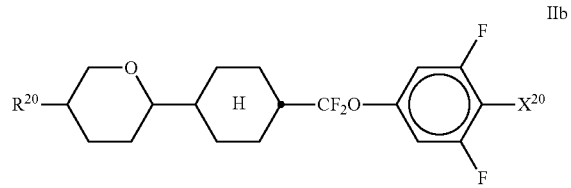
IIb

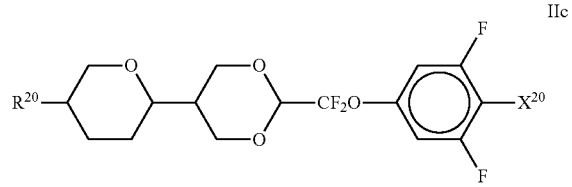
IIc

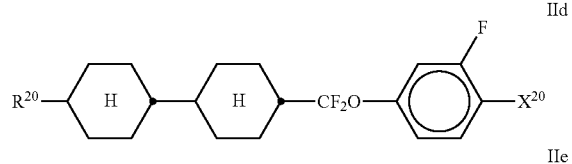
IId

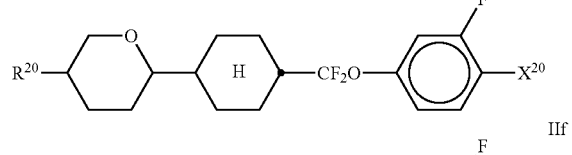
IIe

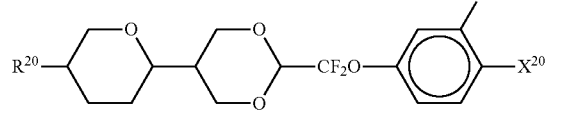
IIf wherein $R^{20}$ and $X^{20}$ have the meanings indicated above.

$R^{20}$ preferably denotes alkyl having 1 to 6 C atoms. $X^{20}$ preferably denotes F. Particular preference is given to compounds of the formulae IIa and IIb, in particular compounds of the formulae IIa and IIb wherein X denotes F.

The compounds of the formula III are preferably selected from the following formulae:

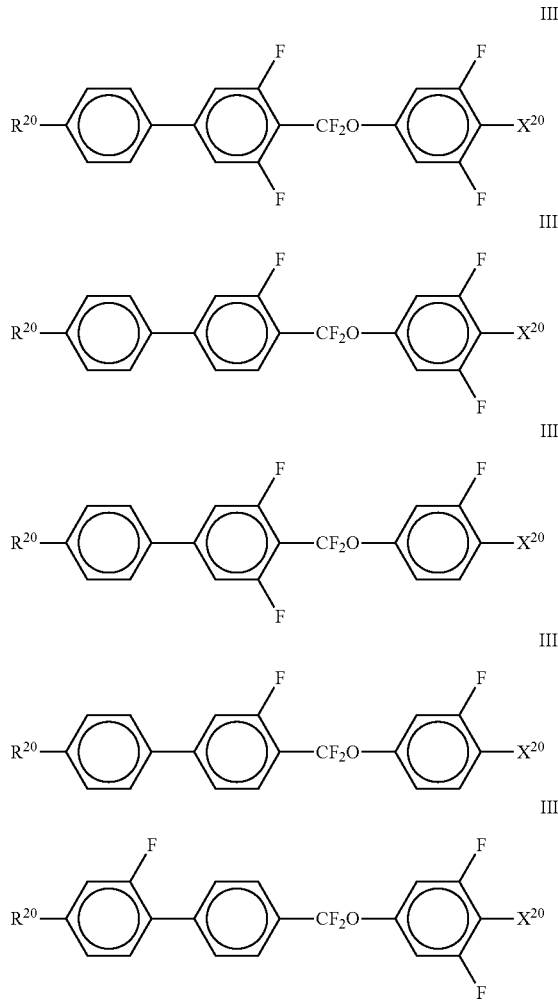

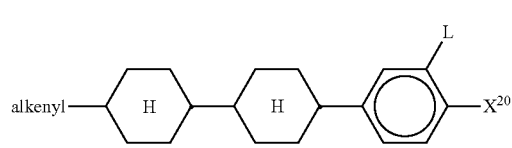

wherein $R^{20}$ and $X^{20}$ have the meanings indicated above. $R^{20}$ preferably denotes alkyl having 1 to 6 C atoms. $X^{20}$ preferably denotes F. Particular preference is given to compounds of the formulae IIIa and IIIe, in particular compounds of the formula IIIa;

cc) The medium additionally comprises one or more compounds selected from the formulae ZK1 to ZK10 given above. Especially preferred are compounds of formula ZK1 and ZK3. Particularly preferred compounds of formula ZK are selected from the subformulae ZK1a, ZK1b, ZK1c, ZK3a, ZK3b, ZK3c and ZK3d.

dd) The medium additionally comprises one or more compounds selected from the formulae DK and 0 given above. Especially preferred compounds are DK1, DK4, DK7, DK9, DK10, DK11, O3, O4 and O5.

ee) The medium additionally comprises one or more compounds selected from the following formulae:

wherein $X^{20}$ has the meanings indicated above, and
L denotes H or F,
"alkenyl" denotes $C_{2-6}$-alkenyl.

ff) The compounds of the formulae DK-3a and IX are preferably selected from the following formulae:

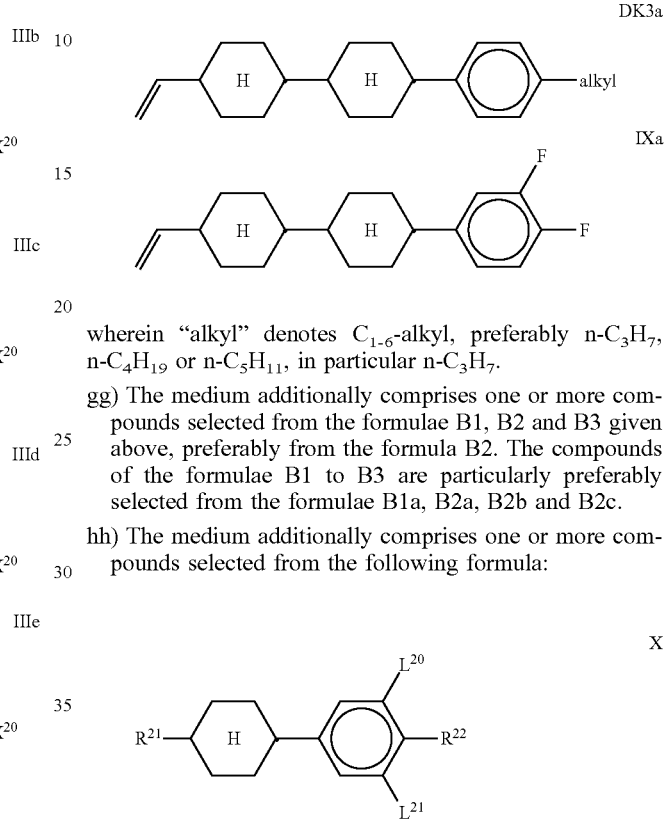

wherein "alkyl" denotes $C_{1-6}$-alkyl, preferably n-$C_3H_7$, n-$C_4H_{19}$ or n-$C_5H_{11}$, in particular n-$C_3H_7$.

gg) The medium additionally comprises one or more compounds selected from the formulae B1, B2 and B3 given above, preferably from the formula B2. The compounds of the formulae B1 to B3 are particularly preferably selected from the formulae B1a, B2a, B2b and B2c.

hh) The medium additionally comprises one or more compounds selected from the following formula:

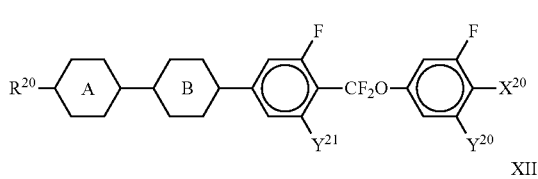

wherein $L^{20}$, $L^{21}$ denote H or F, and $R^{21}$ and $R^{22}$ each, identically or differently, denote n-alkyl, alkoxy, oxaalkyl, fluoroalkyl or alkenyl, each having up to 6 C atoms, and preferably each, identically or differently, denote alkyl having 1 to 6 C atoms.

ii) The medium comprises one or more compounds of the following formulae:

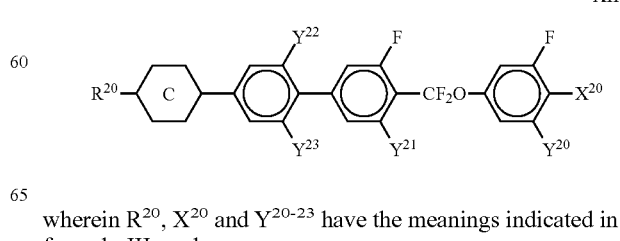

wherein $R^{20}$, $X^{20}$ and $Y^{20-23}$ have the meanings indicated in formula III, and

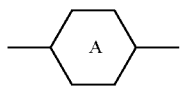
and
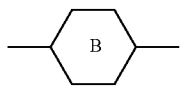
each, independently of one another, denote
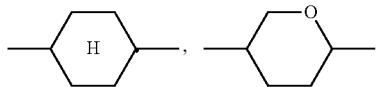
or
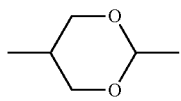
and
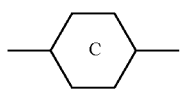
denotes
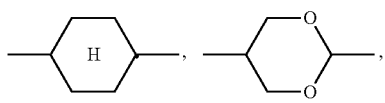
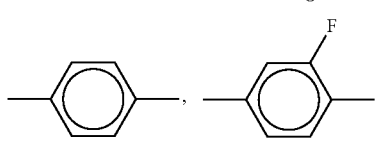
or
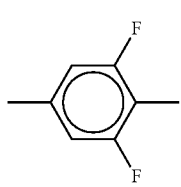
The compounds of the formulae XI and XII are preferably selected from the following formulae:
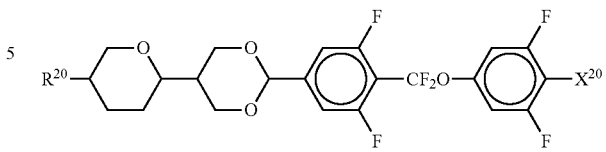
XIa
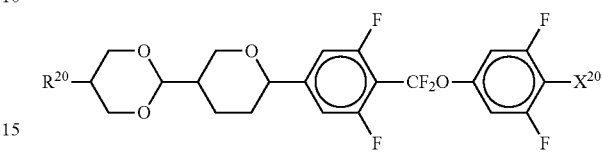
XIb
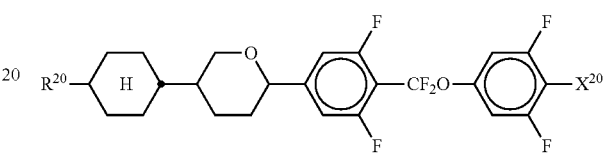
XIc
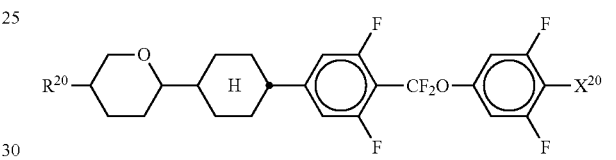
XId
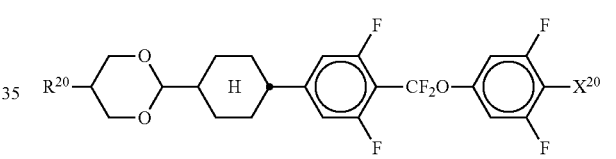
XIe
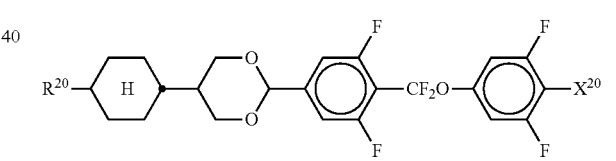
XIf
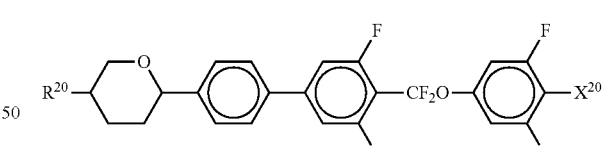
XIIa
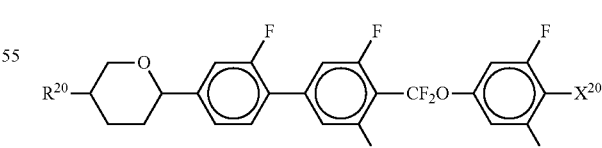
XIIb
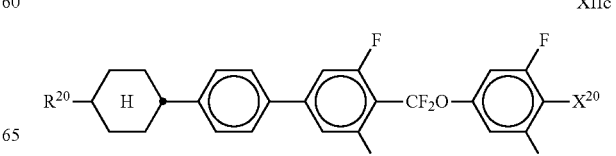
XIIc XIId
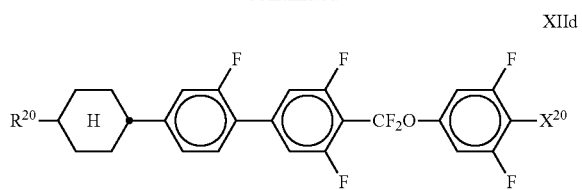

XIIe
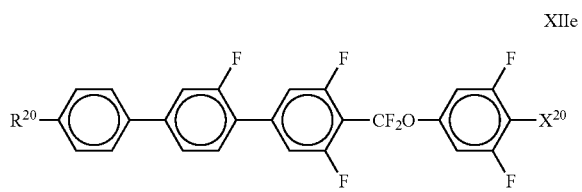

XIIf
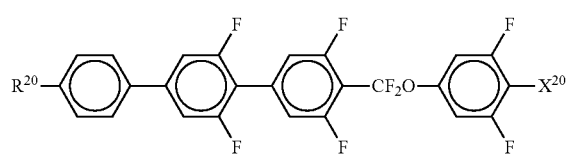

wherein $R^{20}$ and $X^{20}$ have the meaning indicated above and preferably $R^{20}$ denotes alkyl having 1 to 6 C atoms and $X^{20}$ denotes F. In this embodiment, a mixture which comprises at least one compound of the formula XIIa and/or XIIe is preferred.

jj) The medium comprises one or more compounds of formula T given above, preferably selected from the group of compounds of the formulae T21 to T23 and T25 to T27.

Particular preference is given to the compounds of the formulae T21 to T23. Very particular preference is given to the compounds of the formulae

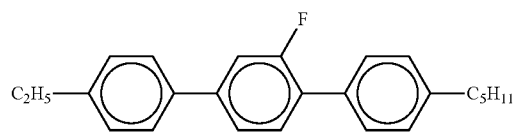
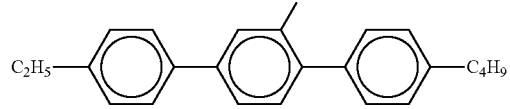
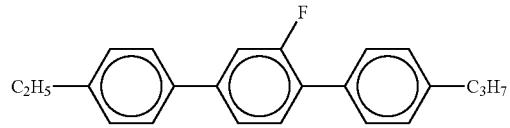
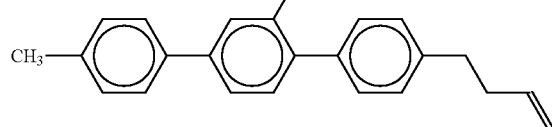
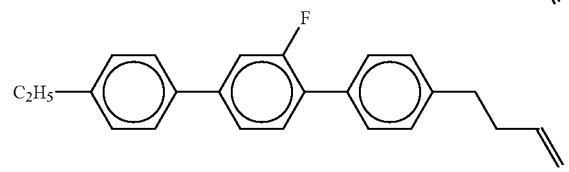

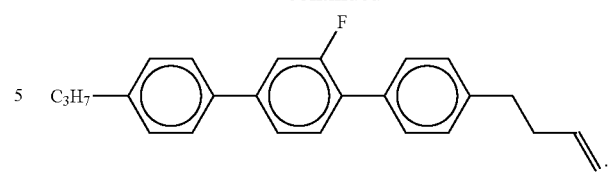

kk) The medium comprises one or more compounds selected from the group of formulae DK9, DK10 and DK11 given above.

ll) The medium additionally comprises one or more compounds selected from the following formulae:

XIII
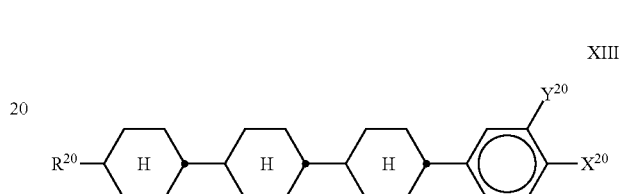

XIV
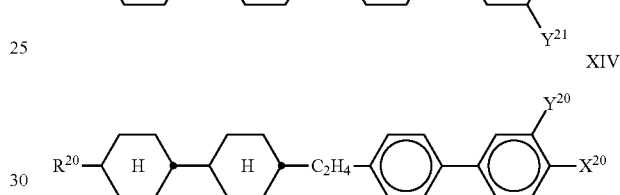

XV
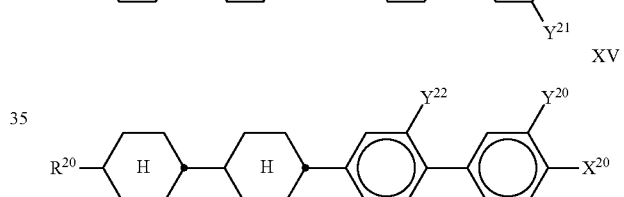

XVI
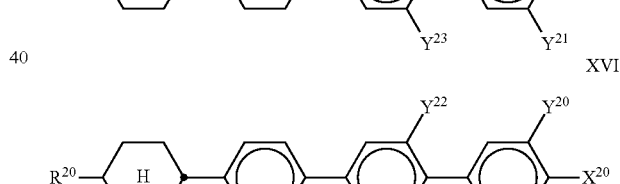

XVII

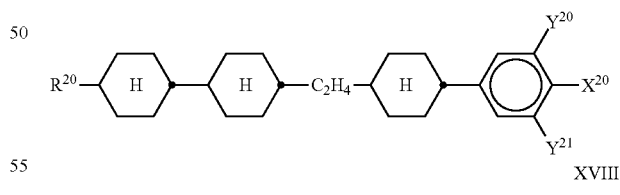

XVIII
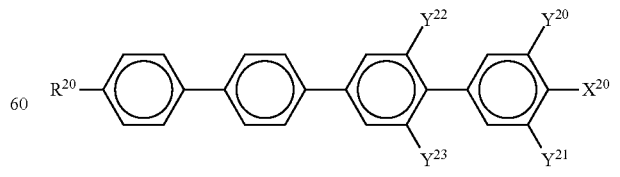

wherein $R^{20}$ and $X^{20}$ each, independently of one another, have one of the meanings indicated above, and $Y^{20\text{-}23}$ each, independently of one another, denote H or F. $X^{20}$ is preferably F, Cl, $CF_3$, $OCF_3$ or $OCHF_2$. $R^{20}$ preferably denotes alkyl, alkoxy, oxaalkyl, fluoroalkyl or alkenyl, each having up to 6 C atoms.

The mixture according to the invention particularly preferably comprises one or more compounds of the formula XV-a or XVIII-a, XV-a
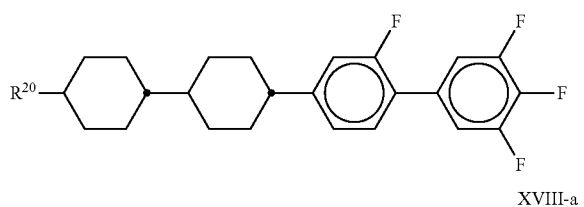

XVIII-a
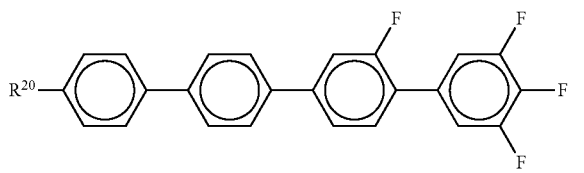

wherein $R^{20}$ has the meanings indicated above. $R^{20}$ preferably denotes straight-chain alkyl, in particular ethyl, n-propyl, n-butyl and n-pentyl and very particularly preferably n-propyl. The compound(s) of the formula XV, in particular of the formula XV-a, is (are) preferably employed in the mixtures according to the invention in amounts of 0.5-20% by weight, particularly preferably 1-15% by weight.

mm) The medium additionally comprises one or more compounds of the formula XIX,

XIX
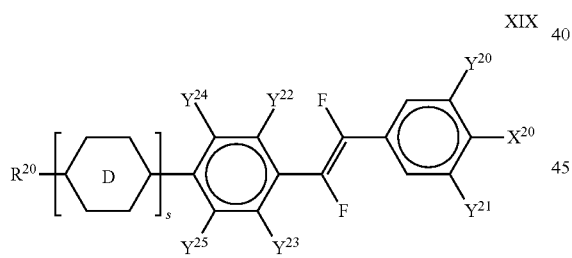

wherein $R^{20}$, $X^{20}$ and $Y^{20-25}$ have the meanings indicated in formula I, s denotes 0 or 1, and

denotes

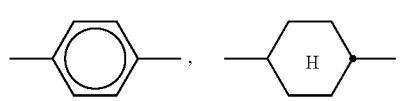

or

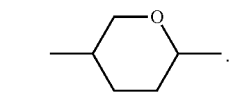

In the formula XIX, $X^{20}$ may also denote an alkyl radical having 1-6 C atoms or an alkoxy radical having 1-6 C atoms. The alkyl or alkoxy radical is preferably straight-chain.

$R^{20}$ preferably denotes alkyl having 1 to 6 C atoms. $X^{20}$ preferably denotes F;

The compounds of the formula XIX are preferably selected from the following formulae:

XIXa
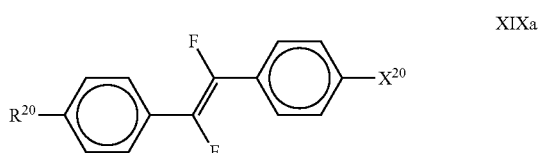

XIXb
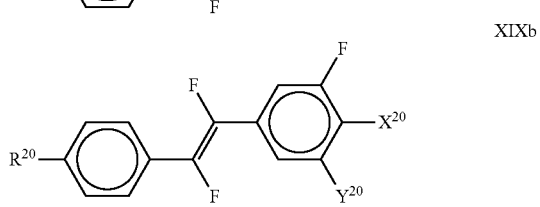

XIXc
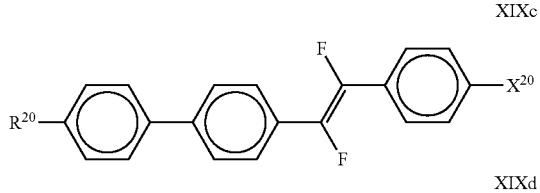

XIXd
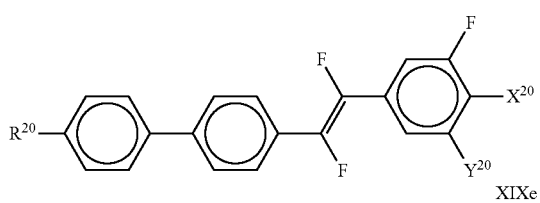

XIXe
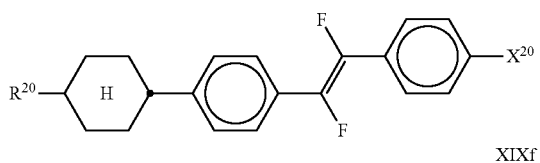

XIXf
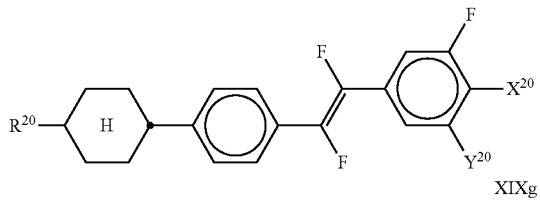

XIXg
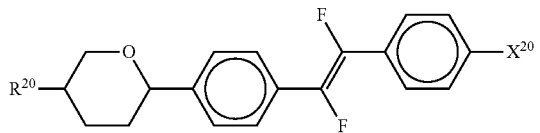

-continued

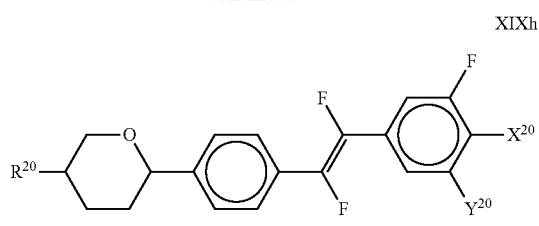

wherein $R^{20}$, $X^{20}$ and $Y^{20}$ have the meanings indicated above. $R^{20}$ preferably denotes alkyl having 1 to 6 C atoms. $X^{20}$ preferably denotes F, and $Y^{20}$ is preferably F;

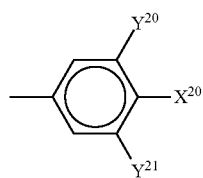

is preferably

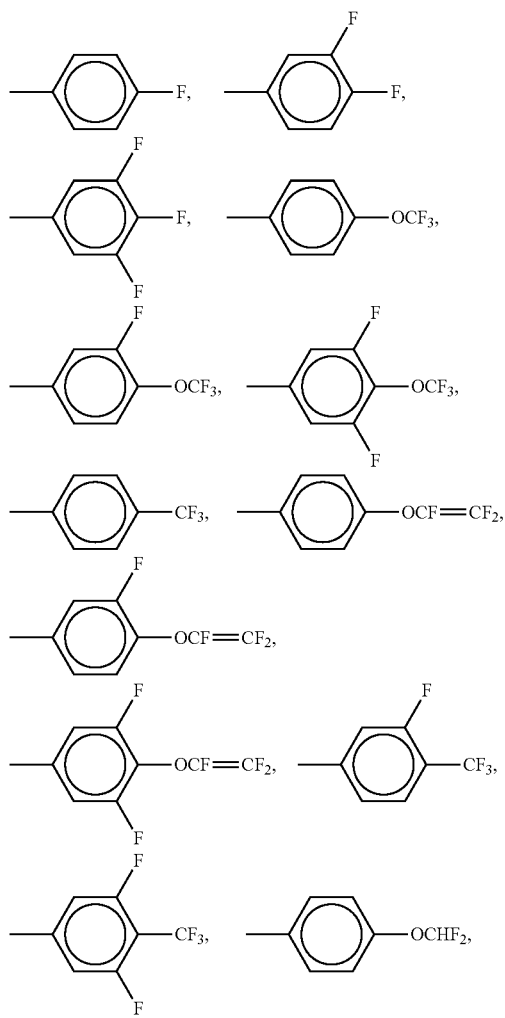

$R^{20}$ is straight-chain alkyl or alkenyl having 2 to 6 C atoms;

nn) The medium comprises one or more compounds of the formulae G1 to G4 given above, preferably selected from G1 and G2 wherein alkyl denotes $C_{1-6}$-alkyl, Lx denotes H and X denotes F or $C_1$. In G2, X particularly preferably denotes Cl.

oo) The medium comprises one or more compounds of the following formulae:

wherein $R^{20}$ and $X^{20}$ have the meanings indicated above. $R^{20}$ preferably denotes alkyl having 1 to 6 C atoms. $X^{20}$ preferably denotes F. The medium according to the invention particularly preferably comprises one or more compounds of the formula XXII wherein $X^{20}$ preferably denotes F. The compound(s) of the formulae XX-XXII is (are) preferably employed in the mixtures according to the invention in amounts of 1-20% by weight, particularly preferably 1-15% by weight. Particularly preferred mixtures comprise at least one compound of the formula XXII.

pp) The medium comprises one or more compounds of the following formulae

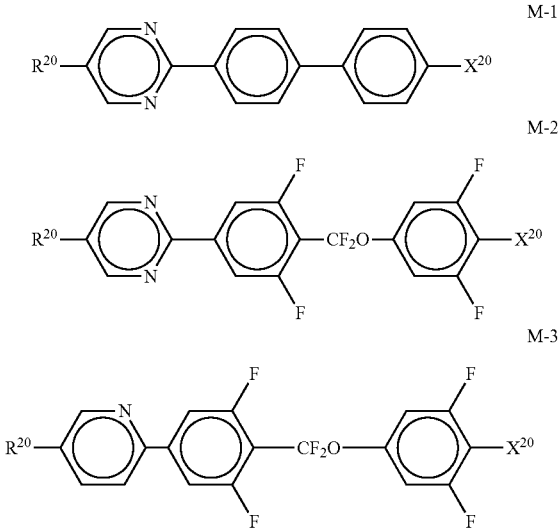

wherein R²⁰ and X²⁰ have the meanings indicated above. R²⁰ preferably denotes alkyl having 1 to 6 C atoms. X²⁰ preferably denotes F. The medium according to the invention particularly preferably comprises one or more compounds of the formula M-1, wherein X²⁰ preferably denotes F. The compound(s) of the formulae M-1-M-3 is (are) preferably employed in the mixtures according to the invention in amounts of 1-20% by weight, particularly preferably 1-15% by weight.

Further preferred embodiments are indicated below:
qq) The medium comprises two or more compounds of the formula XII, in particular of the formula XIIa and/or XIIe;
rr) The medium comprises 2-30% by weight, preferably 3-20% by weight, particularly preferably 3-15% by weight, of compounds of the formula XII;
ss) Besides the compounds of the formulae XII, the medium comprises further compounds selected from the group of the compounds of the formulae II-XVIII;
tt) The proportion of compounds of the formulae II-XVIII in the mixture as a whole is 40 to 95%, preferably 50 to 90%, particularly preferably 55 to 88% by weight;
uu) The medium preferably comprises 10-40%, more preferably 12-30%, particularly preferably 15 to 25% by weight of compounds of the formulae II and/or III;
vv) The medium comprises 1-10% by weight, particularly preferably 2-7% by weight, of compounds of the formula XV and/or XVI;
ww) The medium comprises at least one compound of the formula XIIa and/or at least one compound of the formula XIIe and at least one compound of the formula IIIa and/or IIa.
xx) Preferred media comprise one or more compounds of formula O, preferably selected from the formulae O3, O4 and O5 in a total concentration of 2 to 25%, preferably 3 to 20%, particularly preferably 5 to 15%.
yy) Preferred media comprise one or more compounds of formula DK, preferably selected from the formulae DK1, DK4, DK7, DK 9, DK10 and DK11. The total concentration of compounds of formulae DK9, DK10 and DK11 is preferably 2 to 25%, more preferably 3 to 20%, particularly preferably 5 to 15%.
zz) Preferred media comprise one or more compounds of formulae IV to VI, preferably selected from the group of compounds of formulae IVa, IVb, IVc, IVd, Va, Vc and VIb in a concentration of 10 to 80%, preferably 12 to 75% particularly preferably 15 to 70% by weight.

In case the medium has negative dielectric anisotropy (As), the value for Δε is preferably in the range from −2.0 to −8.0, more preferably in the range from −3.0 to −6.0, and particularly preferably from −3.5 to 5.0.

In case the medium has positive dielectric anisotropy, the value for Δε is preferably in the range from 3.0 to 60.0, more preferably in the range from 5.0 to 30.0, and particularly preferably from 8.0 to 15.0.

The liquid-crystal media in accordance with the present invention preferably have a clearing point of 80° C. or more, more preferably 90° C. or more, even more preferably 105° C. or more, and particularly preferably 110° C. or more.

The nematic phase of the media according to the invention preferably extends at least from −10° C. or less to 80° C. or more, preferably up to 90° C. or more, more preferably at least from −20° C. or less to 100° C. or more and particularly preferably from −30° C. or less to 110° C. or more.

In a preferred embodiment of the present invention the birefringence (An) of the liquid crystal media is in the range of 0.040 or more to 0.080 or less, more preferably in the range of 0.045 or more to 0.070 or less and most preferably in the range of 0.050 or more to 0.060 or less. In this embodiment, the dielectric anisotropy is positive or negative, preferably negative.

In another preferred embodiment of the present invention the Δn of the liquid crystal media is n the range of 0.075 or more to 0.130 or less, more preferably in the range of 0.090 or more to 0.125 or less and most preferably in the range of 0.095 or more to 0.120 or less.

In yet another preferred embodiment of the present invention the Δn of the liquid crystal media is n the range of 0.100 or more to 0.200 or less, more preferably in the range of 0.110 or more to 0.180 or less and most preferably in the range of 0.120 or more to 0.160 or less.

The dichroic compound of the formula I is preferably present in the switching layer in a proportion of 0.01 to 10% by weight, particularly preferably 0.05 to 7% by weight and very particularly preferably 0.1 to 7% by weight. The media preferably comprise one, two, three, four or five compounds of the formula I according to the invention.

The LC medium according to the invention is preferably a nematic liquid crystal.

The media according to the invention are prepared in a manner conventional per se. In general, the components are dissolved in one another, preferably at elevated temperature. The mixing is preferably carried out under inert gas, for example under nitrogen or argon. One or more dyes of the formula I and optionally further dichroic dyes are subsequently added, preferably at elevated temperature, particularly preferably at above 40° C. and very particularly preferably at above 50° C. In general, the desired amount of the components used in smaller amount is dissolved in the components making up the principal constituent. It is also possible to mix solutions of the components in an organic solvent, for example in acetone, toluene, chloroform or methanol, and to remove the solvent again, for example by distillation, after mixing. The invention furthermore relates to the process for the preparation of the LC media according to the invention.

The invention furthermore relates to the use of an LC medium comprising at least one compound of the formula I in a liquid-crystal display of the guest-host type.

The invention furthermore relates to a liquid-crystal display of the guest-host type containing an LC medium which comprises at least one compound of the formula I.

The invention furthermore relates to the use of a mixture comprising a liquid-crystalline medium and at least one compound of a formula I in a device for regulating the passage of energy from an outside space into an inside space, preferably in a window pane.

The device according to the invention, in addition to one or more compounds of the formula I, and preferably a liquid-crystalline medium, preferably also comprises further dichroic dyes having a different structure to formula I in the switching layer. It particularly preferably comprises one, two, three or four further dyes, very particularly preferably two or three further dyes and most preferably three further dyes having a different structure to formula I.

With respect to the property of dichroism, the preferred properties described for the compound of the formula I are also preferred for the optional further dichroic dyes.

The absorption spectra of the dichroic dyes of the switching layer preferably complement one another in such a way that the impression of a black colour arises for the eye. The two or more dichroic dyes of the liquid-crystalline medium according to the invention preferably cover a large part of the visible spectrum. The precise way in which a mixture of dyes which appears black or grey to the eye can be prepared is known to the person skilled in the art and is described, for example, in Manfred Richter, Einfuhrung in die Farbmetrik [Introduction to Colorimetry], 2nd Edition, 1981, ISBN 3-11-008209-8, Verlag Walter de Gruyter & Co.

The setting of the colour location of a mixture of dyes is described in the area of colorimetry. To this end, the spectra of the individual dyes are calculated taking into account the Lambert-Beer law to give an overall spectrum and converted into the corresponding colour locations and luminance values under the associated illumination, for example illuminant D65 for daylight, in accordance with the rules of colorimetry. The position of the white point is fixed by the respective illuminant, for example D65, and is quoted in tables (for example reference above). Different colour locations can be set by changing the proportions of the various dyes.

According to a preferred embodiment, the switching layer comprises one or more dichroic dyes which absorb light in the red and NIR region, i.e. at a wavelength of 600 to 2000 nm, preferably in the range from 650 to 1800 nm, particularly preferably in the range from 650 to 1300 nm. In a preferred embodiment, these dichroic dyes are selected from azo compounds, anthraquinones, methine compounds, azomethine compounds, merocyanine compounds, naphthoquinones, tetrazines, perylenes, terrylenes, quaterrylenes, higher rylenes, pyrromethenes, azo dyes, nickel dithiolenes, (metal) phthalocyanines, (metal) naphthalocyanines and (metal) porphyrins. Of these, particular preference is given to perylenes and terrylenes.

The further dichroic dyes of the switching layer having a different structure to the formula I are preferably selected from the dye classes indicated in B. Bahadur, Liquid Crystals—Applications and Uses, Vol. 3, 1992, World Scientific Publishing, Section 11.2.1, and particularly preferably from the explicit compounds given in the table present therein.

The said dyes belong to the classes of dichroic dyes which are known to the person skilled in the art and have been described many times in the literature. Thus, for example, anthraquinone dyes are described in EP 34832, EP 44893, EP 48583, EP 54217, EP 56492, EP 59036, GB 2065158, GB 2065695, GB 2081736, GB 2082196, GB 2094822, GB 2094825, JP-A 55-123673, DE 3017877, DE 3040102, DE 3115147, DE 3115762, DE 3150803 and DE 3201120, naphthoquinone dyes are described in DE 3126108 and DE 3202761, azo dyes in EP 43904, DE 3123519, WO 82/2054, GB 2079770, JP-A 56-57850, JP-A 56-104984, U.S. Pat. Nos. 4,308,161, 4,308,162, 4,340,973, T. Uchida, C. Shishido, H. Seki and M. Wada: Mol. Cryst. Liq. Cryst. 39, 39-52 (1977), and H. Seki, C. Shishido, S. Yasui and T. Uchida: Jpn. J. Appl. Phys. 21, 191-192 (1982), and perylenes are described in EP 60895, EP 68427 and WO 82/1191. Rylene dyes as described, for example, in EP 2166040, US 2011/0042651, EP 68427, EP 47027, EP 60895, DE 3110960 and EP 698649.

According to a preferred embodiment, the switching layer of the device according to the invention comprises, besides compounds of the formula I, exclusively dichroic dyes selected from rylene dyes.

Examples of preferred further dichroic dyes which may be present in the switching layer of the device are shown in Table 1 below:

TABLE 1

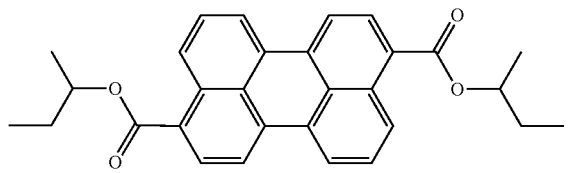 [SMILES: CCC(C)OC(=O)c1ccc2c3cccc4c(C(=O)OC(C)CC)ccc(c5cccc1c52)c43]

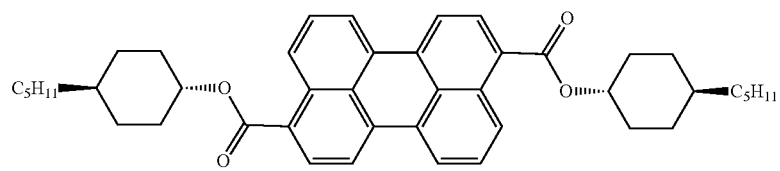

TABLE 1-continued
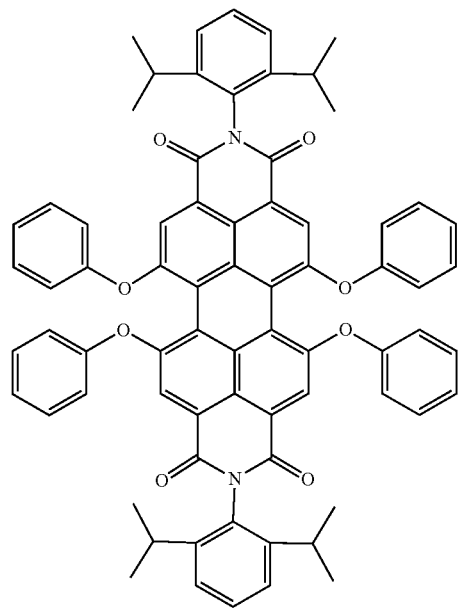 [SMILES: CC(C)c1cccc(C(C)C)c1N1C(=O)c2cc(Oc3ccccc3)c3c4c(Oc5ccccc5)cc5c6c(cc(Oc7ccccc7)c(c7c(Oc8ccccc8)cc(c2c37)C1=O)c64)C(=O)N(c1c(C(C)C)cccc1C(C)C)C5=O]
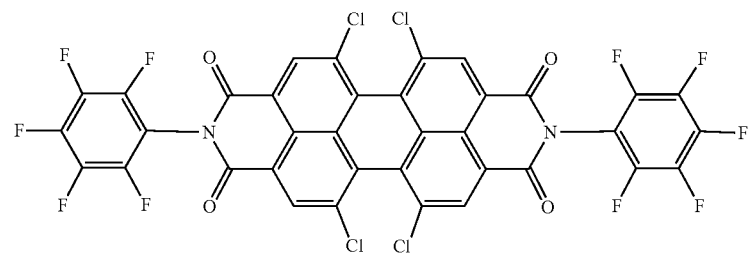 [SMILES: O=C1c2cc(Cl)c3c4c(Cl)cc5c6c(cc(Cl)c(c7c(Cl)cc(c2c37)C(=O)N1c1c(F)c(F)c(F)c(F)c1F)c64)C(=O)N(c1c(F)c(F)c(F)c(F)c1F)C5=O]
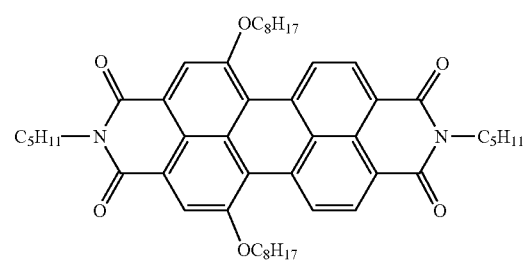
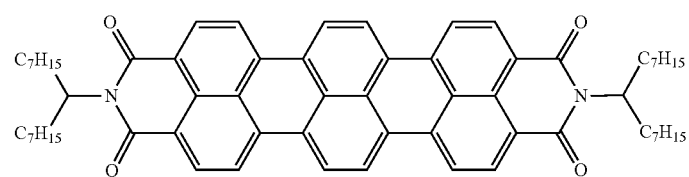

TABLE 1-continued
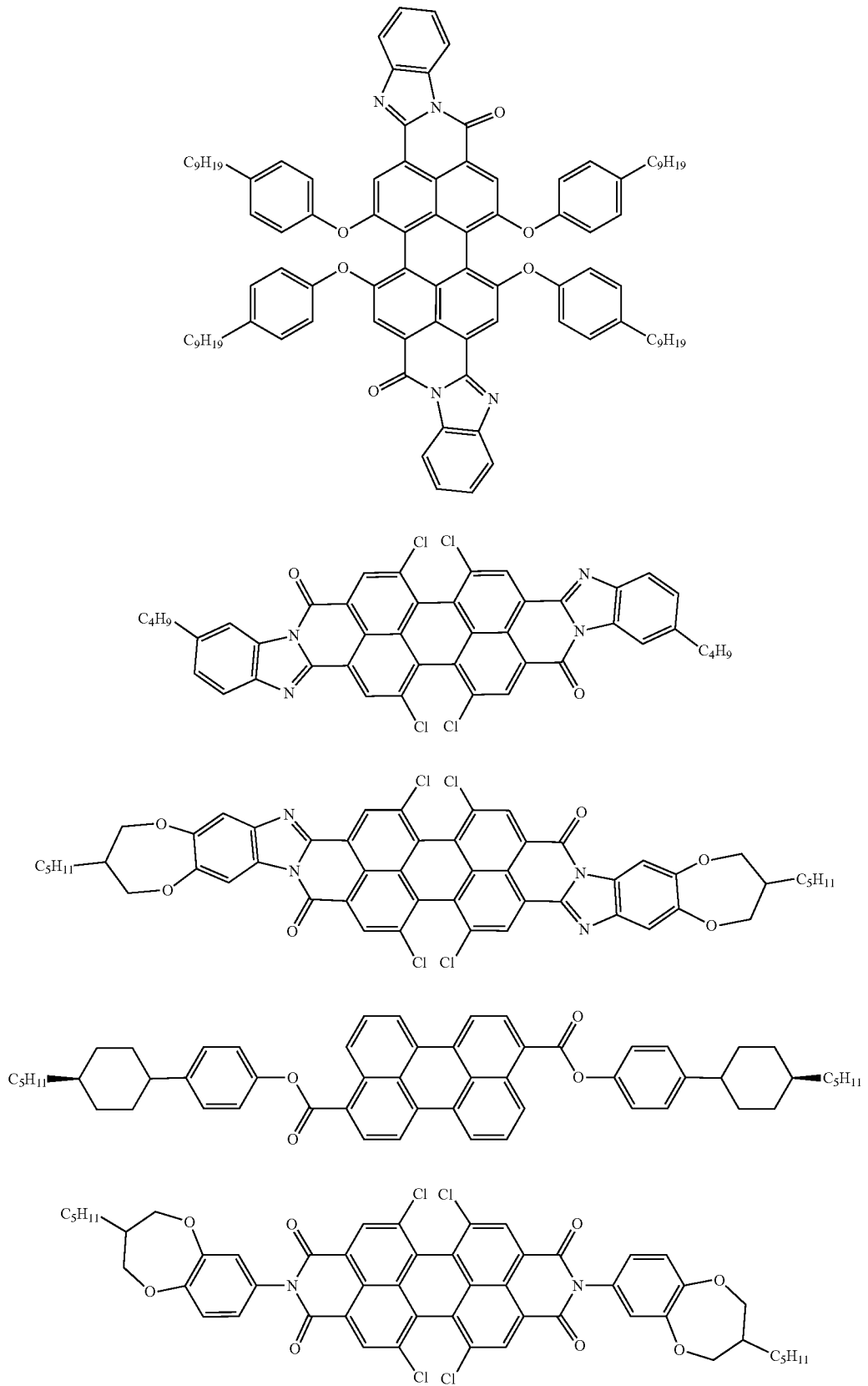

TABLE 1-continued
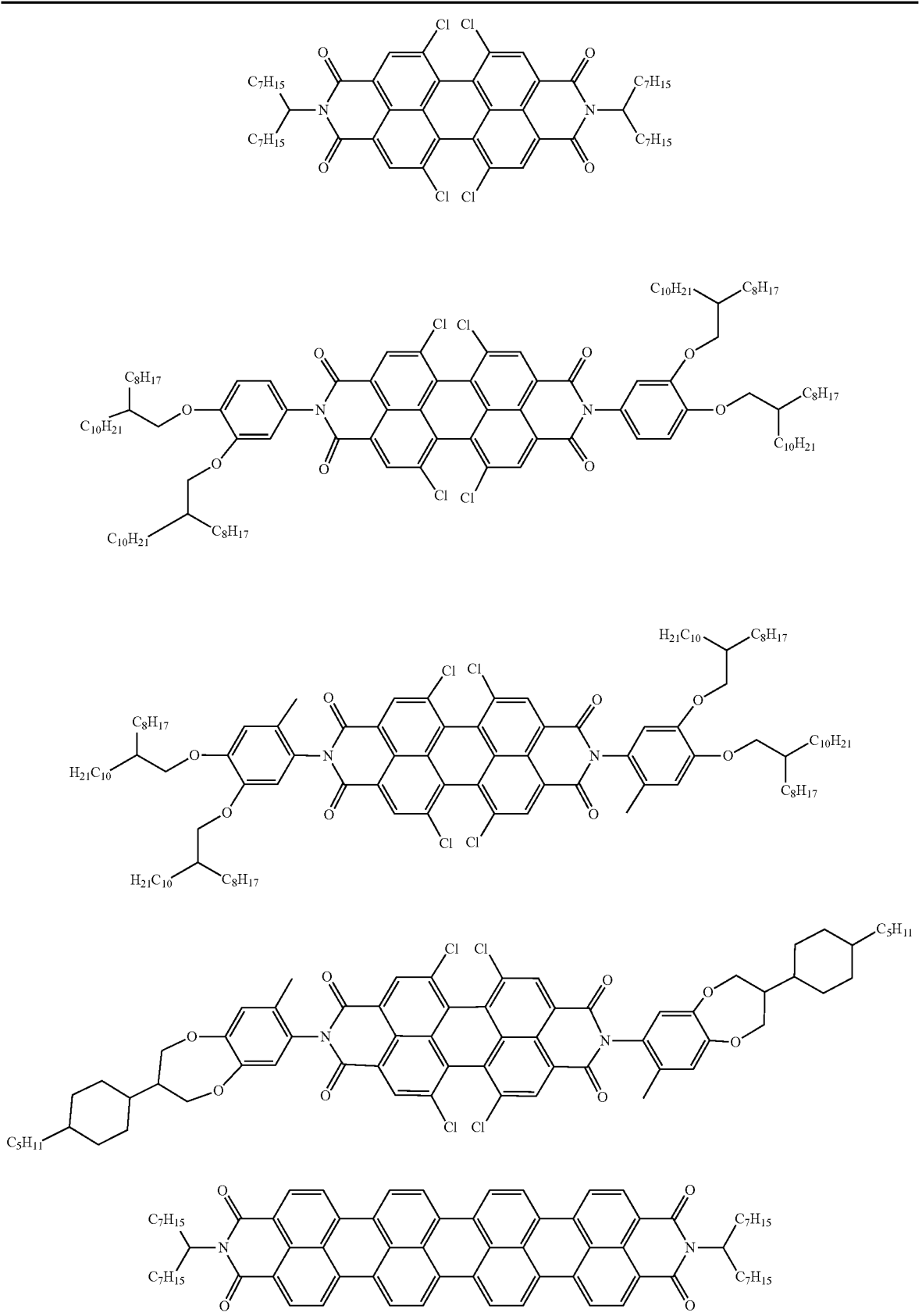

TABLE 1-continued
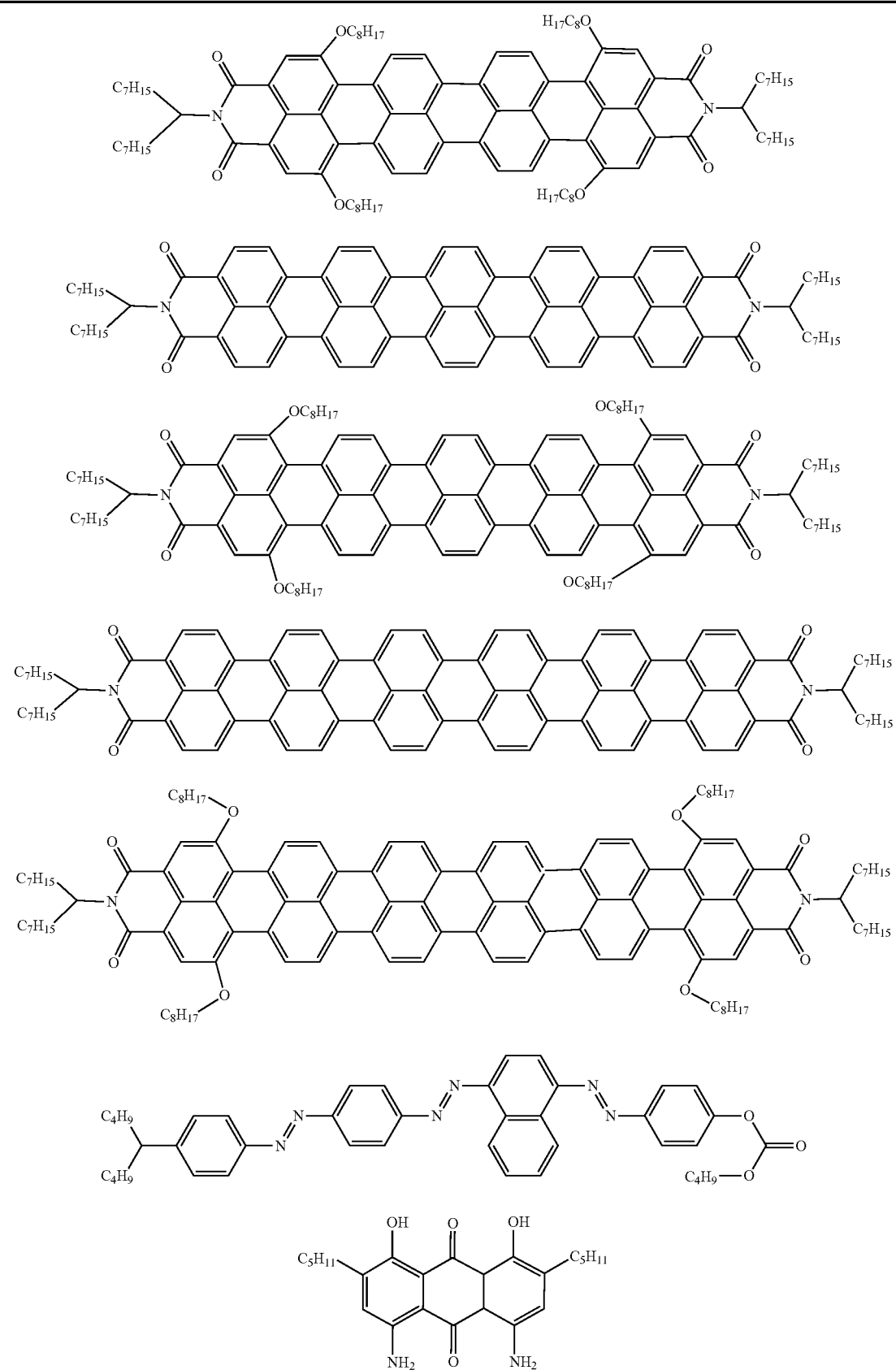

TABLE 1-continued

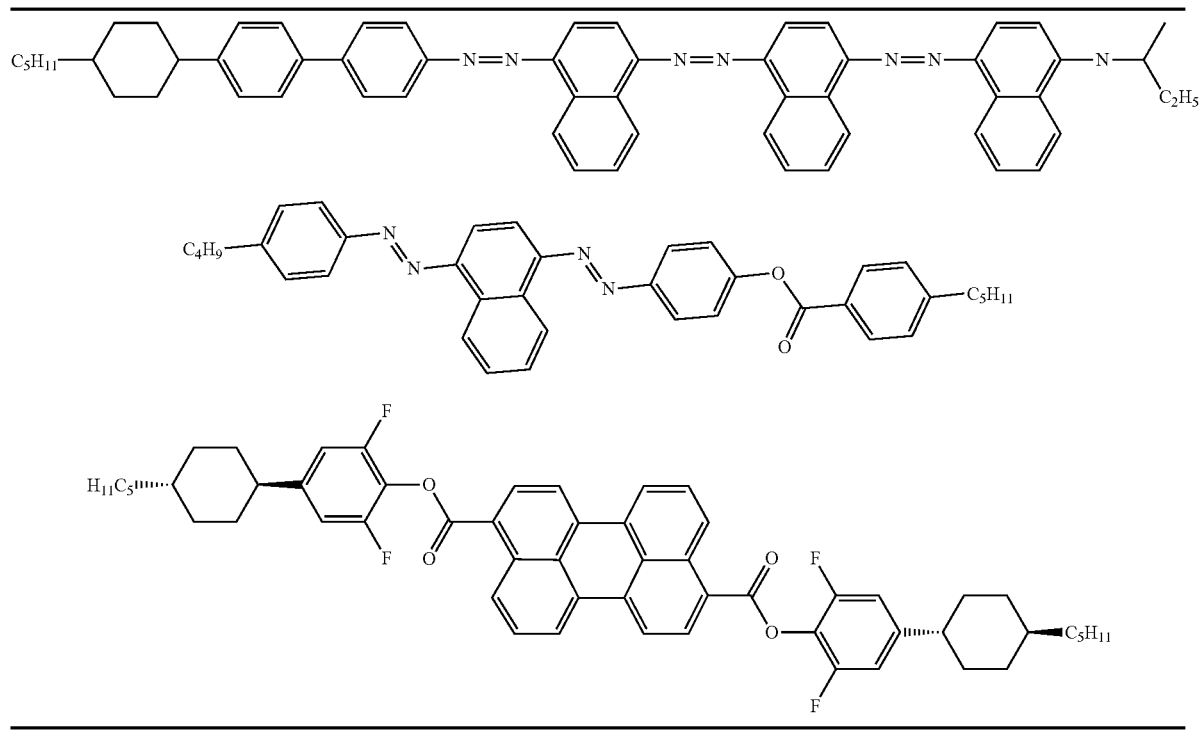

In a preferred embodiment, the switching layer of the device according to the invention comprises one or more quencher compounds. This is particularly preferred if the device according to the invention comprises one or more fluorescent dyes in its switching layer.

Quencher compounds are compounds which quench the fluorescence. The quencher compounds can take on the electronic excitation energy of adjacent molecules, such as, for example, fluorescent dyes, in the switching layer and undergo a transition into an electronically excited state in the process. The quenched fluorescent dye is thus converted into the electronic ground state and is thus prevented from emitting fluorescence or undergoing a subsequent reaction. The quencher compound itself returns to the ground state through radiation-free deactivation or by emission of light and is again available for further quenching.

The quencher compound may have various functions in the switching layer of the device according to the invention. Firstly, the quencher compound may contribute to extending the lifetime of a dye system, by deactivation of electronic excitation energy. Secondly, the quencher compound eliminates additional colour effects which may be aesthetically undesired, for example coloured emission in the inside space emanating from the fluorescent dyes in the switching layer.

In order to achieve effective quenching, the quencher compound should be adapted to the respective dye system, in particular the dye absorbing at the longest wavelength in a dye combination. The way to do this is known to the person skilled in the art.

Preferred quencher compounds are described, for example, in Table 8.1 on page 279 in Joseph R. Lakowicz, Principles of Fluorescence Spectroscopy, $3^{rd}$ Edition, 2010, ISBN 10: 0-387-31278-1, Verlag Springer Science+ Business Media LLC. Further classes of molecule are familiar to the person skilled in the art, for example under the key words dark quencher or black hole quencher. Examples are azo dyes and aminoanthraquinones. The quencher compounds used in the switching layer of the device according to the invention may also be non-fluorescent dyes or dyes which only fluoresce in the NIR.

In a preferred embodiment of the switching layer according to the invention, any quencher compounds present are selected so that fluorescence in the visible part of the spectrum is suppressed.

The device according to the invention is preferably suitable for regulating the passage of energy in the form of sunlight from the environment into an inside space. The passage of energy to be regulated here takes place from the environment (the outside space) into an inside space.

The inside space here can be any desired space that is substantially sealed off from the environment, for example a building, a vehicle or a container.

The invention therefore furthermore relates to the use of the device for regulating the passage of energy from an outside space into an inside space.

However, the device can also be employed for aesthetic room design, for example for light and colour effects. For example, door and wall elements containing the device according to the invention in grey or in colour can be switched to transparent. Furthermore, the device may also comprise white or coloured flat backlighting which is modulated in brightness or yellow flat backlighting which is modulated in colour by means of a blue guest-host display. One or both glass sides of the device according to the invention may be provided with roughened or structured glass for the coupling-out of light and/or for the generation of light effects.

In a further alternative use, the device is employed for regulating the incidence of light on the eyes, for example in protective goggles, visors or sunglasses, where the device keeps the incidence of light on the eyes low in one switching state and reduces the incidence of light less in another switching state.

The device according to the invention is preferably arranged in an opening in a relatively large two-dimensional structure, where the two-dimensional structure itself only allows slight passage of energy, or none at all, and where the opening has relatively high energy transmissivity. The two-dimensional structure is preferably a wall or another boundary of an inside space to the outside. Furthermore, the two-dimensional structure preferably covers an area of at least equal size, particularly preferably an area at least twice as large as the opening in it in which the device according to the invention is disposed.

The device is preferably characterised in that it has an area of at least 0.05 m$^2$, preferably at least 0.1 m$^2$, particularly preferably at least 0.5 m$^2$ and very particularly preferably at least 0.8 m$^2$.

The device is preferably accommodated in an opening having relatively high energy transmissivity, as described above, in a building, a container, a vehicle or another substantially closed space. The device can generally be used for any desired inside spaces, particularly if they have only limited exchange of air with the environment and have light-transmitting boundary surfaces through which input of energy from the outside in the form of light energy can take place. The use of the device for inside spaces which are subjected to strong insolation through light-transmitting areas, for example through window areas, is particularly relevant.

The device according to the invention is switchable. Switching here is taken to mean a change in the passage of energy through the device. The device according to the invention is preferably electrically switchable, as described, for example, in WO 2009/141295 and in WO 2014/090373.

However, it may also be thermally switchable, as described, for example, in WO 2010/118422. In this case, the switching preferably takes place through a transition from a nematic state to an isotropic state through a change in the temperature of the switching layer comprising the compound of the formula I and a liquid-crystalline medium. In the nematic state, the molecules of the liquid-crystalline medium are in ordered form and thus so is the compound of the formula I, for example aligned parallel to the surface of the device through the action of an alignment layer. In the isotropic state, the molecules are in unordered form, and thus so is the compound of the formula I. The difference between ordered and unordered presence of the dichroic compound of the formula I causes a difference in the light transmissivity of the switching layer of the device according to the invention, in accordance with the principle that dichroic compounds have a higher or lower absorption coefficient depending on the alignment in relation to the plane of vibration of the light.

If the device is electrically switchable, it preferably comprises two or more electrodes, which are installed on both sides of the switching layer. The electrodes preferably consist of ITO or a thin, preferably transparent metal and/or metal-oxide layer, for example silver or FTO (fluorine-doped tin oxide) or an alternative material known to the person skilled in the art for this use. The electrodes are preferably provided with electrical connections. The voltage is preferably provided by a battery, a rechargeable battery or an external power supply.

The switching operation in the case of electrical switching takes place through an alignment of the molecules of the liquid-crystalline medium by the application of voltage.

In a preferred embodiment, the device is converted from a state having high absorption, i.e. low light transmissivity, which is present without voltage, into a state having lower absorption, i.e. higher light transmissivity. The liquid-crystalline medium of the switching layer is preferably nematic in both states. The voltage-free state is preferably characterised in that the molecules of the liquid-crystalline medium, and thus the molecules of the compound of the formula I, are aligned parallel to the plane of the switching layer. This is preferably achieved by a correspondingly selected alignment layer. The state under voltage is preferably characterised in that the molecules of the liquid-crystalline medium, and thus the molecules of the compound of the formula I, are perpendicular to the plane of the switching layer.

In an alternative embodiment to the embodiment mentioned above, the device is converted from a state having low absorption, i.e. high light transmissivity, which is present without voltage, into a state having higher absorption, i.e. lower light transmissivity. The liquid-crystalline medium of the switching layer is preferably nematic in both states. The voltage-free state is preferably characterised in that the molecules of the liquid-crystalline medium of the switching layer, and thus the molecules of the compound of the formula I, are aligned perpendicular to the plane of the switching layer. This is preferably achieved by a correspondingly selected alignment layer or by self-alignment additives for vertical alignment. The state under voltage is preferably characterised in that the molecules of the liquid-crystalline medium of the switching layer, and thus the molecules of the compound of the formula I, are parallel to the plane of the switching layer.

According to a preferred embodiment of the invention, the device can be operated without an external power supply by providing the energy required by means of a solar cell or another device for conversion of light and/or heat energy into electrical energy which is connected to the device. The provision of the energy by means of the solar cell can take place directly or indirectly, i.e. via a battery or rechargeable battery or other unit for the storage of energy connected in-between. The solar cell is preferably mounted on the outside of the device or is an internal component of the device, as disclosed, for example, in WO 2009/141295. Particular preference is given here to solar cells which are particularly efficient in the case of diffuse light, and transparent solar cells.

The device according to the invention preferably has the following layer sequence, where further layers may additionally be present. The layers indicated below are preferably directly adjacent to one another in the device:

substrate layer, preferably comprising glass or polymer
electrically conductive transparent layer, preferably comprising ITO
alignment layer
switching layer comprising one or more compounds of the formula I
alignment layer
electrically conductive transparent layer, preferably comprising ITO
substrate layer, preferably comprising glass or polymer The preferred embodiments of the individual layers are described below.

The device according to the invention preferably comprises one or more, particularly preferably two, alignment layers. The alignment layers are preferably directly adjacent to the two sides of the switching layer comprising the compound of the formula I.

The alignment layers used in the device according to the invention can be any desired layers known to the person skilled in the art for this purpose.

Preference is given to polyimide layers, particularly preferably layers comprising rubbed polyimide. Polyimide rubbed in a certain manner known to the person skilled in the art results in alignment of the molecules of the liquid-crystalline medium in the rubbing direction if the molecules are parallel to the alignment layer (planar alignment). It is preferred here for the molecules of the liquid-crystalline medium not to be completely planar on the alignment layer, but instead to have a slight pretilt angle. In order to achieve vertical alignment of the compounds of the liquid-crystalline medium to the surface of the alignment layer (homeotropic alignment), polyimide treated in a certain manner is preferably employed as material for the alignment layer (polyimide for very high pretilt angles). Furthermore, polymers obtained by an exposure process to polarised light can be used as alignment layer in order to achieve alignment of the compounds of the liquid-crystalline medium in accordance with an alignment axis (photoalignment). In alternative to vertical alignment layers a self-alignment additive for vertical alignment can be used which is added to the liquid crystalline medium.

The switching layer in the device according to the invention is furthermore preferably arranged between two substrate layers or enclosed thereby. The substrate layers can consist, for example, of glass or a polymer, preferably a light-transmitting polymer.

The device is preferably characterised in that it does not comprise a polymer-based polariser, particularly preferably does not comprise a polariser in the solid material phase and very particularly preferably comprises no polariser at all.

However, in accordance with an alternative embodiment, the device may also comprise one or more polarisers. The polarisers in this case are preferably linear polarisers.

If precisely one polariser is present, its absorption direction is preferably perpendicular to the orientation axis of the compounds of the liquid-crystalline medium of the device according to the invention on the side of the switching layer on which the polariser is located.

In the device according to the invention both absorptive and also reflective polarisers can be employed. Preference is given to the use of polarisers which are in the form of thin optical films. Examples of reflective polarisers which can be used in the device according to the invention are DRPF (diffusive reflective polariser film, 3M), DBEF (dual brightness enhanced film, 3M), DBR (layered-polymer distributed Bragg reflectors, as described in U.S. Pat. Nos. 7,038,745 and 6,099,758) and APF films (advanced polariser film, 3M, cf. Technical Digest SID 2006, 45.1, US 2011/0043732 and U.S. Pat. No. 7,023,602). It is furthermore possible to employ polarisers based on wire grids (WGPs, wire-grid polarisers) which reflect infrared light. Examples of absorptive polarisers which can be employed in the devices according to the invention are the Itos XP38 polariser film and the Nitto Denko GU-1220DUN polariser film. An example of a circular polariser which can be used in accordance with the invention is the APNCP37-035-STD polariser (American Polarizers). A further example is the CP42 polariser (ITOS).

The device according to the invention furthermore may comprise an optical waveguide system which transports the light to a solar cell or another device for the conversion of light and/or heat energy into electrical energy, preferably as described in WO 2009/141295. The optical waveguide system collects and concentrates light hitting the device. It preferably collects and concentrates light emitted by fluorescent dichroic dyes in the switching layer. The optical waveguide system is in contact with a device for the conversion of light energy into electrical energy, preferably a solar cell, so that the collected light hits the latter in concentrated form. In a preferred embodiment of the invention, the device for the conversion of light energy into electrical energy is mounted at the edge of the device according to the invention, integrated into the latter and electrically connected to means for the electrical switching of the device.

In a preferred embodiment, the device according to the invention is a constituent of a window, particularly preferably a window comprising at least one glass surface, very particularly preferably a window which comprises multi-pane insulating glass.

Window here is taken to mean, in particular, a structure in a building which comprises a frame and at least one glass pane surrounded by this frame. It preferably comprises a heat-insulating frame and two or more glass panes (multi-pane insulating glass).

According to a preferred embodiment, the device according to the invention is applied directly to a glass surface of a window, particularly preferably in the interspace between two glass panes of multipane insulating glass.

The invention furthermore relates to a window comprising a device according to the invention, preferably having the preferred features indicated above.

Owing to the electronic properties of the compounds according to the invention, they are also suitable, besides the use as dye, as organic semiconductors.

The invention therefore furthermore relates to the use of compounds of the formula I in organic electronic components, such as, for example, organic light-emitting diodes (OLEDs), organic field-effect transistors (OFETs), printed circuits, radio frequency identification elements (RFIDs), lighting elements, photovoltaic devices and optical sensors.

Owing to their coloured nature and good solubility in organic materials, the compounds according to the invention are eminently suitable as dyes. The invention therefore likewise relates to the use of dyes of the formula I for colouring a polymer.

In the present invention and especially in the following examples, the structures of the mesogenic compounds are indicated by means of abbreviations, also called acronyms. In these acronyms, the chemical formulae are abbreviated as follows using Tables A to C below. All groups $C_nH_{2n+1}$, $C_mH_{2m+1}$ and $C_lH_{2l+1}$ or $C_nH_{2n-1}$, $C_mH_{2m-1}$ and $C_lH_{2l-1}$ denote straight-chain alkyl or alkenyl, preferably 1E-alkenyl, each having n, m and l C atoms respectively. Table A lists the codes used for the ring elements of the core structures of the compounds, while Table B shows the linking groups. Table C gives the meanings of the codes for the left-hand or right-hand end groups. The acronyms are composed of the codes for the ring elements with optional linking groups, followed by a first hyphen and the codes for the left-hand end group, and a second hyphen and the codes for the right-hand end group. Table D shows illustrative structures of compounds together with their respective abbreviations.

TABLE A

Ring elements

C    C(CN)    CN

TABLE A-continued

| Ring elements | | | |
|---|---|---|---|
| P | 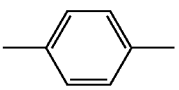 | P(F,CN) | 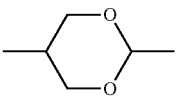 |
| D | 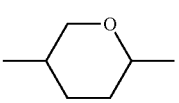 | DI | 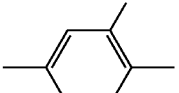 |
| A | 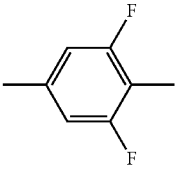 | AI | 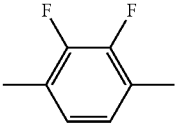 |
| G | 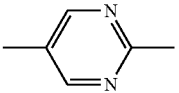 | GI | 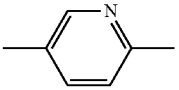 |
| U | 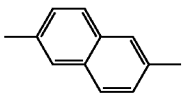 | UI | 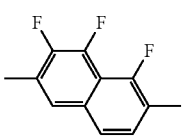 |
| Y | 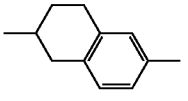 | | |
| M | 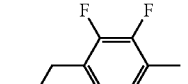 | MI | 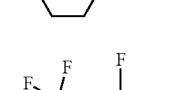 |
| N | 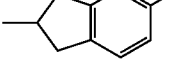 | NI |  |
| Np | 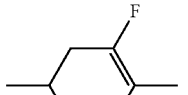 | dH | 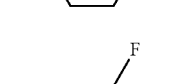 |
| N3f | 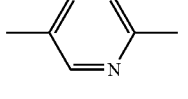 | N3fl | 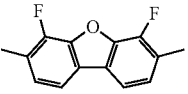 |
| tH | | tHl | |
| tH2f | | tH2fl | |
| K | | Kl | |
| L | | Ll | |
| F | | Fl | |
| Nf | | Nfl | |
| B |  | | |

TABLE B

| Linking groups | | | |
|---|---|---|---|
| E | —$CH_2CH_2$— | Z | —CO—O— |
| V | —CH=CH— | Zl | —O—CO— |
| X | —CF=CH— | O | —$CH_2$—O— |
| Xl | —CH=CF— | Ol | —O—$CH_2$— |
| B | —CF=CF— | Q | —$CF_2$—O— |
| T | —C≡C— | Ql | —O—$CF_2$— |
| W | —$CF_2CF_2$— | T | —C≡C— |

TABLE C

| End groups | | | |
|---|---|---|---|
| Left-hand side | | Right-hand side | |
| Use alone | | | |
| -n- | $C_nH_{2n+1}$— | -n | —$CnH_{2n+1}$ |
| -nO— | $C_nH_{2n+1}$—O— | —On | —O—$C_nH_{2n+1}$ |
| —V— | $CH_2$=CH— | —V | —CH=$CH_2$ |
| -nV— | $C_nH_{2n+1}$—CH=CH— | -nV | —$C_nH_{2n}$—CH=$CH_2$ |
| —Vn- | $CH_2$=CH—$CnH_{2n+1}$ | —Vn | —CH=CH—$CnH_{2n+1}$ |
| -nVm- | $C_nH_{2n+1}$—CH=CH—$C_mH_{2m}$— | -nVm | —$C_nH_{2n}$—CH=CH—$C_mH_{2m+1}$ |

TABLE C-continued

| End groups | | | |
|---|---|---|---|
| Left-hand side | | Right-hand side | |
| —N— | N≡C | —N | —C≡N |
| —S— | S=C=N— | —S | —N=C=S |
| —F— | F— | —F | —F |
| —CL— | Cl— | —CL | —Cl |
| —M— | CFH$_2$— | —M | —CFH$_2$ |
| —D— | CF$_2$H— | —D | —CF$_2$H |
| —T— | CF$_3$— | —T | —CF$_3$ |
| —MO— | CFH$_2$O— | —OM | —OCFH$_2$ |
| —DO— | CF$_2$HO— | —OD | —OCF$_2$H |
| —TO— | CF$_3$O— | —OT | —OCF$_3$ |
| —OXF— | CF$_2$=CH—O— | —OXF | —O—CH=CF$_2$ |
| —A— | H—C≡C— | —A | —C≡C—H |
| -nA— | C$n$H$_{2n+1}$—C≡C— | —An | —C≡C—C$_n$H$_{2n+1}$ |
| —NA— | N≡C—C≡C— | —AN | —C≡C—C≡N |
| Use together with one another and with others | | | |
| -…A…- | —C≡C— | -…A… | —C≡C— |
| -…V…- | CH=CH— | -…V… | —CH=CH— |
| -…Z…- | —CO—O— | -…Z… | —CO—O— |
| -…ZI…- | —O—CO— | -…ZI… | —O—CO— |
| -…K…- | —CO— | -…K… | —CO— |
| -…W…- | —CF=CF— | -…W… | —CF=CF— | in which n and m each denote integers, and the three dots "…" are placeholders for other abbreviations from this table.

The following table shows illustrative structures together with their respective abbreviations. These are shown in order to illustrate the meaning of the rules for the abbreviations. They furthermore represent compounds which are preferably used.

TABLE D

Illustrative structures

C$_n$H$_{2n+1}$—[Cy]—[Cy]—C$_m$H$_{2m+1}$     CC-n-m

C$_n$H$_{2n+1}$—[Cy]—[Cy]—O—C$_m$H$_{2m+1}$     CC-n-Om

C$_n$H$_{2n+1}$—[Cy]—[Cy]—CH=CH$_2$     CC-n-V

C$_n$H$_{2n+1}$—[Cy]—[Cy]—CH=CH—C$_m$H$_{2m+1}$     CC-n-Vm

C$_n$H$_{2n+1}$—[Cy]—[Cy]—(CH$_2$)$_m$—CH=CH$_2$     CC-n-mV

C$_n$H$_{2n+1}$—[Cy]—[Cy]—(CH$_2$)$_m$—CH=CH—C$_l$H$_{2l+1}$     CC-n-mVl

TABLE D-continued

| Illustrative structures | |
|---|---|
| H₂C=CH—[Cy]—[Cy]—CH=CH₂ | CC-V-V |
| CH₂=CH—[Cy]—[Cy]—(CH₂)$_m$—CH=CH₂ | CC-V-mV |
| CH₂=CH—[Cy]—[Cy]—CH=CH—C$_m$H$_{2m+1}$ | CC-V-Vm |
| CH₂=CH—(CH₂)$_n$—[Cy]—[Cy]—(CH₂)$_m$—CH=CH₂ | CC-Vn-mV |
| C$_n$H$_{2n+1}$—CH=CH—[Cy]—[Cy]—(CH₂)$_m$—CH=CH₂ | CC-nV-mV |
| C$_n$H$_{2n+1}$—CH=CH—[Cy]—[Cy]—CH=CH—C$_m$H$_{2m+1}$ | CC-nV-Vm |
| C$_n$H$_{2n+1}$—[Cy]—[Ph]—C$_m$H$_{2m+1}$ | CP-n-m |
| C$_n$H$_{2n+1}$O—[Cy]—[Ph]—C$_m$H$_{2m+1}$ | CP-nO-m |
| C$_n$H$_{2n+1}$—[Cy]—[Ph]—OC$_m$H$_{2m+1}$ | CP-n-Om |
| CH₂=CH—[Cy]—[Ph]—C$_m$H$_{2m+1}$ | CP-V-m |
| CH₂=CH—(CH₂)$_n$—[Cy]—[Ph]—C$_m$H$_{2m+1}$ | CP-Vn-m |
| C$_n$H$_{2n+1}$—CH=CH—[Cy]—[Ph]—C$_m$H$_{2m+1}$ | CP-nV-m |
| H₂C=CH—[Cy]—[Ph]—CH=CH₂ | CP-V-V |

TABLE D-continued
Illustrative structures
| | |
|---|---|
| 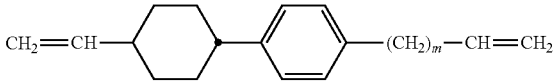 | CP-V-mV |
| 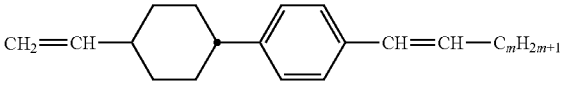 | CP-V-Vm |
| 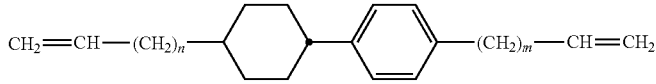 | CP-Vn-mV |
| 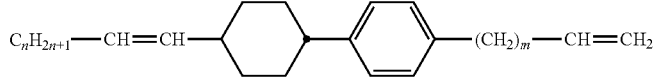 | CP-nV-mV |
| 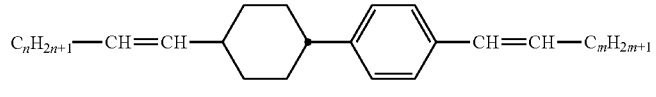 | CP-nV-Vm |
| 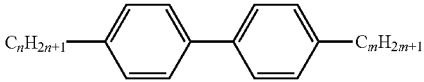 | PP-n-m |
| 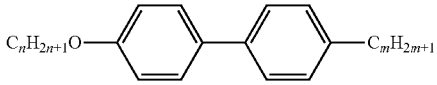 | PP-nO-m |
| 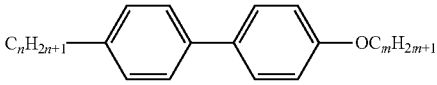 | PP-n-Om |
| 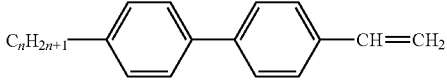 | PP-n-V |
| 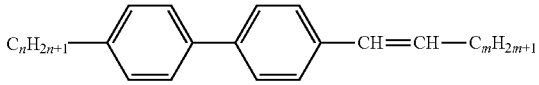 | PP-n-Vm |
| 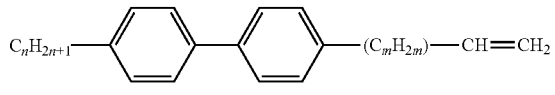 | PP-n-mV |
| 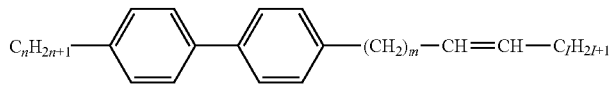 | PP-n-mVl |
|  | CCP-n-m |

TABLE D-continued
Illustrative structures
 CCP-nO-m
 CCP-n-Om
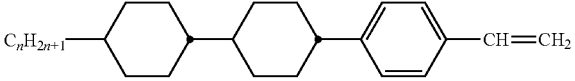 CCP-n-V
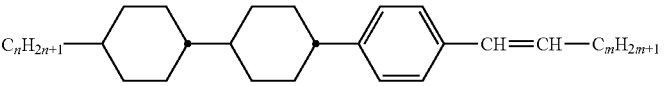 CCP-n-Vm
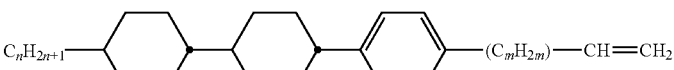 CCP-n-mV
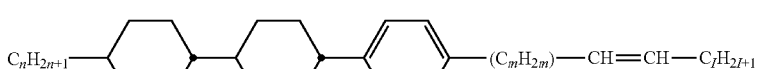 CCP-n-mVl
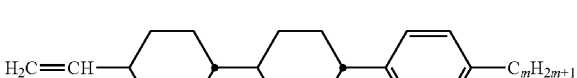 CCP-V-m
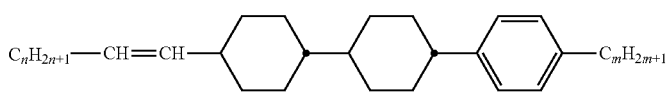 CCP-nV-m
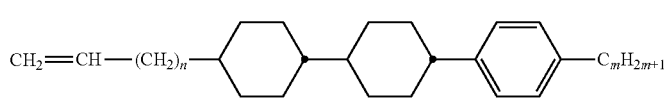 CCP-Vn-m
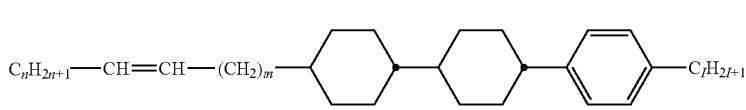 CCP-nVm-l
 CPP-n-m
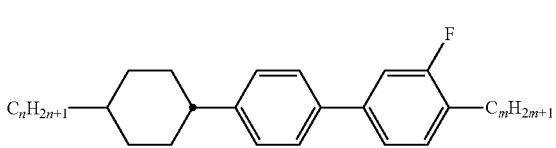 CPG-n-m TABLE D-continued

| Illustrative structures | |
|---|---|
| [structure: C$_n$H$_{2n+1}$–cyclohexyl–(2-F-phenyl)–phenyl–C$_m$H$_{2m+1}$] | CGP-n-m |
| [structure: C$_n$H$_{2n+1}$O–cyclohexyl–phenyl–phenyl–C$_m$H$_{2m+1}$] | CPP-nO-m |
| [structure: C$_n$H$_{2n+1}$–cyclohexyl–phenyl–phenyl–OC$_m$H$_{2m+1}$] | CPP-n-Om |
| [structure: H$_2$C=CH–cyclohexyl–phenyl–phenyl–C$_m$H$_{2m+1}$] | CPP-V-m |
| [structure: C$_n$H$_{2n+1}$–CH=CH–cyclohexyl–phenyl–phenyl–C$_m$H$_{2m+1}$] | CPP-nV-m |
| [structure: CH$_2$=CH–(C$_n$H$_{2n}$)–cyclohexyl–phenyl–phenyl–C$_m$H$_{2m+1}$] | CPP-Vn-m |
| [structure: C$_n$H$_{2n+1}$–CH=CH–(C$_m$H$_{2m}$)–cyclohexyl–phenyl–phenyl–C$_l$H$_{2l+1}$] | CPP-nVm-I |
| [structure: C$_n$H$_{2n+1}$–phenyl–(2-F-phenyl)–phenyl–C$_m$H$_{2m+1}$] | PGP-n-m |
| [structure: C$_n$H$_{2n+1}$–phenyl–(2-F-phenyl)–phenyl–CH=CH$_2$] | PGP-n-V |
| [structure: C$_n$H$_{2n+1}$–phenyl–(2-F-phenyl)–phenyl–CH=CH–C$_m$H$_{2m+1}$] | PGP-n-Vm |
| [structure: C$_n$H$_{2n+1}$–phenyl–(2-F-phenyl)–phenyl–(CH$_2$)$_m$–CH=CH$_2$] | PGP-n-mV |

TABLE D-continued
Illustrative structures
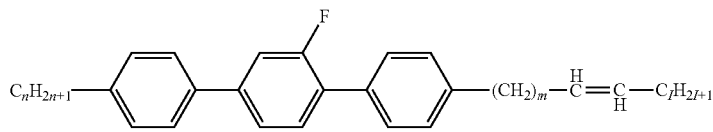 PGP-n-mVl
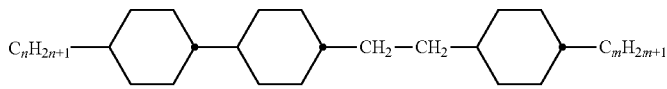 CCEC-n-m
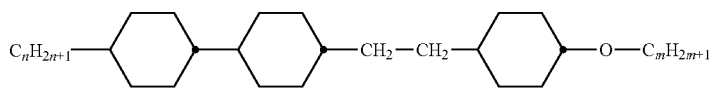 CCEC-n-Om
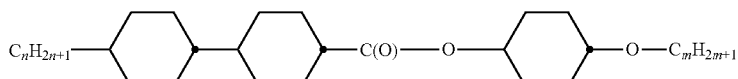 CCZC-n-Om
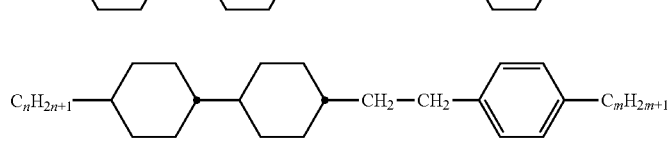 CCEP-n-m
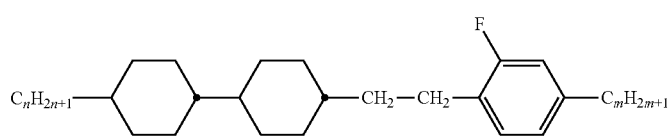 CCEG-n-m
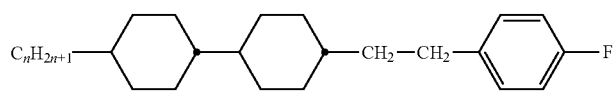 CCEU-n-F
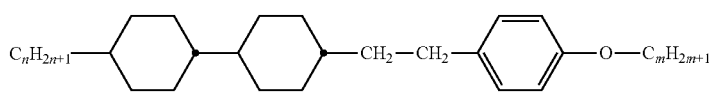 CCEP-n-Om
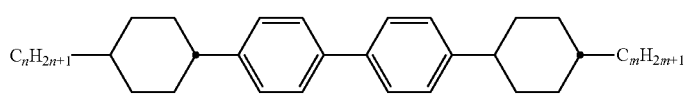 CPPC-n-m
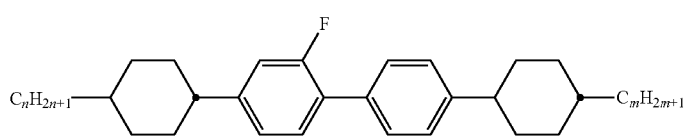 CGPC-n-m
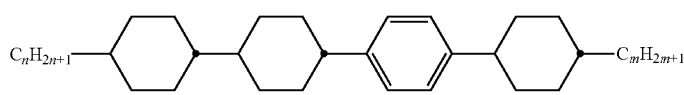 CCPC-n-m
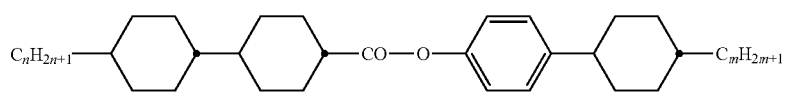 CCZPC-n-m TABLE D-continued

| Illustrative structures | |
|---|---|
| $C_nH_{2n+1}$—⬡—⬡—CO—O—⌬—$C_mH_{2m+1}$ | CCZP-n-m |
| $C_nH_{2n+1}$—⬡—⬡—CO—O—⌬(F)—$C_mH_{2m+1}$ | CCZGI-n-m |
| $C_nH_{2n+1}$—⬡—⌬—⌬(F)—⌬—$C_mH_{2m+1}$ | CPGP-n-m |
| $C_nH_{2n+1}$—⬡—⌬—⌬(F)—⌬—$(CH_2)_m$—CH=$CH_2$ | CPGP-n-mV |
| $C_nH_{2n+1}$—⬡—⌬—⌬(F)—⌬—$(CH_2)_m$—CH=CH—$C_lH_{2l+1}$ | CPGP-n-mVI |
| $C_nH_{2n+1}$—⬡—⌬(F)—⌬(F)—⌬—$C_mH_{2m+1}$ | PGIGP-n-m |
| $C_nH_{2n+1}$—⬡—⌬—F | CP-n-F |
| $C_nH_{2n+1}$—⬡—⌬—CN | CP-n-N |
| $C_nH_{2n+1}$—⬡—⌬—Cl | CP-n-CL |
| $C_nH_{2n+1}$—⌬(F)—⌬—F | GP-n-F |
| $C_nH_{2n+1}$—⌬(F)—⌬—Cl | GP-n-CL |

TABLE D-continued

Illustrative structures

PZG-n-N $C_nH_{2n+1}$—[benzene]—C(=O)O—[benzene(3-F, 4-CN)]

CCP-n-OT $C_nH_{2n+1}$—[cyclohexane]—[cyclohexane]—[benzene]—OCF$_3$

CCG-n-OT $C_nH_{2n+1}$—[cyclohexane]—[cyclohexane]—[benzene(3-F)]—OCF$_3$

CCP-n-T $C_nH_{2n+1}$—[cyclohexane]—[cyclohexane]—[benzene]—CF$_3$

CCG-n-F $C_nH_{2n+1}$—[cyclohexane]—[cyclohexane]—[benzene(3,4-diF)]

CCG-V-F $H_2C{=}CH$—[cyclohexane]—[cyclohexane]—[benzene(3,4-diF)]

CCG-V-F $H_2C{=}CH$—[cyclohexane]—[cyclohexane]—[benzene(3,4-diF)]

CCU-n-F $C_nH_{2n+1}$—[cyclohexane]—[cyclohexane]—[benzene(3,4,5-triF)]

CDU-n-F $C_nH_{2n+1}$—[cyclohexane]—[1,3-dioxane]—[benzene(3,4,5-triF)]

TABLE D-continued
Illustrative structures
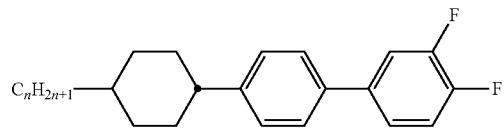
CPG-n-F
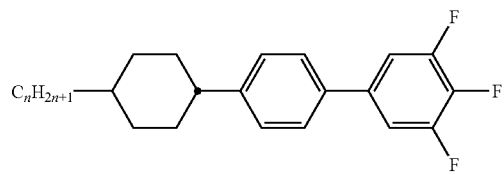
CPU-n-F
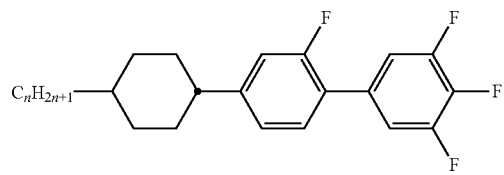
CGU-n-F
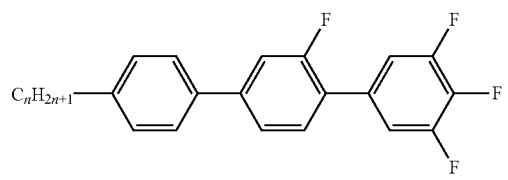
PGU-n-F
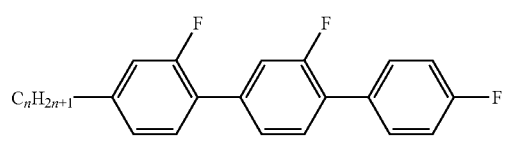
GGP-n-F
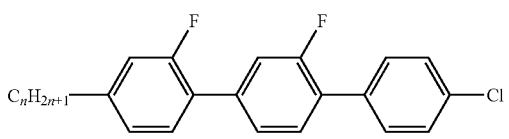
GGP-n-CL
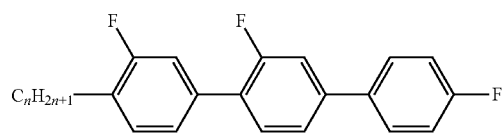
PGIGI-n-F
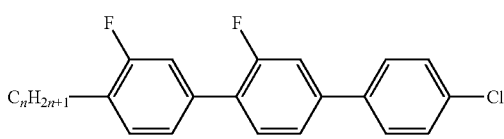
PGIGI-n-CL TABLE D-continued
Illustrative structures
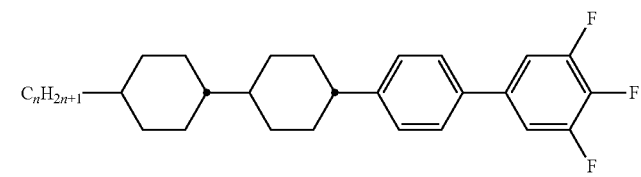 CCPU-n-F
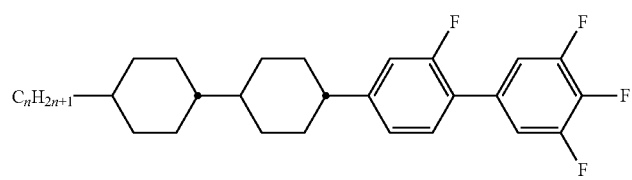 CCGU-n-F
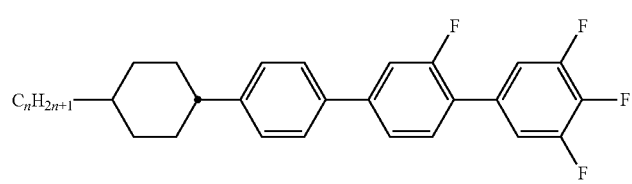 CPGU-n-F
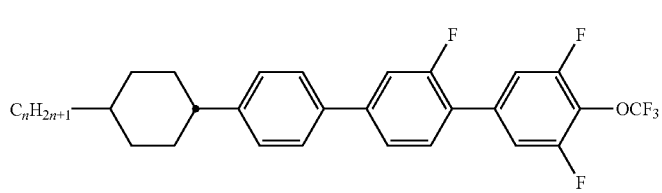 CPGU-n-OT
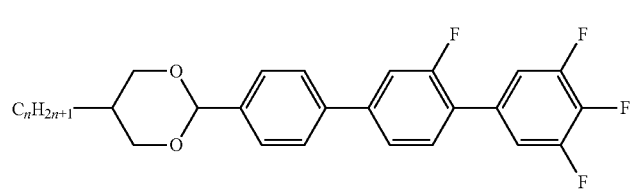 DPGU-n-F
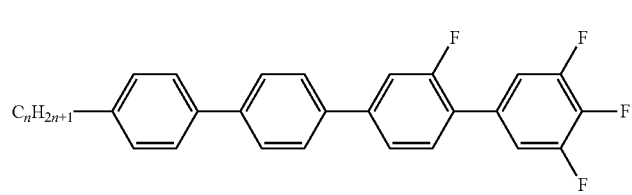 PPGU-n-F
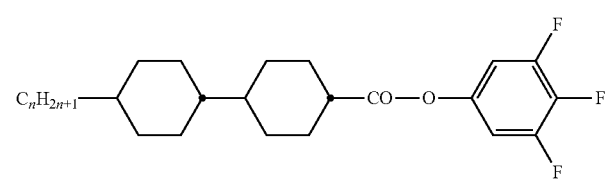 CCZU-n-F
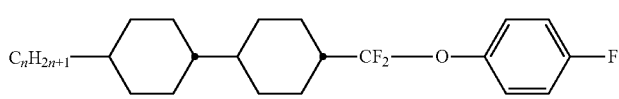 CCCIP-n-F TABLE D-continued
Illustrative structures
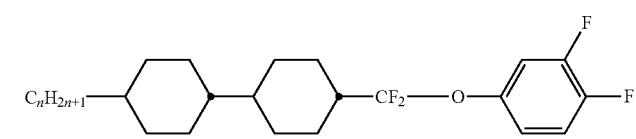
CCQG-n-F
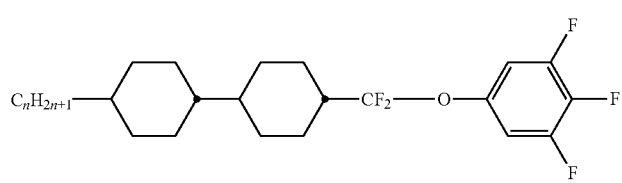
CCQU-n-F
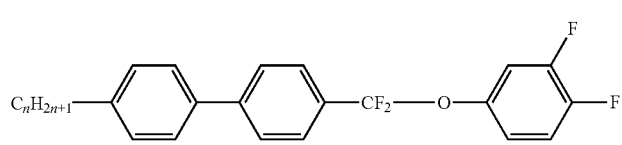
PPCIG-n-F
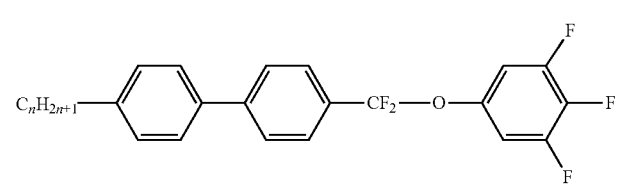
PPOU-n-F
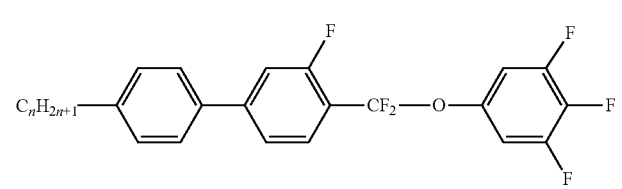
PGQU-n-F
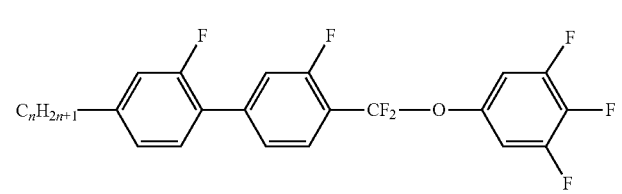
GGQU-n-F
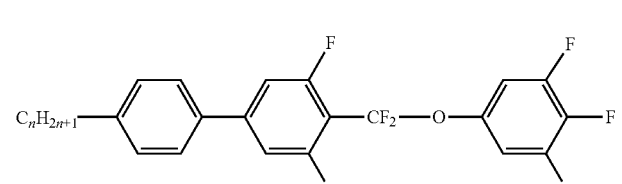
PUQU-n-F
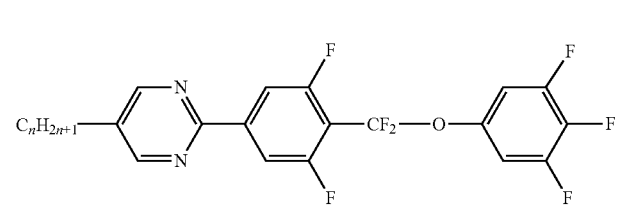
MUQU-n-F TABLE D-continued
| Illustrative structures | |
|---|---|
| 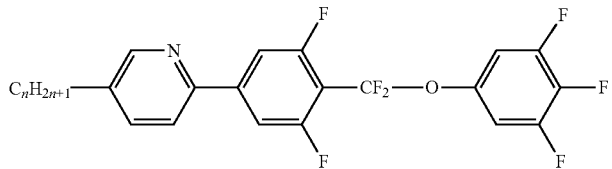 | NUQU-n-F |
| 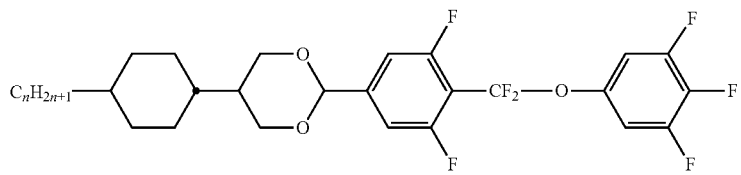 | CDUQU-n-F |
| 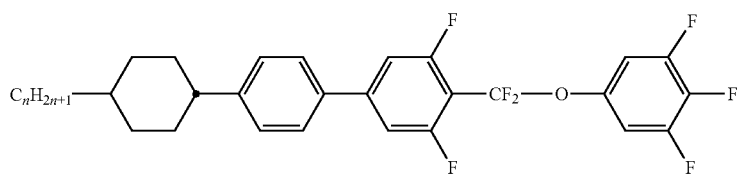 | CPUQU-n-F |
| 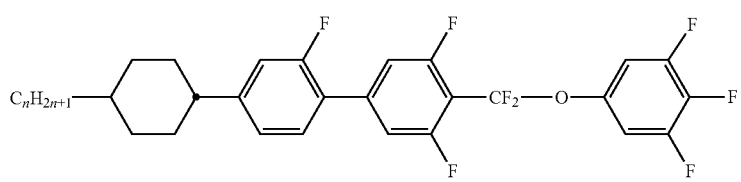 | CGUQU-n-F |
| 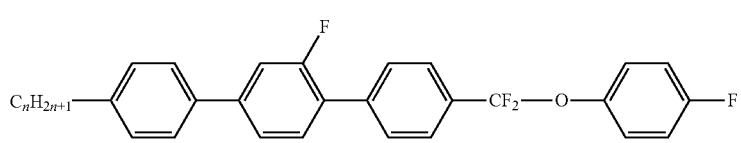 | PGPQP-n-F |
| 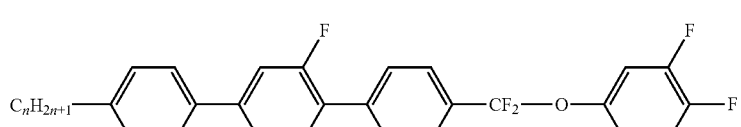 | PGPCIG-n-F |
| 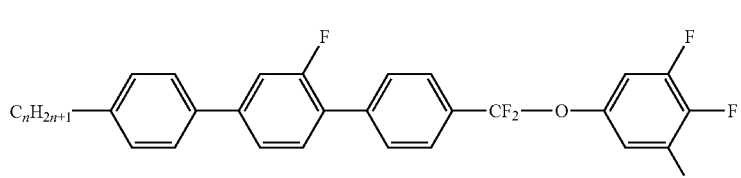 | PGIDQU-n-F |
| 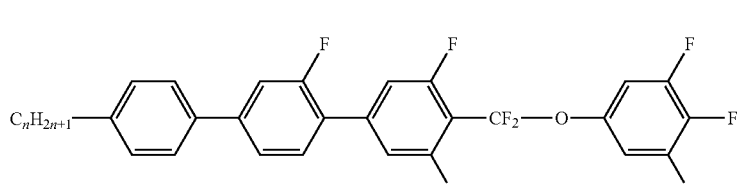 | PGUQU-n-F |

TABLE D-continued
Illustrative structures
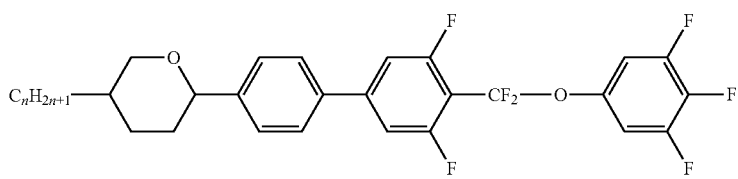
APUQU-n-F
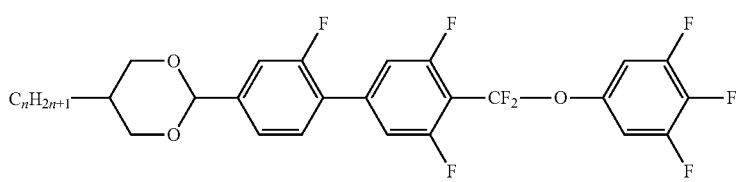
DGUQU-n-F
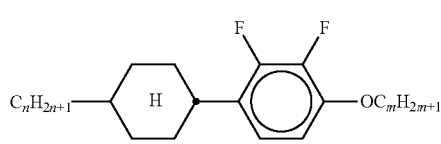
CY-n-Om
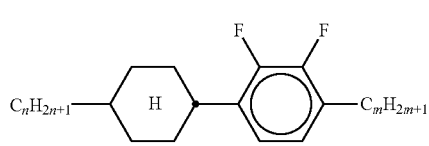
CY-n-m
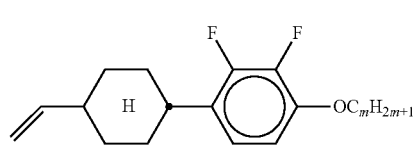
CY-V-Om
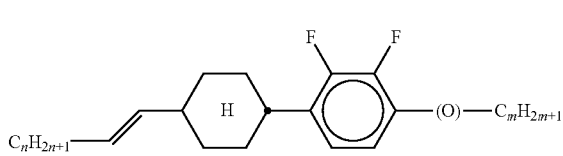
CY-nV-(O)m
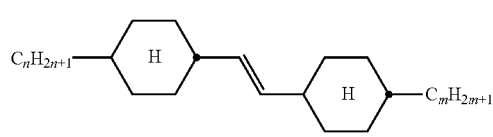
CVC-n-m
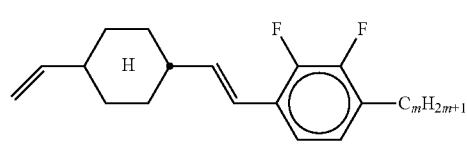
CVY-V-m
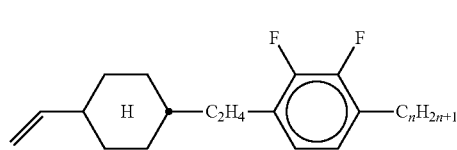
CEY-V-m TABLE D-continued
Illustrative structures
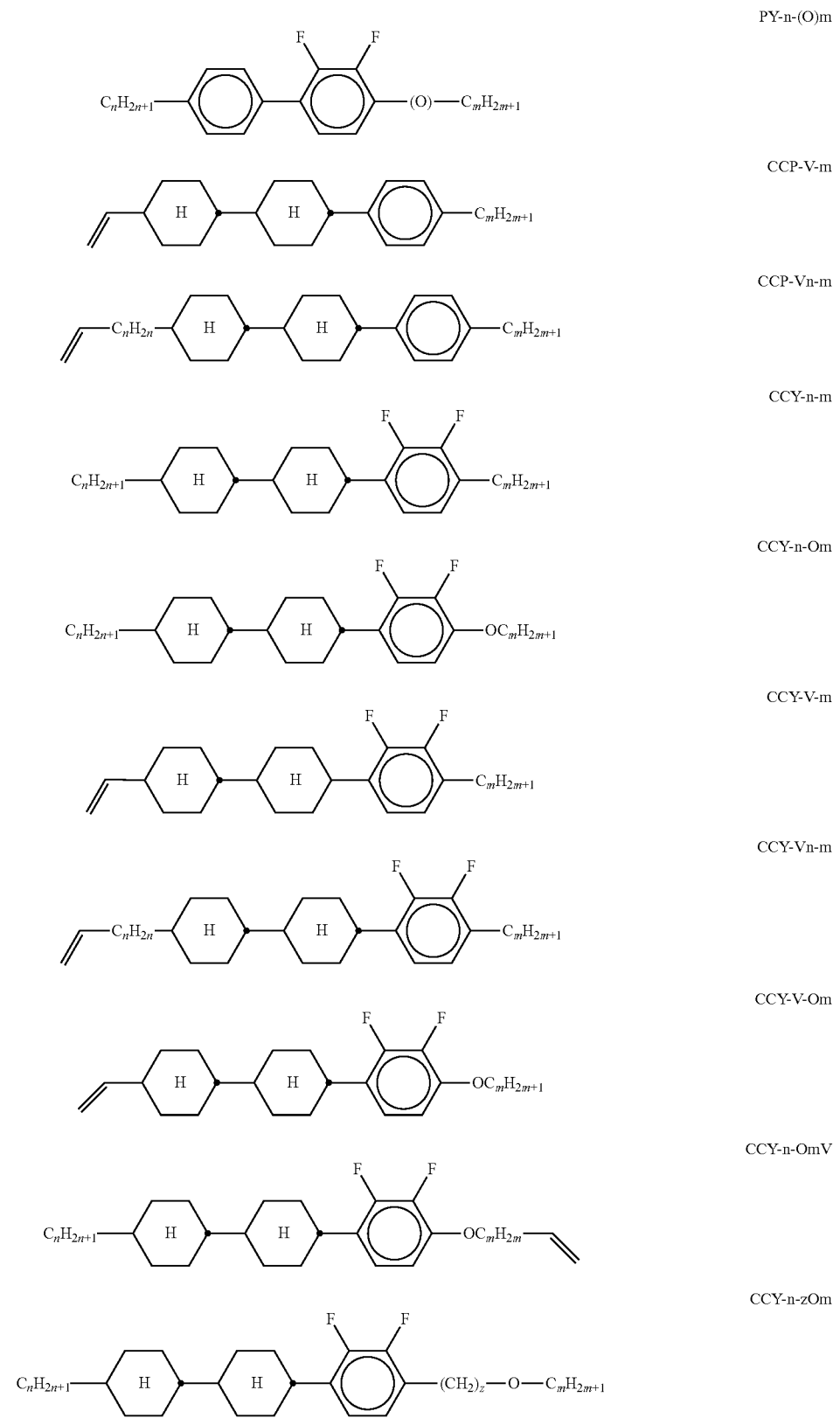
PY-n-(O)m
CCP-V-m
CCP-Vn-m
CCY-n-m
CCY-n-Om
CCY-V-m
CCY-Vn-m
CCY-V-Om
CCY-n-OmV
CCY-n-zOm TABLE D-continued
Illustrative structures
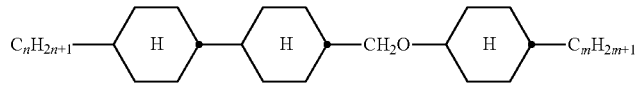   CCOC-n-m
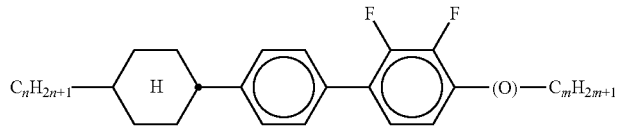   CPY-n-(O)m
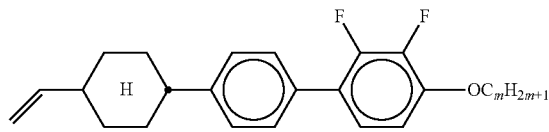   CPY-V-Om
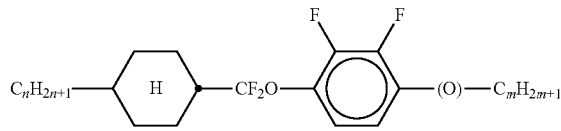   CQY-n-(O)m
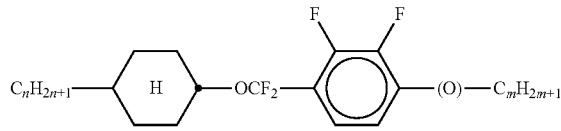   CQIY-n-(O)m
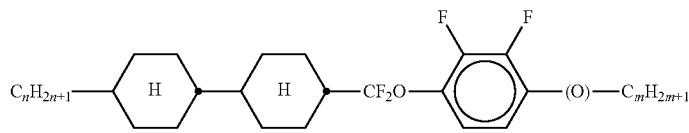   CCQY-n-(O)m
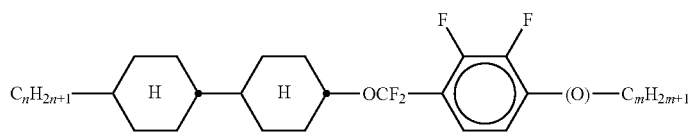   CCQIY-n-(O)m
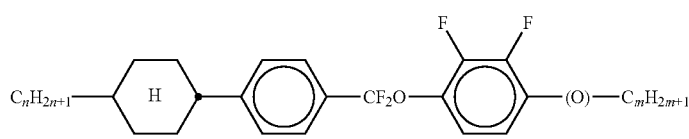   CPQY-n-(O)m
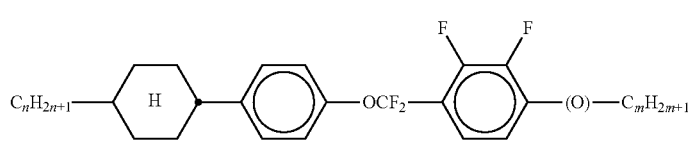   CPQIY-n-Om
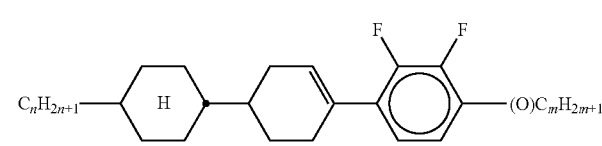   CLY-n-(O)m TABLE D-continued Illustrative structures CYLI-n-m LYLI-n-m LY-n-(O)m PGIGI-n-F PGP-n-m PYP-n-(O)m PYP-n-mV YPY-n-m YPY-n-mV BCH-nm TABLE D-continued Illustrative structures BCH-nmF CPYP-n-(O)m CPGP-n-m CPYC-n-m CYYC-n-m CCYY-n-m CPYG-n-(O)m CBC-nm CBC-nmF TABLE D-continued
Illustrative structures
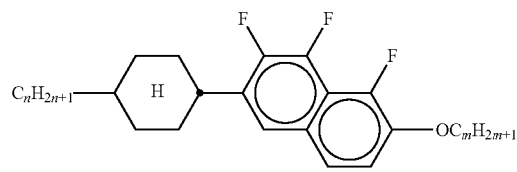 CNap-n-Om
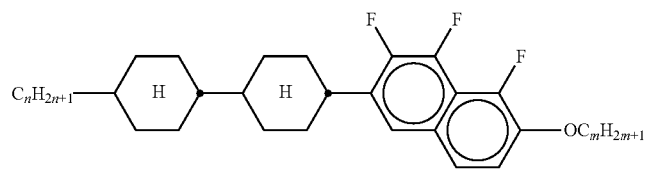 CCNap-n-Om
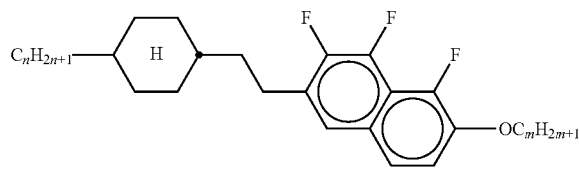 CENap-n-Om
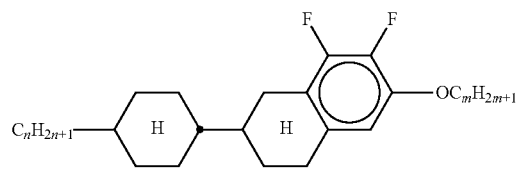 CTNap-n-Om
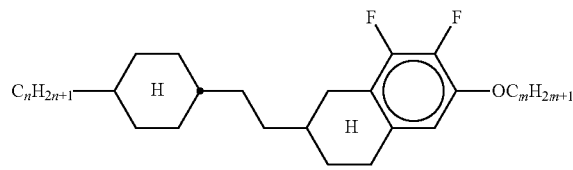 CETNap-n-Om
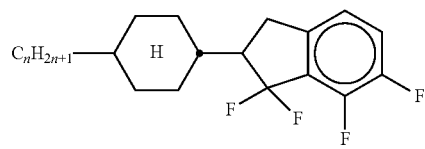 CK-n-F
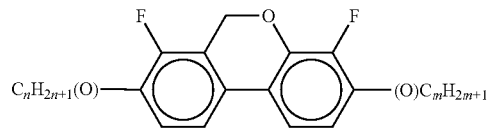 DFDBC-n(O)-(O)m
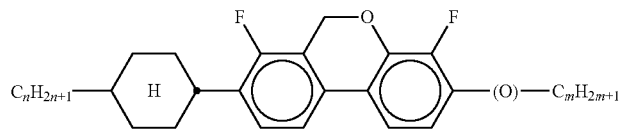 C-DFDBF-n-(O)m TABLE D-continued Illustrative structures

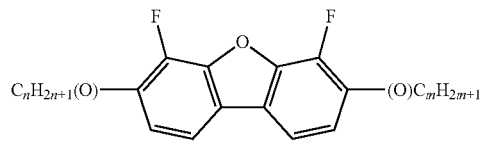  B-n(O)-(O)m

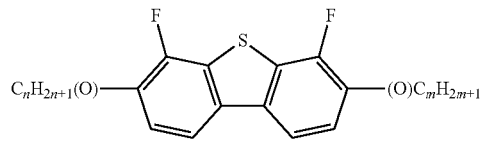  B(S)-n(O)-(O)m

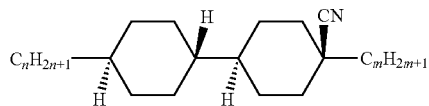  CC(CN)-n-m

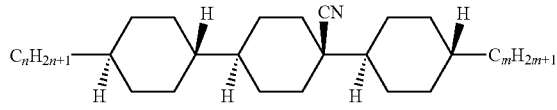  CC(CN)C-n-m

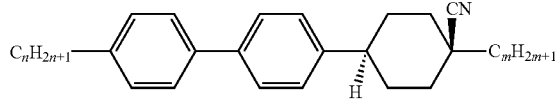  PPC(CN)-n-m

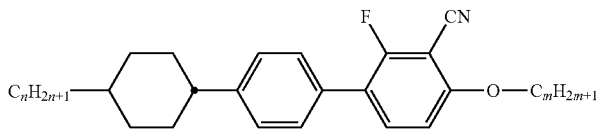  CPP(F,CN)-n-Om in which n, m and l preferably, independently of one another, denote 1 to 7.

The following table, Table E, shows illustrative compounds which can be used as additional stabilisers in the mesogenic media according to the present invention.

TABLE E

Table E shows possible stabilisers which can be added to the LC media according to the invention. (n here denotes an integer from 1 to 12, preferably 1, 2, 3, 4, 5, 6, 7 or 8, terminal methyl groups are not shown).

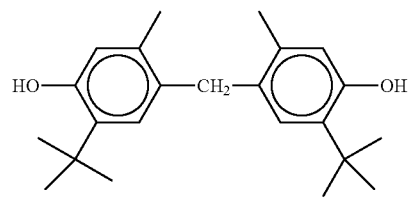

TABLE E-continued
Table E shows possible stabilisers which can be added to the LC media according to the invention. (n here denotes an integer from 1 to 12, preferably 1, 2, 3, 4, 5, 6, 7 or 8, terminal methyl groups are not shown).
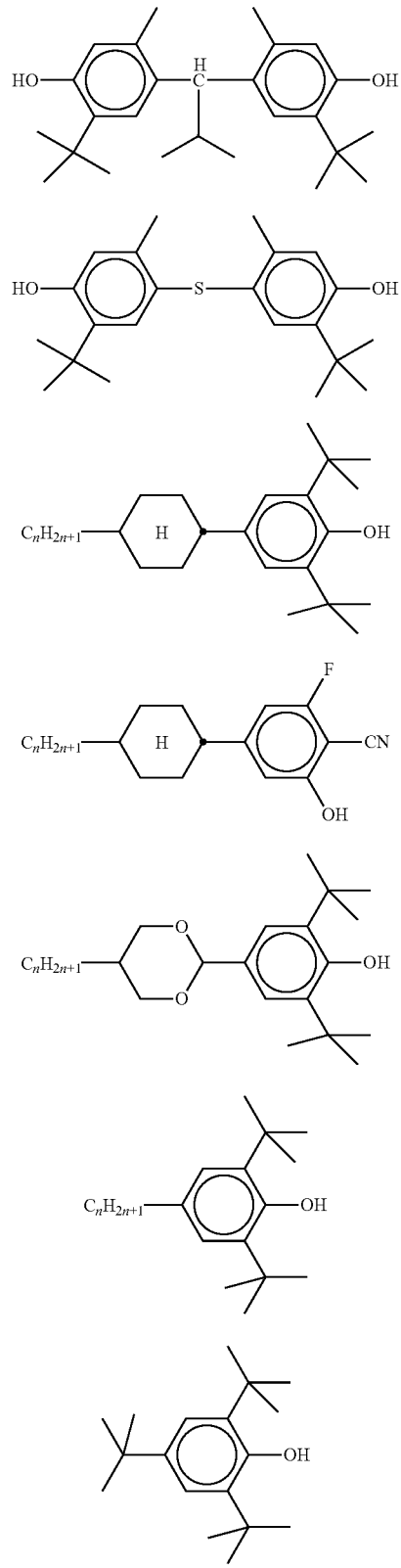

TABLE E-continued
Table E shows possible stabilisers which can be added to the LC media according to the invention. (n here denotes an integer from 1 to 12, preferably 1, 2, 3, 4, 5, 6, 7 or 8, terminal methyl groups are not shown).
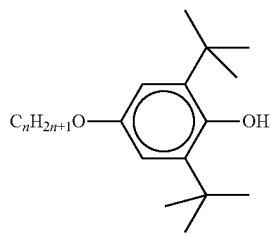
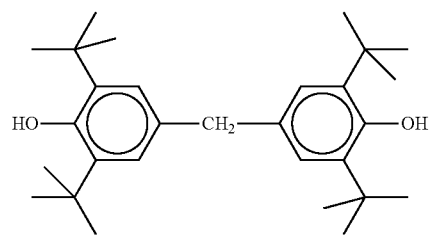
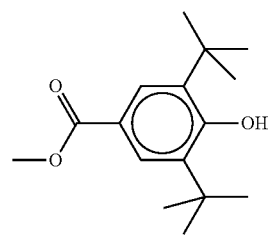
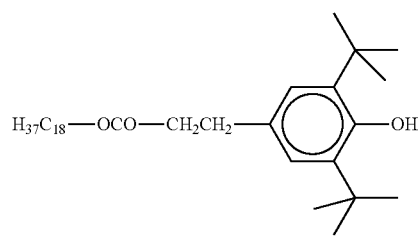
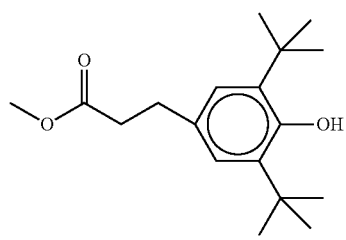
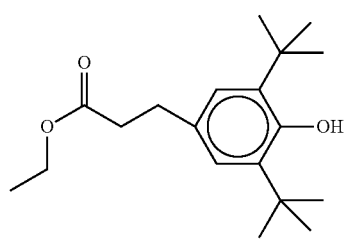

TABLE E-continued
Table E shows possible stabilisers which can be added to the LC media according to the invention. (n here denotes an integer from 1 to 12, preferably 1, 2, 3, 4, 5, 6, 7 or 8, terminal methyl groups are not shown).
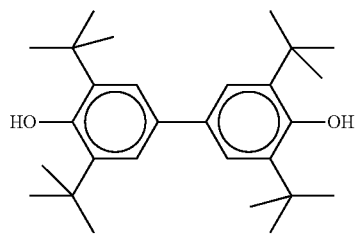
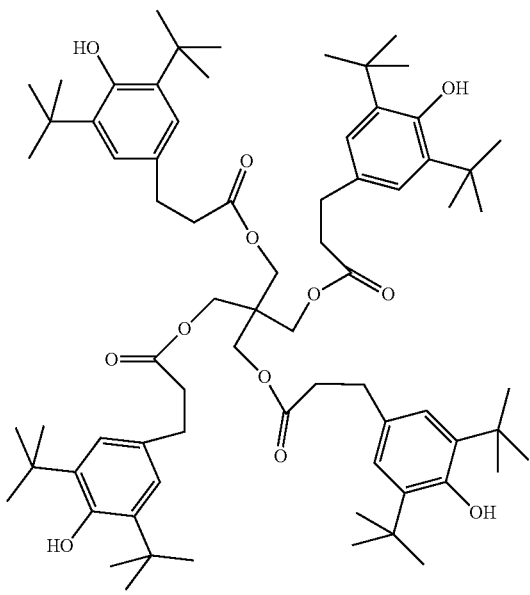 [SMILES: CC(C)(C)c1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]
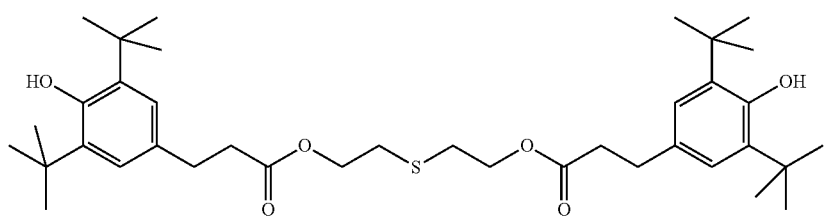 [SMILES: CC(C)(C)c1cc(CCC(=O)OCCSCCOC(=O)CCc2cc(C(C)(C)C)c(O)c(C(C)(C)C)c2)cc(C(C)(C)C)c1O]
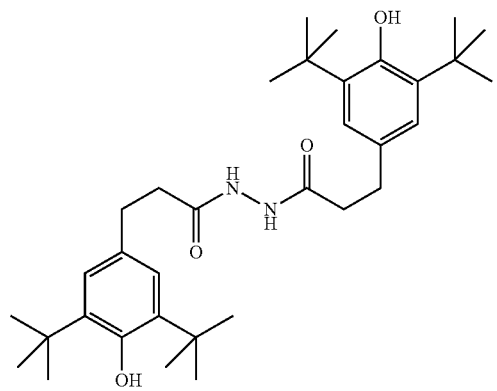 [SMILES: CC(C)(C)c1cc(CCC(=O)NNC(=O)CCc2cc(C(C)(C)C)c(O)c(C(C)(C)C)c2)cc(C(C)(C)C)c1O]

TABLE E-continued
Table E shows possible stabilisers which can be added to the LC media according to the invention. (n here denotes an integer from 1 to 12, preferably 1, 2, 3, 4, 5, 6, 7 or 8, terminal methyl groups are not shown).
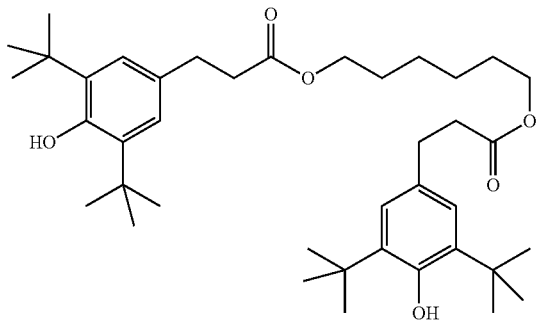 [SMILES: CC(C)(C)c1cc(CCC(=O)OCCCCCCOC(=O)CCc2cc(C(C)(C)C)c(O)c(C(C)(C)C)c2)cc(C(C)(C)C)c1O]
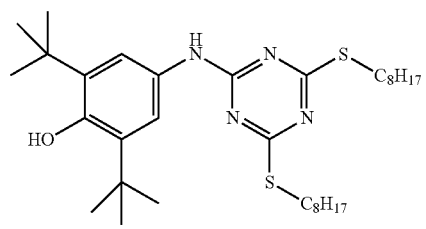
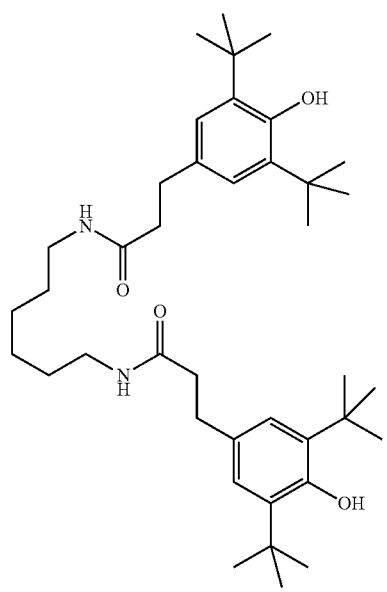 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]

TABLE E-continued
Table E shows possible stabilisers which can be added to the LC media according to the invention. (n here denotes an integer from 1 to 12, preferably 1, 2, 3, 4, 5, 6, 7 or 8, terminal methyl groups are not shown).
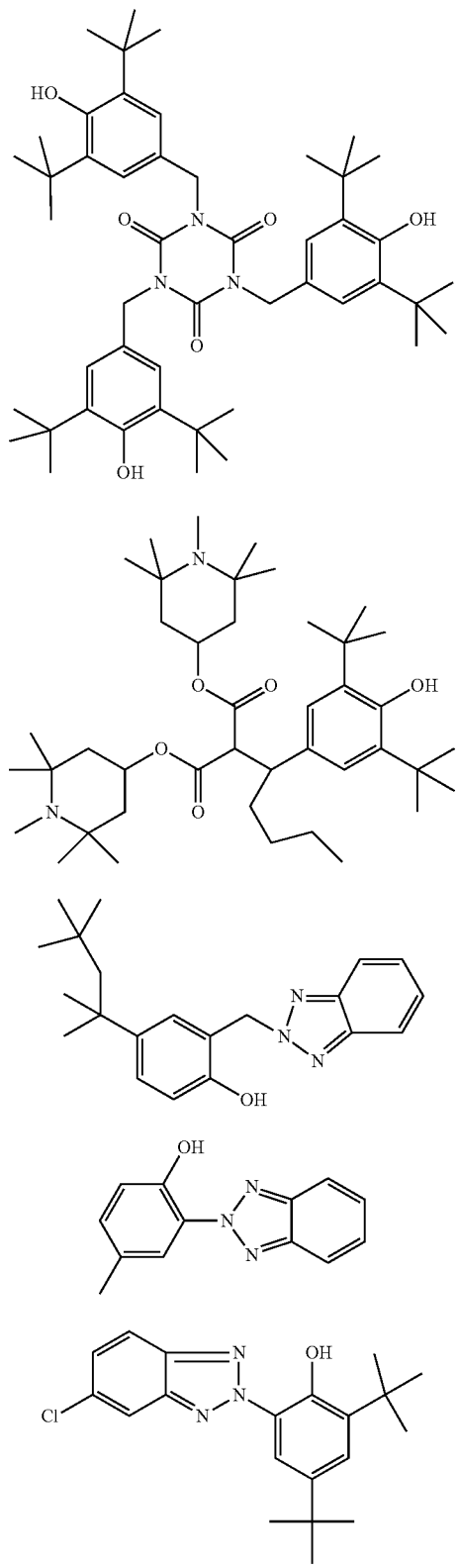

TABLE E-continued
Table E shows possible stabilisers which can be added to the LC media according to the invention. (n here denotes an integer from 1 to 12, preferably 1, 2, 3, 4, 5, 6, 7 or 8, terminal methyl groups are not shown).
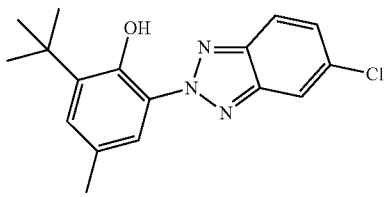 [SMILES: Cc1cc(-n2nc3ccc(Cl)cc3n2)c(O)c(C(C)(C)C)c1]
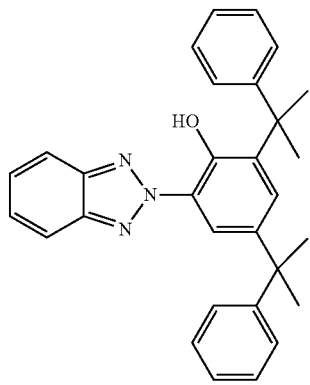 [SMILES: CC(C)(c1ccccc1)c1cc(-n2nc3ccccc3n2)c(O)c(C(C)(C)c2ccccc2)c1]
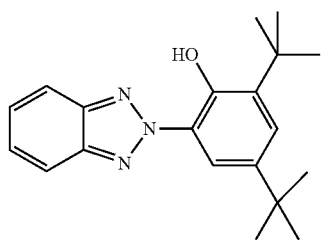 [SMILES: CC(C)(C)c1cc(-n2nc3ccccc3n2)c(O)c(C(C)(C)C)c1]
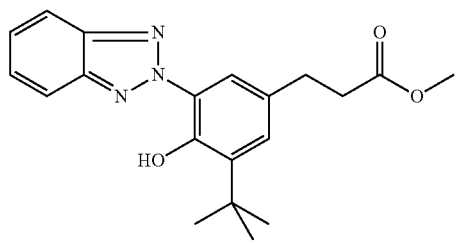 [SMILES: COC(=O)CCc1cc(-n2nc3ccccc3n2)c(O)c(C(C)(C)C)c1]
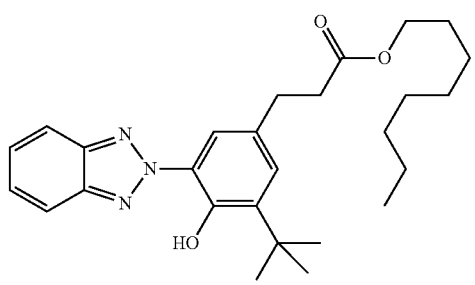 [SMILES: CCCCCCCCOC(=O)CCc1cc(-n2nc3ccccc3n2)c(O)c(C(C)(C)C)c1]

TABLE E-continued
Table E shows possible stabilisers which can be added to the LC media according to the invention. (n here denotes an integer from 1 to 12, preferably 1, 2, 3, 4, 5, 6, 7 or 8, terminal methyl groups are not shown).
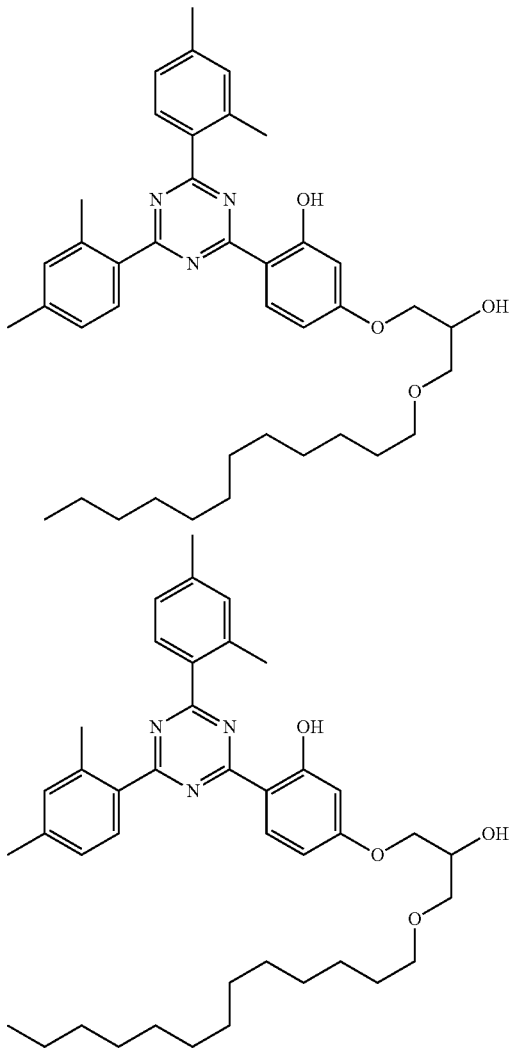
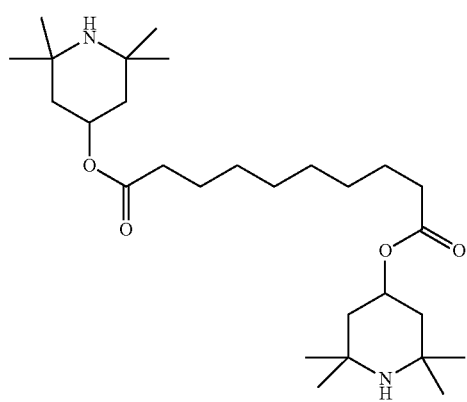

TABLE E-continued
Table E shows possible stabilisers which can be added to the LC media according to the invention. (n here denotes an integer from 1 to 12, preferably 1, 2, 3, 4, 5, 6, 7 or 8, terminal methyl groups are not shown).
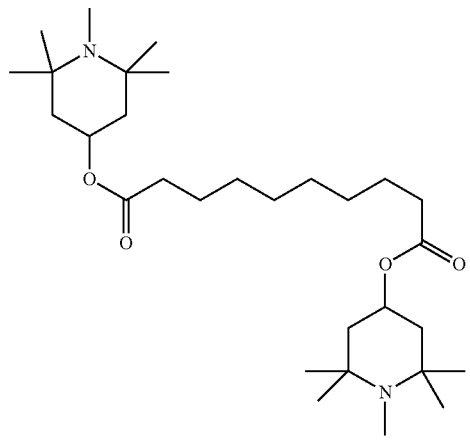
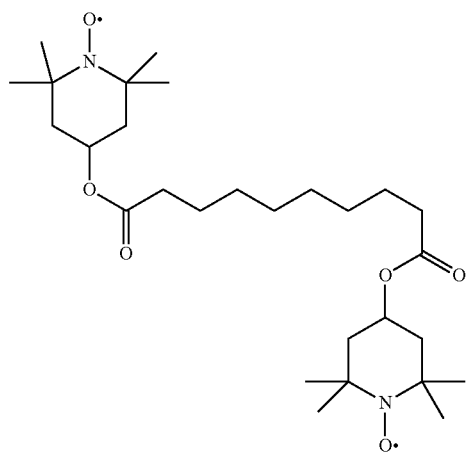
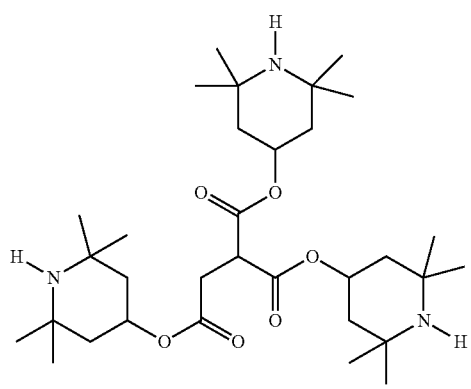

TABLE E-continued
Table E shows possible stabilisers which can be added to the LC media according to the invention. (n here denotes an integer from 1 to 12, preferably 1, 2, 3, 4, 5, 6, 7 or 8, terminal methyl groups are not shown).
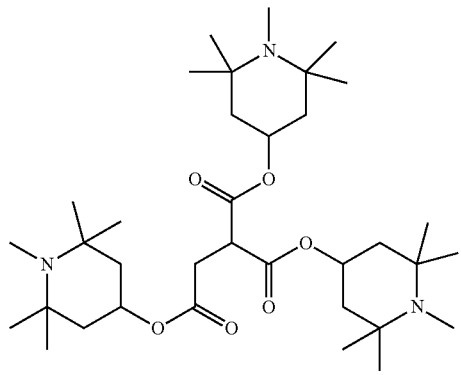
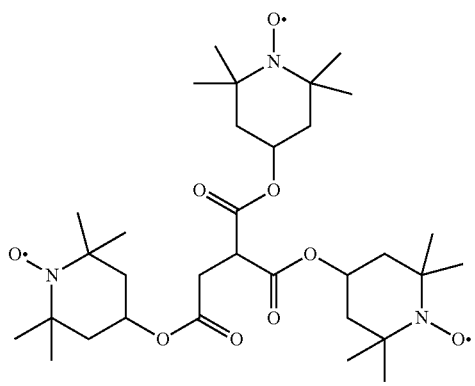
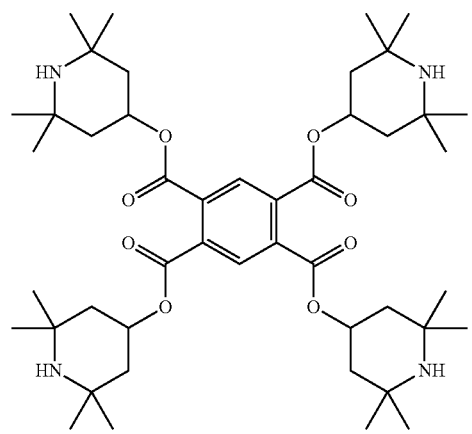

TABLE E-continued

Table E shows possible stabilisers which can be added to the LC media according to the invention. (n here denotes an integer from 1 to 12, preferably 1, 2, 3, 4, 5, 6, 7 or 8, terminal methyl groups are not shown).

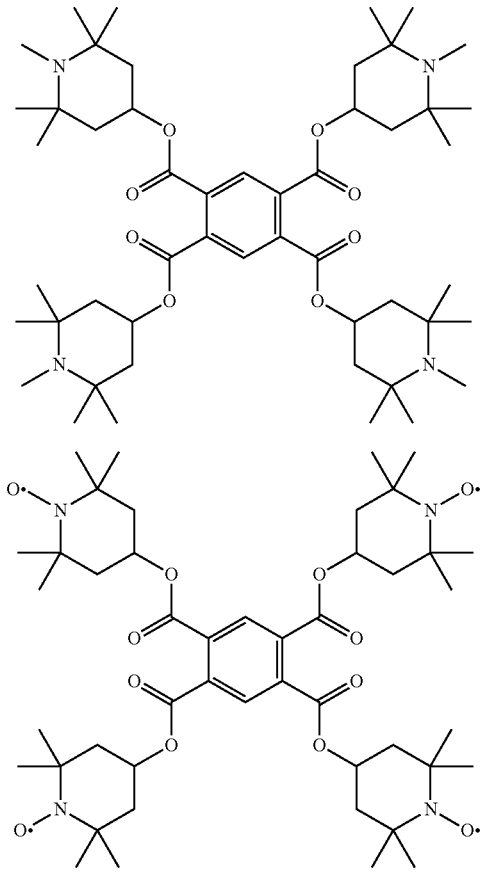

The LC media preferably comprise 0 to 10% by weight, in particular 1 ppm to 5% by weight, particularly preferably 1 ppm to 1% by weight, of stabilisers.

Table F below shows illustrative compounds which can preferably be used as chiral dopants in the mesogenic media according to the present invention.

TABLE F

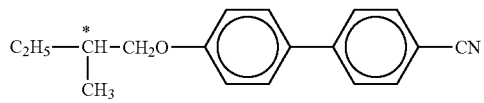

C 15

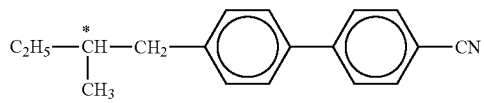

CB15

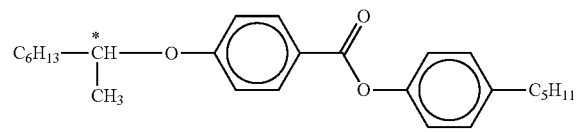

CM 21

TABLE F-continued
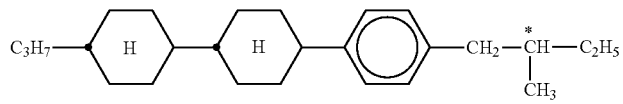 CM 44
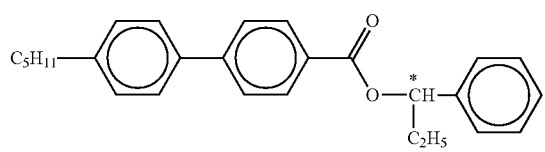 CM 45
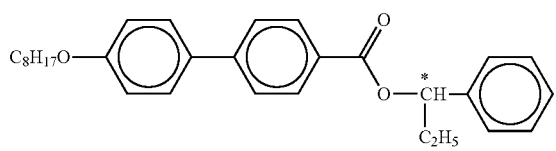 CM 47
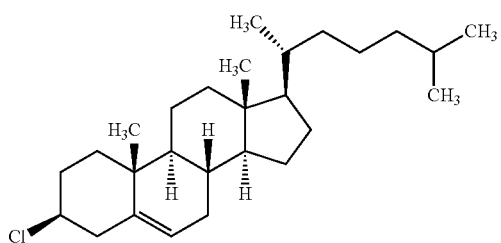 CC
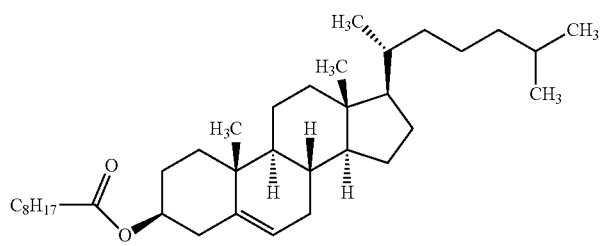 CN
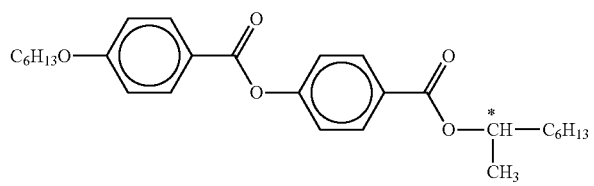 R/S-811
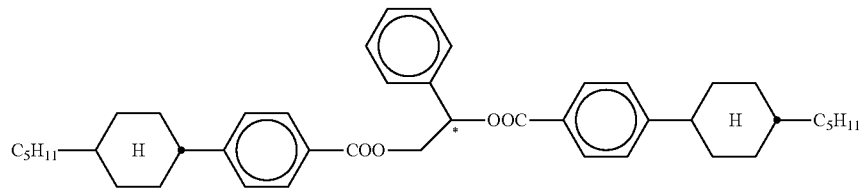 R/S-1011

TABLE F-continued

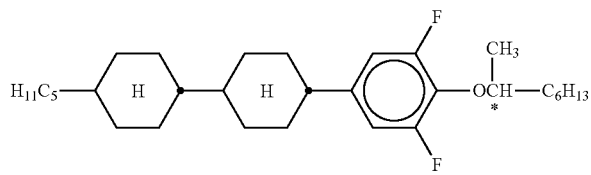
R/S-2011

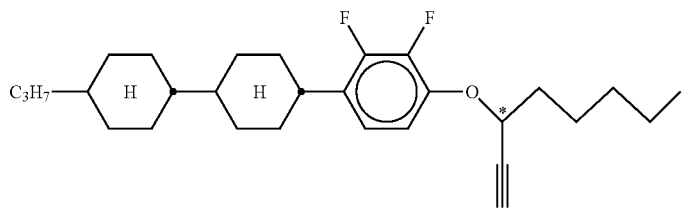
R/S-3011

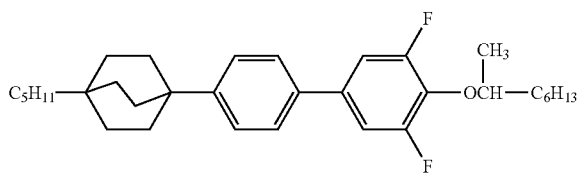
R/S-4011

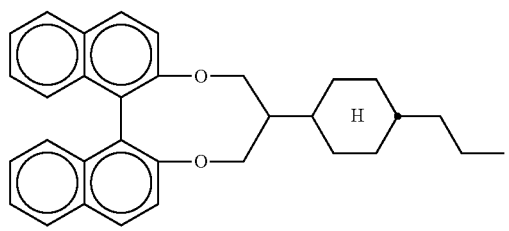
R/S-5011

In a preferred embodiment of the present invention, the mesogenic media comprise one or more compounds selected from the group of the compounds from Table F.

The mesogenic media according to the present application preferably comprise two or more, preferably four or more, compounds selected from the group consisting of the compounds from the above tables.

The liquid-crystal media according to the present invention preferably comprise seven or more, preferably eight or more, individual compounds, preferably of three or more, particularly preferably of four or more, different formulae, selected from the group of the compounds from Table D. The proportions of these compounds and other components present in minor amounts are neglected when indicating the proportions of the liquid-crystalline compounds and the dichroic dyes.

It goes without saying to the person skilled in the art that the LC media according to the invention may also comprise compounds in which, for example, H, N, O, Cl or F have been replaced by the corresponding isotopes.

All percent data and amount ratios are percent by weight.

EXAMPLES

The present invention is described in detail by the following, non-restrictive example.

All physical properties are determined in accordance with "Merck Liquid Crystals, Physical Properties of Liquid Crystals", Status Nov. 1997, Merck KGaA, Germany, and apply for a temperature of 20° C. The value of Δn is determined at 589 nm, and the value of □□ is determined at 1 kHz, unless explicitly indicated otherwise in each case. $n_e$ and $n_o$ are in each case the refractive indices of the extraordinary and ordinary light beam under the conditions indicated above.

The degree of anisotropy R is determined from the value for the extinction coefficient E(p) (extinction coefficient of the mixture in the case of parallel alignment of the molecules to the polarisation direction of the light) and the value for the extinction coefficient of the mixture E(s) (extinction coefficient of the mixture in the case of perpendicular alignment of the molecules to the polarisation direction of the light), in each case at the wavelength of the maximum of the absorption band of the dye in question. If the dye has a plurality of absorption bands, the strongest absorption band is selected. The alignment of the molecules of the mixture is achieved by an alignment layer, as known to the person skilled in the art in the area of LC display technology. In order to eliminate influences by liquid-crystalline medium, other absorptions or reflections, each measurement is carried out against an identical mixture comprising no dye, and the value obtained is subtracted.

The measurement is carried out using linear-polarised light whose vibration direction is either parallel to the alignment direction (determination of E(p)) or perpendicular to the alignment direction (determination of E(s)). This can be achieved by a linear polariser, where the polariser is rotated with respect to the device in order to achieve the two different vibration directions. The measurement of E(p) and E(s) is thus carried out via the rotation of the vibration direction of the incident polarised light.

The degree of anisotropy R is calculated from the resultant values for E(s) and E(p) in accordance with the formula $$R = [E(p) - E(s)] / [E(p) + 2*E(s)],$$

as indicated, inter alia, in "Polarized Light in Optics and Spectroscopy", D. S. Kliger et al., Academic Press, 1990. A detailed description of the method for the determination of the degree of anisotropy of liquid-crystalline media comprising a dichroic dye is also given in B. Bahadur, Liquid Crystals—Applications and Uses, Vol. 3, 1992, World Scientific Publishing, Section 11.4.2.

Example 1

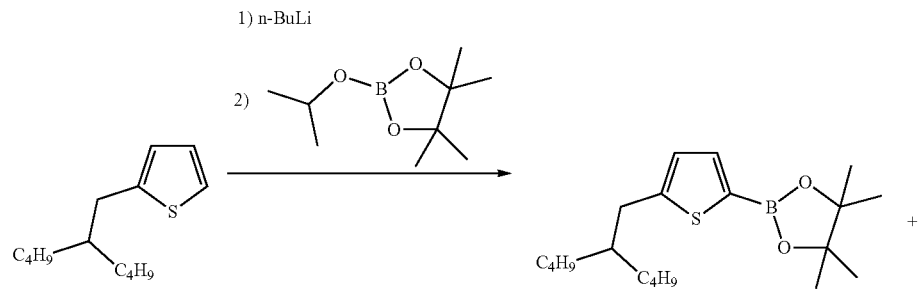

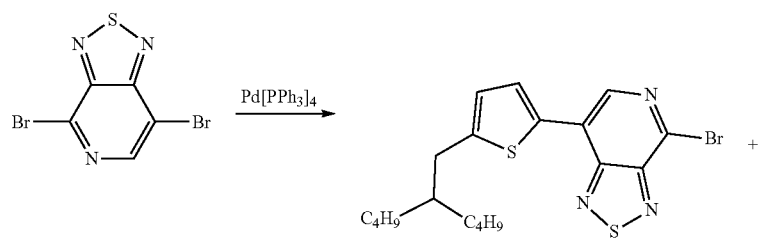

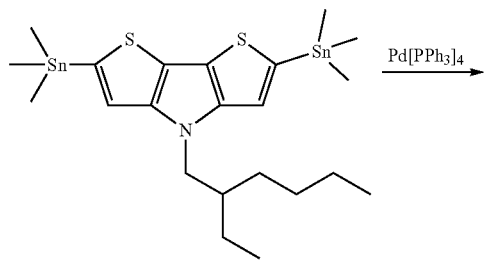

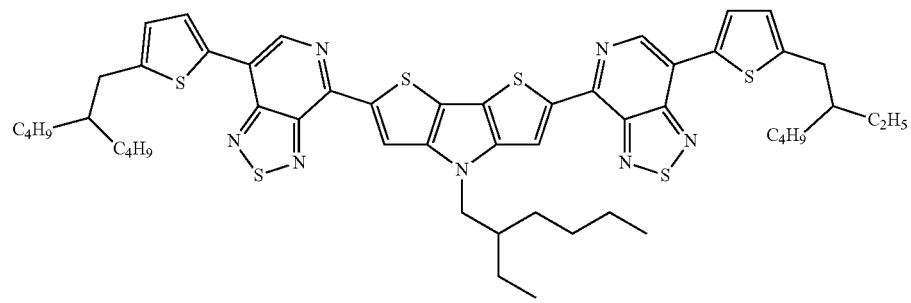

Example 2
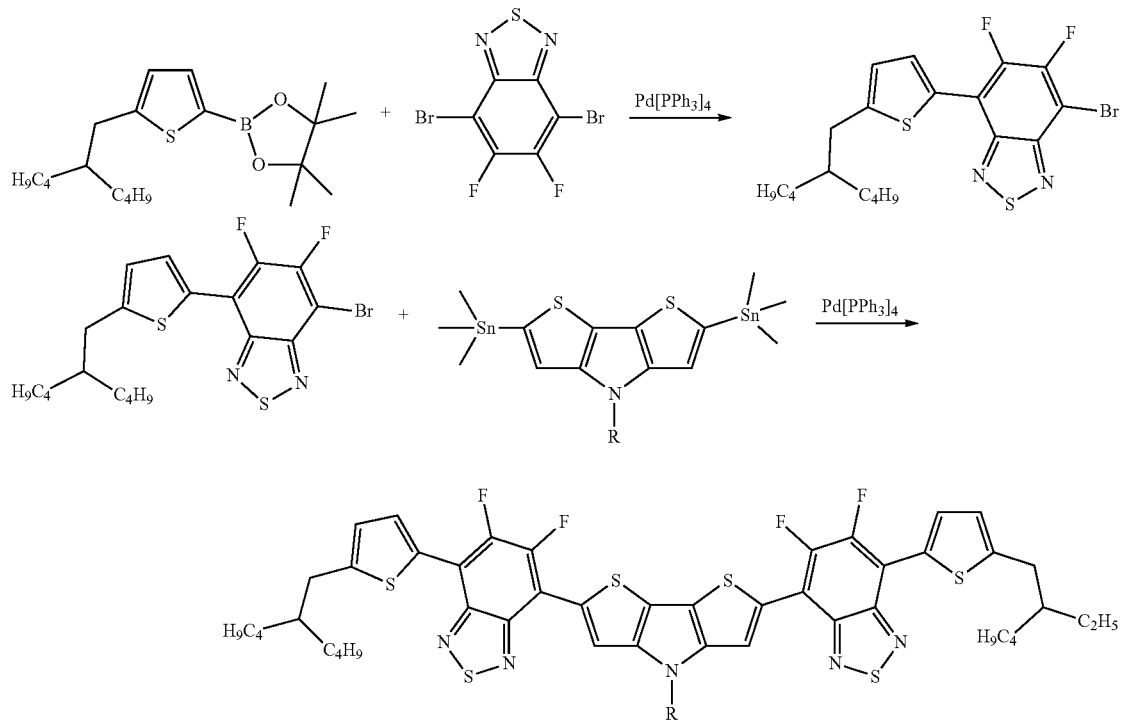
R=2-ethylhexyl
Example 3
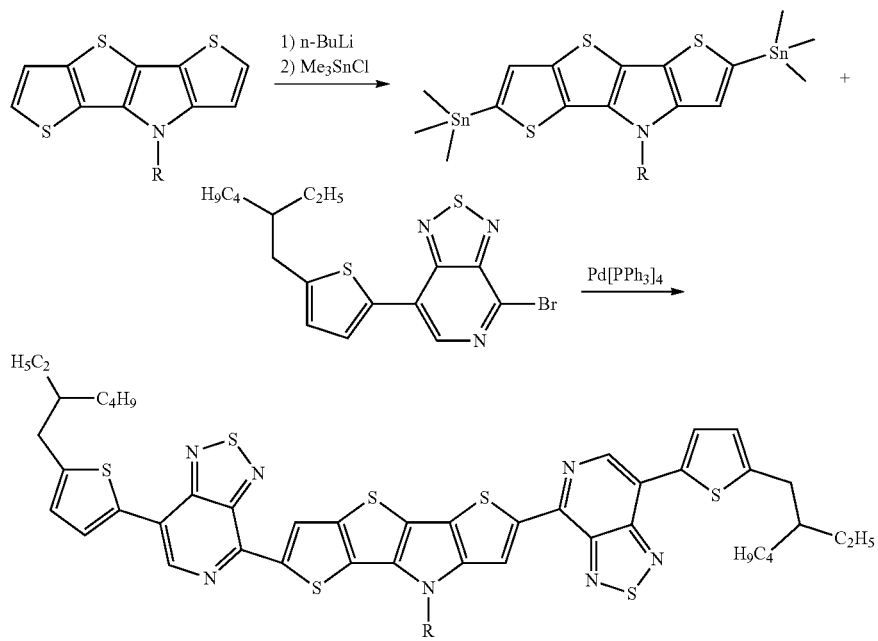
R=2-ethylhexyl
The starting material is available according to C. Wetzel et al., Angew. Chem. Int. Ed. 2015, 54, 12334-12338.

173 174
Example 4
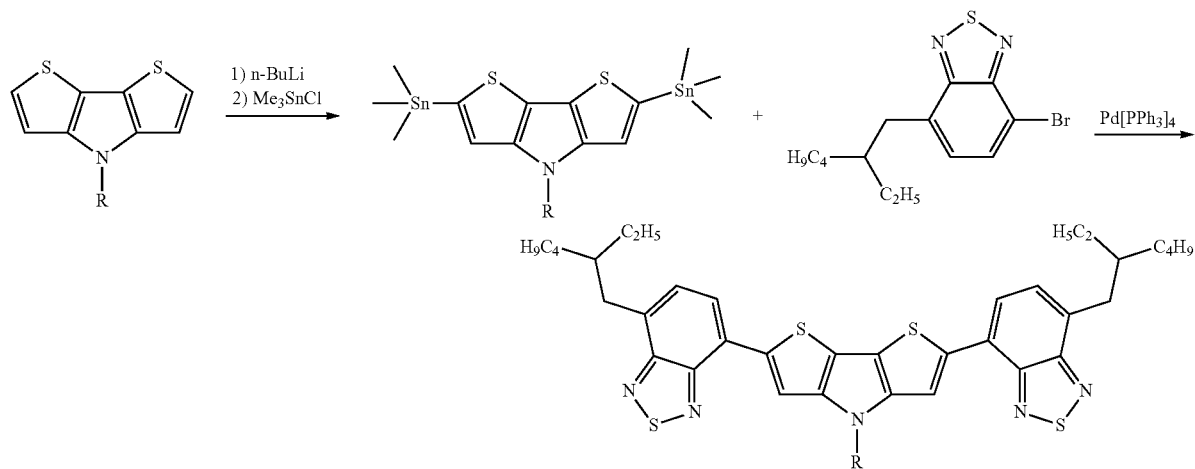
R=2-ethylhexyl
Example 5
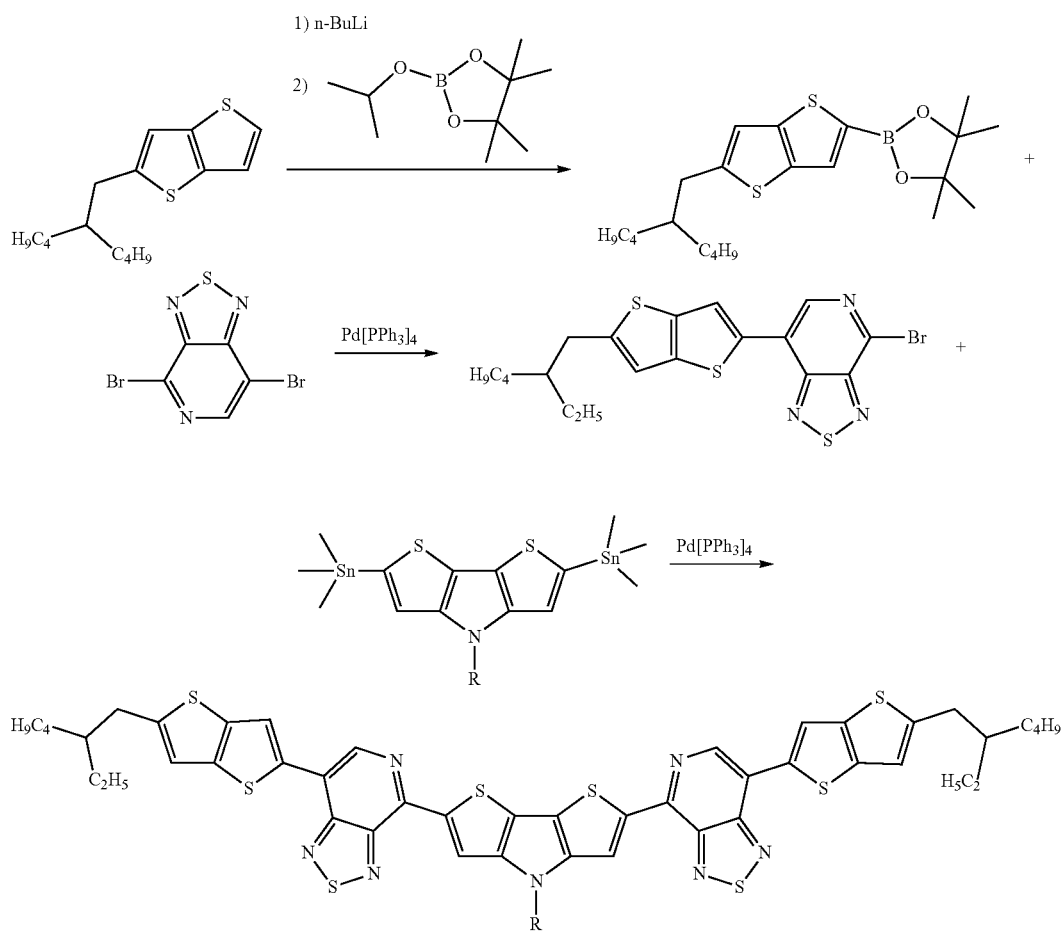
R=2-ethylhexyl Example 6
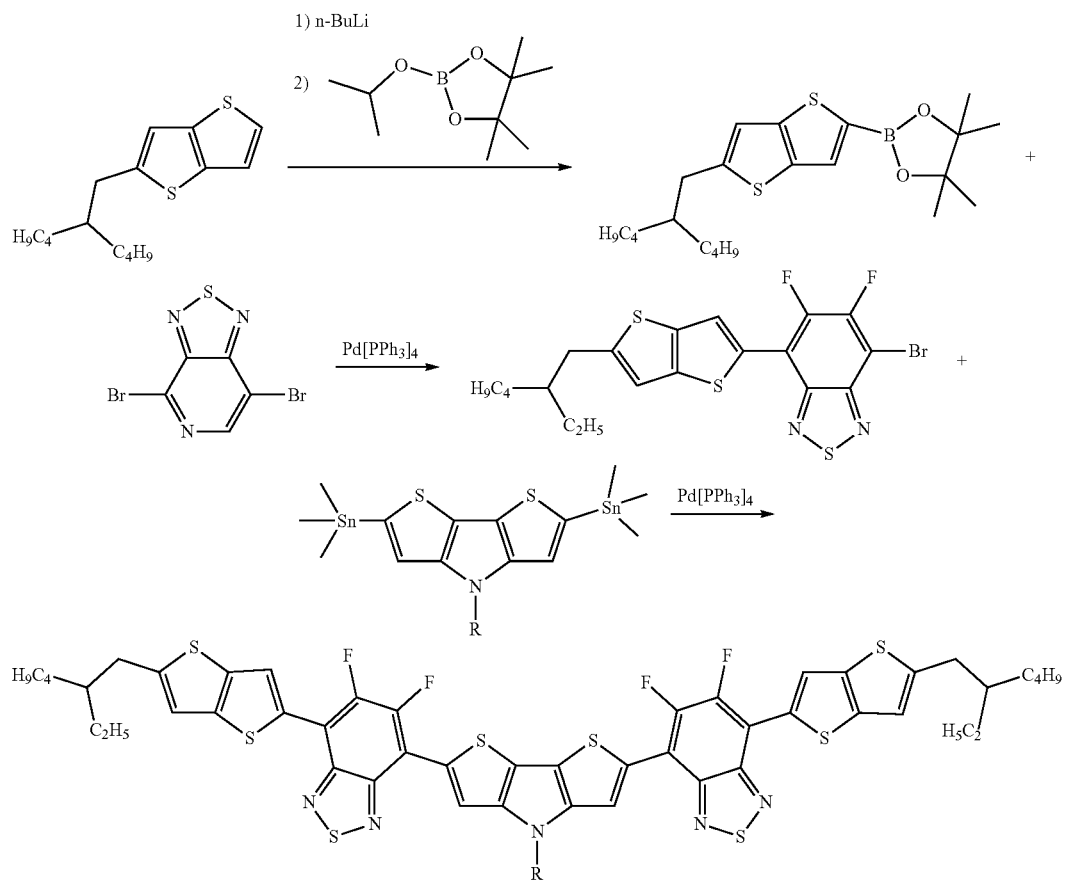
R=2-ethylhexyl
Example 7
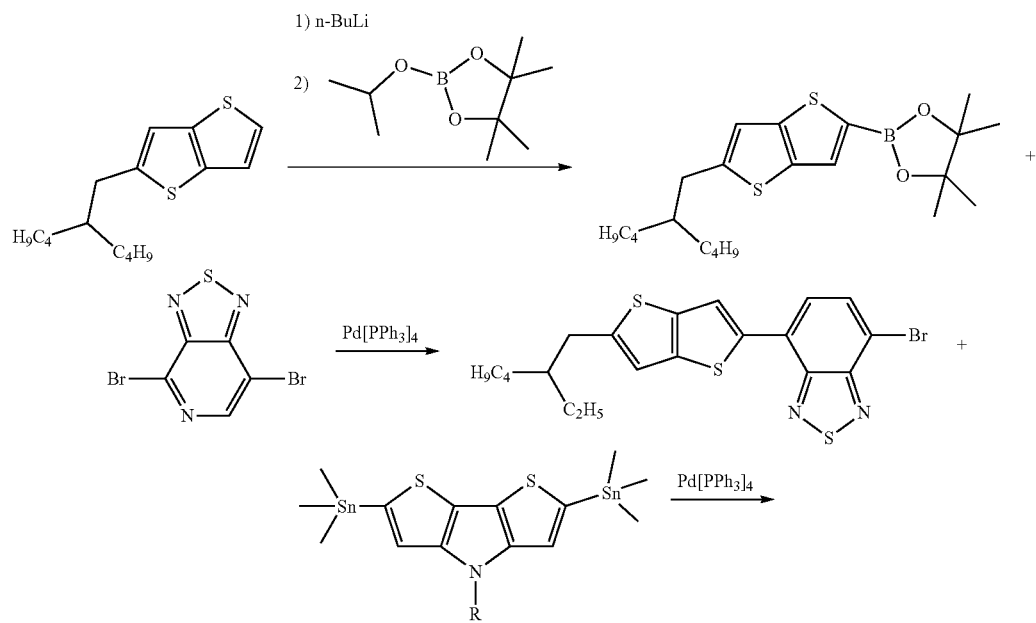

177 178
-continued
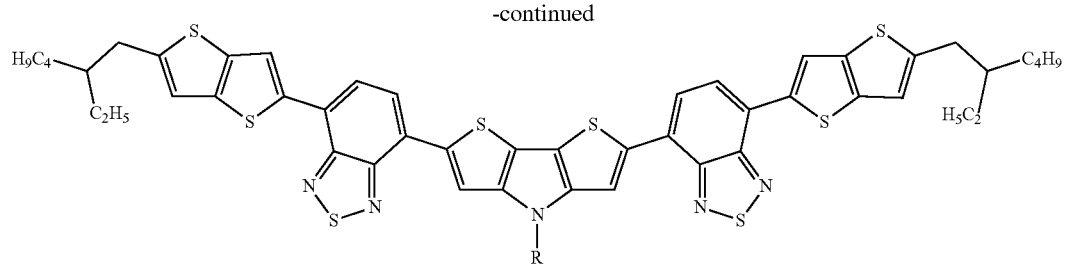
R=2-ethylhexyl
Example 8
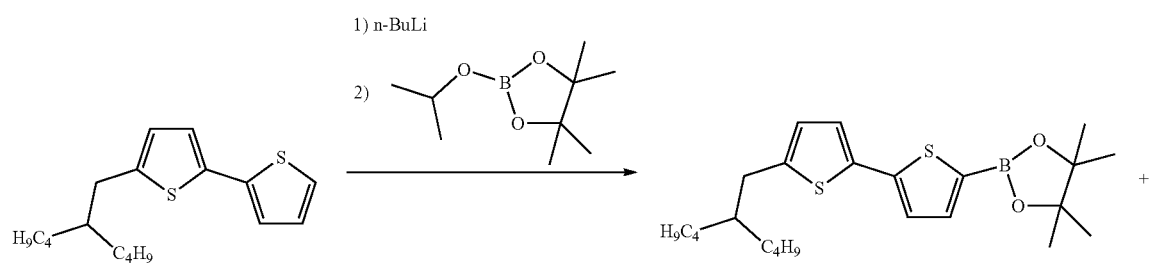
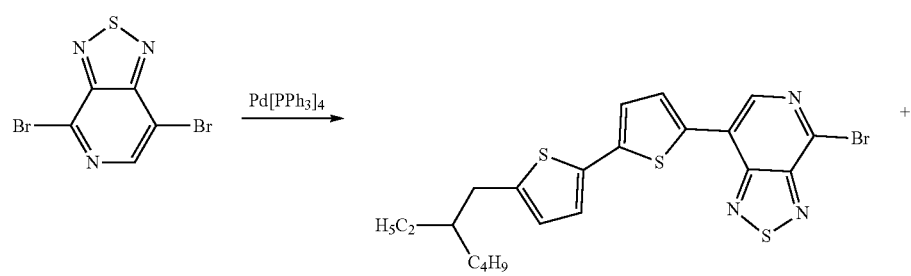
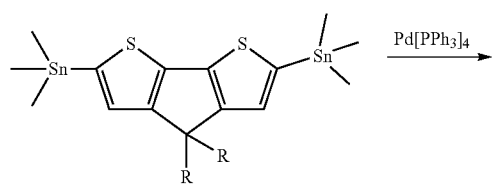
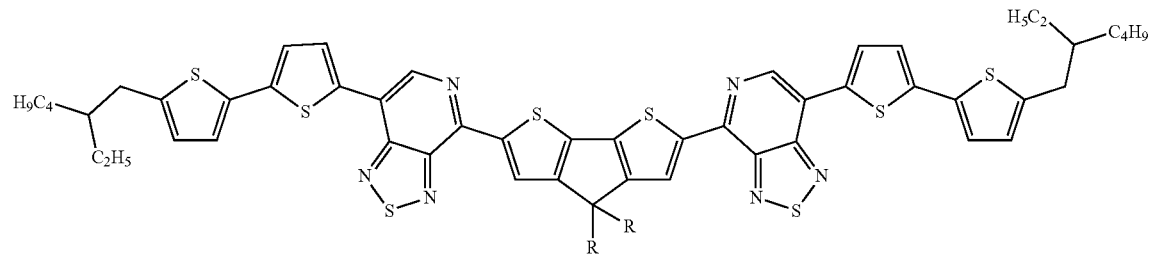
R=2-ethylhexyl Example 9
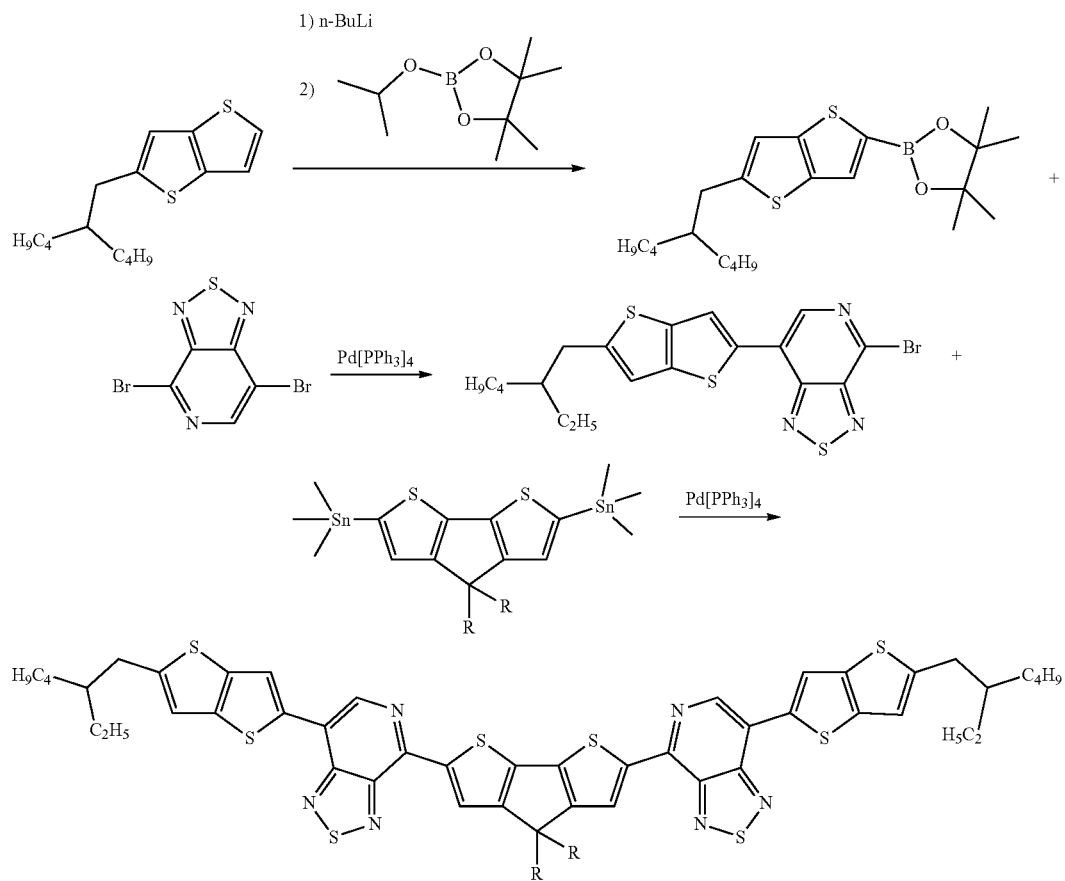
R=2-ethylhexyl
Example 10
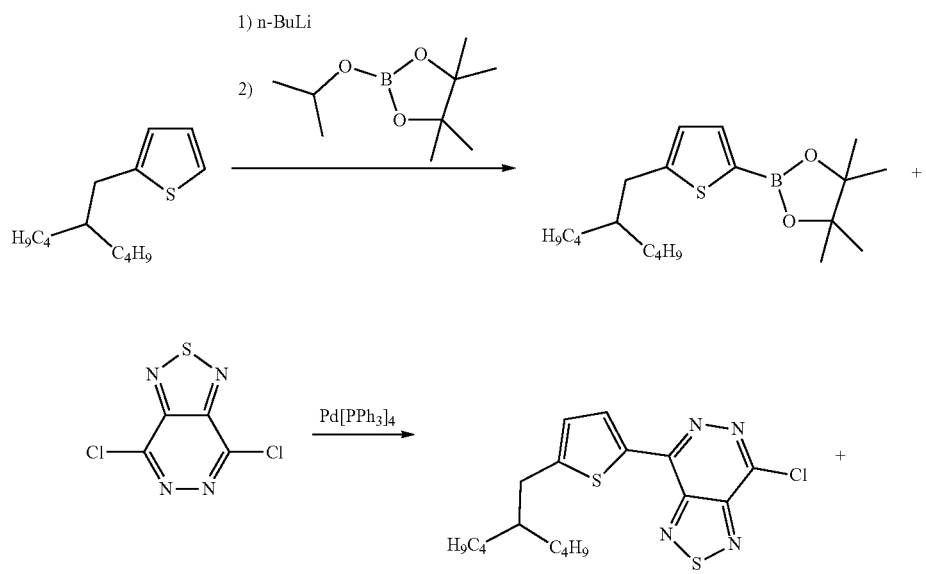

-continued
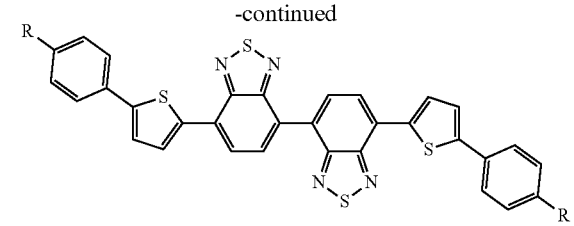
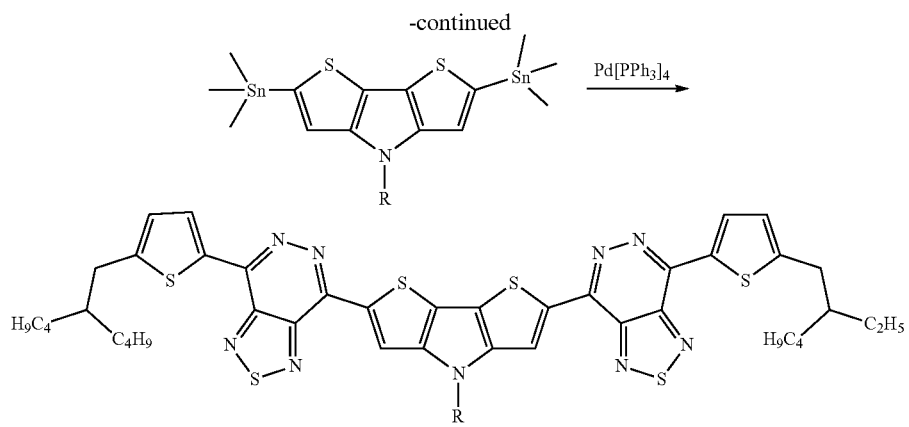
R=2-ethylhexyl
Example 11
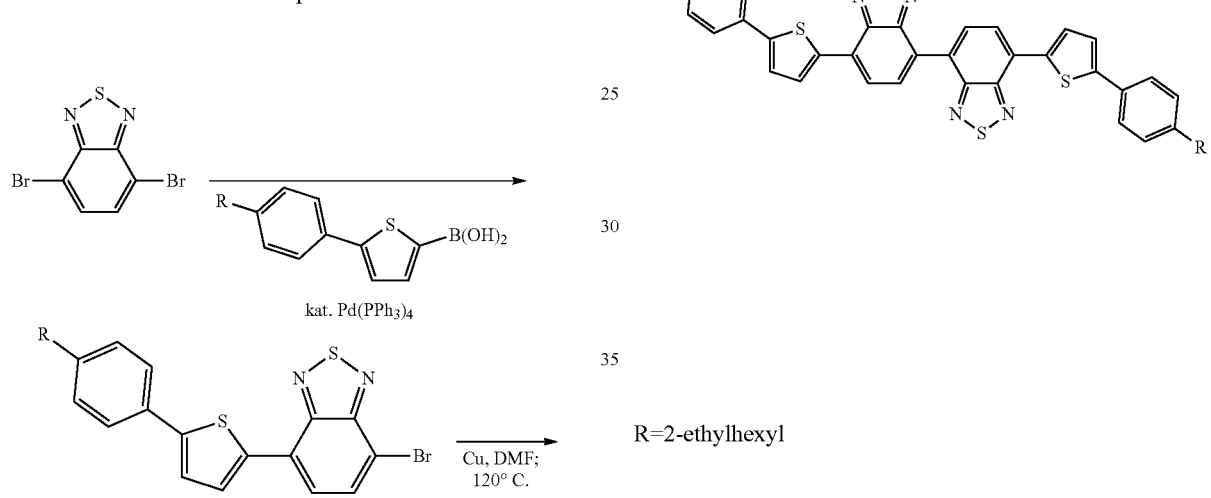
-continued
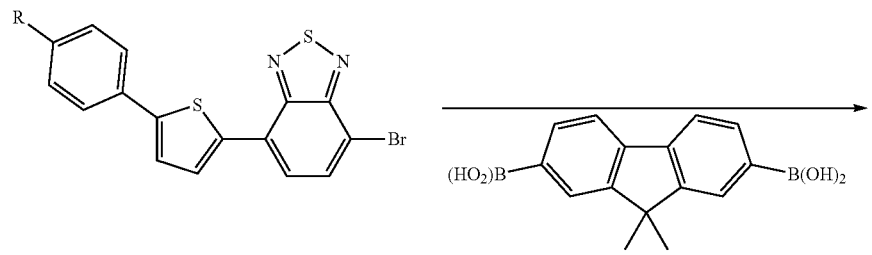
R=2-ethylhexyl
Example 12
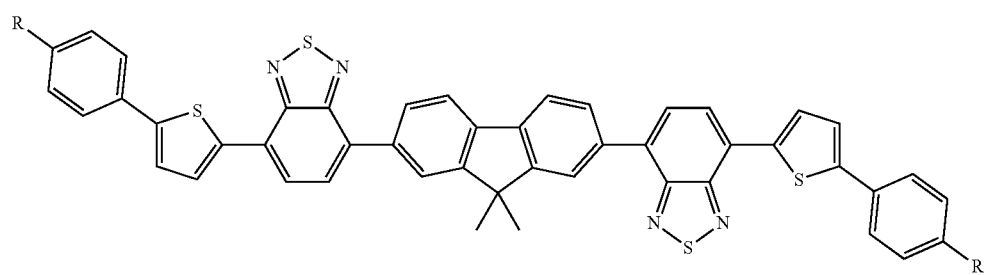
R=2-ethylhexyl

Example 13

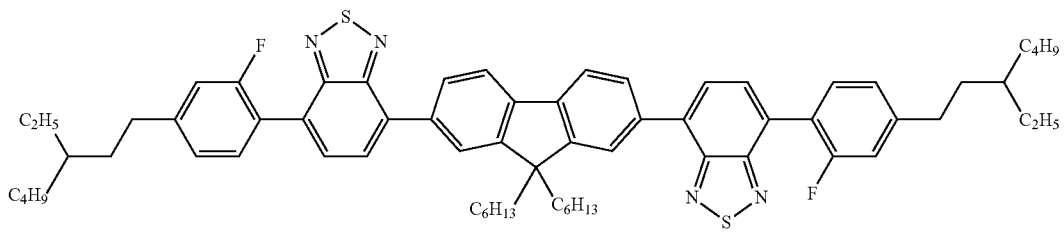

Step 1:

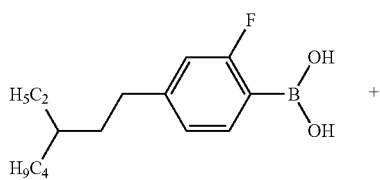

60.05 mmol) and bis(triphenylphosphine)palladium(II) chloride (15.2% of Pd) (562 mg, 0.80 mmol), the reaction mixture is stirred overnight at 70° C. Water and MTBE are added to the cooled reaction mixture. The combined organic phases are dried over sodium sulfate and filtered, and the solvent is removed. After purification by column chromatography (silica gel; chlorobutane), a yellow oil (12.1 g, 0.03 mol, GC: 95.9%) is isolated in a yield of 74%.

El-MS: m/z: 390.5.

The boronic acid is synthesised by procedures known from the literature. Bromochlorobenzothiadiazole is commercially available.

Step 2:

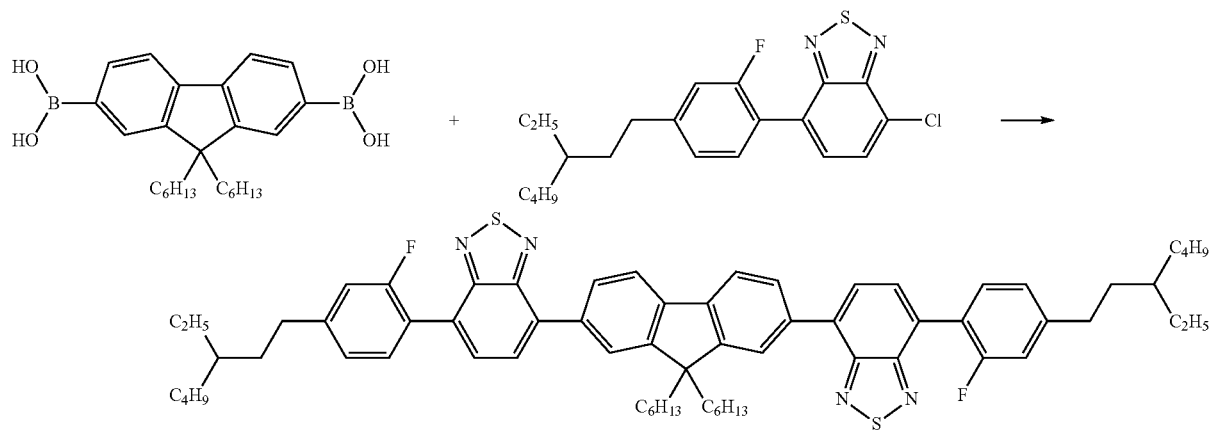

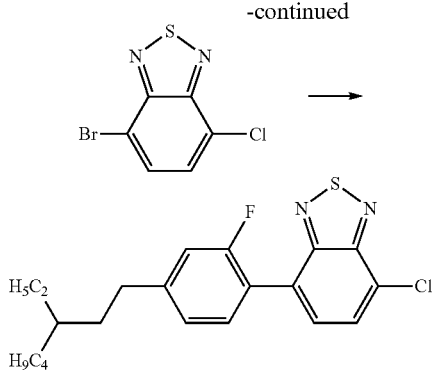

4-Bromo-7-chlorobenzo-1,2,5-thiadiazole (10.10 g, 40.03 mmol) and [4-(3-ethylheptyl)-2-fluorophenyl]boronic acid (10.91 g, 40.03 mol) are dissolved in THF (120 ml). After addition of water (24 ml), hydrazinium hydroxide (49 μl, 0.80 mmol, 80%), sodium metaborate tetrahydrate (8.28 g, 4-Chloro-7-[4-(3-ethylheptyl)-2-fluorophenyl]benzo-1,2,5-thiadiazole (4.70 g, 0.012 mol) and 2-[9,9-dihexyl-7-(4,4,5,5-tetramethyl-1,3,2-dioxaborolan-2-yl)fluoren-2-yl]-4,4,5,5-tetramethyl-1,3,2-dioxaborolane (3.38 g, 0.006 mol) are added to an aqueous $NaHCO_3$ solution (0.97 g in 25 ml $H_2O$). After addition of THF (55 ml) and bis(tri-t-butylphosphine)-palladium(O) (5.89 mg, 11.527 μmol), the reaction mixture is stirred overnight at 65° C. The organic phase is separated off and washed with water (2×200 ml). The further purification is carried out by column chromatography (silica gel; heptane/toluene: 1/1) and recrystallisation from heptane/chlorobutane. A slightly yellowish solid (1.70 g, 1.63 mmol, HPLC: 99.5%) is isolated in a yield of 28%.

$^1$H-NMR ($CDCl_3$, 500 MHz): δ=8.09 (dd, J=7.8, 1.6 Hz, 2H), 8.03 (d, J=1.5 Hz, 2H), 7.97 (d, J=7.9 Hz, 2H), 7.91 (d, J=7.3 Hz, 2H), 7.85 (dd, J=7.3, 1.4 Hz, 2H), 7.72 (t, J=7.8 Hz, 2H), 7.20 (dd, J=7.8, 1.6 Hz, 2H), 7.15 (dd, J=11.3, 1.6 Hz, 2H), 2.77-2.59 (m, 4H), 2.19-2.11 (m, 4H), 1.67-1.71

(m, 4H), 1.47-1.29 (m, 18H), 1.13-1.21 (m, 12H), 0.92-0.98 (m, 16H), 0.81 ppm (t, J=6.8 Hz, 6H). DSC: TG 10 C 120 I.

Example 14

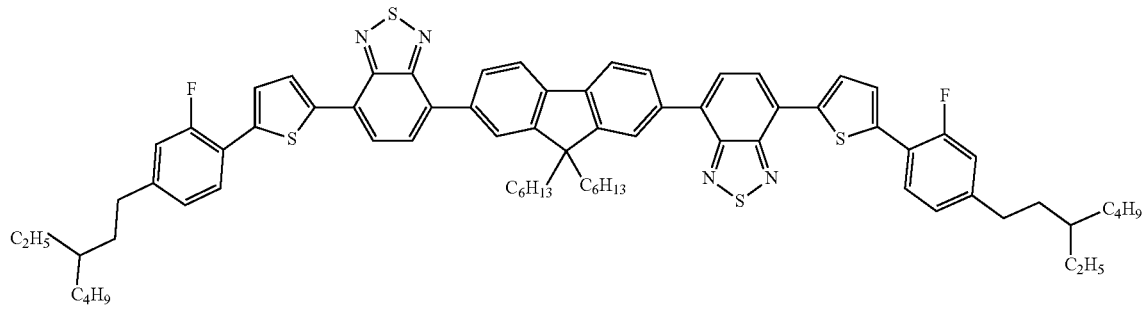

Step 1:

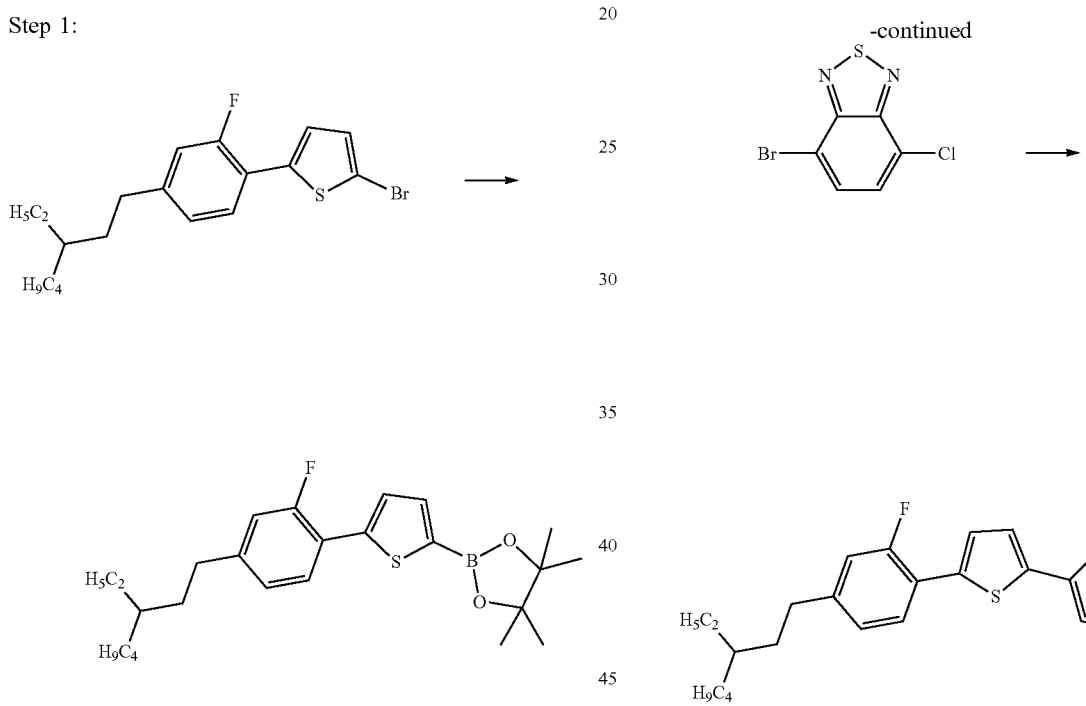

2-Bromo-5-[4-(3-ethylheptyl)-2-fluorophenyl]thiophene (12.00 g, 31.18 mmol) and bis(pinacolato)diboron (10.50 g, 40.52 mmol) are dissolved in 1,4-dioxane (105 ml). After addition of PdCl2-dppf (686 mg, 0.94 mmol) and potassium acetate (9.20 g; 93.73 mmol), the reaction mixture is stirred overnight at 100° C. Water and MTBE are added to the cooled reaction mixture, and the aqueous phase is extracted a number of times with MTBE. After purification by column chromatography (silica gel, heptane/ethyl acetate: 1/1), a brown oil (9.4 g, GC: 82%) is isolated.

Step 2:

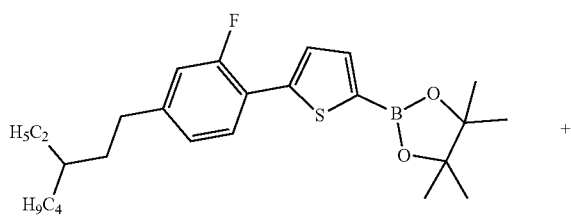

+

4-Bromo-7-chlorobenzo-1,2,5-thiadiazole (6.00 g, 23.78 mmol), 2-{5-[4-(3-ethylheptyl)-2-fluorophenyl]thien-2-yl}-4,4,5,5-tetramethyl-1,3,2-dioxaborolane (12.01 g, 23.78 mmol), bis(triphenylphosphine)palladium(II) chloride (15.2% of Pd) (334 mg, 0.48 mmol), hydrazinium hydroxide (49 µl, 0.48 mmol) and sodium metaborate tetrahydrate (4.92 g, 35.67 mmol) are dissolved in a solvent mixture of water (14 ml) and THF (70 ml) and stirred overnight at 70° C. Water and MTB are added to the cooled reaction mixture. The combined organic phases are dried over sodium sulfate and filtered, and the solvent is removed. After purification by column chromatography, an orange-red solid (9.40 g, 0.02 mol, HPLC: 99.4%) is isolated in a yield of 83%.

Step 3:

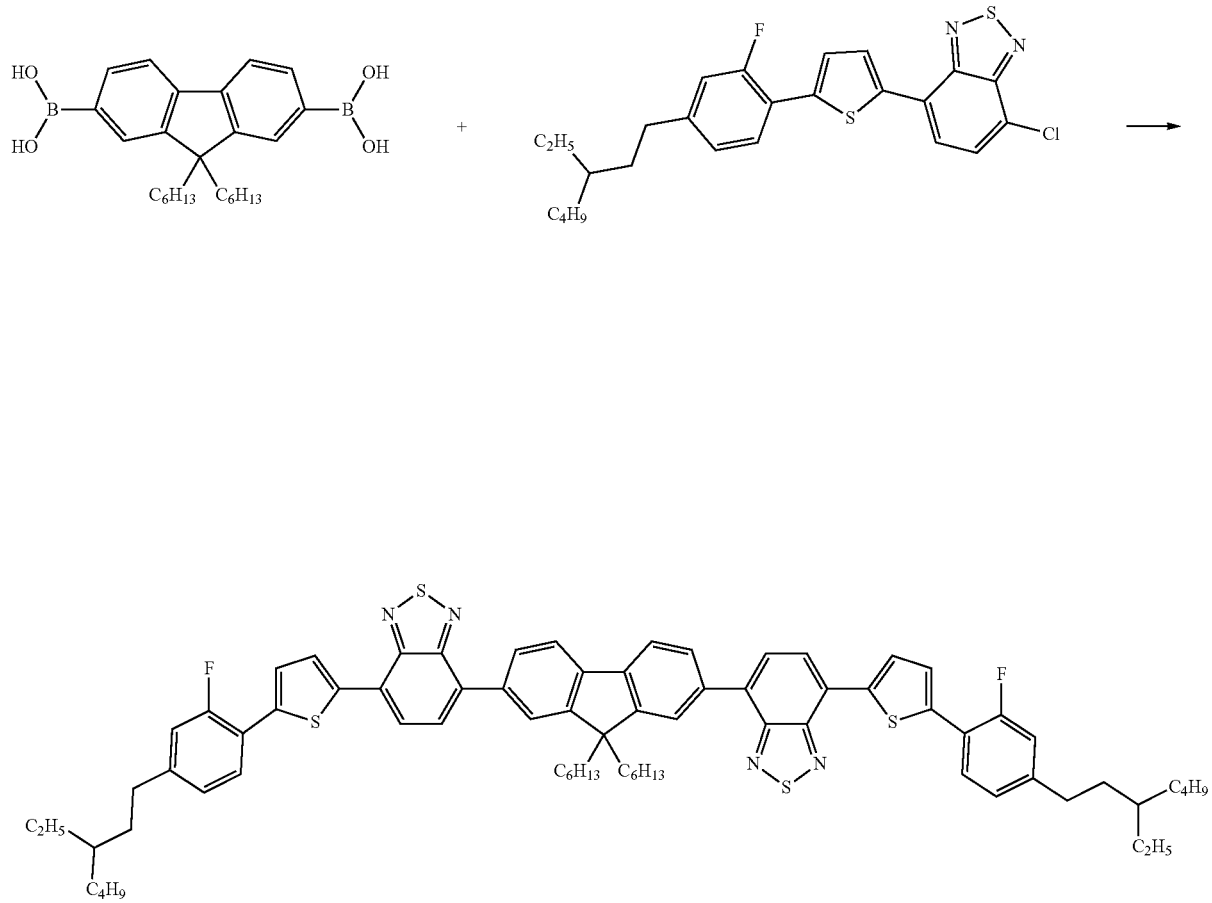

4-Chloro-7-{5-[4-(3-ethylheptyl)-2-fluorophenyl]thien-2-yl}benzo-1,2,5-thiadiazole (1.00 g, 2.10 mmol), 2-[9,9-dihexyl-7-(4,4,5,5-tetramethyl-1,3,2-dioxaborolan-2-yl)fluoren-2-yl]-4,4,5,5-tetramethyl-1,3,2-dioxaborolane (0.59 g, 1.01 mmol), THF (25 ml) and bis(tricyclohexylphosphine)-Pd(II) chloride (31 mg, 0.04 mmol) are added to a solution of sodium tetraborate (0.87 g, 6.31 mmol) in water (2 ml), and the mixture is stirred for 7 h at 65° C. After addition of toluene, the organic phase is separated off, and the solvent is removed. The further purification is carried out by column chromatography (silica gel; chlorobutane). A red resin (0.64 g, 0.53 mmol, HPLC: 99.0%) is isolated in a yield of 24%.

$^1$H-NMR (CDCl$_3$, 700 MHz): δ=8.10 (d, J=3.7 Hz, 2H), 7.99-7.92 (m, 6H), 7.85 (d, J=7.8 Hz, 2H), 7.77 (d, J=7.3 Hz, 2H), 7.58 (t, J=8.0 Hz, 2H), 7.50 (d, J=3.7 Hz, 2H), 6.98-6.94 (m, 4H), 2.55 (dd, J=9.9, 6.4 Hz, 4H), 2.09-2.03 (m, 4H), 1.53 (dt, J=8.2, 5.5 Hz, 4H), 1.33-1.18 (m, 18H), 1.10-1.03 (m, 6H), 0.86-0.80 (m, 18H), 0.71 ppm (t, J=6.9 Hz, 6H). EI-MS: m/z: 1206.7.

DSC: TG −2 I.

UV-Vis (THF): 228, 251, 336, 473 nm.

Example 15

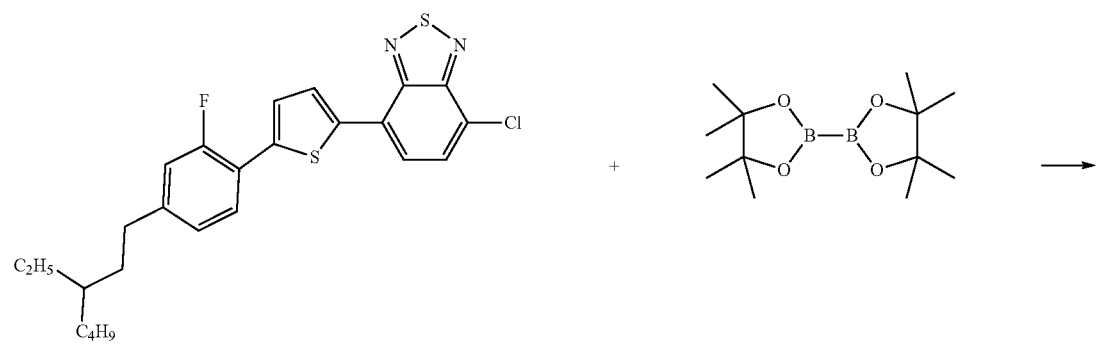

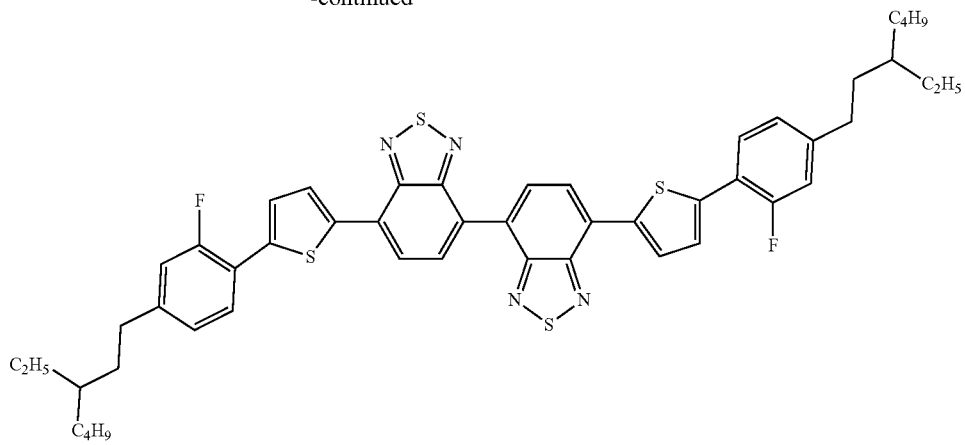

Potassium acetate (6.14, 62.57 mmol), bis(tricyclohexylphosphine)-palladium(II) chloride (205 mg, 0.28 mmol), 1,4-dioxane (60 ml), 4-chloro-7-{5-[4-(3-ethylheptyl)-2-fluorophenyl]thien-2-yl}benzo-1,2,5-thiadiazole (13.16 g, 27.82 mmol) and triethylamine (46 µl, 0.33 mmol) are added to bis(pinacolato)diboron (4.37 g, 16.69 mmol), and the mixture is stirred overnight at 100° C. After addition of toluene and water, the organic phase is separated off, and the solvent is removed. The further purification is carried out by column chromatography (silica gel; toluene) and by recrystallisation from heptane. A red solid (0.58 g, 0.68 mmol, HPLC: 98.5%) is isolated in a yield of 5%.

$^1$H-NMR (CDCl$_3$, 500 MHz): δ=8.47 (d, J=7.6 Hz, 2H), 8.19 (dd, J=3.9, 0.8 Hz, 2H), 8.08 (d, J=7.5 Hz, 2H), 7.65 (t, J=8.1 Hz, 2H), 7.57 (dd, J=4.0, 1.2 Hz, 2H), 7.07-6.99 (m, 4H), 2.67-2.58 (m, 4H), 1.65-1.56 (m, 4H), 1.43-1.19 (m, 18H), 0.93-0.88 ppm (m, 12H). DSC: C 213 I. UV-Vis (THF): 247, 329, 491 nm.

Example 16

Step 1:

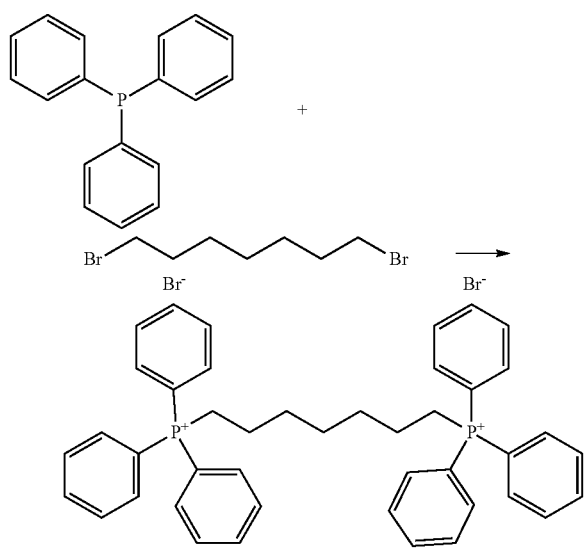

Triphenylphosphine (86.60 g, 368.28 mmol) and 1,7-dibromoheptane (47.50 g, 184.11 mmol) are stirred over-

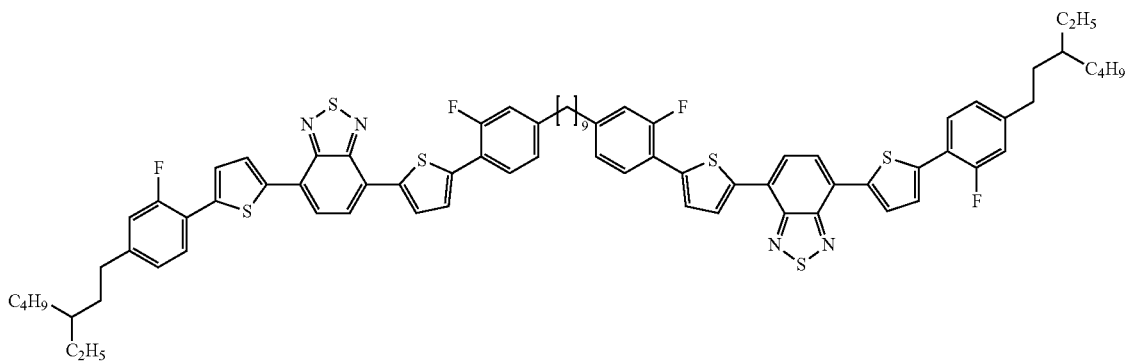

night at 100° C. in DMF (600 ml). After the solvent is distilled off, the residue is stirred under reflux in MTBE (800 ml) and THF (200 ml). The cooled product (130.20 g, 81% yield, HPLC: 89.5%) is filtered off and dried in vacuo.

Step 2:

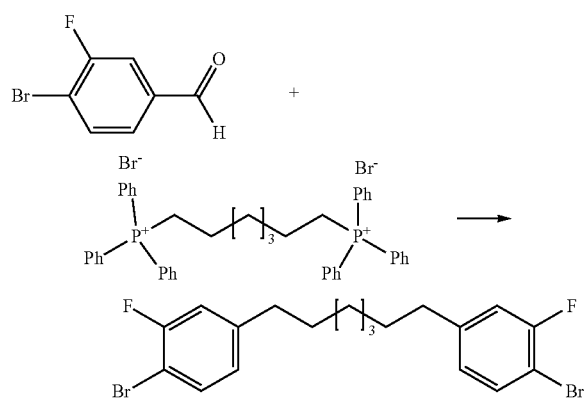

Potassium tert-butoxide (2.55 g, 22.27 mmol), dissolved in THF (20 ml), is added dropwise at 5° C. to a suspension of the phosphonium salt (9.00 g, 10.29 mmol) in THF (60 ml). After the mixture is stirred for 1 h at below 10° C., a solution of 4-bromo-3-fluorobenzaldehyde (4.10 g, 19.79 mmol) in THF (20 ml) is slowly added dropwise, and the mixture is stirred for 18 h at room temperature. A pH of 5 is established by addition of water and 2 N HCl. The phases are separated, and the aqueous phase is extracted with MTBE. The combined organic phases are washed with water, dried over sodium sulfate and filtered, and the solvent is removed. The residue is stirred in hot heptane and filtered, and the solvent is removed. After purification by column chromatography (silica gel, heptane/ethyl acetate: 95/5), a colourless oil (4.00 g, 0.01 mol, GC: 96%) was isolated as an E/Z isomer mixture in a yield of 79%.

Step 3:

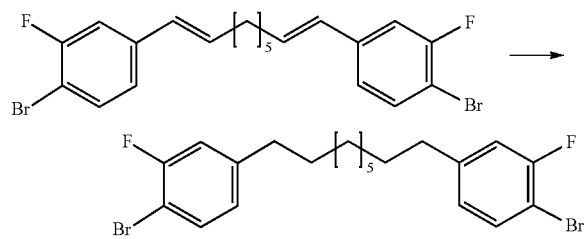

The alkene (43.80 g, 83.84 mmol), conc. hydrochloric acid (0.17 ml, 1.76 mmol) and 5% Pt/C (5.00 g) are stirred in heptane (400 ml) under a hydrogen pressure atmosphere for 30 min at room temperature. The solvent is removed, and the residue obtained is recrystallised from ethanol. The product (38.80 g, 0.08 mol, GC: 93%) is obtained as a colourless solid in a yield of 91%.

$^1$H-NMR (CDCl$_3$, 500 MHz): δ=7.41 (t, J=7.6 Hz, 2H), 6.93 (dd, J=9.7, 2.0 Hz, 2H), 6.83 (dd, J=8.1, 1.9 Hz, 2H), 2.55 (t, J=7.7 Hz, 4H), 1.62-1.52 (m, 4H), 1.30-1.25 ppm (m, 10H).

Step 4:

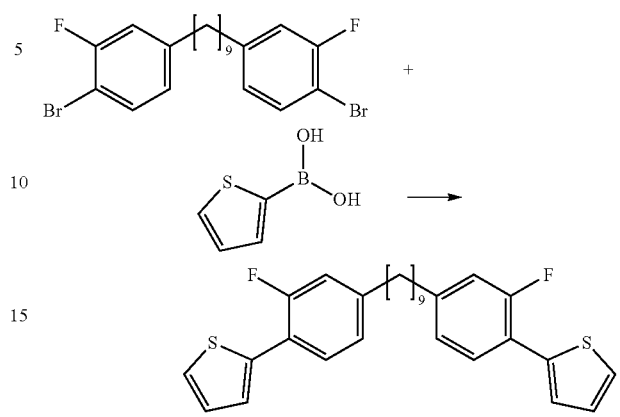

Bis(triphenylphosphine)palladium(II) chloride (15.2% of Pd) (0.70 g, 1.00 mmol), hydrazinium hydroxide (80%) (0.02 ml, 0.40 mmol), the dibromide (9.48 g, 0.02 mol) and THF (90 ml) are added to sodium metaborate tetrahydrate (5.50 g, 0.04 mol) in water (100 ml). A solution of thiophene-2-boronic acid (5.28 g, 0.04 mol) in THF (120 ml) is added to the mixture, which is then stirred overnight at 65° C. The cooled reaction mixture is extracted a number of times with MTBE. The combined organic phases are washed with water, dried over sodium sulfate and filtered, and the solvent is removed. After purification by column chromatography (silica gel, heptane), a crystalline solid (5.10 g, 0.01 mol) was isolated in a yield of 53%.

$^1$H-NMR (CDCl$_3$, 500 MHz): δ=7.50 (t, J=8.0 Hz, 2H), 7.42 (d, J=3.7 Hz, 2H), 7.29 (dd, J=5.2, 1.1 Hz, 2H), 7.08-7.07 (m, 2H), 6.97-6.90 (m, 2H), 2.57 (t, J=7.8 Hz, 4H), 1.58 (m, 4H), 1.33-1.23 ppm (m, 10H). $^{19}$F-NMR (CDCl$_3$, 471 MHz): δ=−114.57−−114.62 ppm (m).

Step 5:

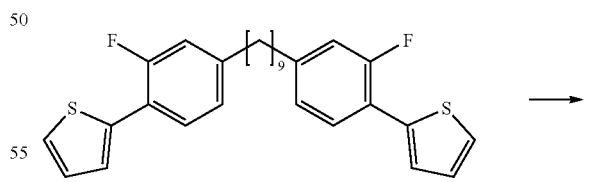

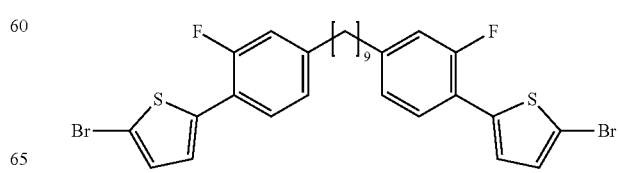

N-Bromosuccinimide is added in portions over the course of 30 min to a solution of compound 1 (21.00 g, 43.16 mmol) in chloroform (500 ml), and the mixture is stirred overnight with exclusion of light. After the solvent is removed, methanol (250 ml) is added, and the reaction mixture is warmed. The cooled residue is filtered off and recrystallised from heptane. The product is isolated as a colourless solid (23.7 g, 0.04 mol, HPLC: 97.6%) in a yield of 84%.

$^1$H-NMR (CDCl$_3$, 500 MHz): δ=7.42 (t, J=8.1 Hz, 2H), 7.15 (dd, J=3.9, 0.8 Hz, 2H), 7.04 (dd, J=4.0, 0.8 Hz, 2H), 6.97-6.91 (m, 4H), 2.59 (t, J=7.7 Hz, 4H), 1.64-1.58 (m, 4H), 1.34-1.29 ppm (m, 10H). $^{19}$F-NMR (CDCl$_3$, 471 MHz): δ=−114.67 ppm (dd, J=11.9, 8.2 Hz).

Step 6:

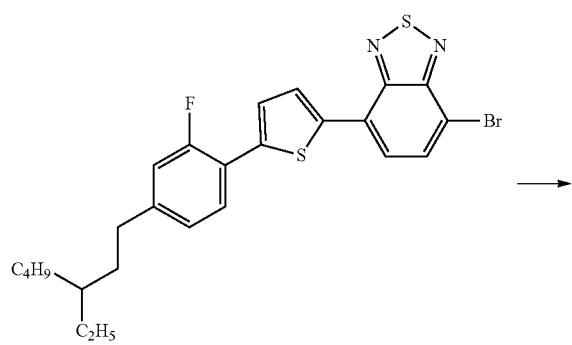

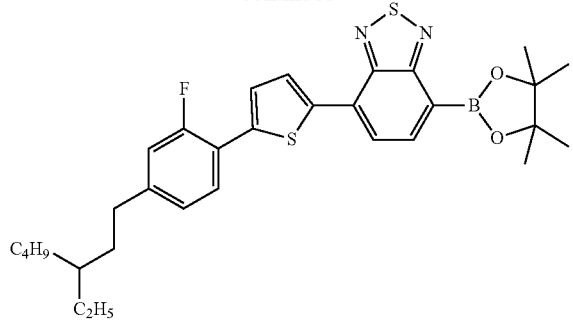

Bis(pinacolato)diboron (134 mg, 0.52 mmol), potassium acetate (114 mg, 1.16 mmol) and Pd(dppf)Cl$_2$ (9 mg, 0.01 mmol) are added to the monobromide (200 mg, 0.39 mmol) in 1,4-dioxane (5 ml), and the mixture is stirred overnight at 100° C. After addition of MTBE (10 ml) and water (20 ml) to the cooled solution, the organic phase is separated off, and the solvent is removed. The further purification is carried out by column chromatography (silica gel; toluene/ethyl acetate: 7/3). A wax-like solid (160 mg, 0.28 mmol, HPLC: 91.5%) is isolated in a yield of 67%.

EI-MS: m/z: 564.3.

Step 7:

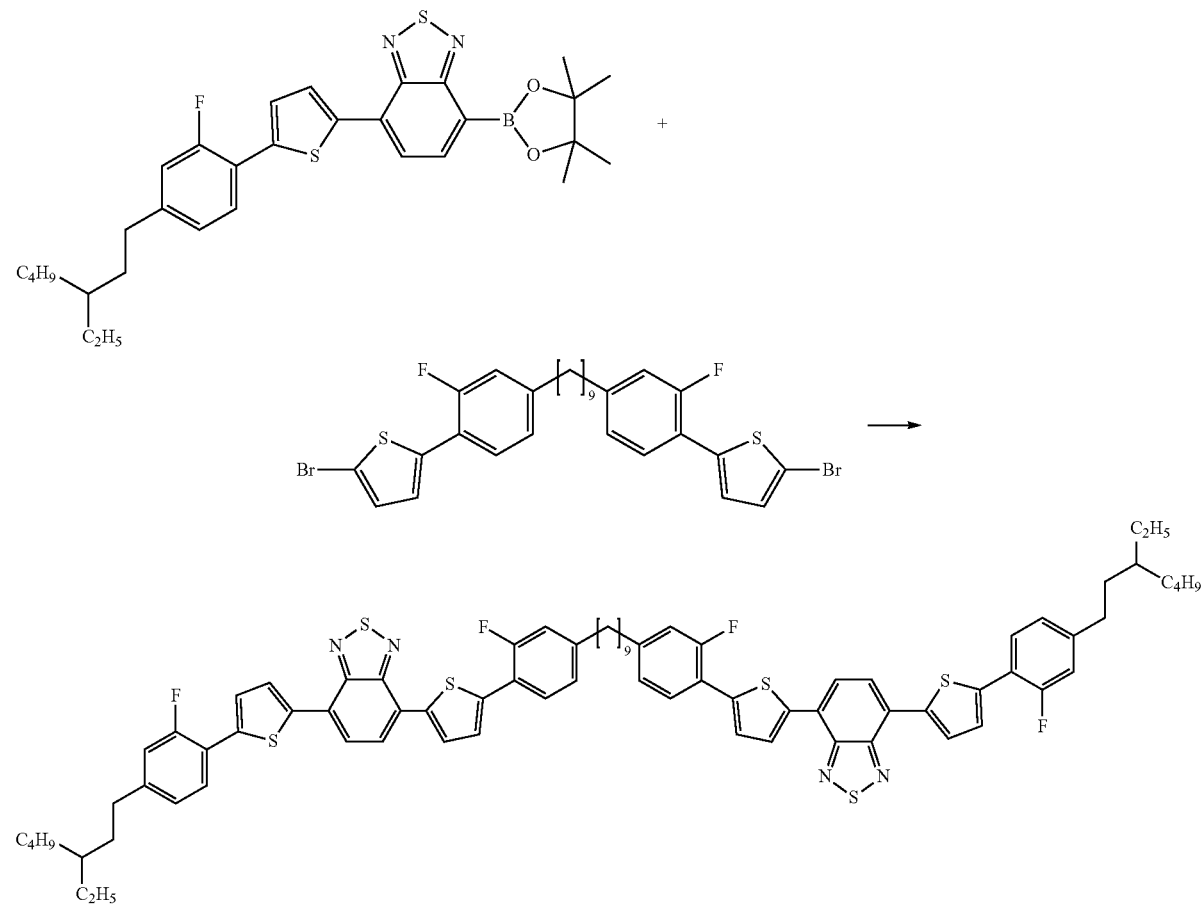

The dibromide (360 mg, 0.56 mmol) and the boronic ester (640 mg, 1.14 mmol) are dissolved in toluene (8 ml). After addition of 2 M $NaCO_3$ solution (1.15 ml), tris(dibenzylideneacetone)dipalladium (5.20 mg, 0.01 mmol) and tris-(o)-tolylphosphine (7.10 mg, 0.02 mmol), the reaction mixture is stirred overnight at 110° C. After addition of hot toluene (50 ml), the mixture is cooled to RT. The solid formed is filtered off and washed with cold toluene, acetone and dichloromethane. A red solid (548 mg, 0.41 mmol, HPLC: 99.2%) is isolated in a yield of 71%.

$^1$H-NMR ($CDCl_3$, 500 MHz): δ=8.10-8.08 (m, 4H), 7.86 (s, 4H), 7.62-7.59 (m, 4H), 7.50 (dd, J=4.0, 1.2 Hz, 4H), 7.02-6.95 (m, 8H), 2.64-2.59 (m, 8H), 1.41-1.23 (m, 34H), 0.93-0.87 ppm (m, 12H). $^{19}$F-NMR ($CDCl_3$, 376 MHz): δ=−113.95−−113.79 ppm (m). DSC: C 176 N (157) I. UV-Vis (THF): 258, 345, 493 nm.

Example 17

1st step:

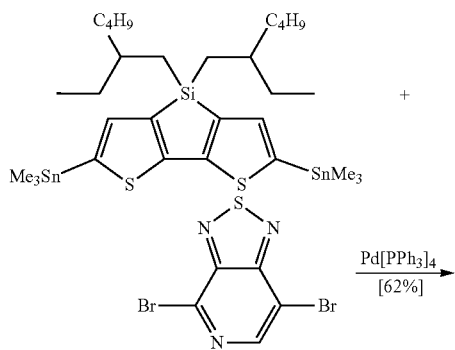

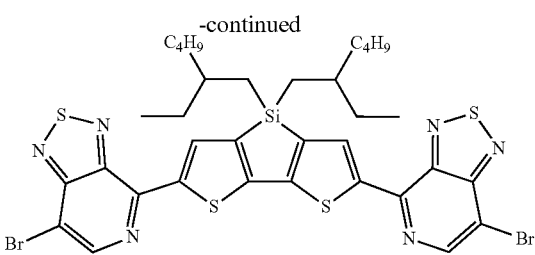

7,7-Bis(2-ethylhexyl)-2,5-bis(trimethylstannyl)-7H-3,4-dithia-7-silacyclopenta[a]pentalene (BTSi) (13.80 g, 0.02 mol) and 4,7-dibromo-1,2,5-thiadiazolo[3,4-c]pyridine (15.01 g, 0.05 mol) are dissolved in THF (35 ml). Tetrakis(triphenylphosphine)-palladium(0) (784 mg, 0.68 mmol) and N,N-dimethylformamide (35 ml) are added. The reaction mixture is stirred at 65° C. overnight. Water (15 ml) is added to the cooled mixture, and the solid formed is filtered off and washed a number of times with methanol. Purification by column chromatography (silica gel; heptane/chlorobutane: 1/1) enables a solid (9.00 g, 0.01 mol; HPLC: 98.7%) to be isolated in 62% yield.

$^1$H-NMR ($CDCl_3$, 700 MHz): δ=8.73-8.75 (m; 2H), 8.63 (s; 2H), 1.51-1.54 (m; 2H), 1.06-1.38 (m; 20H), 0.78-0.82 ppm (m; 12H). $^{13}$C-NMR ($CDCl_3$, 176 MHz) δ 156.35, 153.86, 148.81, 147.95, 147.69, 147.67, 147.46, 146.02, 143.94, 139.96, 136.04, 136.02, 135.99, 107.62, 36.04, 35.78, 34.87, 29.47, 28.99, 28.96, 23.91, 23.00, 17.65, 14.19, 10.83 ppm.

EI-MS: m/z: 846.1.

2nd step

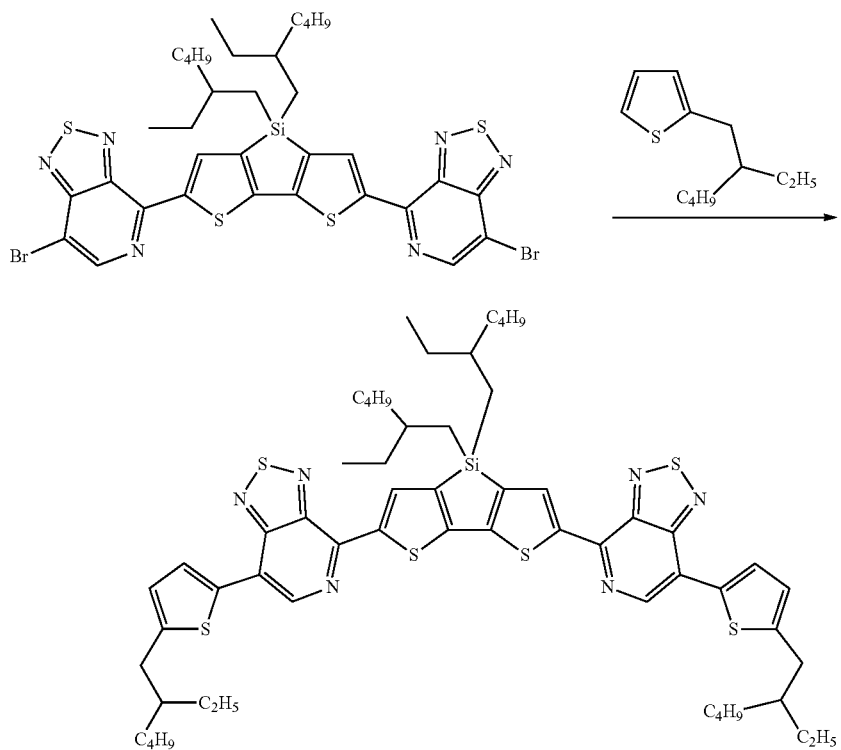

2-(2-Ethylhexyl)thiophene (1.95 g, 0.01 mol) is dissolved in tetrahydrofuran (33 ml) and cooled to −70° C. n-BuLi (6.15 ml, 9.84 mmol; in hexane) is added dropwise, and the mixture is stirred at −70° C. for 1 h. Tributyltin chloride (2.78 ml, 9.84 mmol) is subsequently added, and the reaction mixture is warmed to RT. 5,5′-Bis{(4-(7-bromo-1,2,5-thiadiazolo[3,4-c]pyridinyl)}-3,3′-di-2-ethylhexylsilyl-2,2′-bithiophene (3.50 g, 4.69 mmol), tetrakis(triphenylphosphine)palladium(O) (216.58 mg, 0.19 mmol) and N,N-dimethylformamide (10 ml) are then added, and the mixture is stirred at 65° C. for 72 h. The solid formed is filtered off and purified by column chromatography. A dark-blue solid (620 mg, 0.57 mmol, HPLC: 99.0%) is be isolated.

The following derivatives are prepared by the same procedure:

Example 18

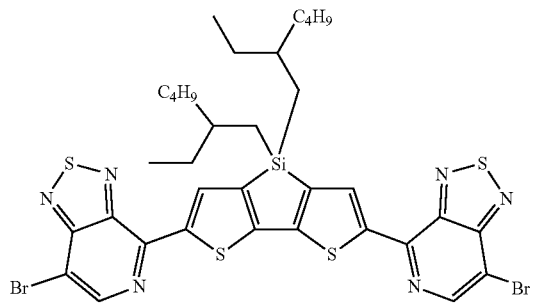
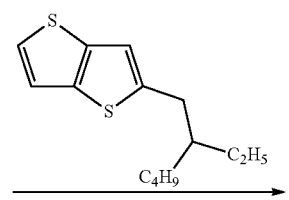

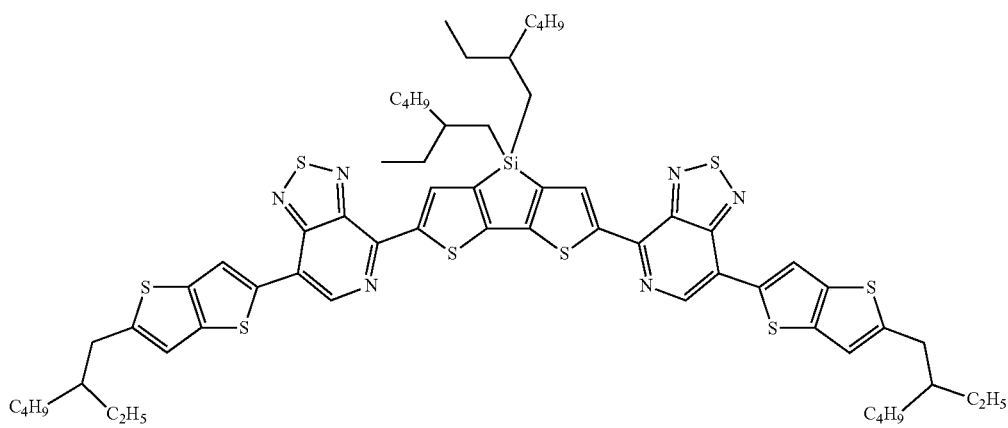

Blue solid, 25% yield, HPLC: 99.0%; $^1$H-NMR (CDCl$_3$, 500 MHz): δ=8.78 (s; 2H), 7.75 (m; 2H), 8.33 (s; 2H), 6.99 (s; 2H), 2.86 (d, J=6.8 Hz; 4H), 1.65-1.70 (m; 4H), 1.55-1.60 (m; 4H), 1.21-1.47 (m; 28H), 1.08-1.20 (m; 4H), 0.90-0.95 (m; 12H), 0.80-0.85 ppm (m; 12H).

UV-VIS (THF): 276, 312, 332, 630 nm.

Example 19

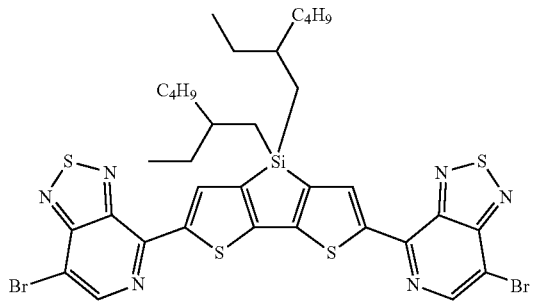
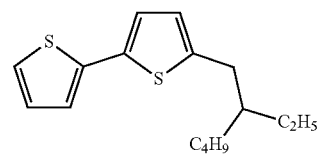

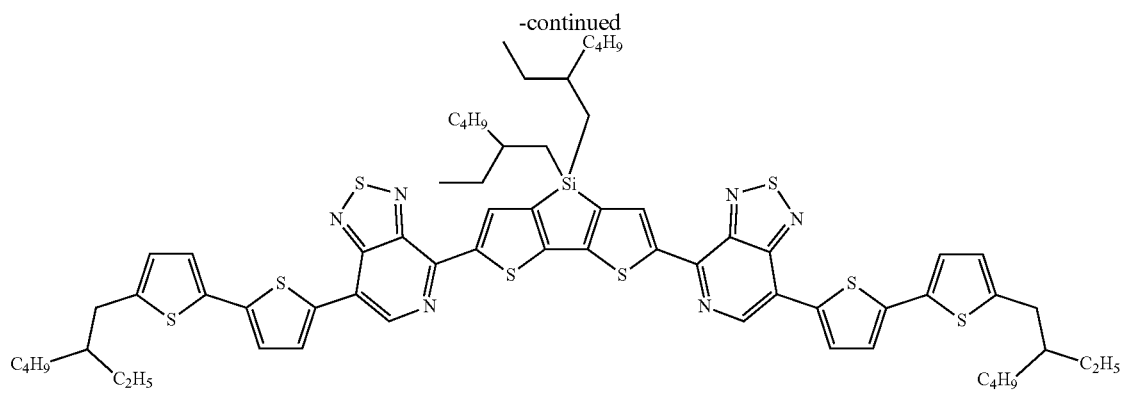

Blue solid, 15% yield, HPLC: 99.4%; $^1$H-NMR (CDCl$_3$, 500 MHz): δ=8.80 (s; 2H), 8.75 (m; 2H), 8.03 (d, J=3.8 Hz; 2H), 7.21 (d, J=3.8 Hz; 2H), 7.13 (d, J=3.5 Hz; 2H), 6.72 (d, J=3.5 Hz; 2H), 2.77 (d, J=6.7 Hz; 4H), 1.53-1.66 (m; 8H), 1.19-1.44 (m; 28H), 1.08-1.20 (m; 4H), 0.88-0.95 (m; 12H), 0.80-0.86 ppm (m; 12H).

UV-VIS (THF): 277, 366, 637 nm.

Example 20

1st step:

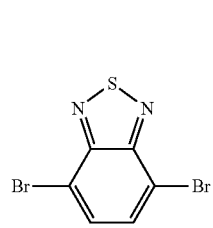

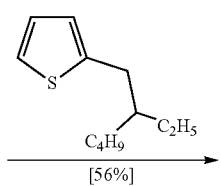

-continued

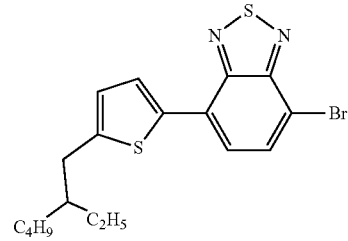

n-BuLi in hexane (1.6 M, 24.5 ml, 0.04 mol) is slowly added dropwise to a solution of 2-(2-ethylhexyl)thiophene (7.00 g, 35.65 mmol) at −70° C., and the reaction mixture is stirred at this temperature for 1 h. After addition of tributyltin chloride (11.08 ml, 0.04 mol), the mixture is stirred at −70° C. for a further 30 min and subsequently warmed to room temperature. After addition of 4,7-dibromobenzo-1,2,5-thiadiazole (10.48 g, 35.65 mmol), tetrakis(triphenylphosphine)palladium(O) (0.82 g, 0.7 mmol) and DMF (18 ml), the reaction mixture is warmed at 70° C. overnight. Water (30 ml) is added to the cooled solution, and the aqueous phase is extracted a number of times with toluene. After purification by column chromatography (silica gel; toluene/heptane: 1/1), a yellow oil (8.2 g, 19.91 mmol, HPLC: 99.4%) can be isolated in 56% yield.

2$^{nd}$ step:

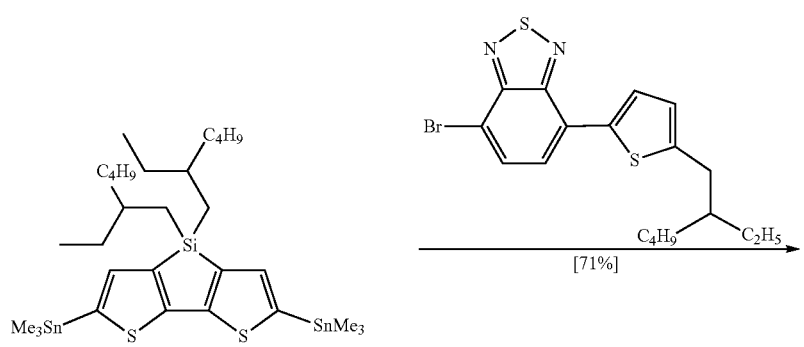

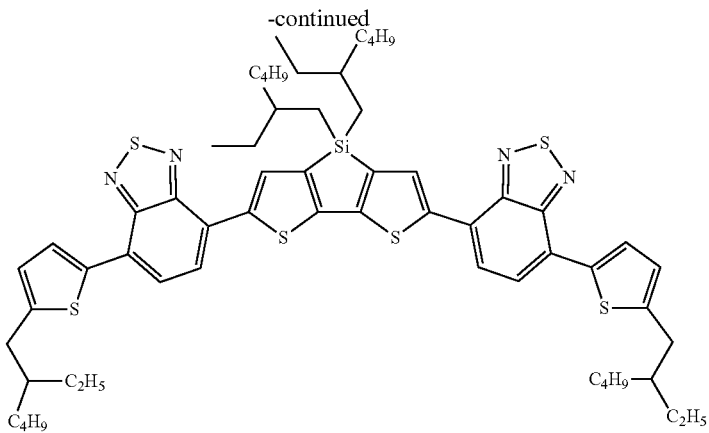

4-Bromo-7-[5-(2-ethylhexyl)thien-2-yl]benzo-1,2,5-thiadiazole (3.02 g, 7.38 mmol), 7,7-bis(2-ethylhexyl)-2,5-bis(trimethylstannyl)-7H-3,4-dithia-7-silapenta[a]pentalene (2.00 g, 2.68 mmol) and tetrakis(triphenylphosphine)palladium(O) (113 mg, 0.10 mmol) are stirred in THF (15 ml) and DMF (5 ml) at 70° C. overnight. Water is added to the cooled reaction mixture, which is then extracted a number of times with MTBE. After purification by column chromatography (silica gel, toluene/heptane: 3/7), a violet oil (1.90 g, 1.75 mmol, HPLC: 99.0%) can be isolated in 71% yield.

$^1$H-NMR (CDCl$_3$, 700 MHz): δ=8.17-8.19 (m; 2H), 7.97 (d, J=3.5 Hz; 4H), 7.84 (d, J=7.6 Hz; 2H), 7.80 (d, J=7.6 Hz; 2H), 6.87 (d, J=3.5 Hz; 2H), 2.83-2.85 (m; 4H), 1.64-1.69 (m; 2H), 1.18-1.43 (m; 34H), 1.03-1.14 (m; 4H), 0.90-0.94 (m; 12H), 0.80-0.86 ppm (m; 12H).

EI-MS: m/z: 1074.8. DSC: TG −30 I. UV-VIS (THF): 316, 401, 474, 561 nm.

The following derivatives are prepared analogously:

Example 21

1st step:

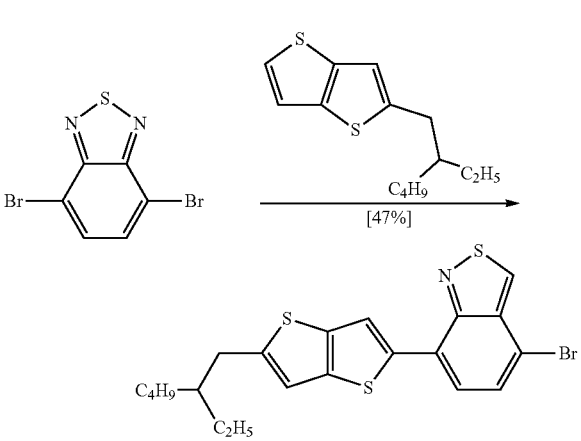

Yellow solid, 47% yield, HPLC: 99.2%

2nd step:

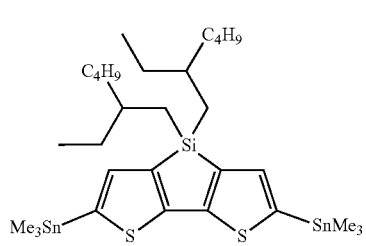

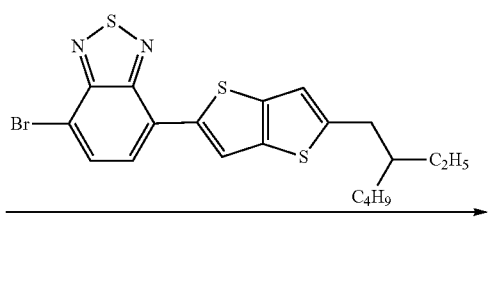

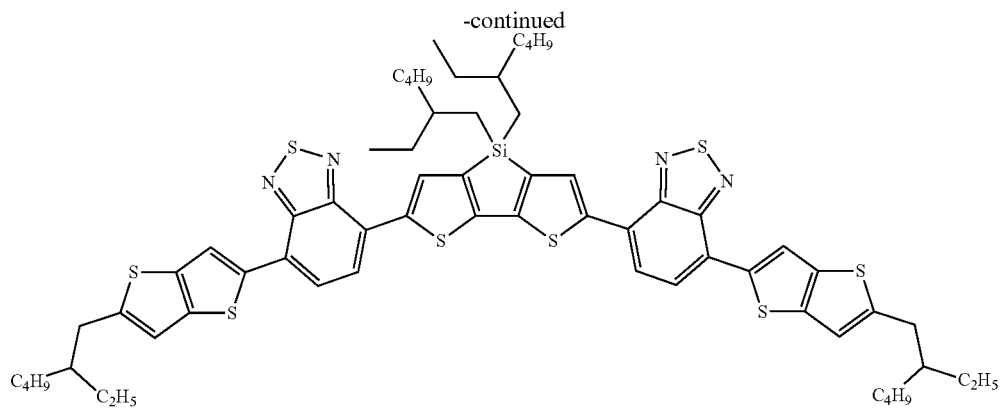
Blue crystals in 85% yield (HPLC: 99.5%); $^1$H-NMR (CDCl$_3$, 700 MHz): δ=8.38 (s, 2H), 8.19-8.21 (m; 2H), 7.80-7.84 (m; 4H), 6.97 (s; 2H) 1.51-1.54 (m, 2H), 2.85-2.86 (m; 4H), 1.64-1.69 (m; 2H), 1.54-1.58 (m; 2H), 1.20-1.45 (m; 32H), 1.05-1.15 (m; 4H), 0.90-0.94 (m; 12H), 0.81-0.85 ppm (m; 12H).
EI-MS: m/z: 1186.4. DSC: TG −26 K 132 I. UV-VIS (THF): 336, 580 nm.
Example 22
1st step:
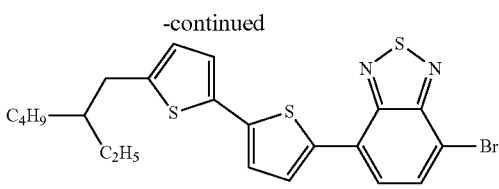
Red oil, 46% yield, HPLC: 99.2%
2nd step:
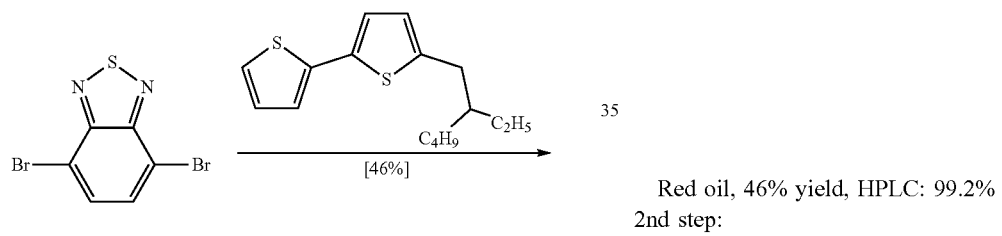
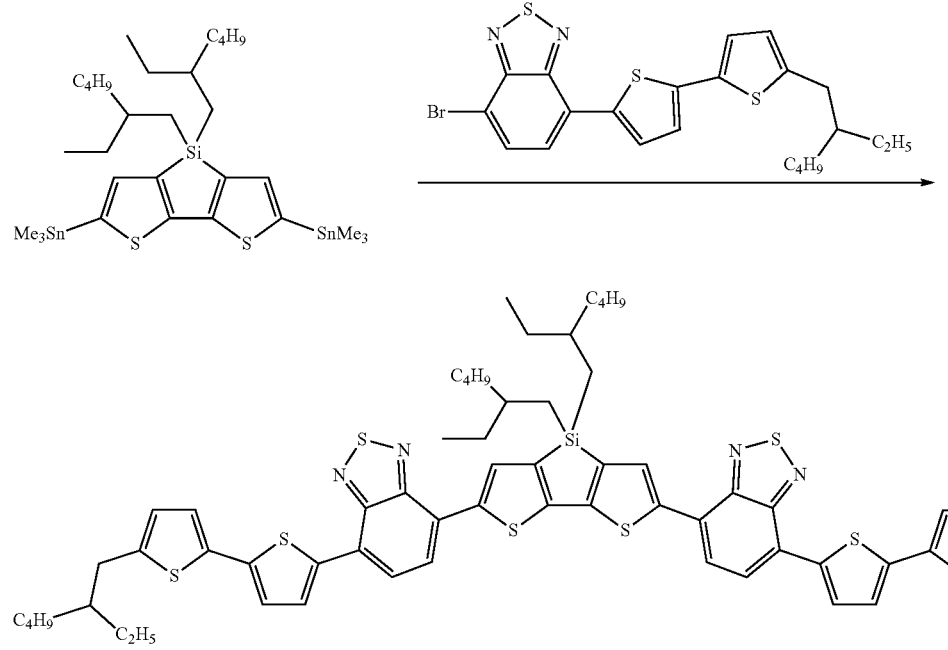

Blue solid in 62% yield (HPLC: 99.6%); ¹H-NMR (CDCl₃, 500 MHz): δ=8.19 (t, J=5.1 Hz; 2H), 8.03 (d, J=3.8 Hz; 2H), 7.79-7.87 (m; 4H), 7.19 (d, J=3.9 Hz; 2H), 7.11 (d, J=3.5 Hz; 2H), 6.68-6.73 (m; 2H), 2.76 (d, J=6.7 Hz; 4H), 1.55-1.63 (m; 4H), 1.26-1.45 (m; 24H), 1.20-1.24 (m; 8H), 1.05-1.15 (m; 4H), 0.90-0.94 (m; 12H), 0.81-0.85 (m; 12H).

EI-MS: m/z: 1238.8. DSC: TG 8 K 117 I. UV-Vis (THF): 365, 592 nm.

Example 23

1st step

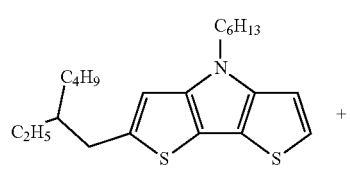

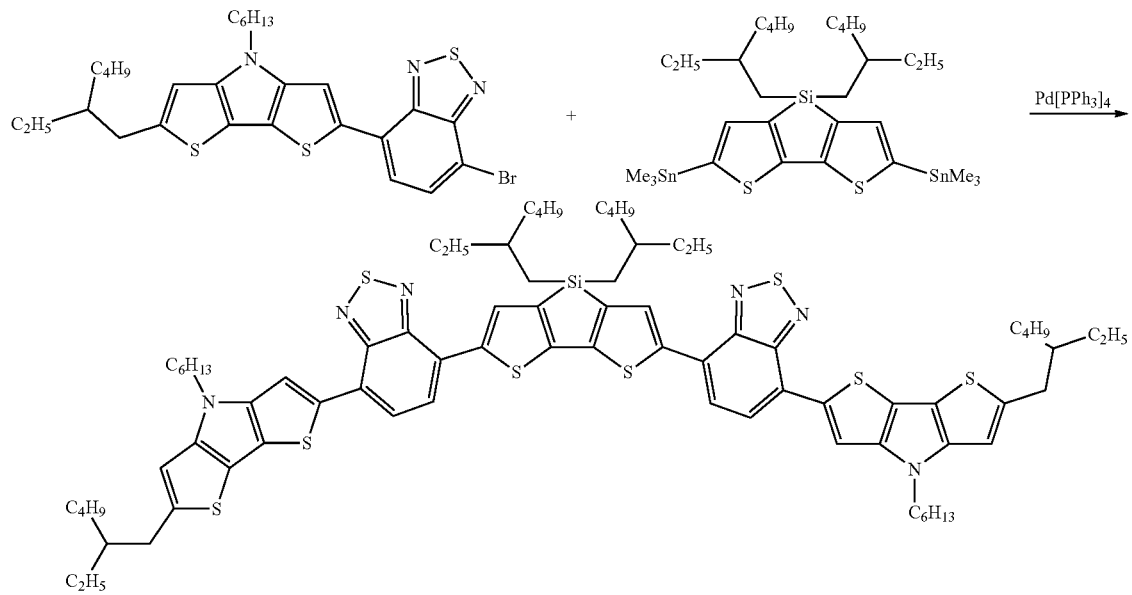

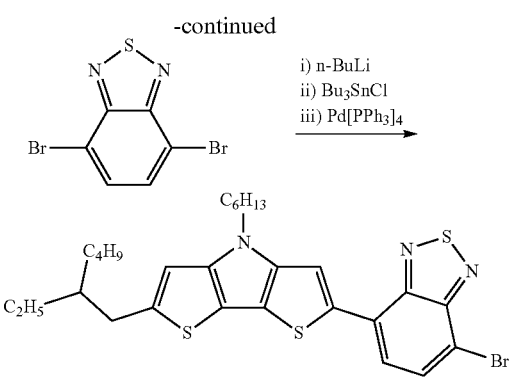

n-BuLi in hexane (1.6 M, 8.71 ml, 0.01 mol) is added dropwise to 2-(2-ethylhexyl)-4-hexyl-dithieno[3,2-b; 2',3'-d]pyrrole (5.00 g, 13.27 mmol) in tetrahydrofuran (80 ml) at −70° C., and the mixture is stirred at this temperature for 45 min. After addition of tributyltin chloride (3.94 ml, 0.01 mol), the reaction mixture is stirred at this temperature for a further 30 min and subsequently warmed to room temperature. 4,7-Dibromobenzo-1,2,5-thiadiazole (11.72 g, 39.81 mmol), tetrakis(triphenylphosphine)palladium(O) (0.61 g, 0.5 mmol) and DMF (7 ml) are added, and the mixture is stirred at 70° C. overnight. Water and MTBE are added to the cooled reaction mixture. The aqueous phase is extracted a number of times with MTBE. The combined organic phases are washed with saturated NaCl solution and water. After purification by column chromatography (silica gel; heptane/toluene: 1/1) and recrystallisation from heptane and acetonitrile, a red solid (4.50 g, 7.61 mmol; HPLC: 99.5%) can be isolated in 57% yield.

¹H-NMR (CDCl₃, 400 MHz): δ=8.28 (s; 1H), 7.80 (d, J=7.8 Hz; 1H), 7.66 (d, J=7.8 Hz; 1H), 6.70 (d, J=1.0 Hz; 1H), 4.23 (t, J=7.1 Hz; 2H), 2.82 (dd, J=6.9, 0.9 Hz; 2H), 1.87-1.93 (m; 2H), 1.65 (q, J=6.1 Hz; 1H), 1.25-1.47 (m, 14H), 0.82-0.96 ppm (m, 9H).

EI-MS: m/z: 587.

Example 24

2-(7-Bromobenzo-1,2,5-thiadiazol-4-yl)-6-(2-ethylhexyl)-4-hexyldithieno[3,2-b;2',3'-d]pyrrole (2.55 g, 4.3 mmol), 7,7-bis(2-ethylhexyl)-2,5-bis(trimethylstannyl)-7H-3,4-dithia-7-silapenta[a]pentalene (1.40 g, 1.88 mmol) and tetrakis(triphenylphosphine)palladium(O) (80 mg, 0.07 mmol) are stirred in THF (15 ml) and DMF (4 ml) at 70° C. overnight. Water and toluene are added to the cooled reaction mixture. The aqueous phase is extracted a number of times with toluene. The combined organic phases are washed with saturated NaCl solution. After purification by column chromatography (silica gel; heptane/toluene:3/2) and recrystallisation from heptane/toluene, a blue solid with a metallic lustre (1.90 g, 1.32 mmol; HPLC: 99.6%) can be isolated in 77% yield.

¹H-NMR (CDCl₃, 500 MHz): δ=8.33 (s; 2H), 8.16-8.18 (m; 2H), 7.83-7.87 (m; 4H), 6.71 (s; 2H), 4.25 (t, J=7.1 Hz; 4H), 2.84 (d, J=6.9 Hz; 4H), 1.88-1.99 (m; 4H), 1.18-1.44 (m; 44H), 1.04-1.10 (m; 6H), 0.78-0.96 ppm (m; 32H).

El-MS: m/z: 1432.7. DSC: K 164 I. UV-VIS (THF): 295, 365, 633 nm.

Example 25

1st step:

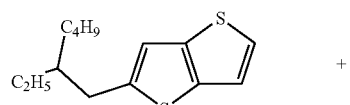 +

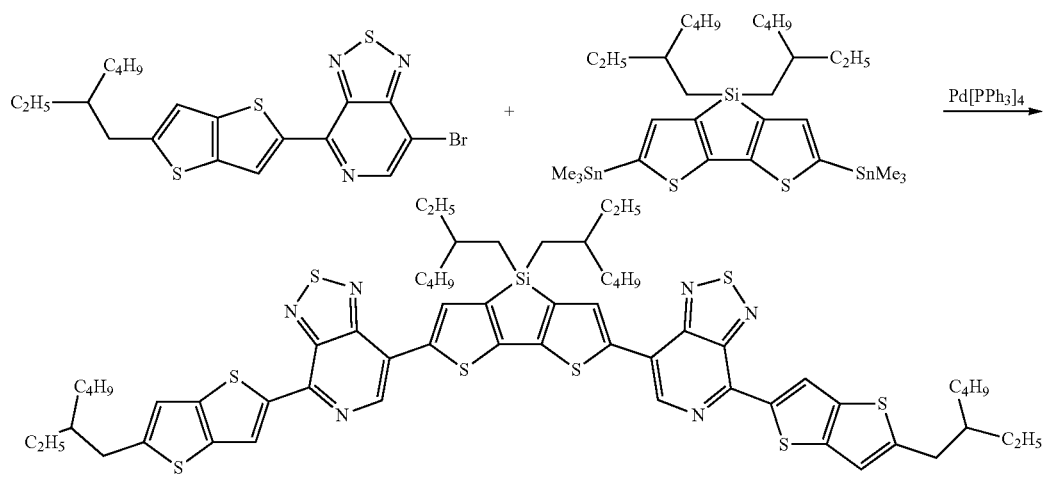

-continued

n-BuLi in hexane (1.6 M, 10.35 ml, 0.02 mol) is added dropwise to 2-(2-ethylhexyl)thieno[3,2-b]thiophene (4.00 g, 15.77 mmol) in tetrahydrofuran (65 ml) at −70° C., and the mixture is stirred at this temperature for 45 min. After addition of tributyltin chloride (4.68 ml, 0.02 mol), the reaction mixture is stirred at this temperature for a further 30 min and subsequently warmed to room temperature. 4,7-Dibromo-1,2,5-thiadiazolo[3,4-c]pyridine (6.98 g, 23.65 mmol), tetrakis(triphenylphosphine)palladium(O) (0.36 g, 0.3 mmol) and DMF (8 ml) are added, and the mixture is stirred at 70° C. overnight. Water and toluene are added to the cooled reaction mixture. The aqueous phase is extracted a number of times with toluene. The combined organic phases are washed with saturated NaCl solution and water. After purification by column chromatography (silica gel; heptane/toluene: 1/1) and recrystallisation from heptane and toluene, a red solid (4.40 g, 9.39 mmol; HPLC: 99.5%) can be isolated in 60% yield.

$^1$H-NMR (CDCl$_3$, 400 MHz): δ=8.87 (s; 1H), 8.63 (s; 1H), 7.01 (s; 1H), 2.86 (d, J=6.8 Hz; 2H), 1.68 (m; 1H), 1.25-1.45 (m; 8H), 0.91 (m; 6H).

El-MS: m/z: 465.

2nd step:

7-Bromo-4-[5-(2-ethylhexyl)thieno[3,2-b]thien-2-yl-1,2,5-thiadiazolo[3,4-c]pyridine (3.27 g, 6.97 mmol), 7,7-bis(2-ethylhexyl)-2,5-bis(trimethylstannyl)-7H-3,4-dithia-7-sila-penta[a]pentalene (2.70 g, 3.32 mmol) and tetrakis (triphenylphosphine)palladium(O) (153 mg, 0.13 mmol) are stirred in DMF (30 ml) at 100° C. overnight. Water and dichloromethane are added to the cooled reaction mixture.

$^1$H-NMR (CDCl$_3$, 700 MHz): δ=8.82 (s; 2H), 8.77 (s; 2H), 8.18-8.20 (m; 2H), 7.02 (s; 2H), 2.87 (d, J=6.9 Hz; 4H), 1.67-1.72 (m; 2H), 1.28-1.46 (m; 26H), 1.20-1.26 (m; 8H), 1.08-1.16 (m; 4H), 0.90-0.95 (m; 12H), 0.80-0.88 ppm (m; 12H).

El-MS: m/z: 1188.7. DSC: K 230 I. UV-VIS (THF): 275, 302, 348, 603 nm.

Example 26

1st step:

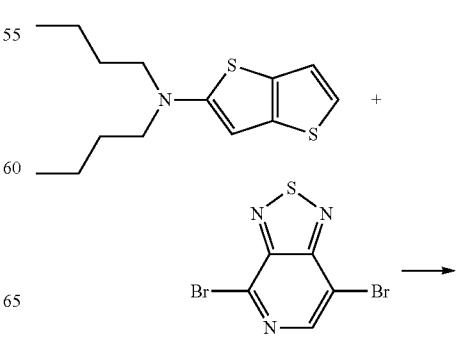

-continued

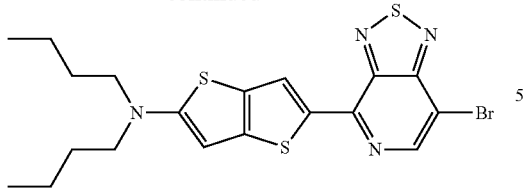

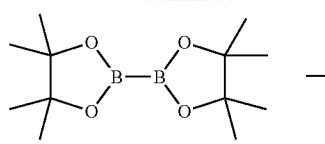

N-BuLi in hexane (1.6 M, 19.6 ml, 0.03 mol) is slowly added dropwise to a solution of 2-(Dibutyl)-amino-thieno[3,2-b]thiophene (8.00 g, 0.03 mol) at −70° C., and the reaction mixture is stirred at this temperature for 1 h. After addition of tributyltin chloride (8.8 ml, 0.03 mol), the mixture is stirred at −70° C. for a further 30 min and subsequently warmed to room temperature. After addition of 4,7-dibromo-[1,2,5]thiadiazolo[3,4-c]pyridine (13.44 g, 0.04 mol), tetrakis(triphenylphosphine)palladium(O) (0.69 g, 0.7 mmol) and DMF (15 ml), the reaction mixture is warmed at 70° C. overnight. Water (30 ml) is added to the cooled solution, and the aqueous phase is extracted a number of times with toluene. After purification by column chromatography (silica gel; toluene/heptane: 7/3), a blue solid (9.0 g, 0.02 mol, HPLC: 99.0%) can be isolated in 62% yield.

2nd step:

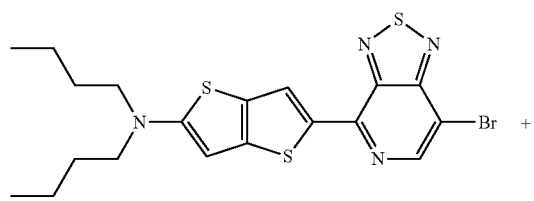

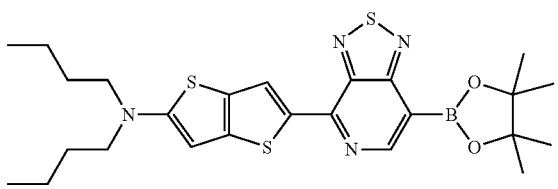

Bis-(pinacolato)-diborane (5.90 g, 22.77 mmol), Pd(dppf)Cl$_2$ (0.33 g, 0.45 mmol), and K$_2$CO$_3$ (4.50 g, 45.85 mmol) were added to a solution of 2-(7-bromo-[1,2,5]thiadiazolo[3,4-c]pyridin-4-yl)-N,N-dibutyl-thieno[3,2-b]thiophen-5-amine (7.30 g, 15.16 mmol) in 1,4-dioxane (110 ml) and stirred at 100° C. overnight. Water is added to the cooled reaction mixture, which is then extracted a number of times with toluene. The combined organic phases were dried over Na$_2$SO$_4$ and filtrated. After removal of the solvent, a red solid (6.10 g, 11.45 mmol) can be isolated in 76% yield.

$^1$H-NMR (CDCl$_3$, 500 MHz): δ=8.82 (s, 1H), 8.81 (s, 1H), 6.03 (s, 1H), 3.32 (t, J=7.6 Hz, 4H), 1.72-1.64 (m, 4H), 1.42 (s, 12H), 1.42-1.36 (m, 4H), 0.98 (t, J=7.4 Hz, 6H).

El-MS: m/z: 528.0.

3rd step:

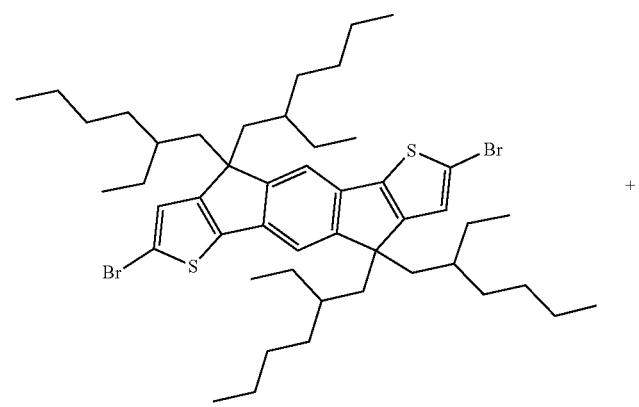

+

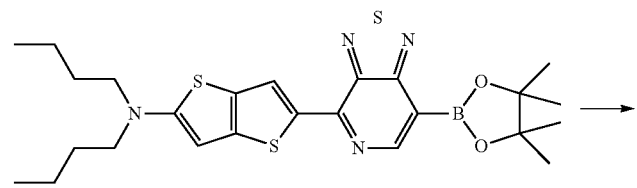

-continued

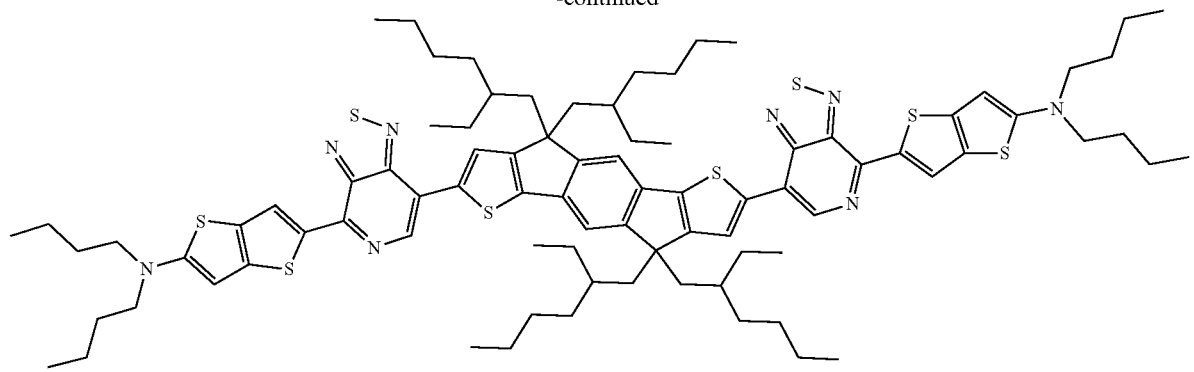

2,7-Dibromo-4,9-dihydro-4,4,9,9-tetra(2-ethylhexyl)-s-indaceno[1,2-b:5,6-b]-dithiophene (0.50 g, 0.57 mmol), N,N-dibutyl-2-[7-(4,4,5,5-tetramethyl-1,3,2-dioxaborolan-2-yl)-[1,2,5]thiadiazolo[3,4-c]pyridin-4-yl]thieno[3,2-b]thiophen-5-amine (0.88 g, 1.67 mmol) and $Pd_2dba_3$ (11 mg, 0.01 mmol), SPhos (14 mg, 0.03 mmol), and Aliquat 336 (0.10 g, 0.25 mmol) are stirred in toluene (18 ml) and $Na_2CO_3$ solution (2M, 2.3 ml, 4.58 mmol) at 100° C. overnight. Water and toluene are added to the warm reaction mixture, which is then extracted a number of times with toluene. After purification by column chromatography (silica gel, toluene/heptane:1/1) and recrystallization (toluene/heptane), a green solid (0.70 g, 0.46 mmol, HPLC: 99.6%) can be isolated in 80% yield.

$^1$H-NMR ($CDCl_3$, 700 MHz): δ=8.78 (t, J=4.3 Hz, 2H), 8.75 (s, 1H), 8.11-7.89 (m, 2H), 7.41 (s, 2H), 6.05 (s, 2H), 3.33 (t, J=7.7 Hz, 8H), 2.11-1.98 (m, 8H), 1.67-1.71 (m, 8H), 1.38-1.42 (m, 8H), 1.03-0.84 (m, 48H), 0.71-0.48 (m, 24H).

APCI-MS: m/z: 1515.7. DSC: TG 96 K 206 I. UV-VIS (THF): 279, 415, 687 nm.

2,7-Dibromo-4,9-dihydro-4,4,9,9-tetra(2-ethylhexyl)-s-indaceno[1,2-b:5,6-b']-dithiophene is available according McCulloch et al. *J. Am. Chem. Soc.* 2010, 132, 11437-11439.

The following derivatives are prepared analogously:

Example 27

1st step:

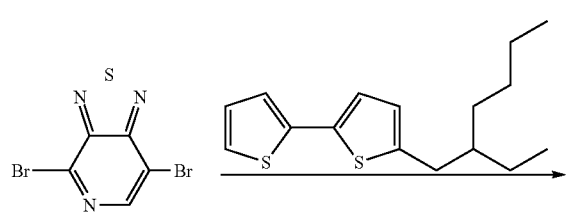

-continued

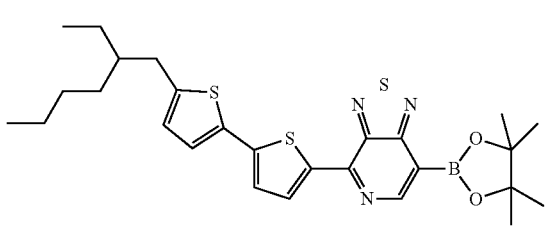

Red solid, 51% yield, HPLC: 99.8%

$^1$H-NMR ($CDCl_3$, 700 MHz): δ=8.63 (s, 1H), 8.59 (d, J=3.9 Hz, 1H), 7.24 (d, J=3.9 Hz, 1H), 7.19 (d, J=3.6 Hz, 1H), 6.73 (d, J=3.5 Hz, 1H), 2.77 (d, J=6.8 Hz, 2H), 1.59-1.62 (m, 1H), 1.35-1.41 (m, 2H), 1.29-1.34 (m, 6H), 0.87-0.94 (m, 6H).

El-MS: m/z: 491.0.

2nd step:

Red oil, 51% yield

El-MS: m/z: 539.4.

3rd step:

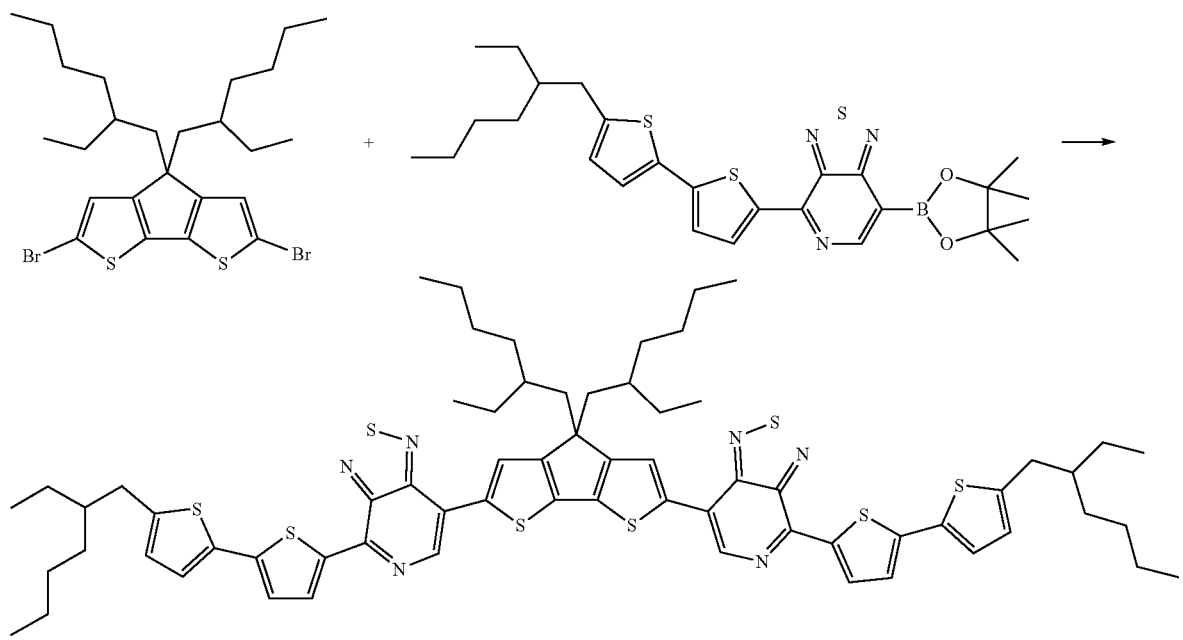

2,6-Dibromo-4,4-bis(2-ethylhexyl)-4H-cyclopenta[1,2-b:5,4-b']dithiophene (1.70 g, 3.03 mmol), 4-[5-[5-(2-ethylhexyl)-2-thienyl]-2-thienyl]-7-(4,4,5,5-tetramethyl-1,3,2-dioxaborolan-2-yl)-[1,2,5]thiadiazolo[3,4-c]pyridine (4.10 g, 7.60 mmol) and Pd$_2$dba$_3$ (55 mg, 0.06 mmol), P(o-Tol)$_3$ (73 mg, 0.24 mmol), and Na$_2$CO$_3$ solution (2M, 12.1 ml, 24.2 mmol) at 100° C. overnight. Water and toluene are added to the cooled reaction mixture, which is then extracted a number of times with toluene. After purification by column chromatography (silica gel, toluene/heptane:1/1) and recrystallization (toluene/heptane), a blue solid (1.80 g, 1.47 mmol, HPLC: 99.9%) can be isolated in 48% yield.

$^1$H-NMR (CDCl$_3$, 700 MHz): δ=8.83 (t, J=4.1 Hz, 2H), 8.60-8.57 (m, 2H), 8.10 (t, J=15.4 Hz, 2H), 7.26 (s, 2H), 7.20 (d, J=3.5 Hz, 2H), 6.73 (d, J=3.5 Hz, 2H), 2.78 (d, J=6.8 Hz, 4H), 2.10-2.04 (m, 4H), 1.64-1.60 (m, 2H), 1.42-1.27 (m, 16H), 1.10-0.95 (m, 16H), 0.94-0.89 (m, 12H), 0.84-0.80 (m, 2H), 0.67-0.64 (m, 12H).

APCI-MS: m/z: 1225.4. DSC: K 169 I. UV-VIS (THF): 279, 389, 639 nm.

Example 28

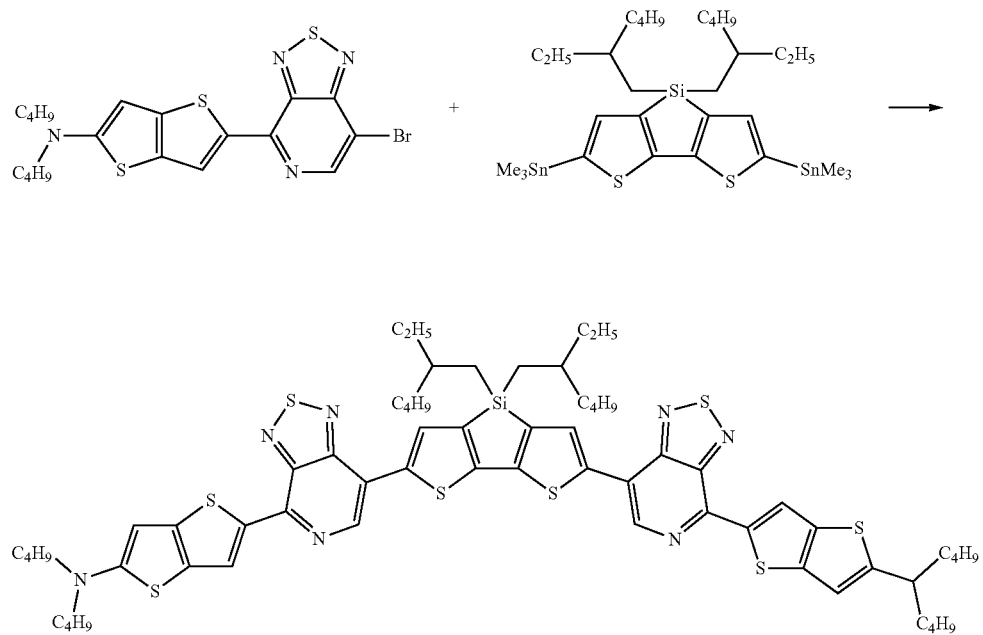

[5-(7-Bromo-[1,2,5]thiadiazolo[3,4-c]pyridin-4-yl)-thieno[3,2-b]thiophen-2-yl]-dibutyl-amine (4.03 g, 8.37 mmol), 7,7-bis(2-ethylhexyl)-2,5-bis(trimethylstannyl)-7H-3,4-dithia-7-silapenta[a]pentalene (3.05 g, 4.10 mmol) and tetrakis(triphenylphosphine)palladium(O) (173 mg, 0.15 mmol) are stirred in DMF (32 ml) at 100° C. overnight. Water is added to the cooled reaction mixture. The resulting solid is filtered off and further purified by column chromatography (silica gel, toluene/heptane: 1/1). The target compound is isolated as a green solid (1.69 g, 1.39 mmol) in 36% yield.

$^1$H-NMR (CDCl$_3$, 700 MHz): δ=8.71 (s; 4H), 8.08-8.12 (m; 2H), 8.18-8.20 (m; 2H), 6.04 (s; 2H), 3.32 (t, J=7.7 Hz; 8H), 1.67-1.71 (m; 8H), 1.38-1.42 (m; 8H), 1.28-1.36 (m; 8H), 1.20-1.26 (m; 8H), 1.08-1.14 (m; 4H), 0.99 (t, J=7.5 Hz; 12H), 0.80-0.88 ppm (m; 12H).

EI-MS: m/z: 1218.8. DSC: TG 45 K 243 I. UV-VIS (THF): 401, 703 nm.

Example 29

1st step:

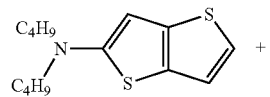
+
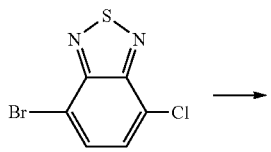
→

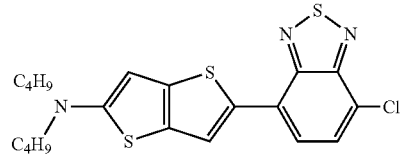

N-BuLi in hexane (1.6 M, 12.61 ml, 0.06 mol) is slowly added dropwise to a solution of 2-(Dibutyl)-amino-thieno[3,2-b]thiophene (5.00 g, 0.02 mol) in THF (130 ml) at −70° C., and the reaction mixture is stirred at this temperature for 1 h. After addition of tributyltin chloride (5.7 ml, 0.02 mol), the mixture is stirred at −70° C. for a further 30 min and subsequently warmed to room temperature. After addition of 4-bromo-7-chlorobenzo[1,2,5]thiadiazole (5.07 g, 0.02 mol), tetrakis(triphenylphosphine)palladium(O) (0.42 g) and DMF (19 ml), the reaction mixture is warmed at 70° C. overnight. Water (30 ml) is added to the cooled solution, and the aqueous phase is extracted a number of times with toluene. After purification by column chromatography (silica gel; toluene/heptane:1/1) and recrystallization from THF/acetonitrile, a blue solid (3.3 g, 0.01 mol, HPLC: 96.7%) can be isolated in 40% yield.

APCI-MS: m/z: 436.0.

2nd step:

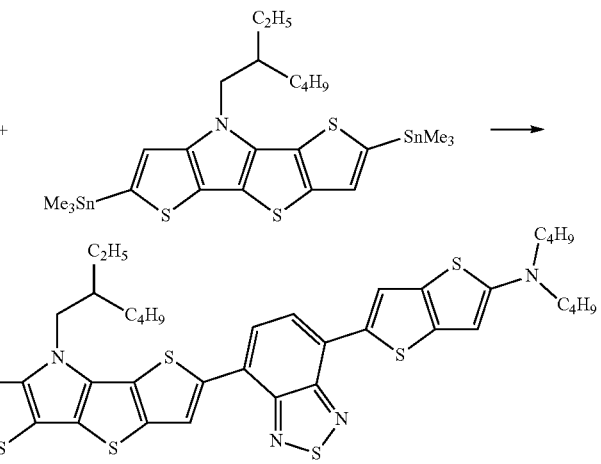

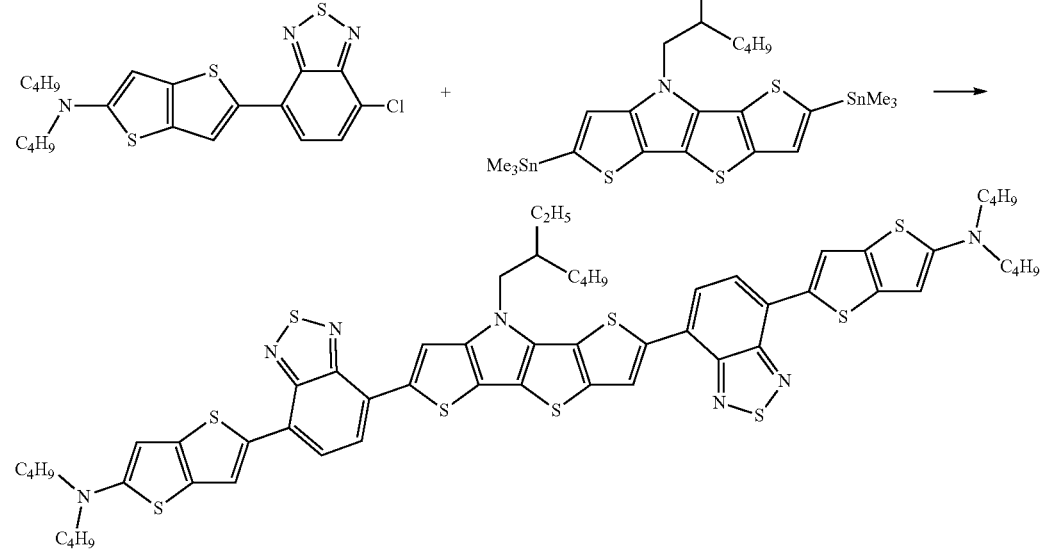

The distannane (0.39 g, 0.58 mmol) and dibutyl-[5-(7-chlorobenzo[1,2,5]thiadiazol-4-yl)-thieno[3,2-b]thiophen-2-yl]-amine (0.56 g, 1.28 mmol) were dissolved in toluene (10 ml) and placed under nitrogen. The reaction mixture was heated to 50° C. then Pd(OAc) (3 mg) and SPhos (10 mg) were added and the reaction heated to reflux for 24 hours. After cooling to room temperature, the product had precipitated out of solution. The toluene was reduced under vacuum then heptane was added and the mixture triturated then filtered. The dark purple solid was washed with heptane until no more purple filtrate came through (150 ml).

The crude material was applied to 5 g silica as a slurry in DCM. The pad was washed with heptane then 50% DCM/heptane, eluting some blue impurities until the clean product began to elute. Neat DCM then THF was used to elute the product. The solvent was removed to leave 0.5 g dark purple solid. The solid was triturated with methanol then collected by filtration and dried in a vacuum oven to leave dark purple solid (0.33 g, 0.29 mmol, HPLC: 99.9%) in 49% yield.

APCI-MS: m/z: 1146.27. DSC: K 249 I. UV-VIS (THF): 287, 401, 660 nm.

Example 30

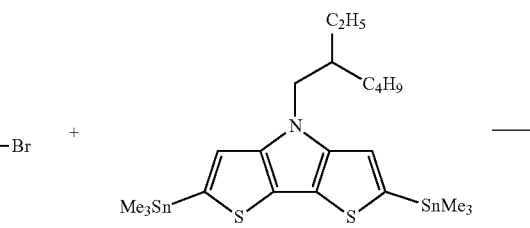

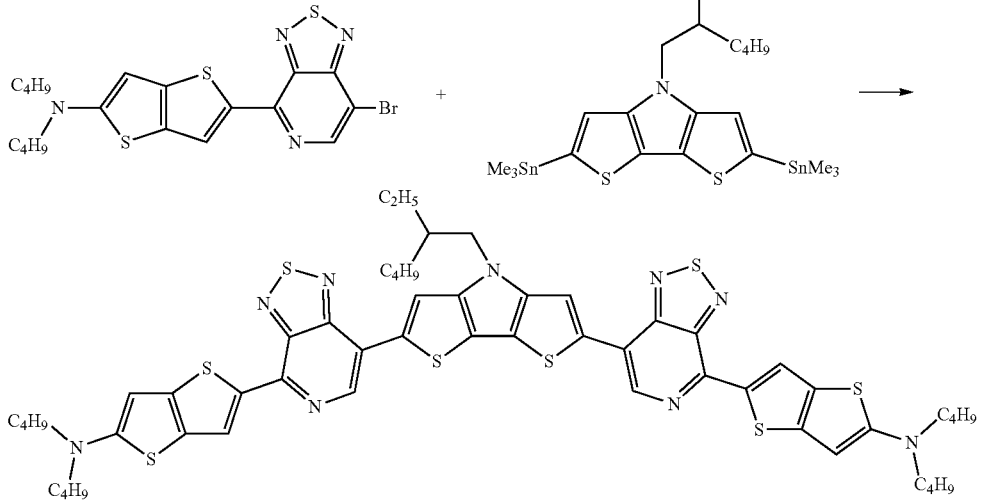

[4-(2-ethylhexyl)-6-trimethylstannyl-dithieno[4,2-c:2',4'-e]pyrrol-2-yl]-trimethyl-stannane (0.1 g, 0.11 mmol) and 2-(7-bromo-[1,2,5]thiadiazolo[3,4-c]pyridin-4-yl)-N,N-dibutyl-thieno[3,2-b]thiophen-5-amine (0.13 g, 0.26 mmol) were dissolved in toluene (5 ml), placed under nitrogen and heated to 60° C. Pd(PPh$_3$)$_2$Cl$_2$ (3 mg) was added and the reaction was refluxed overnight. After purification by column chromatography (silica gel; DCM/ethyl acetate: 2:1), a blue solid (0.085 g, 0.08 mmol, HPLC: 98.9%) can be isolated in 70% yield.

EI-MS: m/z: 1091.3. UV-VIS (THF): 281, 405, 723 nm.

The following compounds are made analogously:

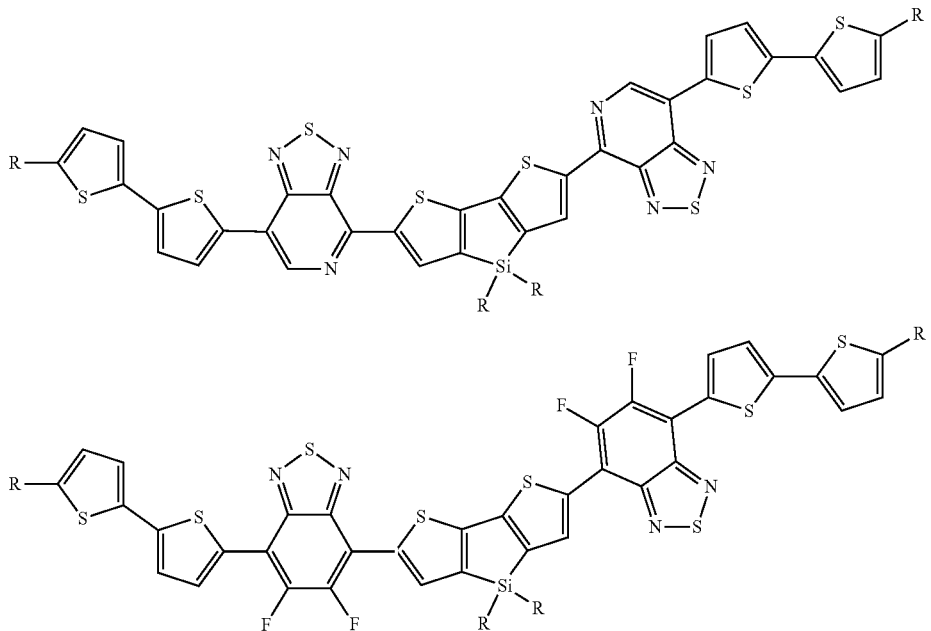

-continued
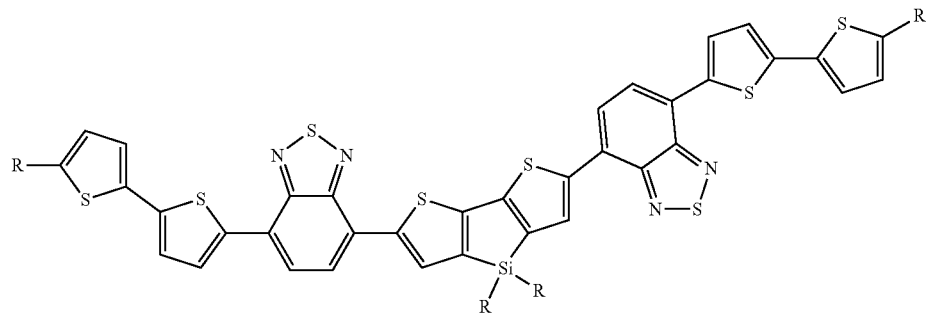
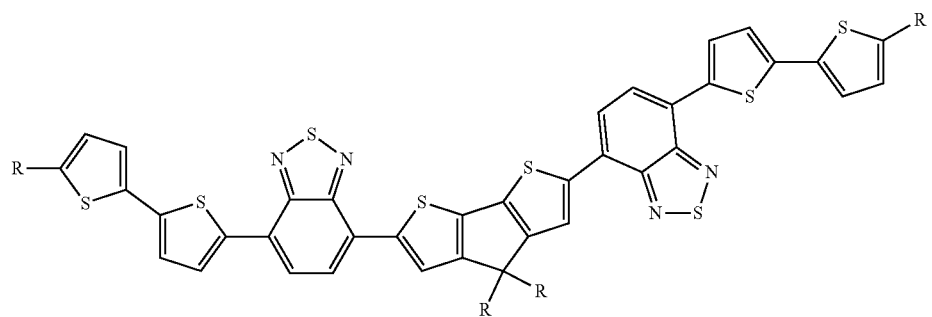
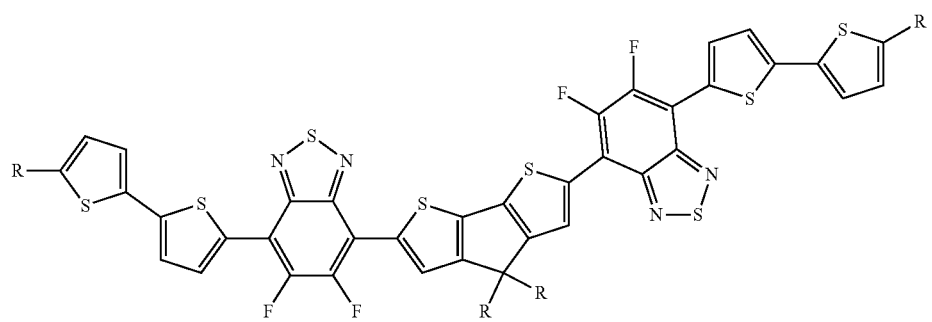
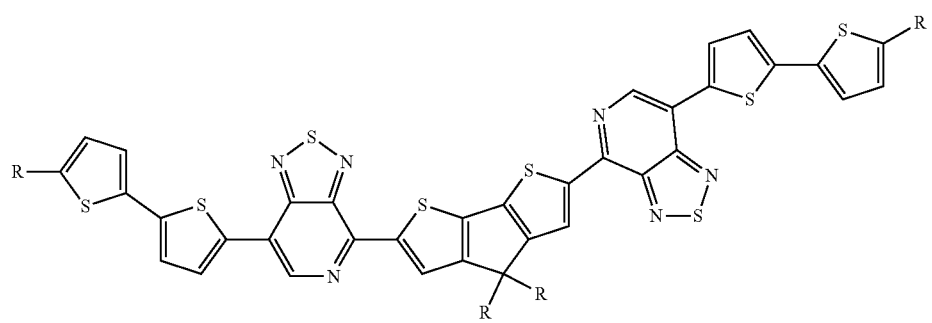
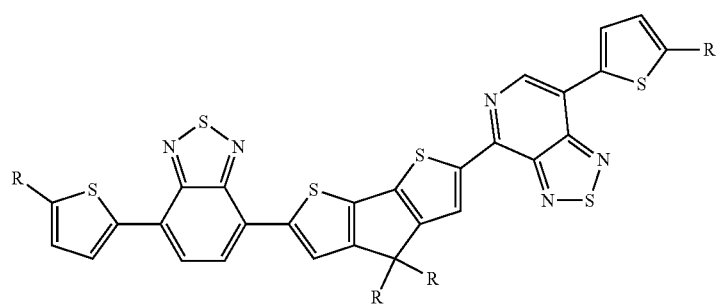

-continued
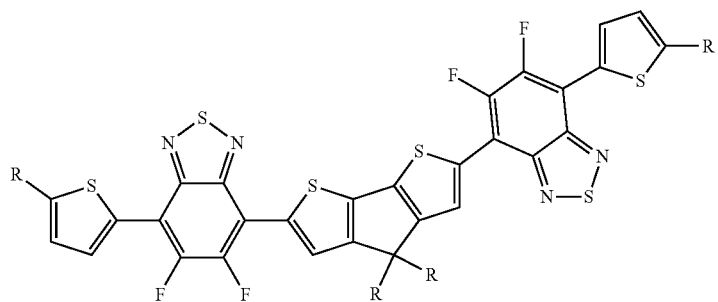
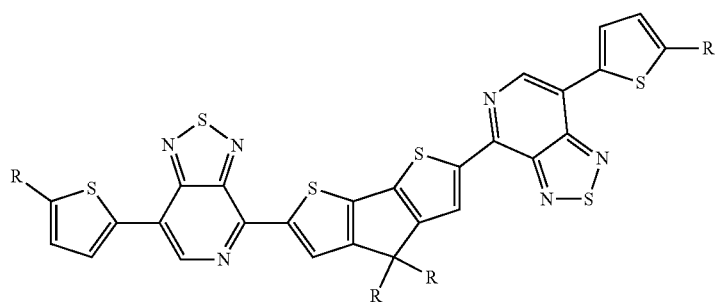
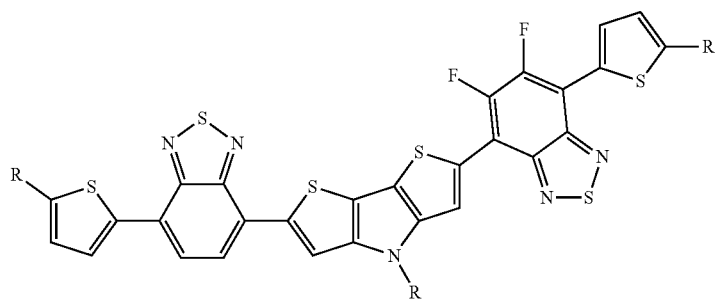
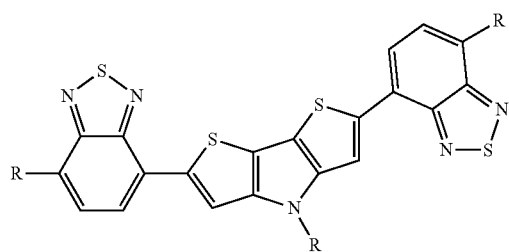
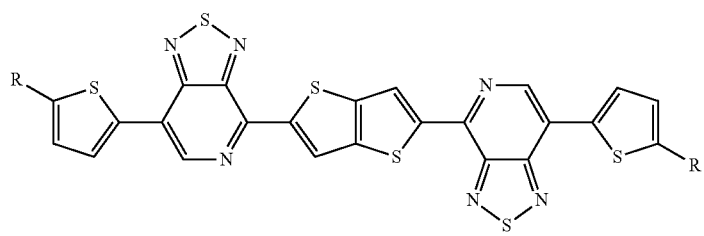
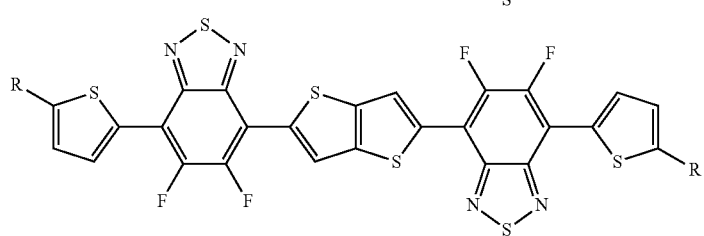

-continued
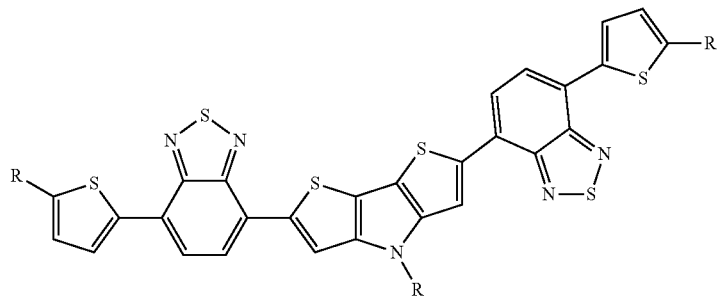
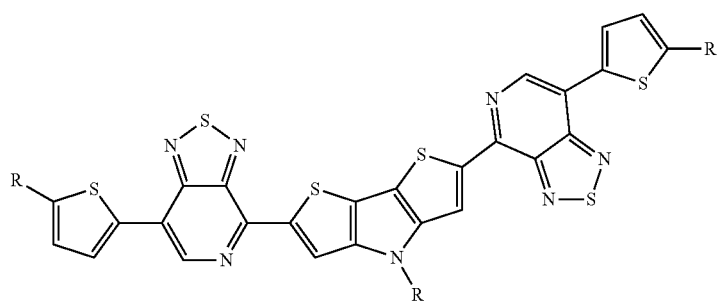
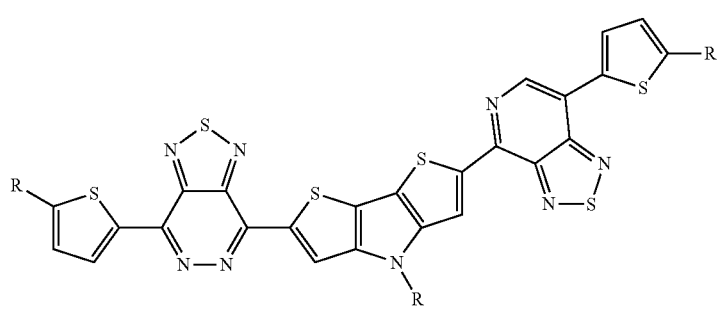
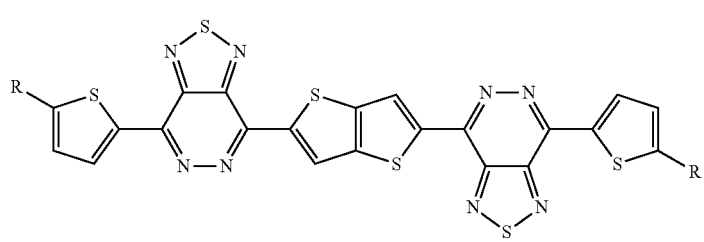
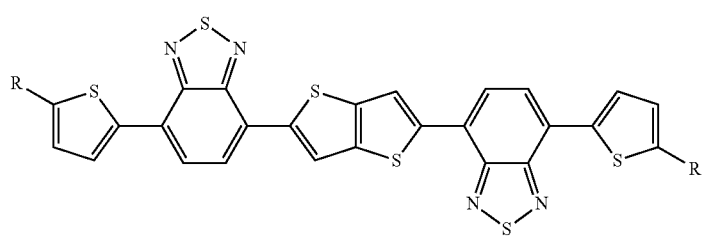
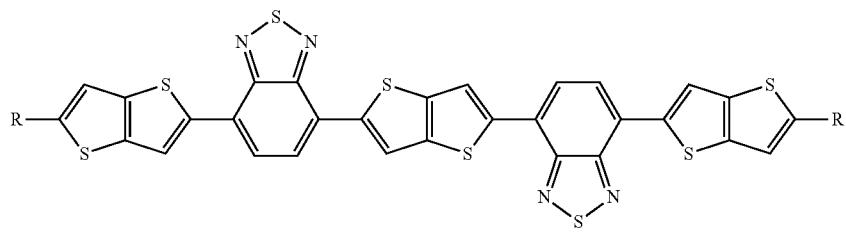

-continued
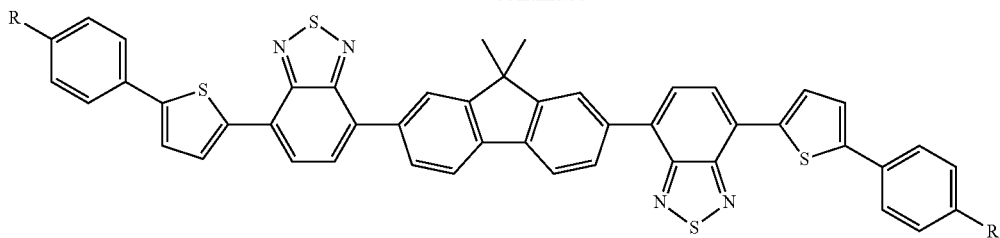
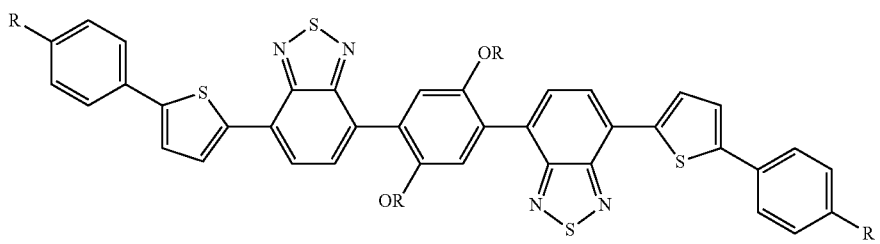
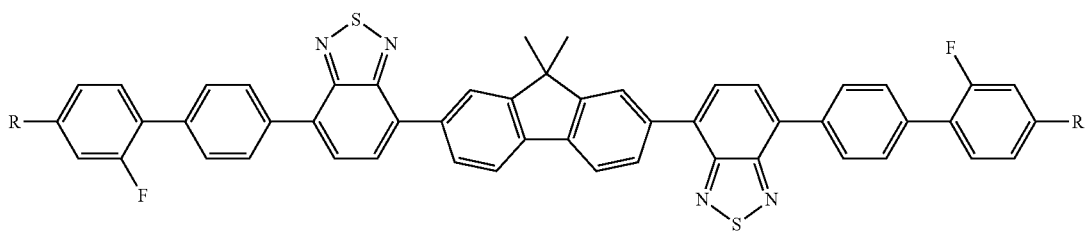
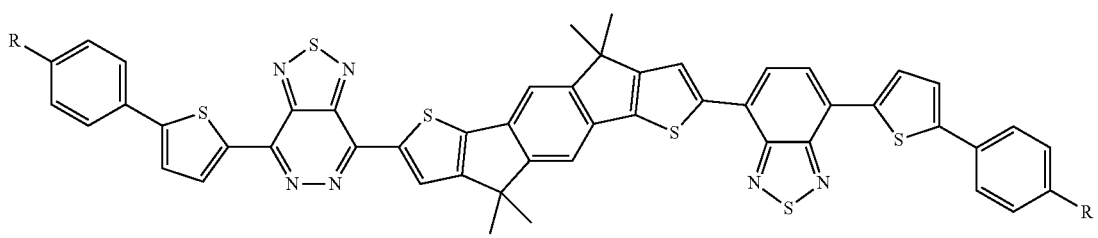
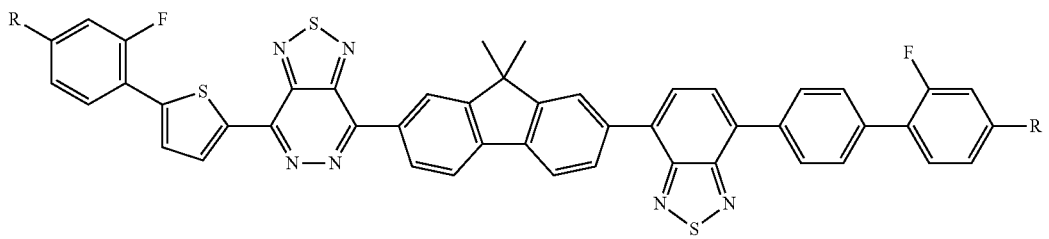
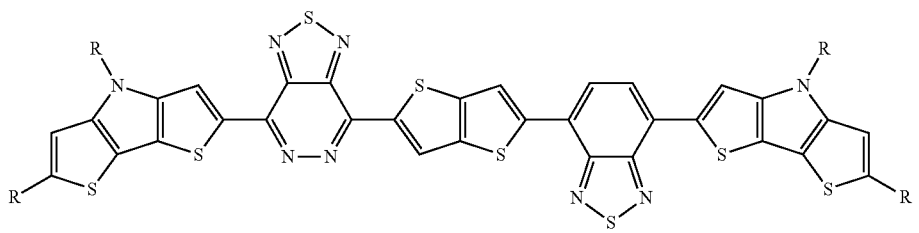
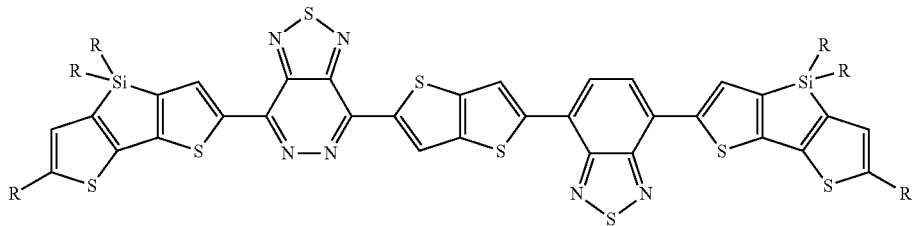

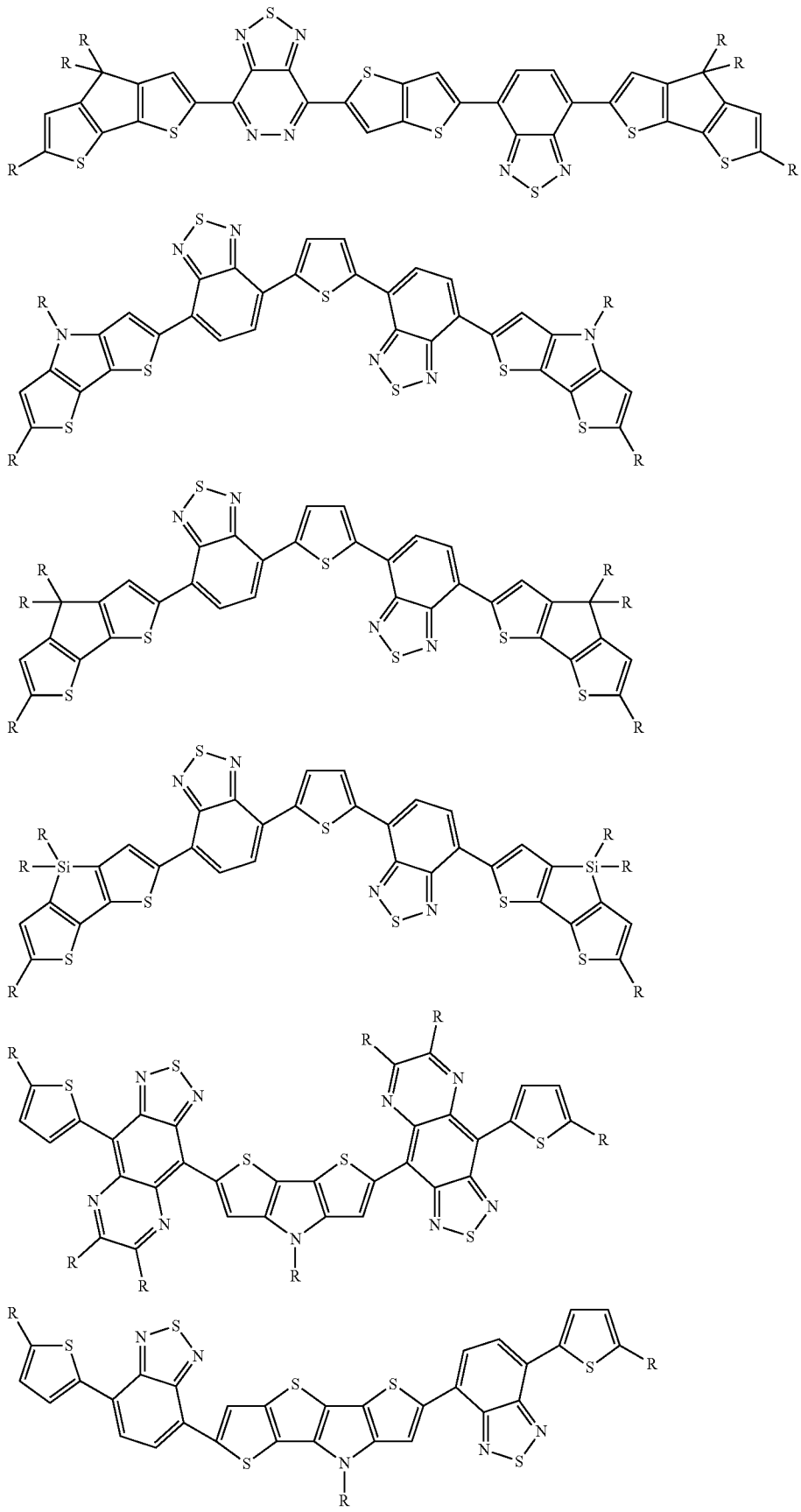

-continued
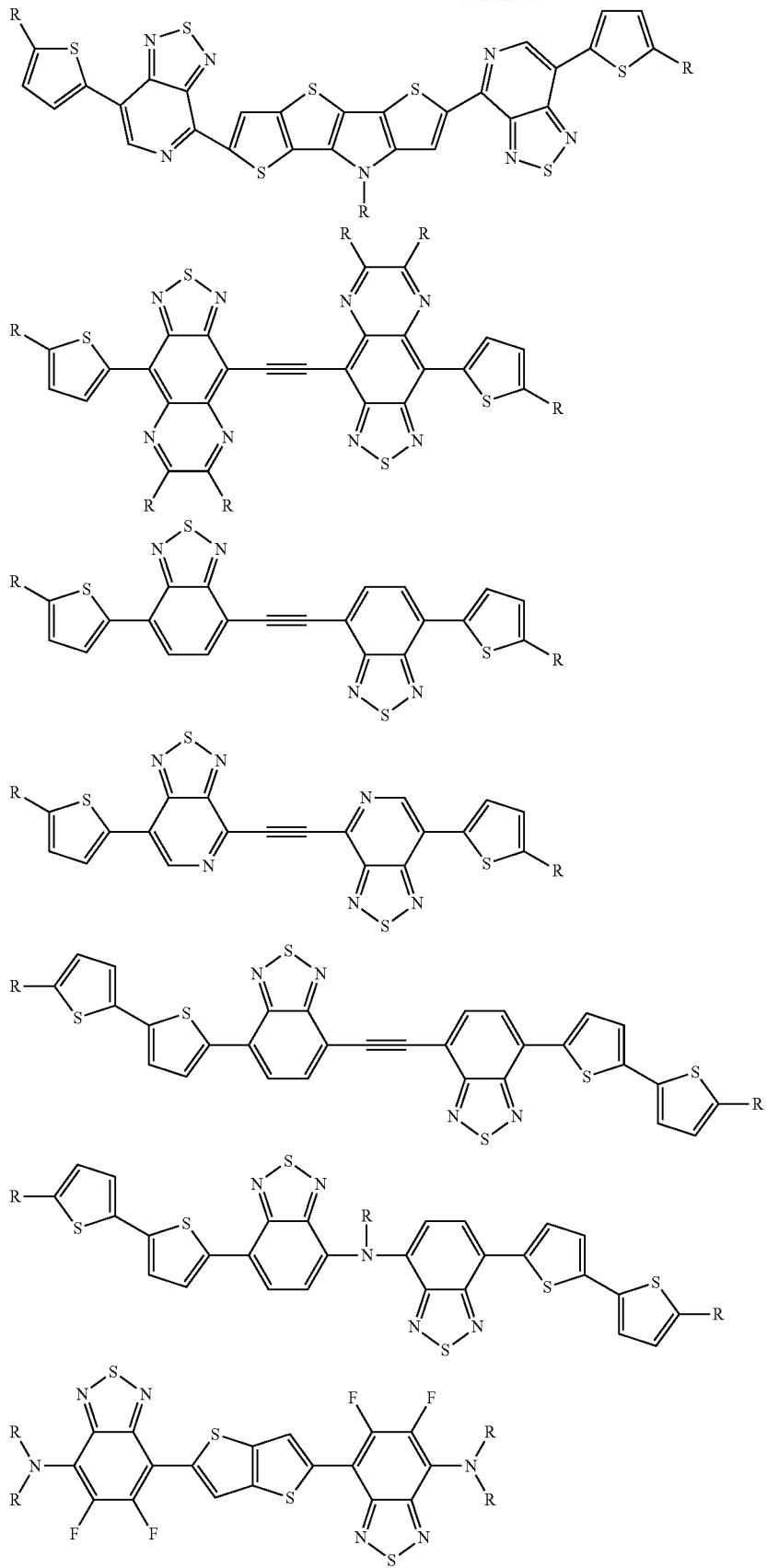

wherein
R denotes branched or linear alkyl with 1 to 12 C-atoms, preferably ethyl, n-propyl, iso-propyl, n-butyl, pentyl, hexyl or 3-ethylheptyl.
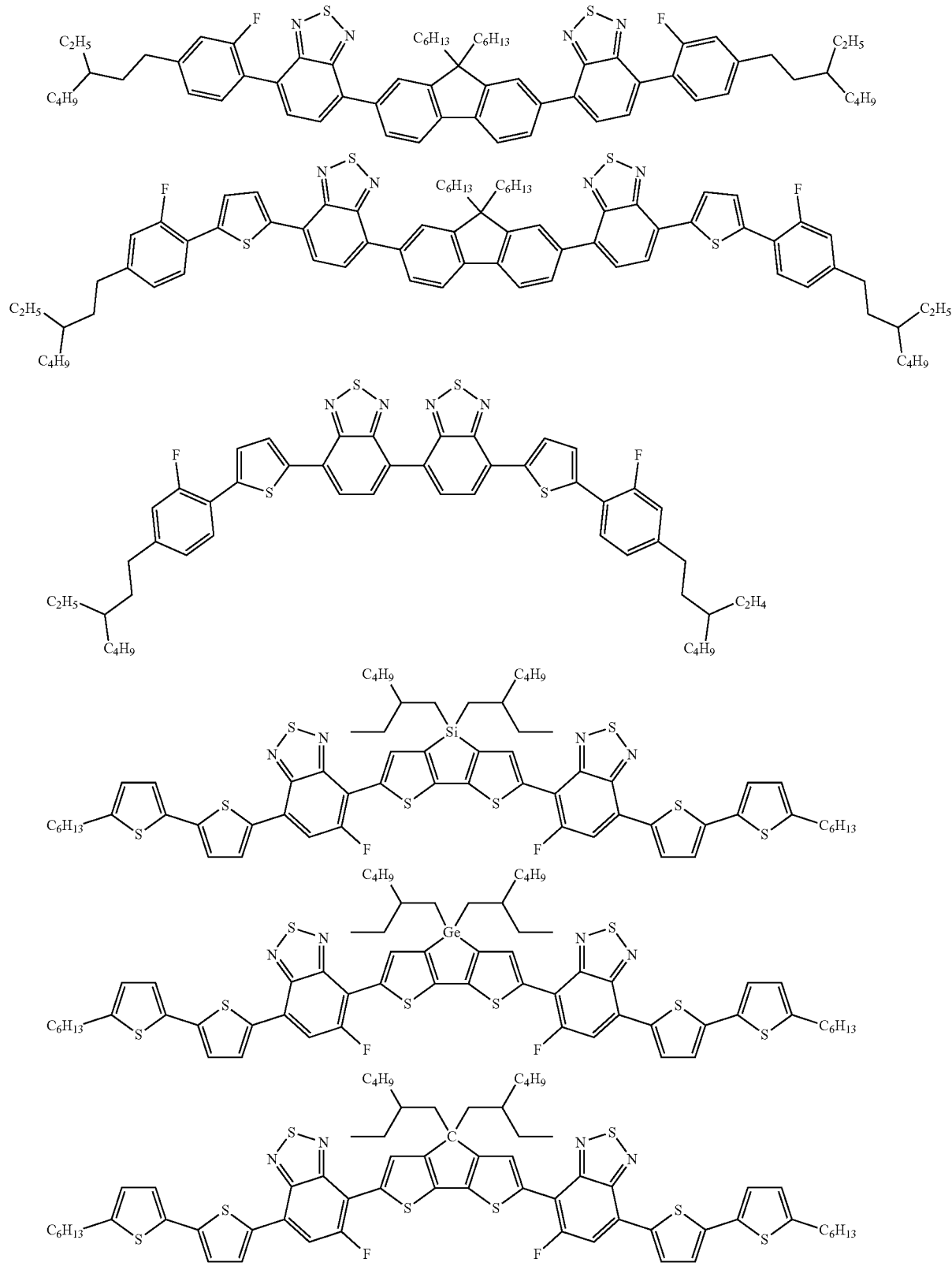

-continued
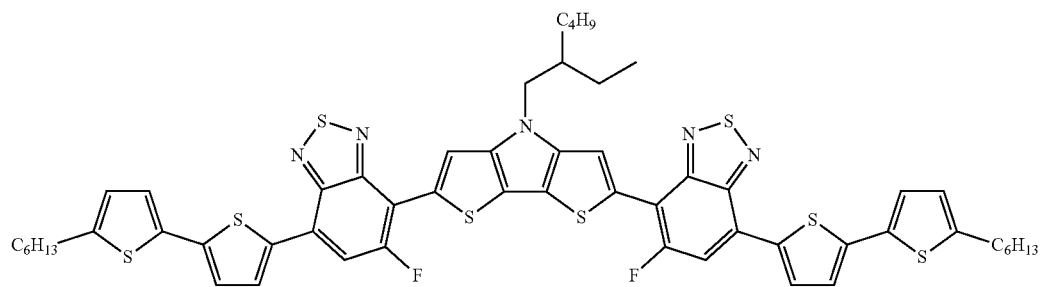
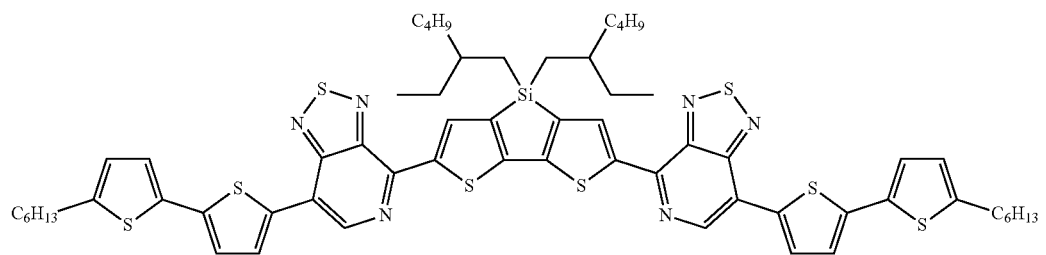
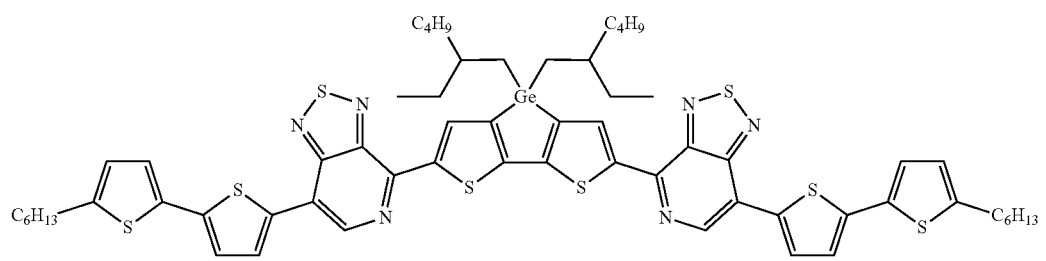
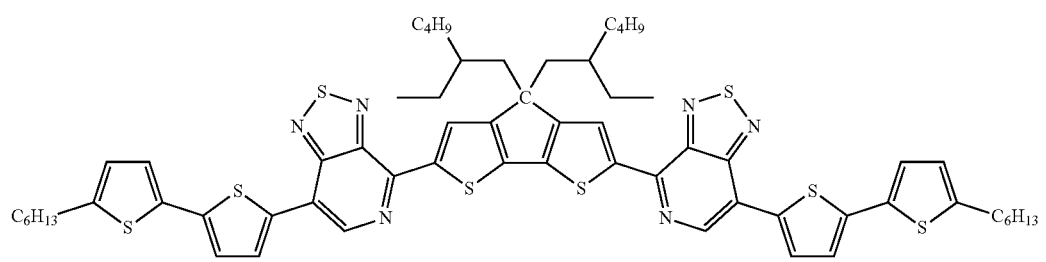
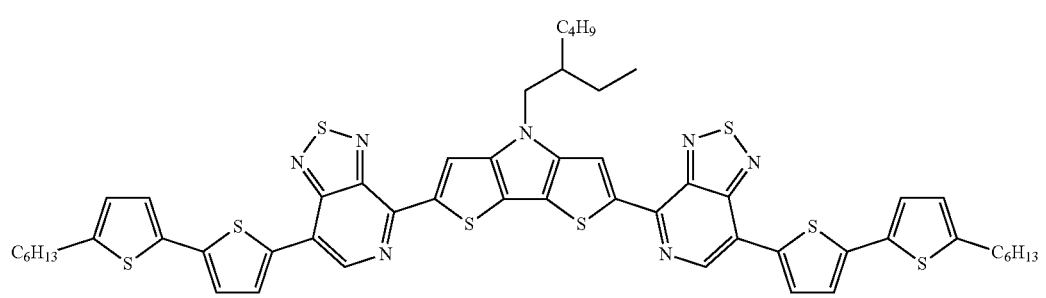
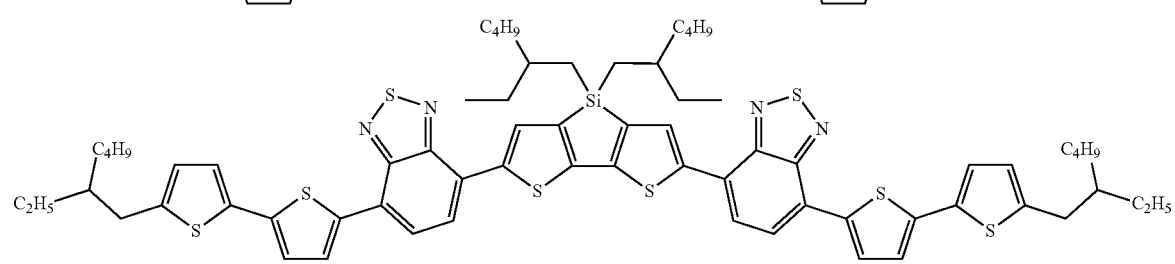

-continued
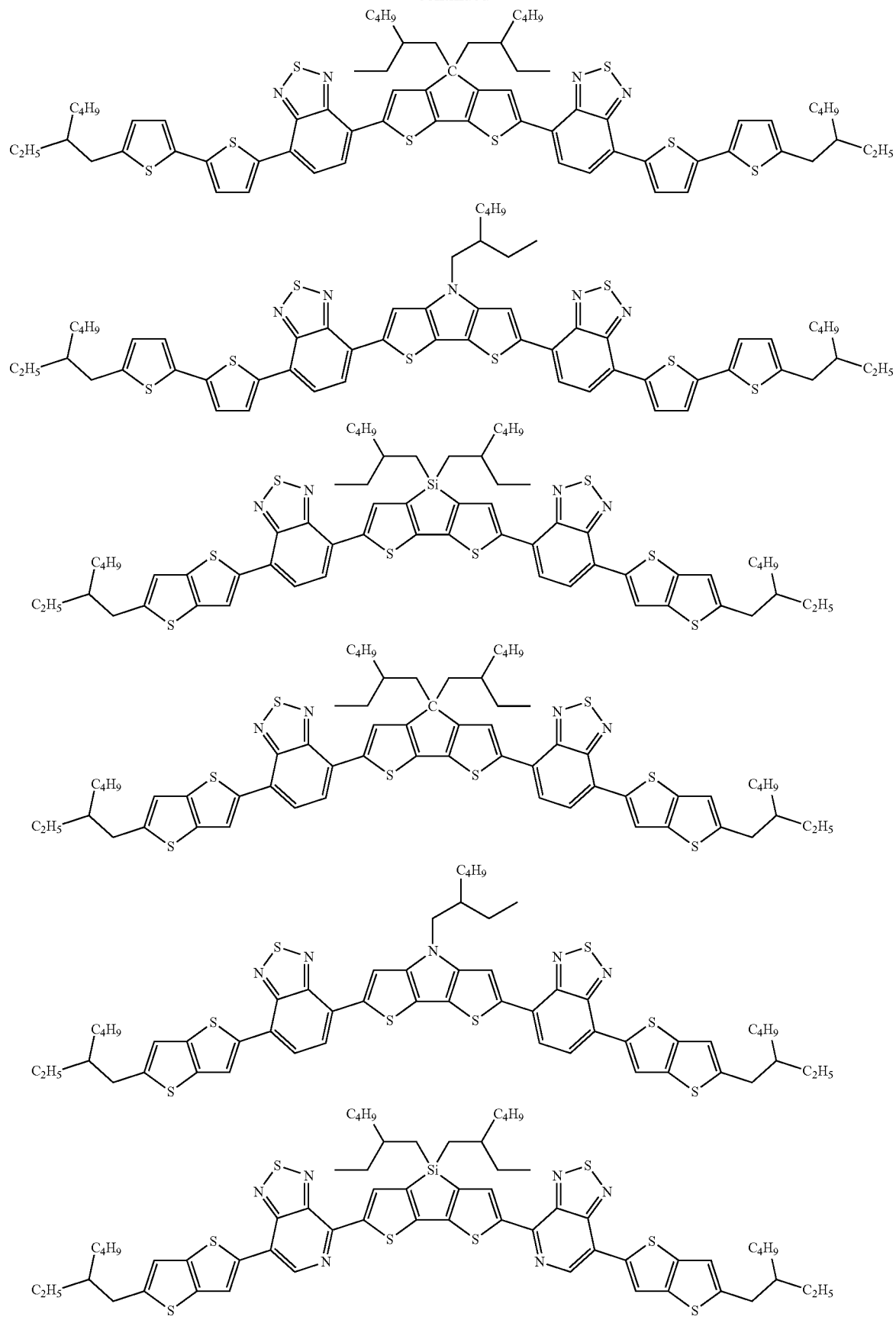

-continued
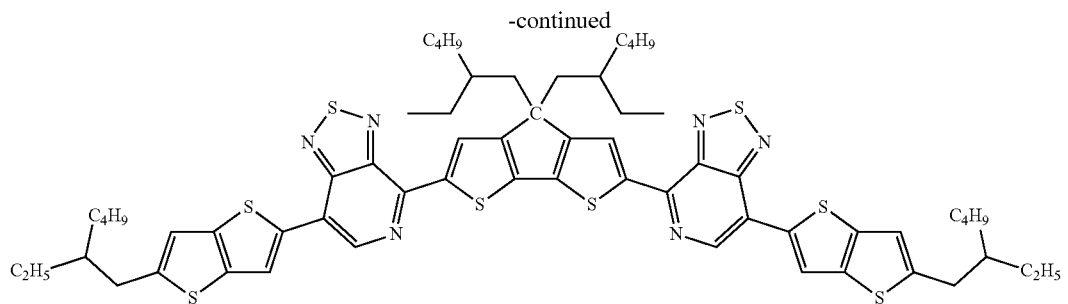
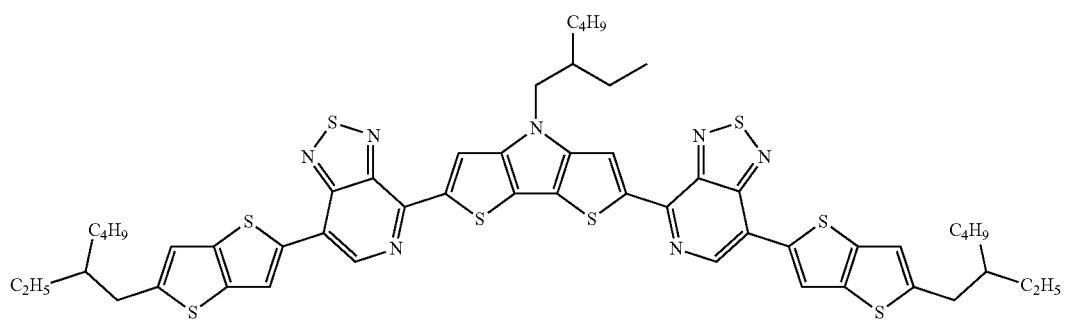
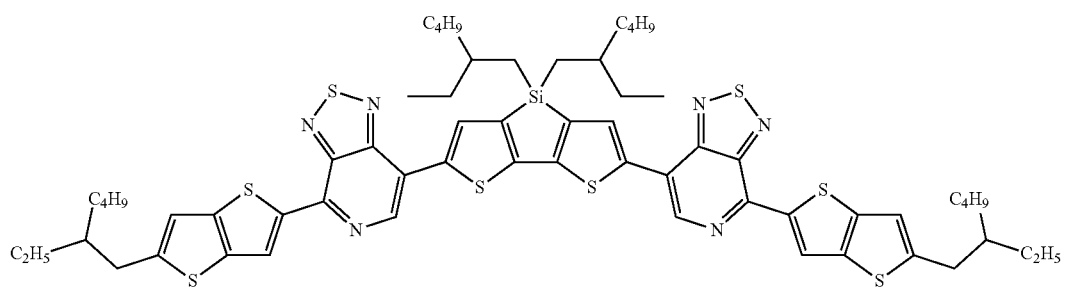
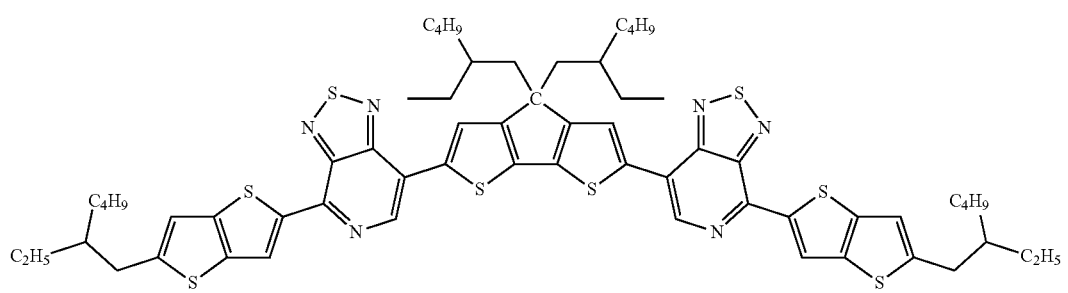
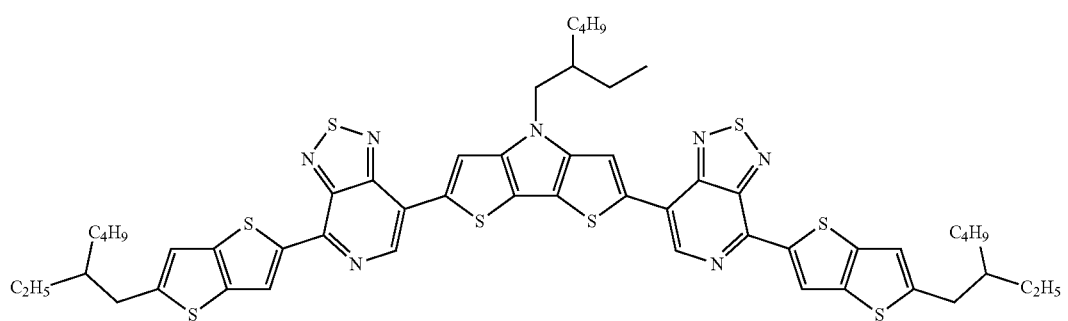

-continued
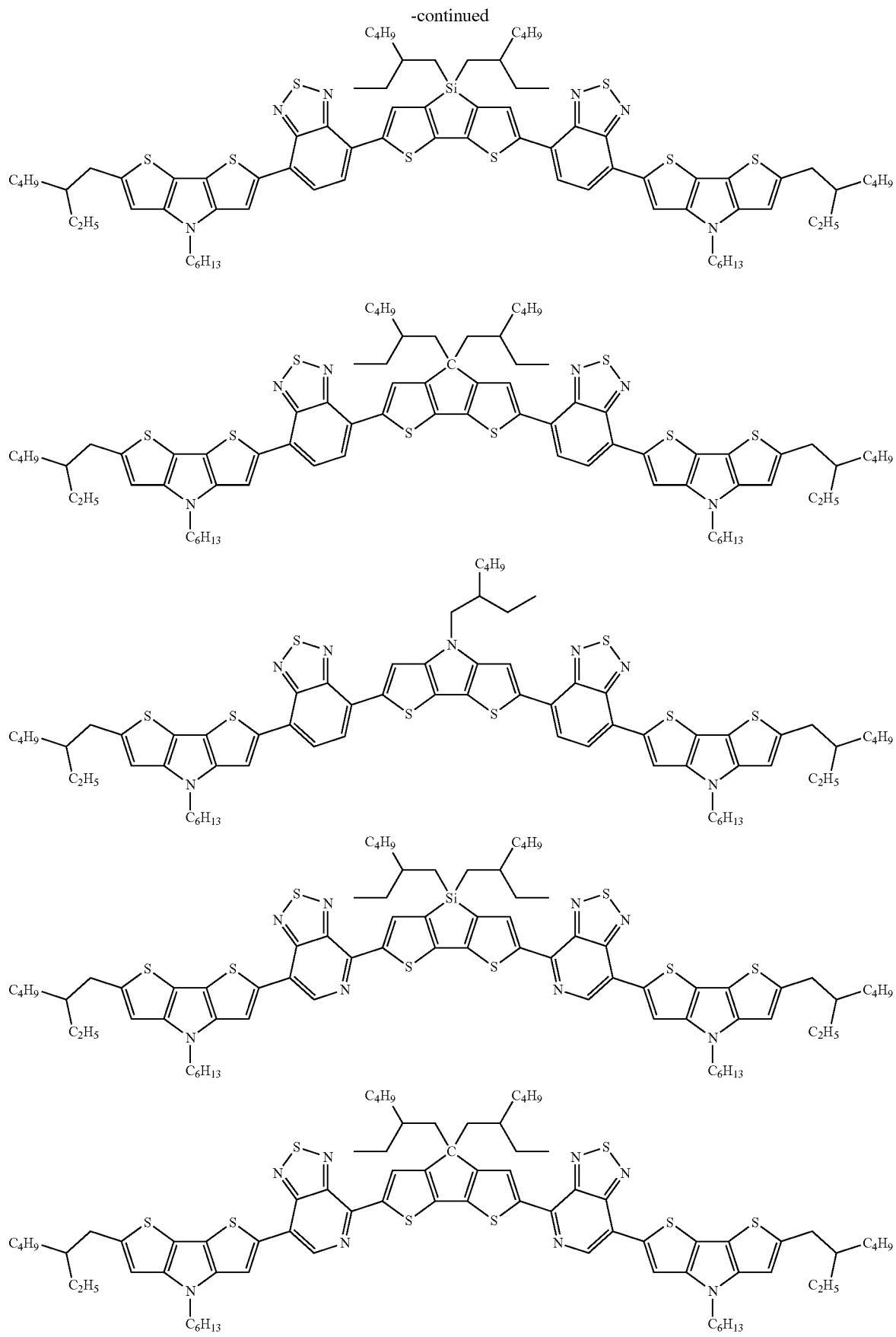

-continued
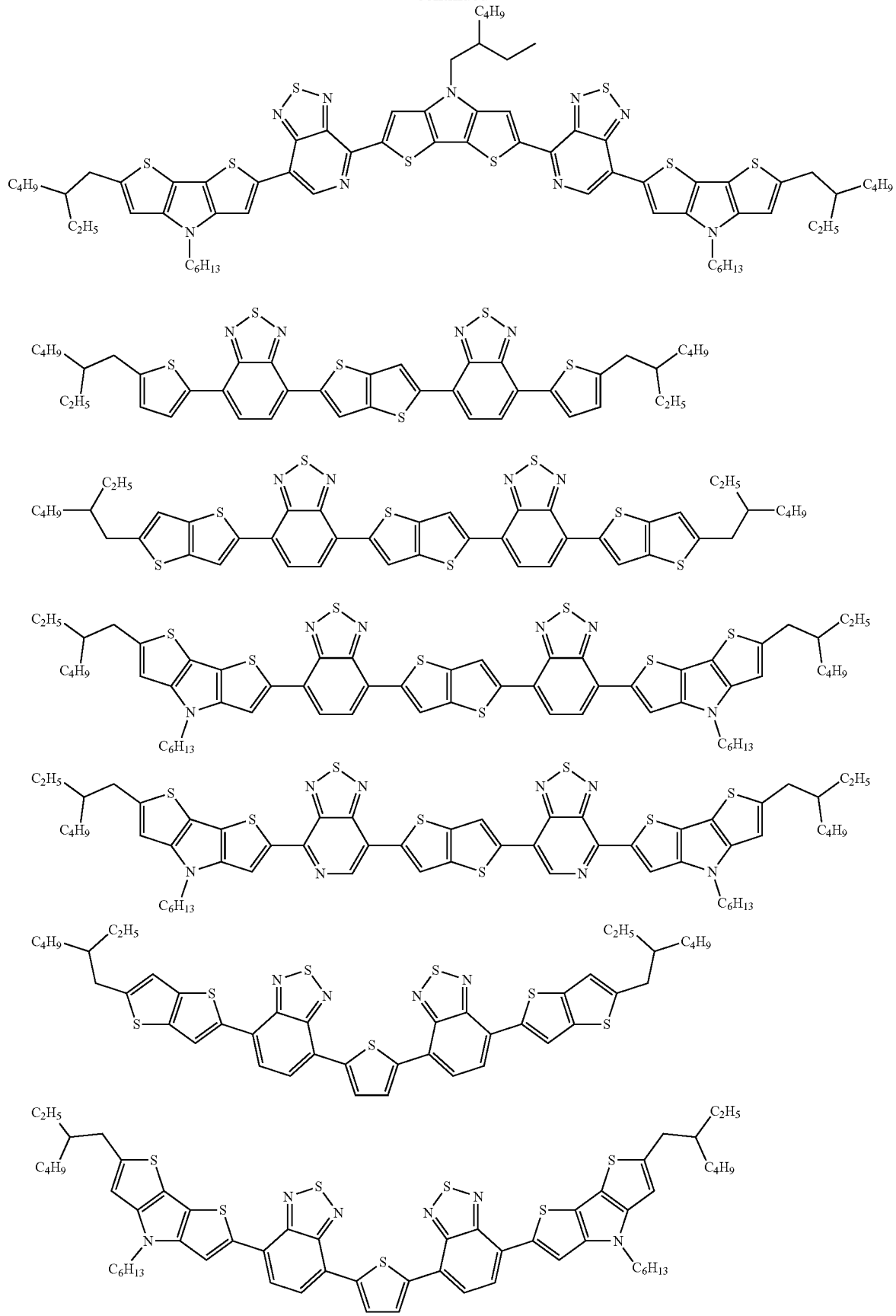

-continued
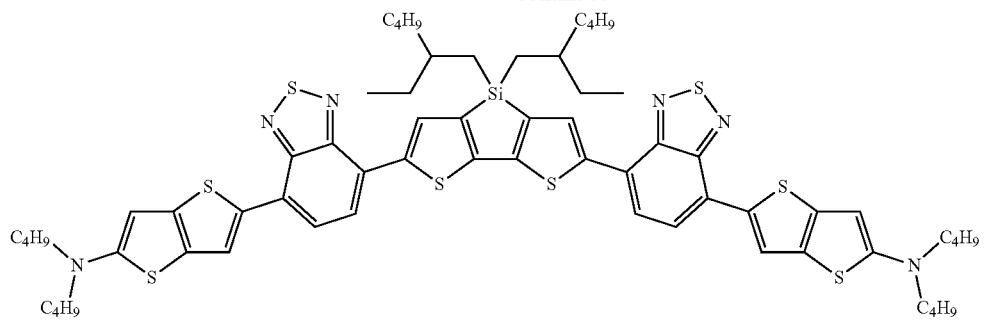
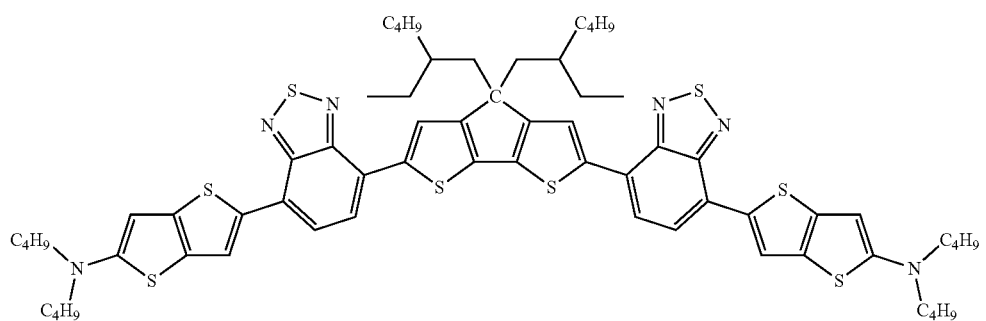
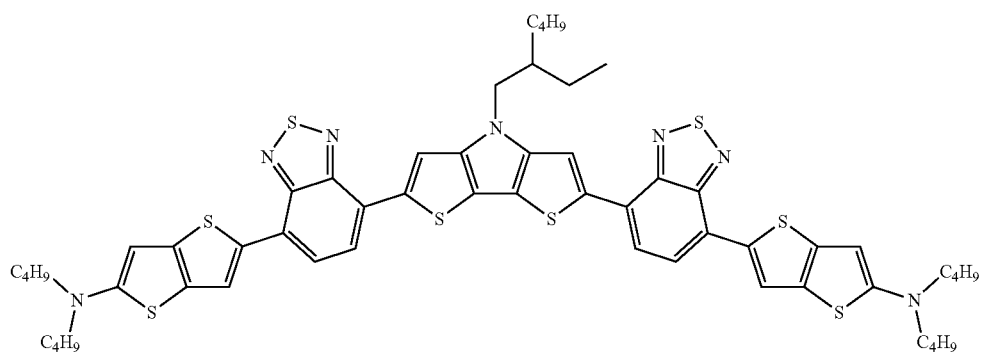
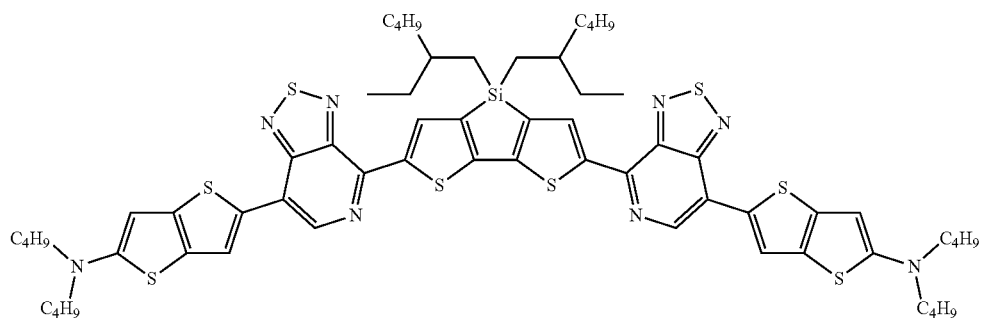
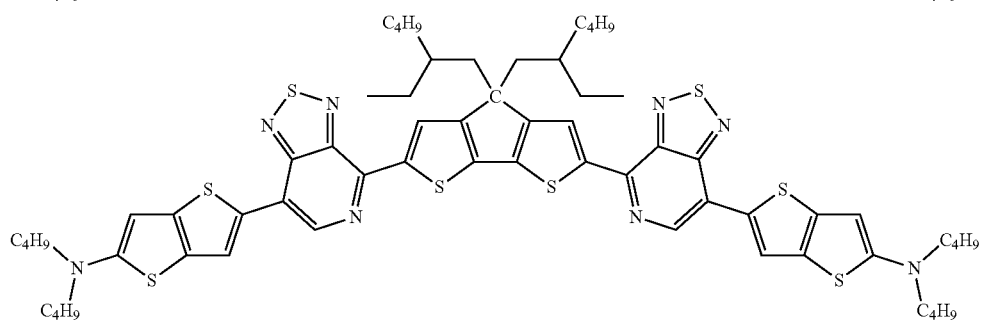

-continued
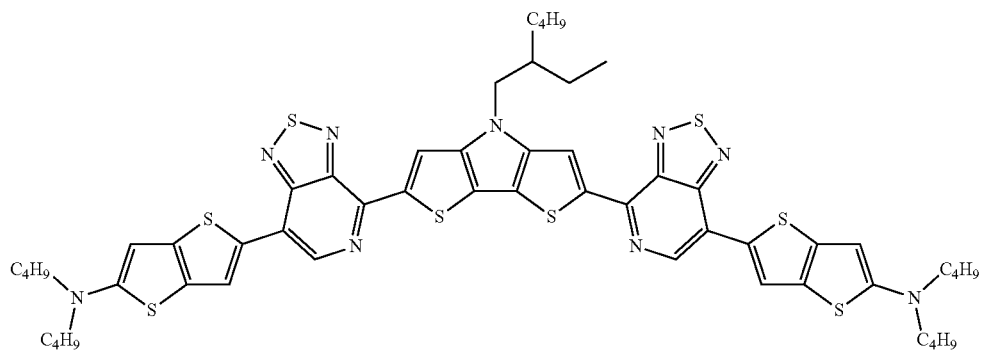
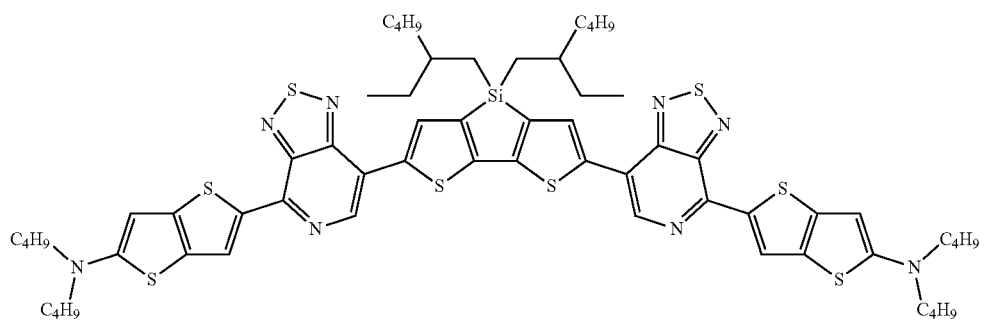
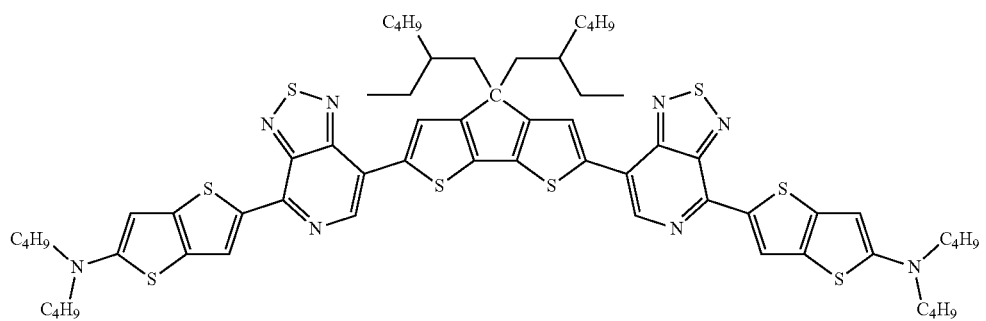
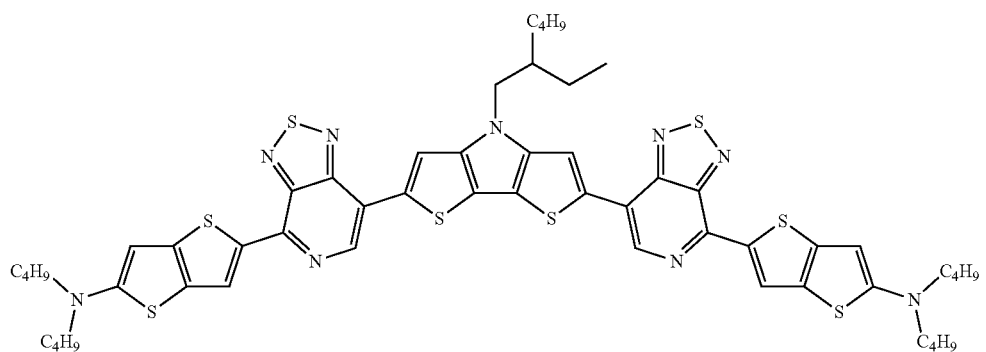
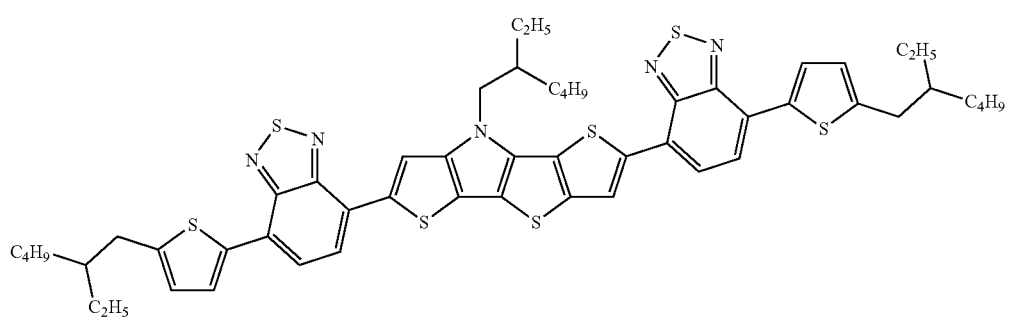

-continued
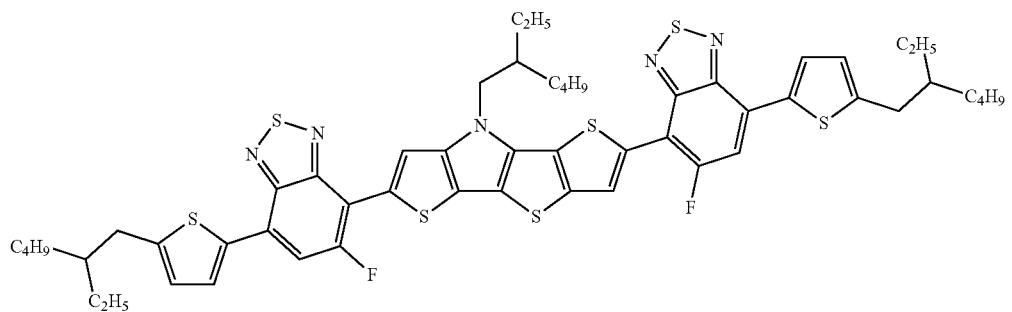
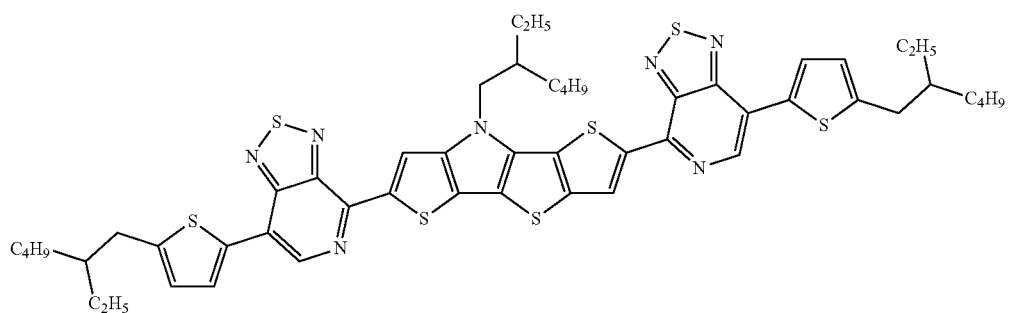
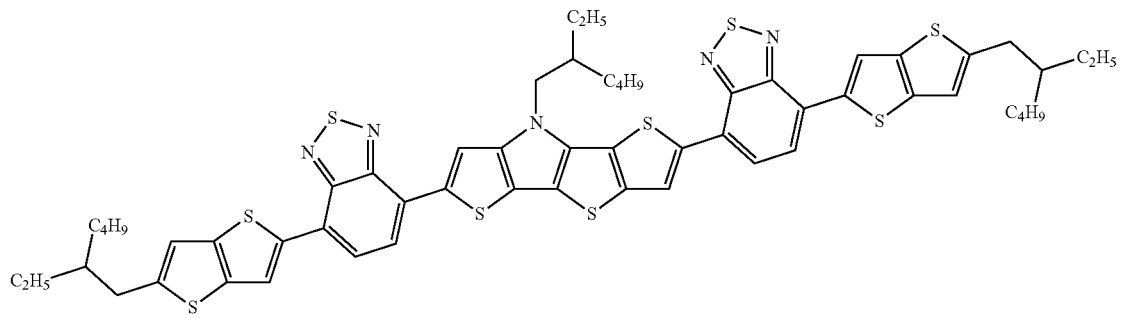
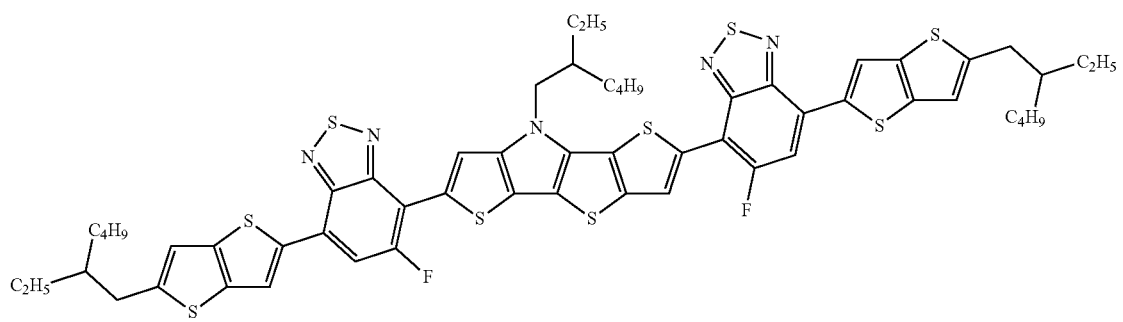
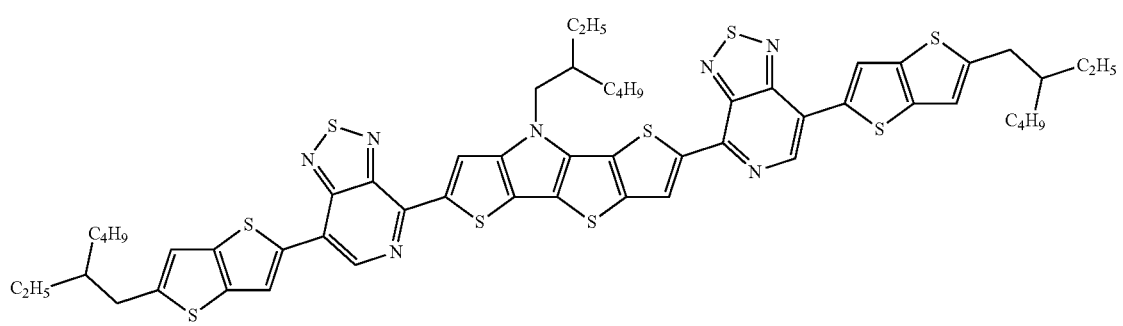

-continued
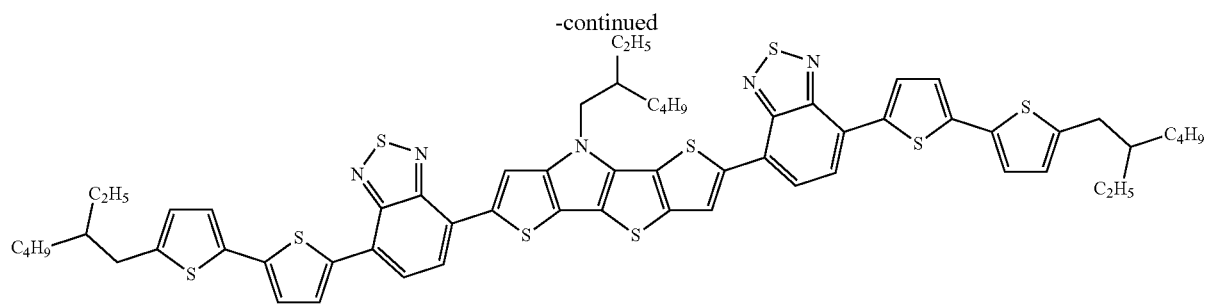
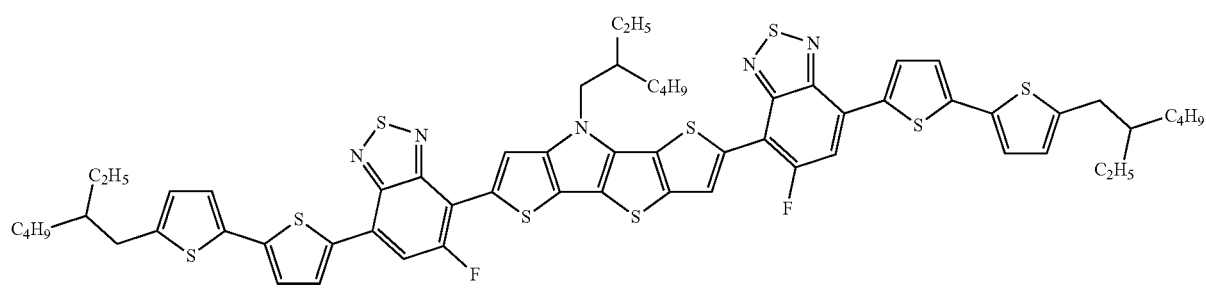
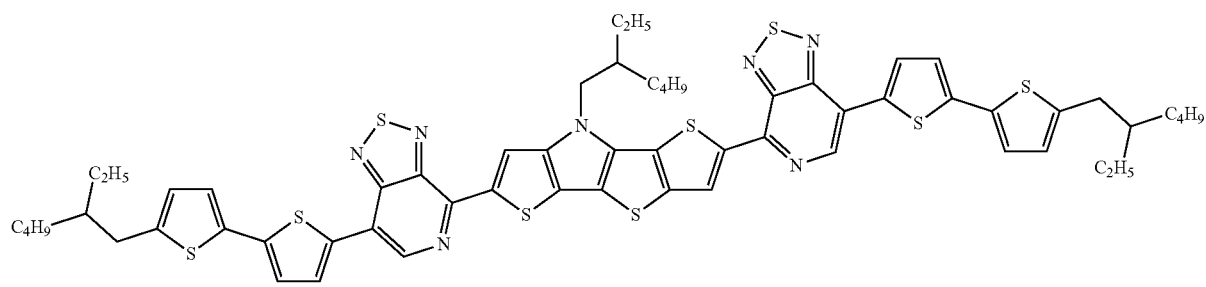
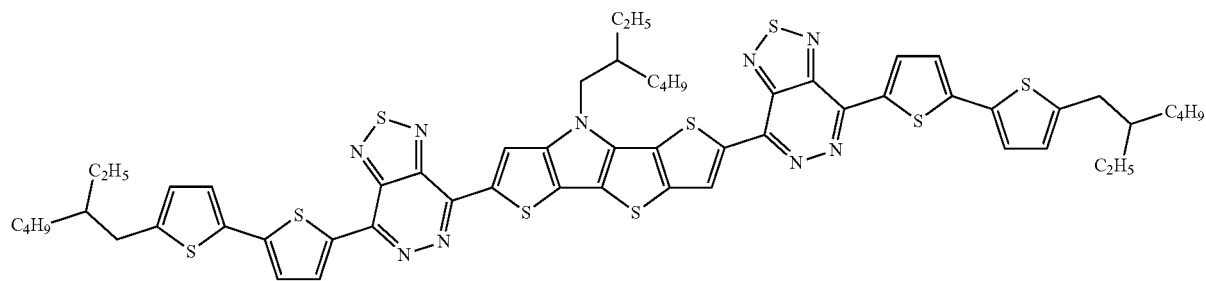
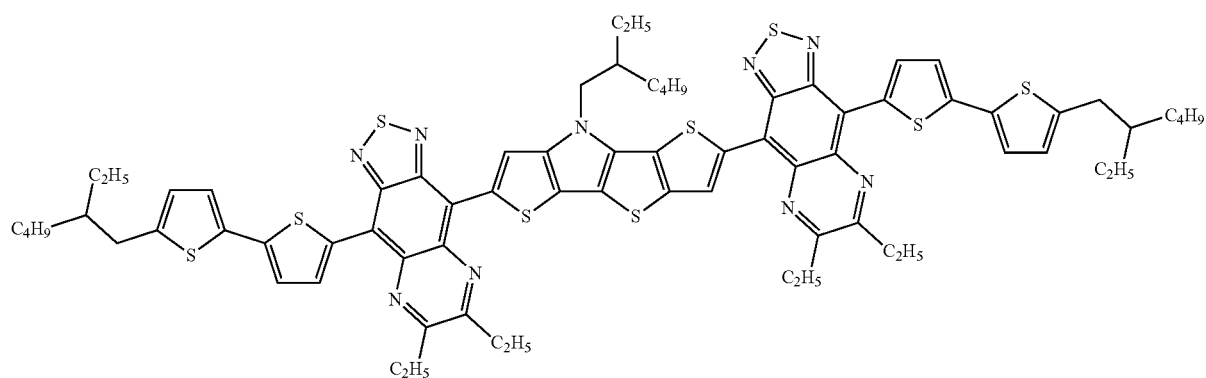

-continued
251 252
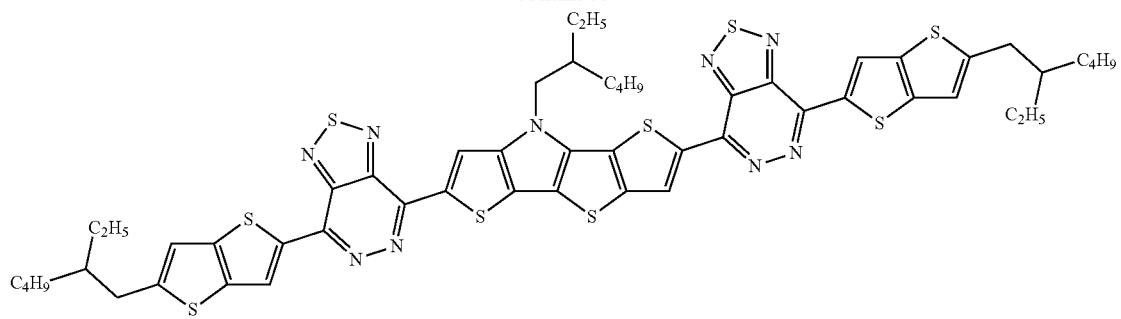
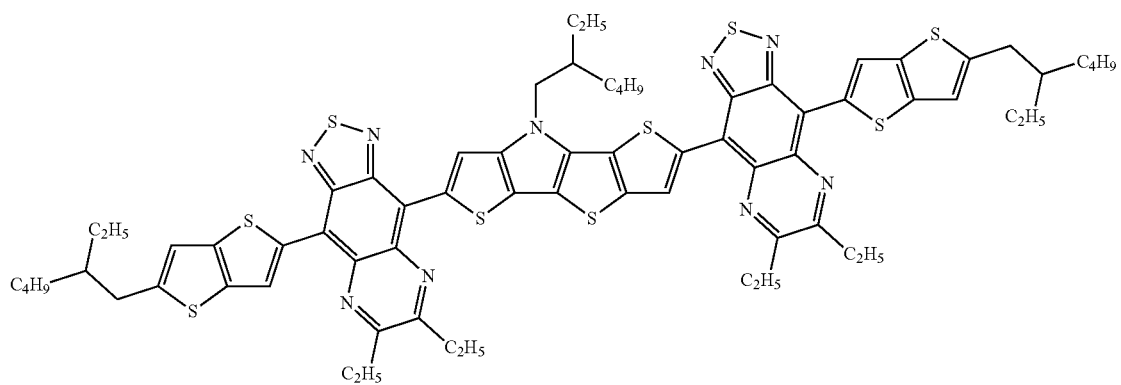
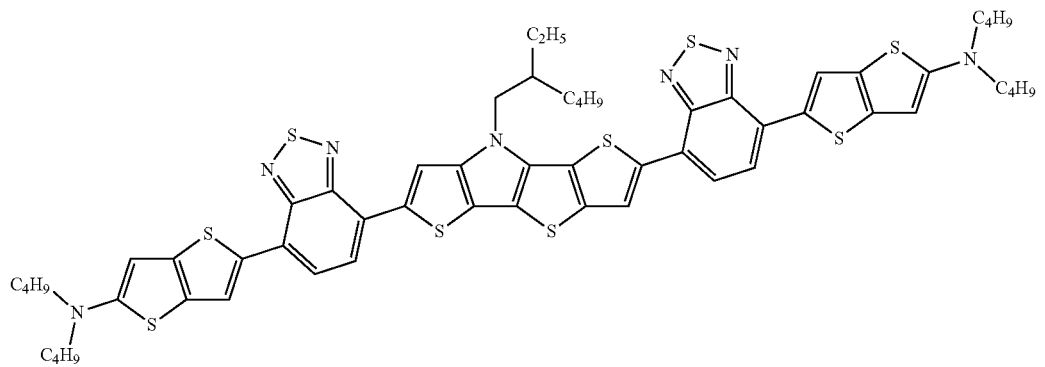
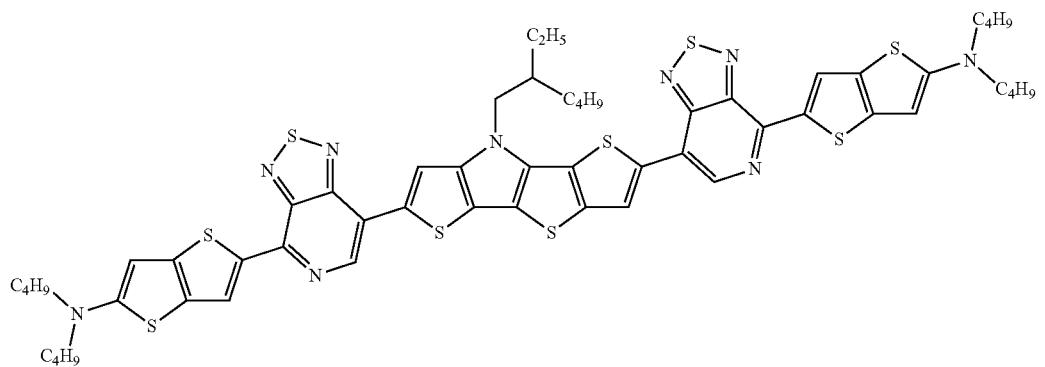

253 254
-continued
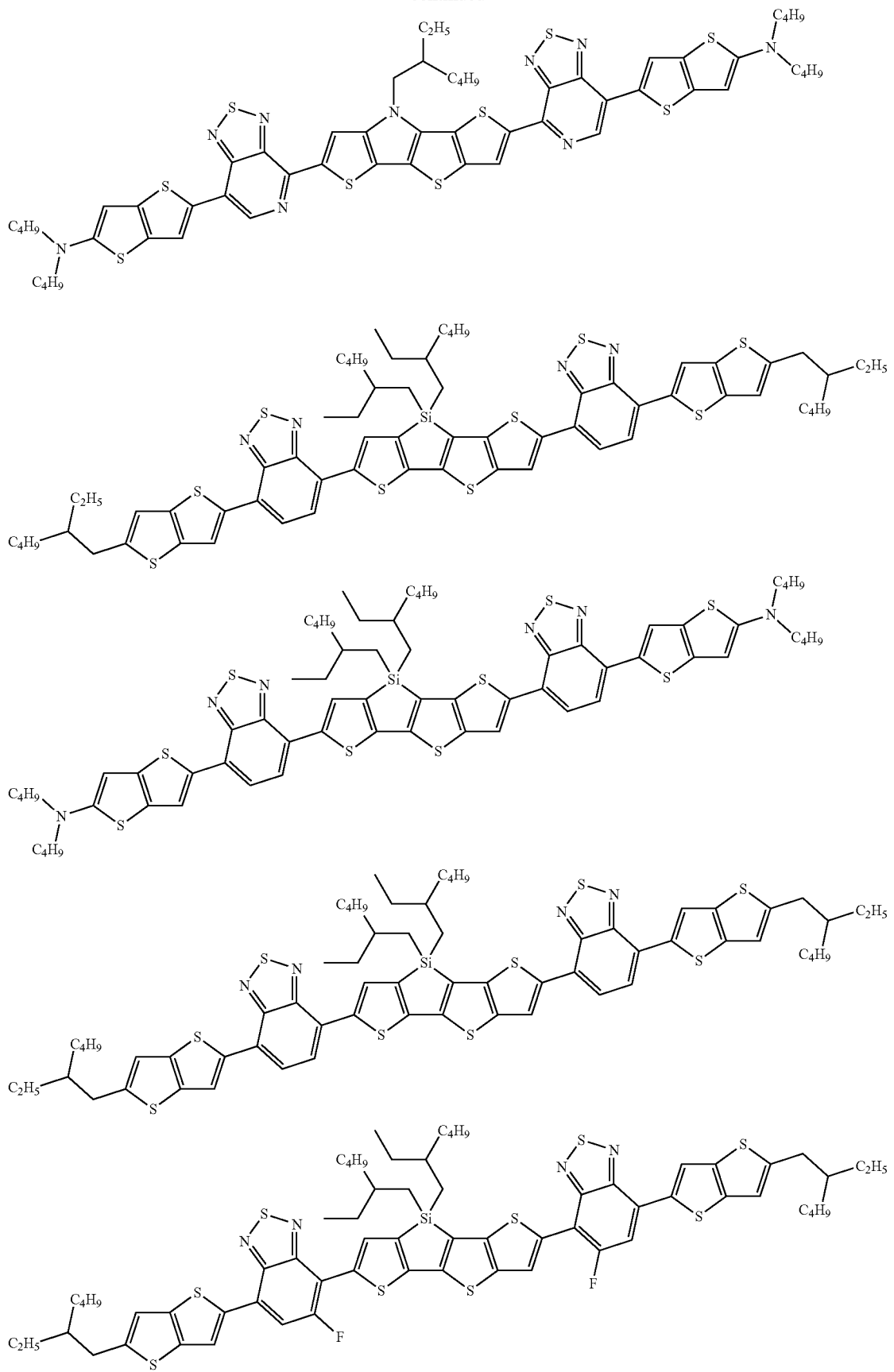

-continued
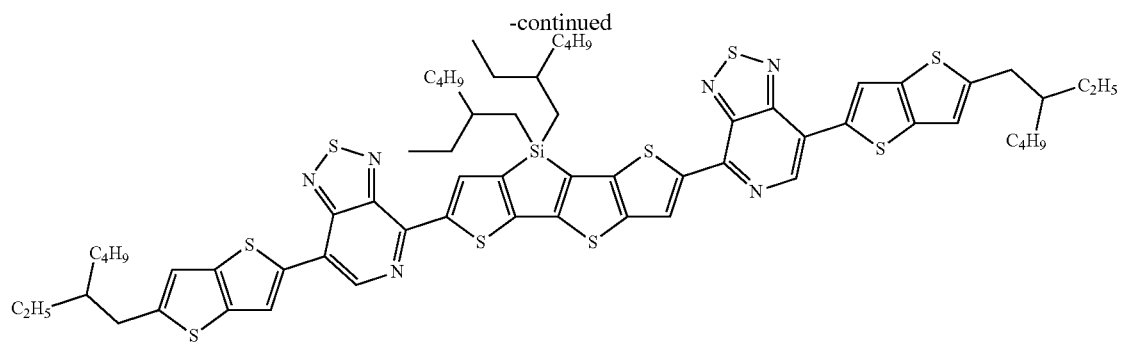
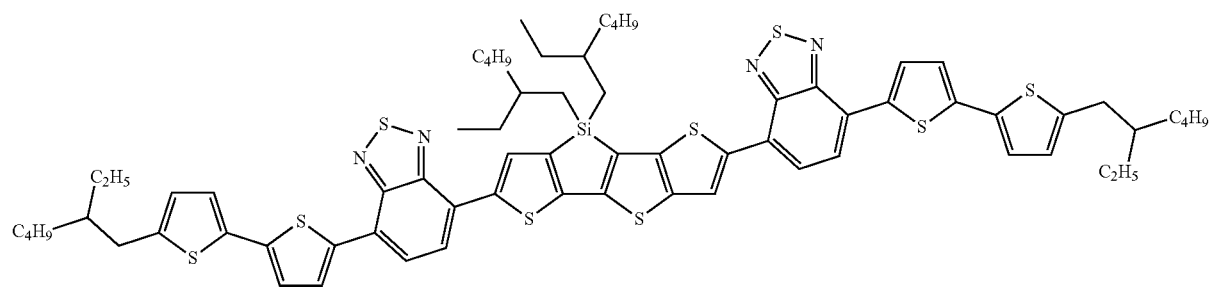
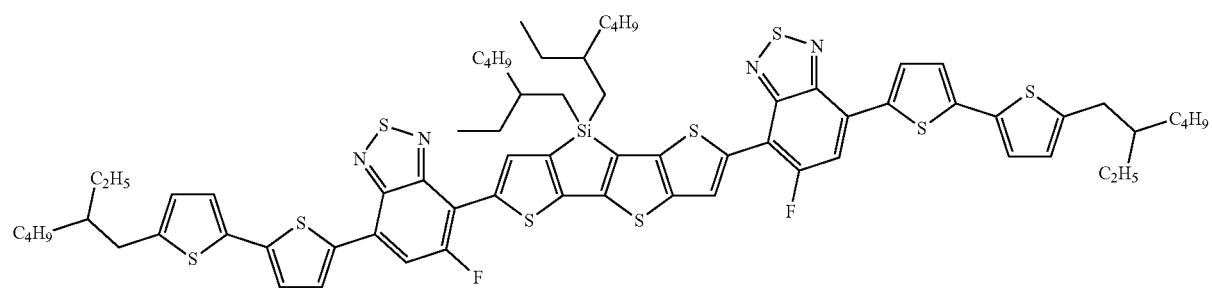
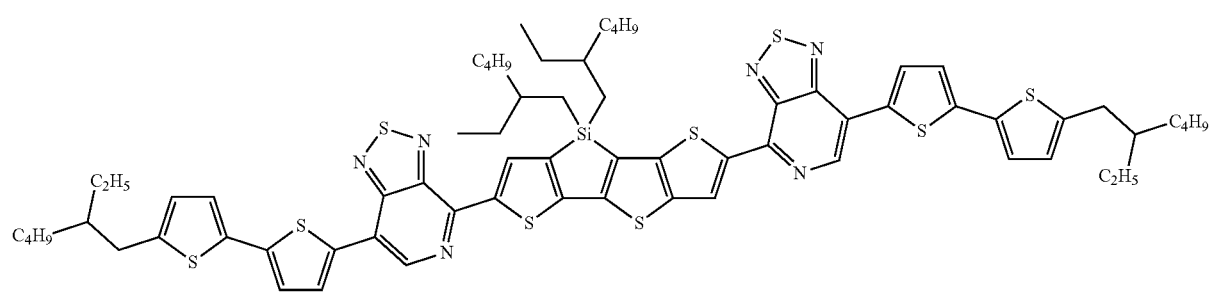
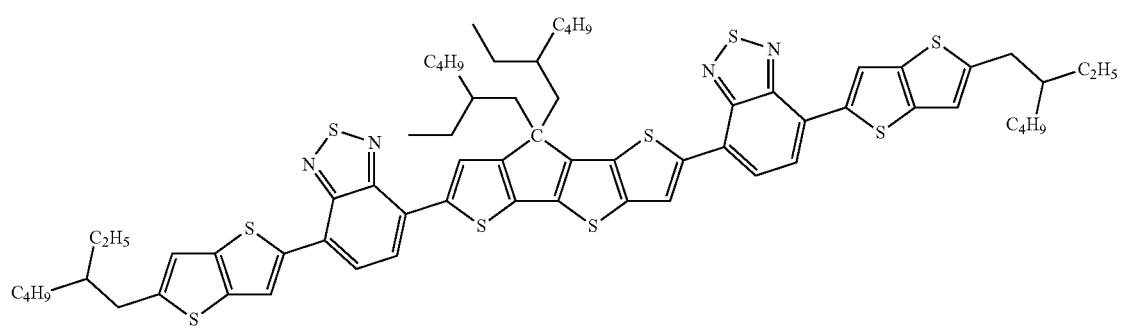

-continued
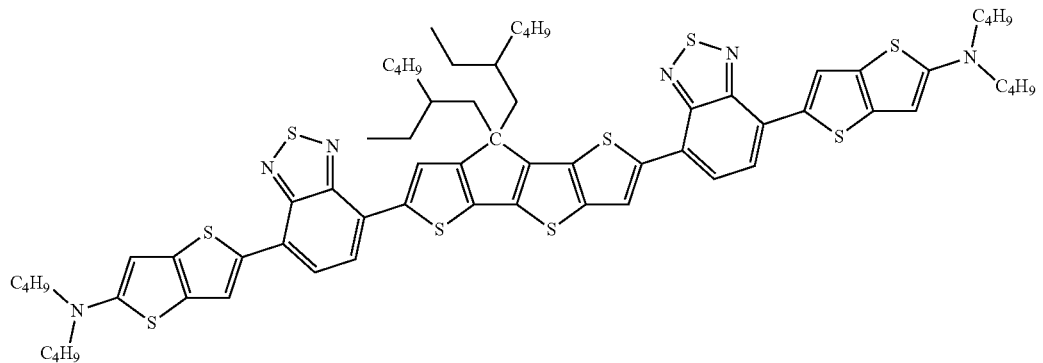
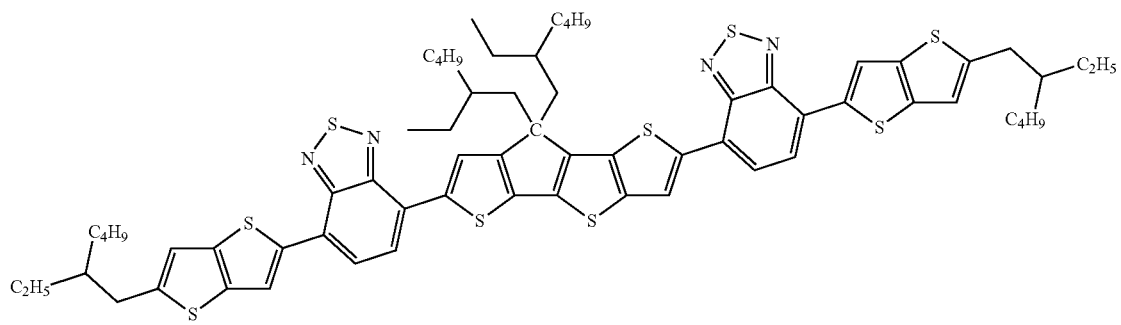
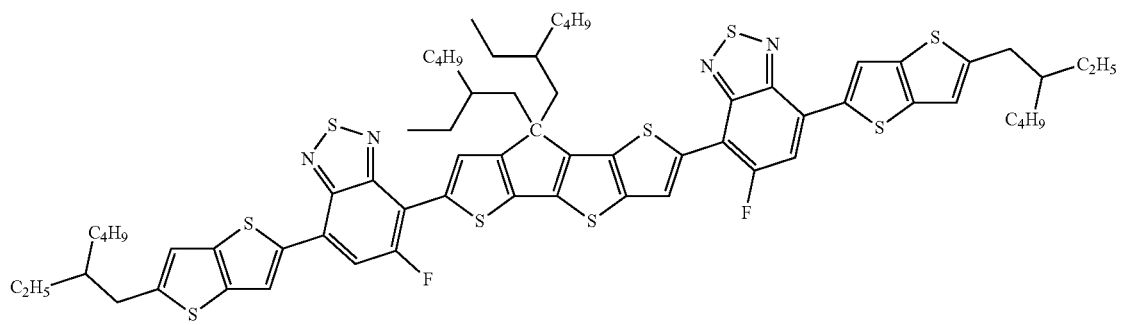
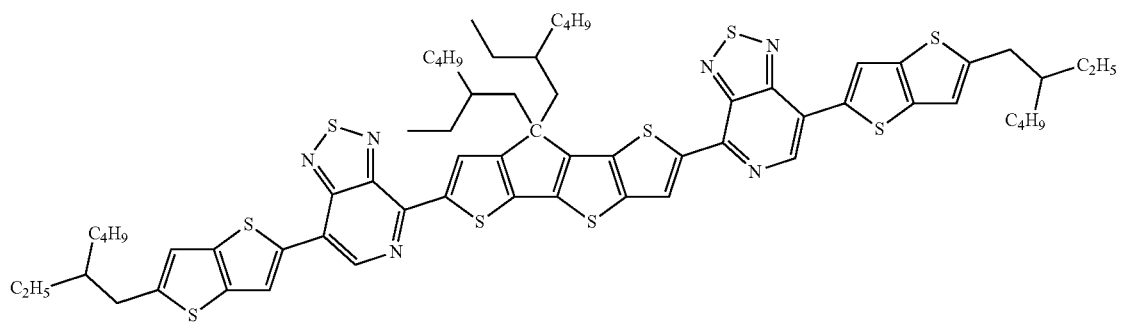
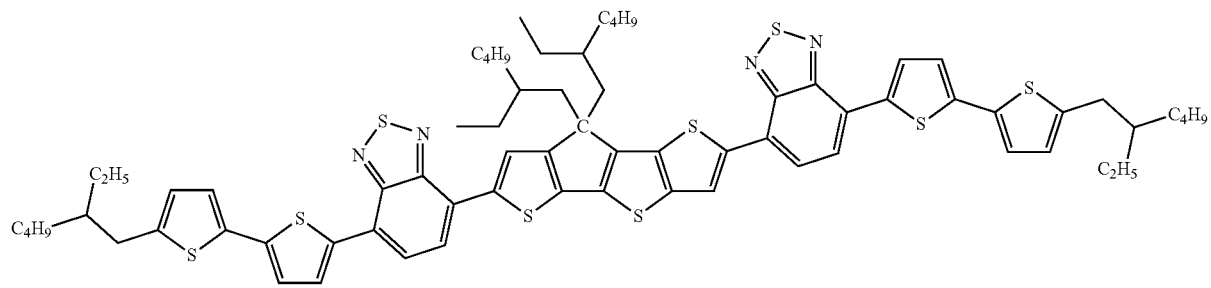

-continued
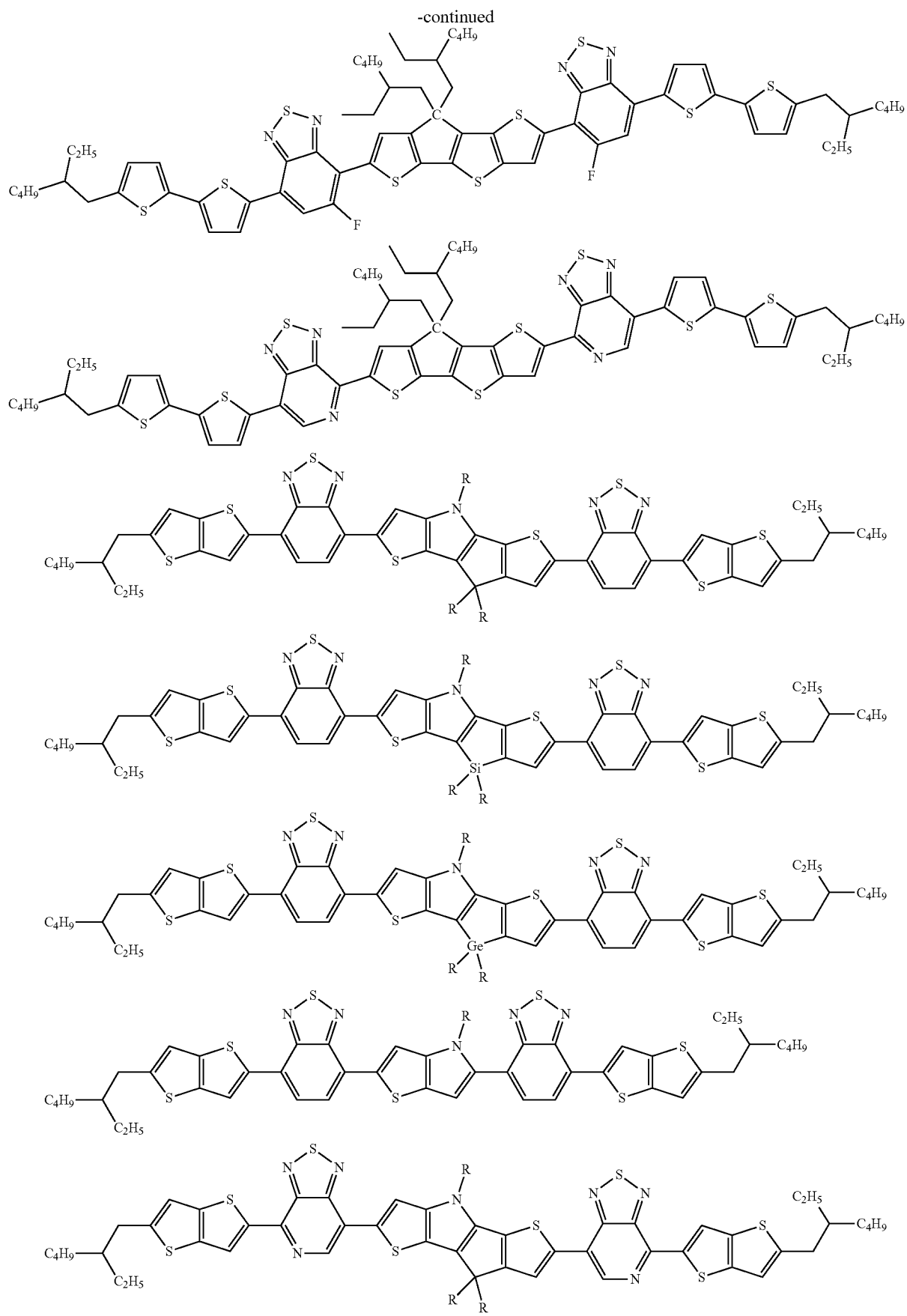

-continued
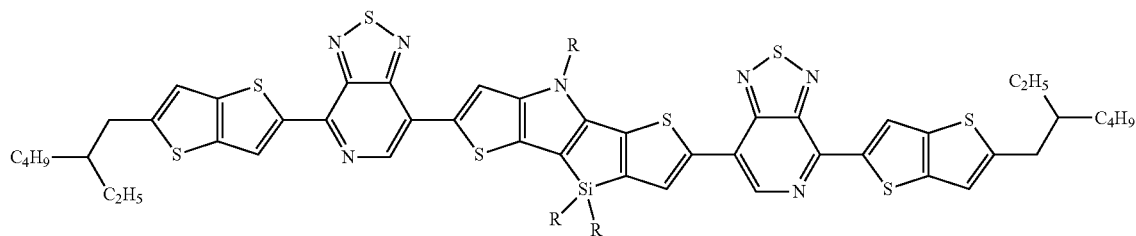
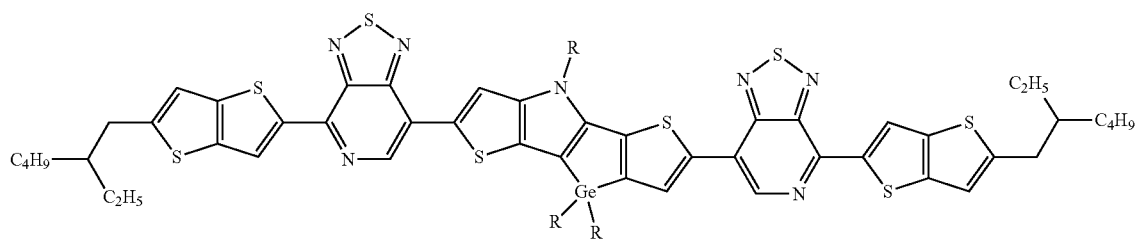
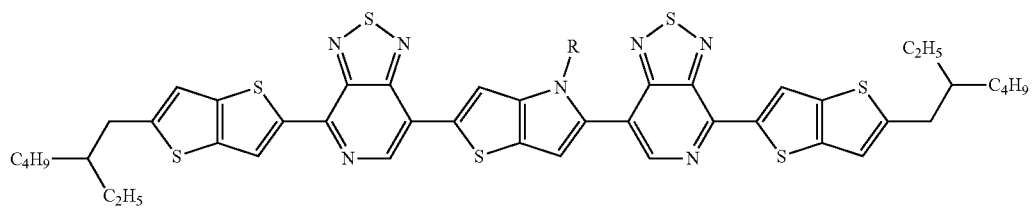
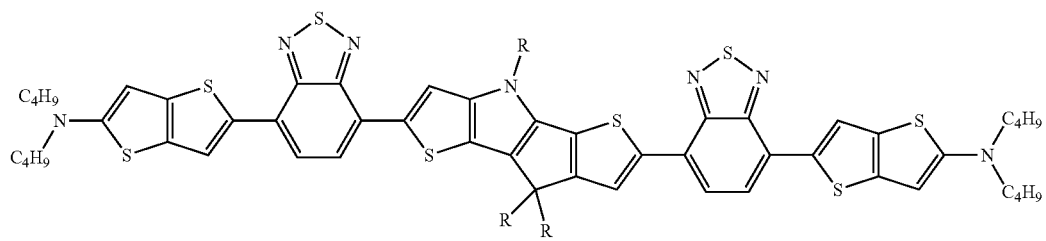
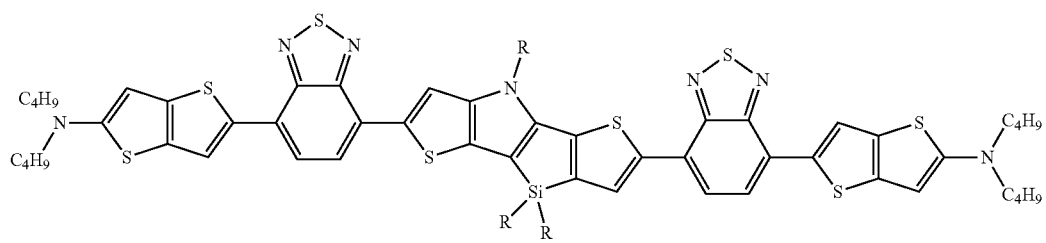
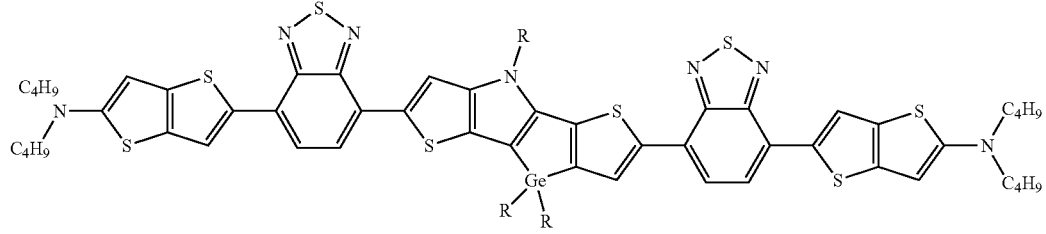
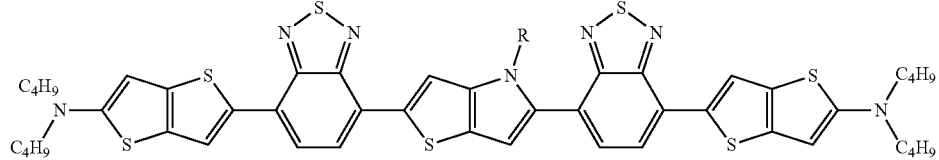

-continued
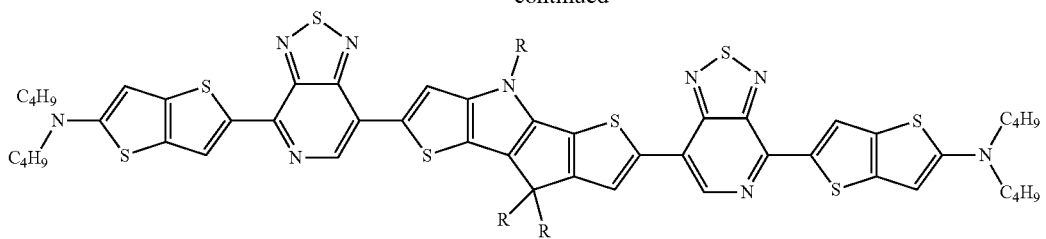
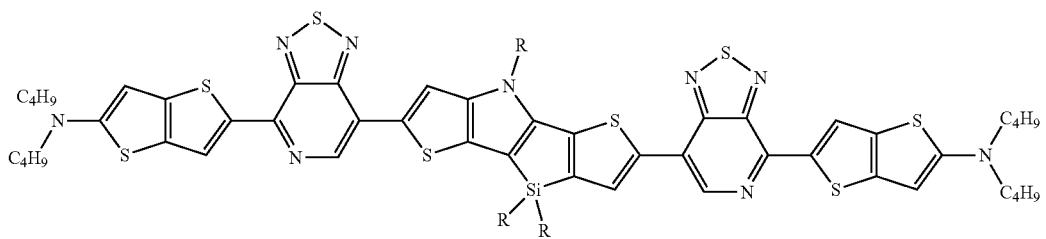
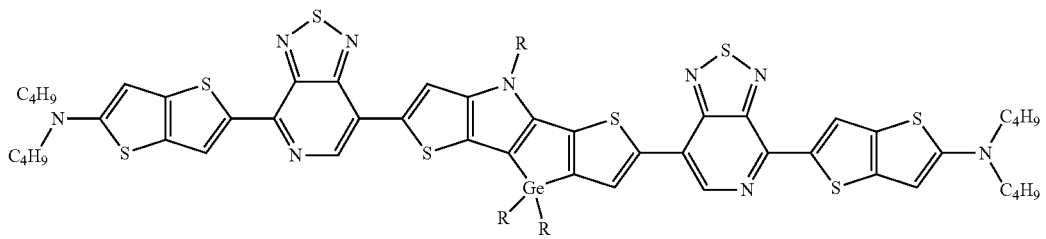
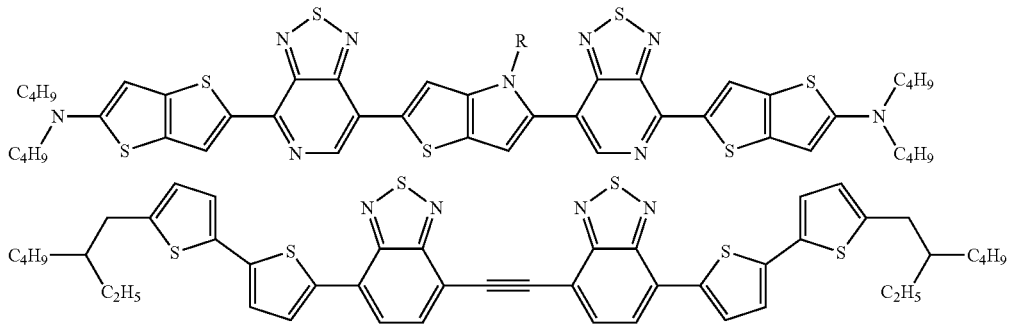
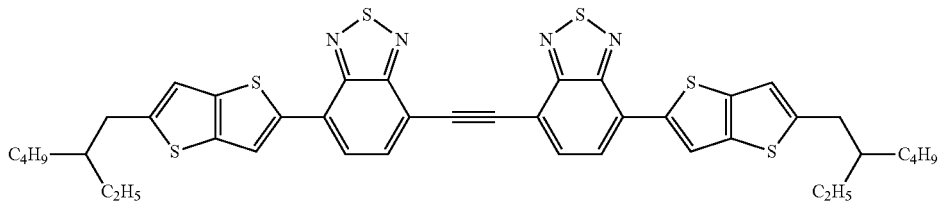
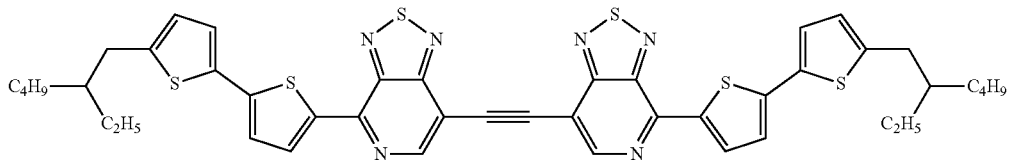
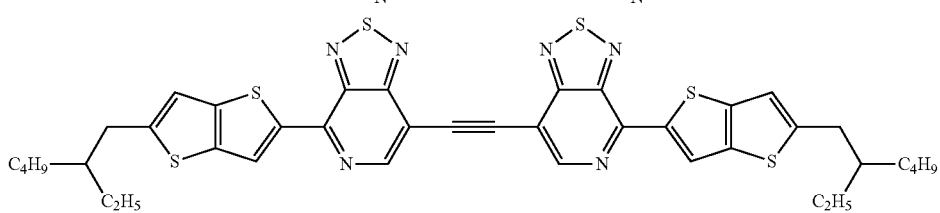

-continued
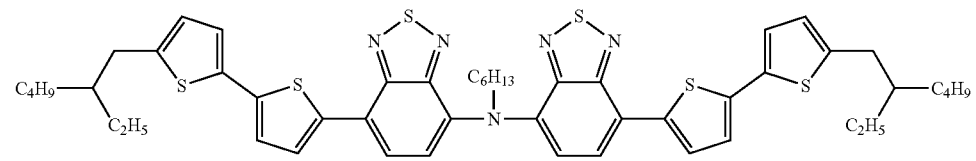
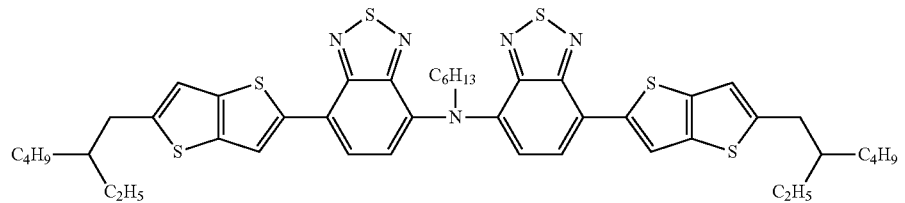
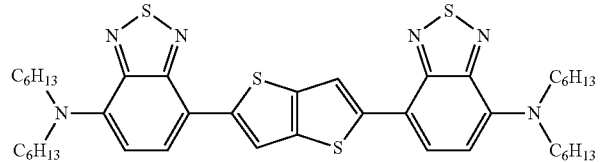
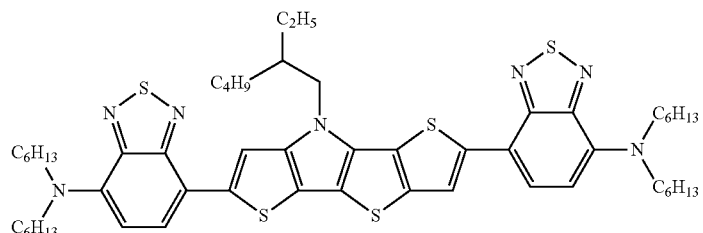
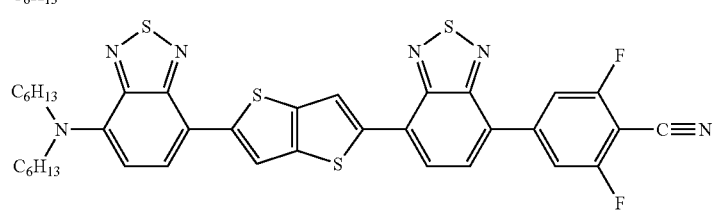
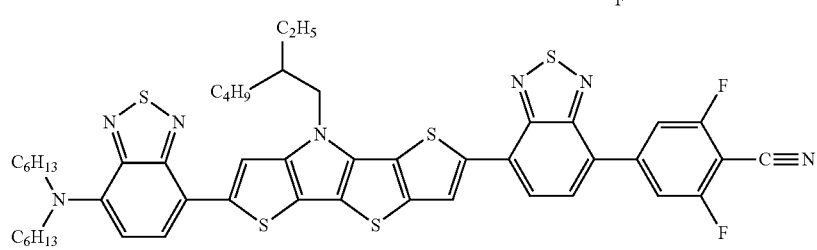
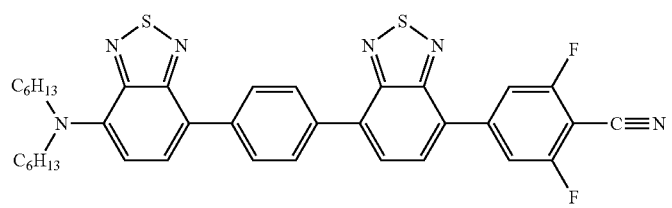
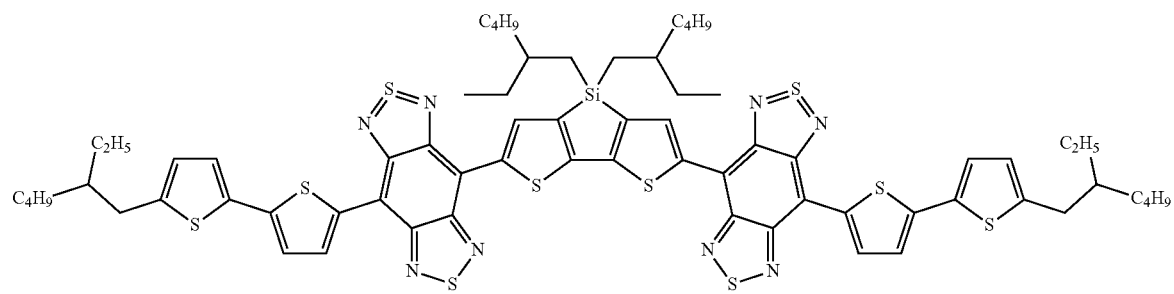

-continued
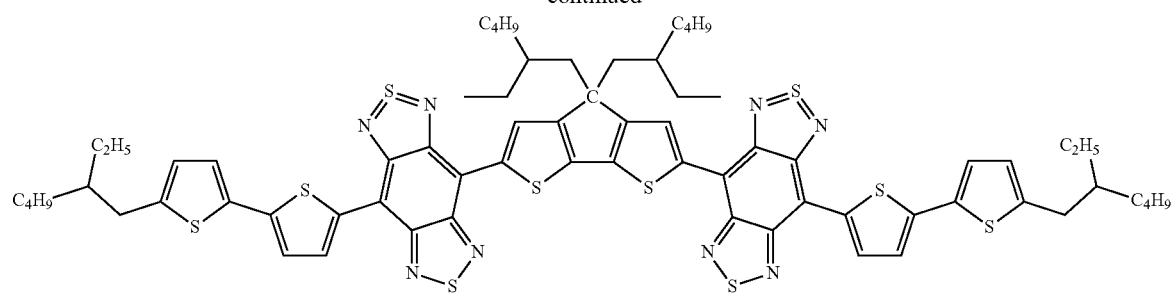
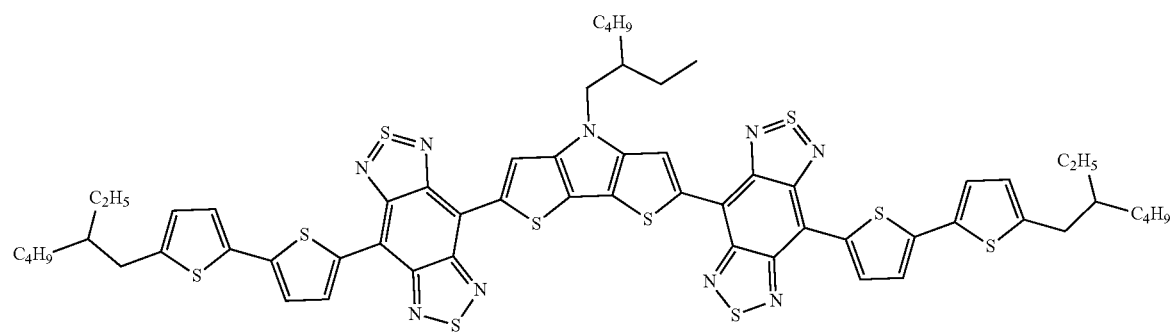
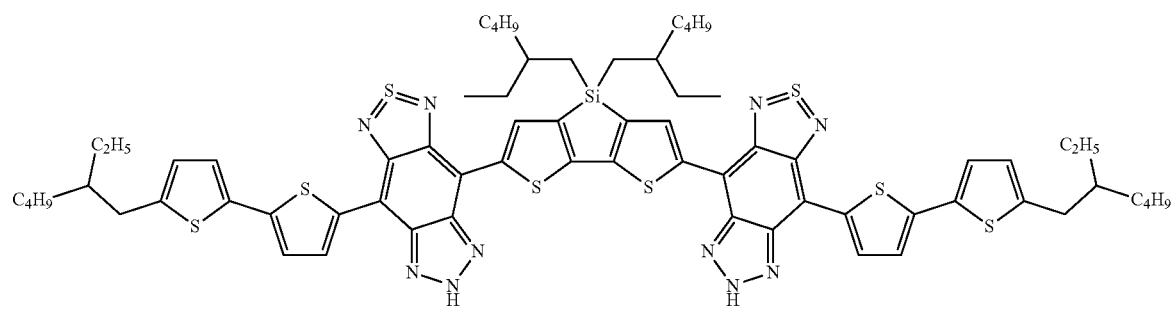
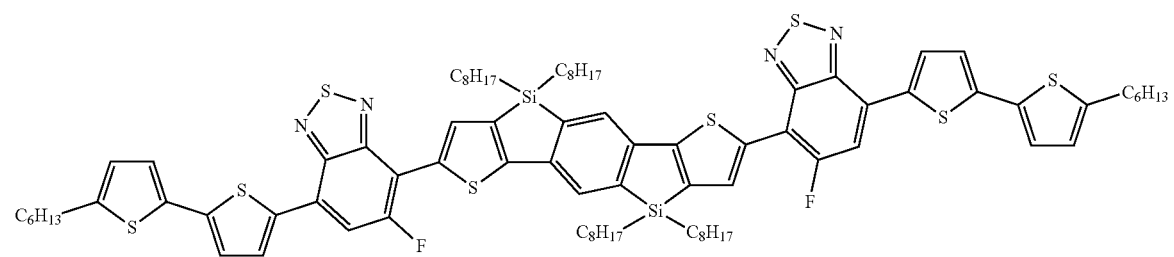
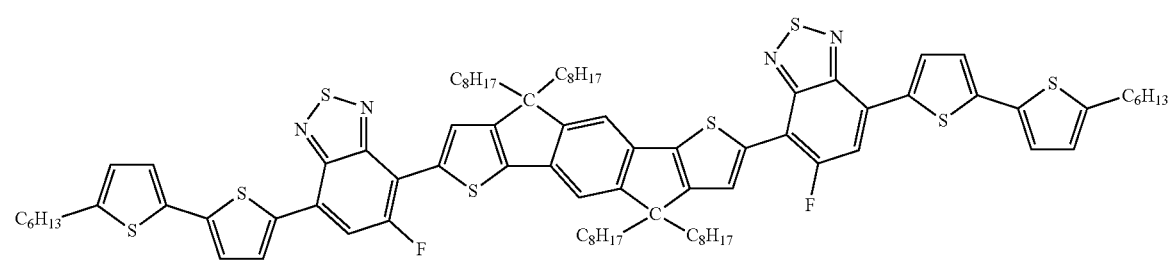

-continued
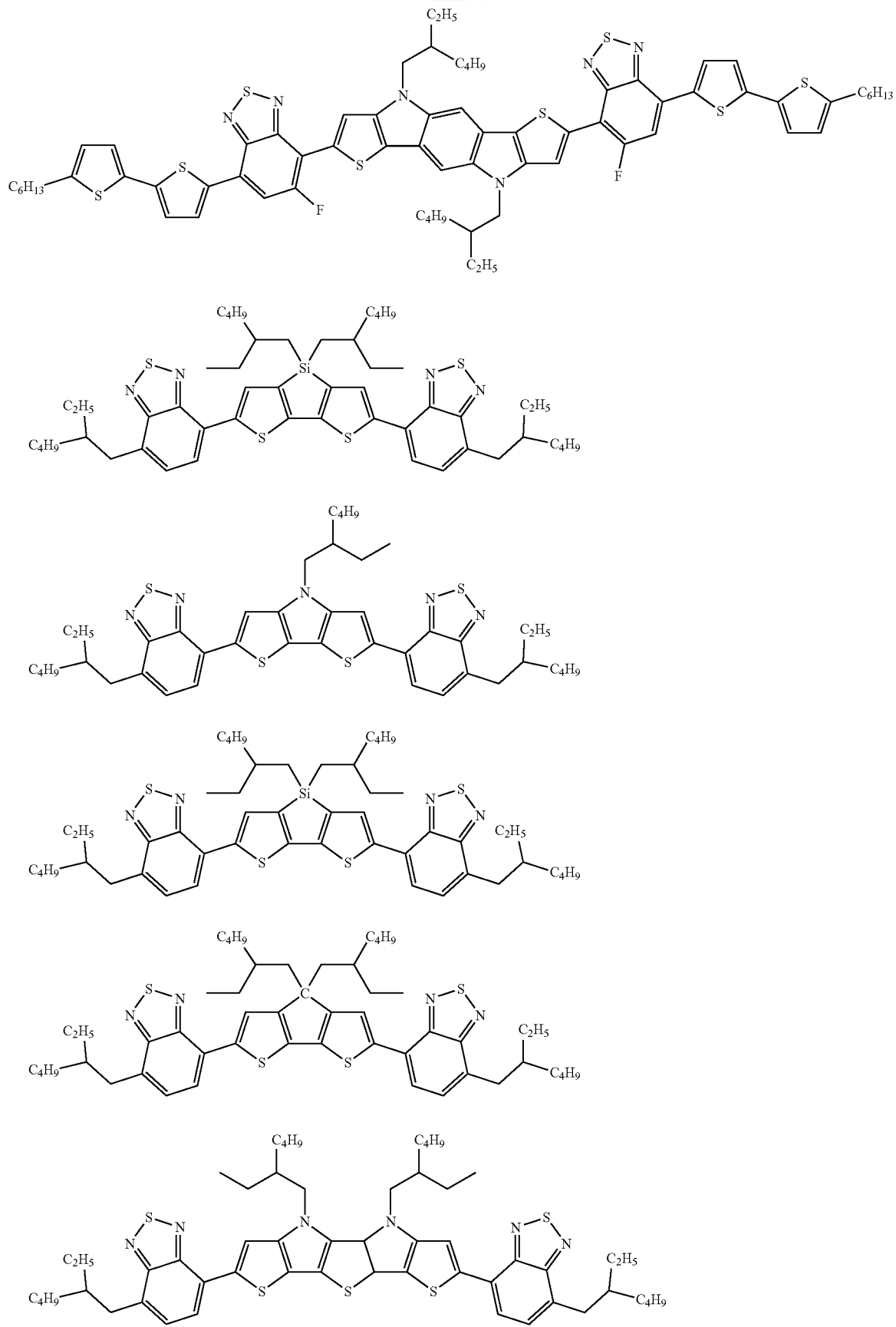

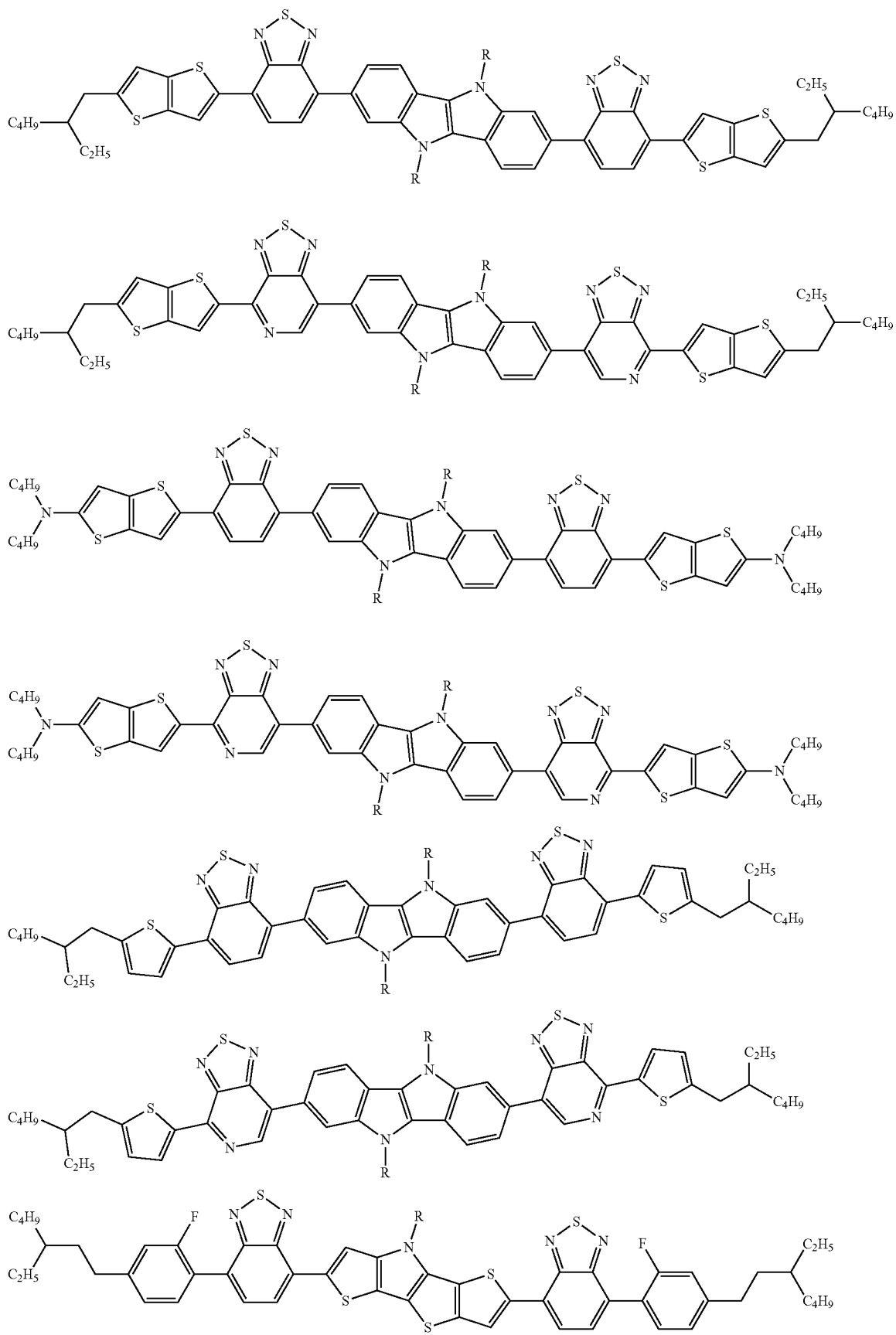

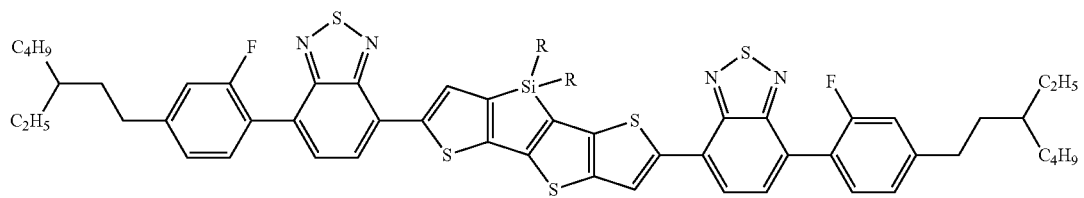
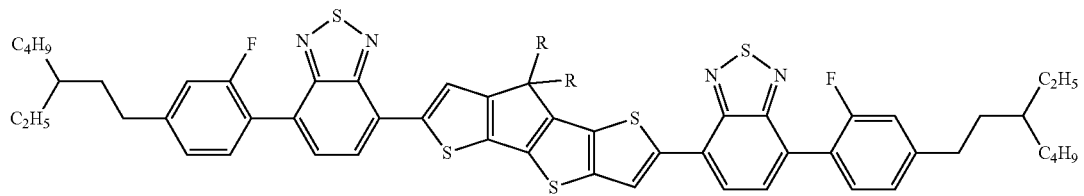
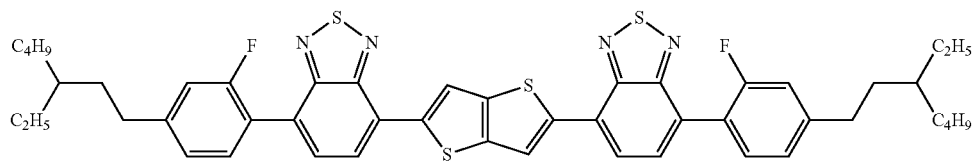
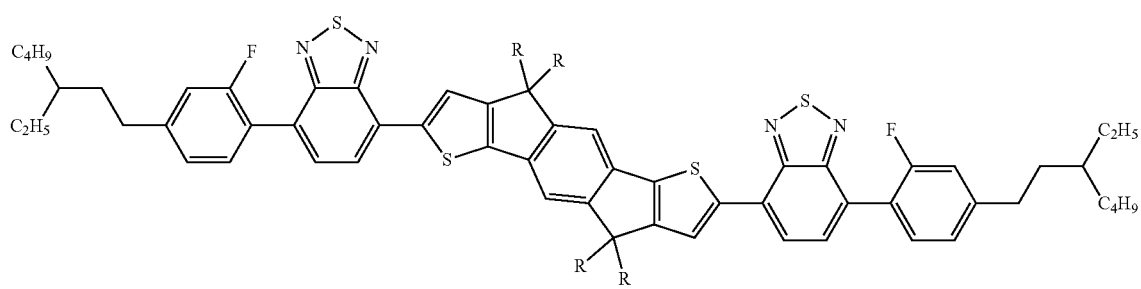
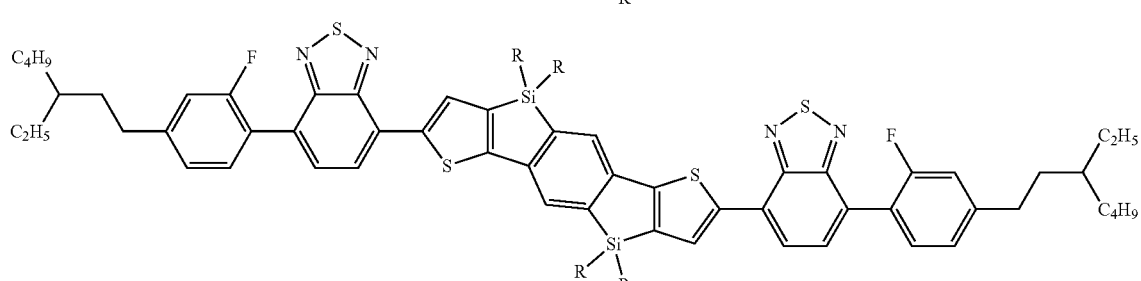
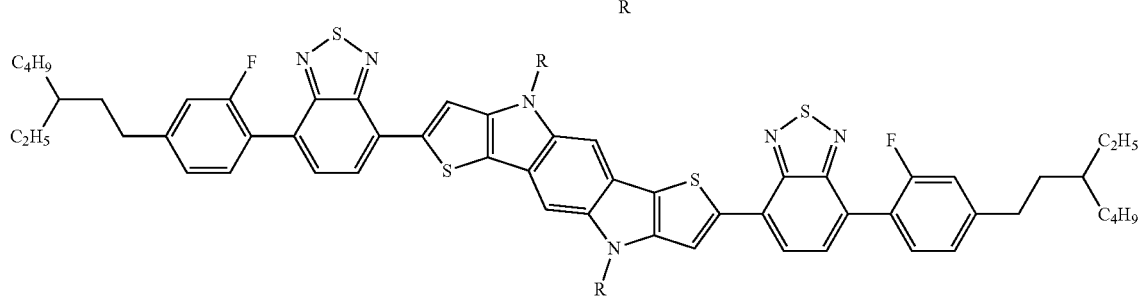
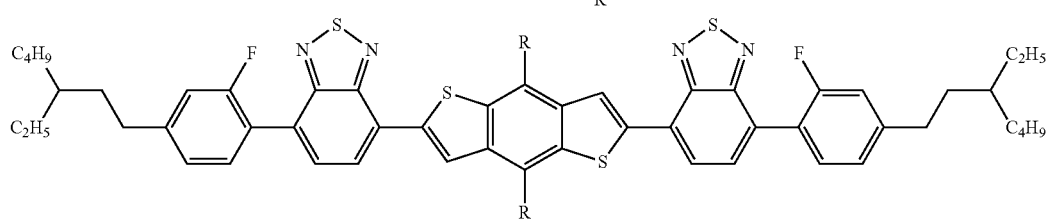

-continued
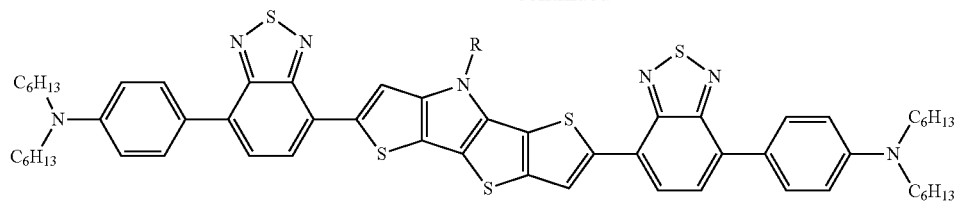
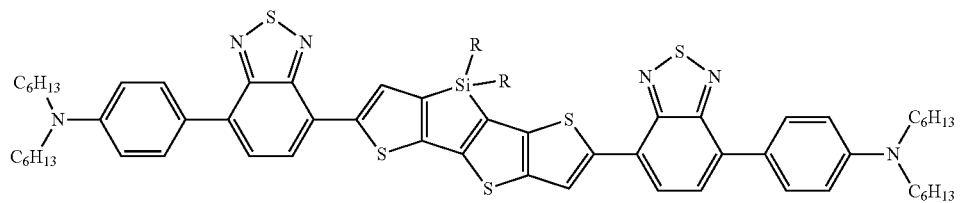
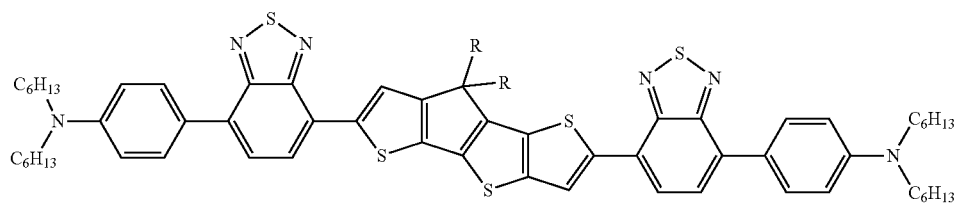
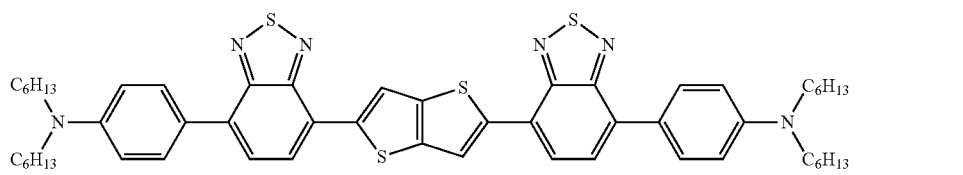
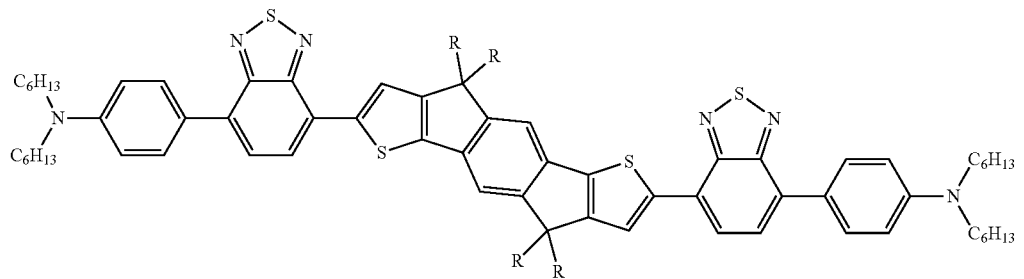
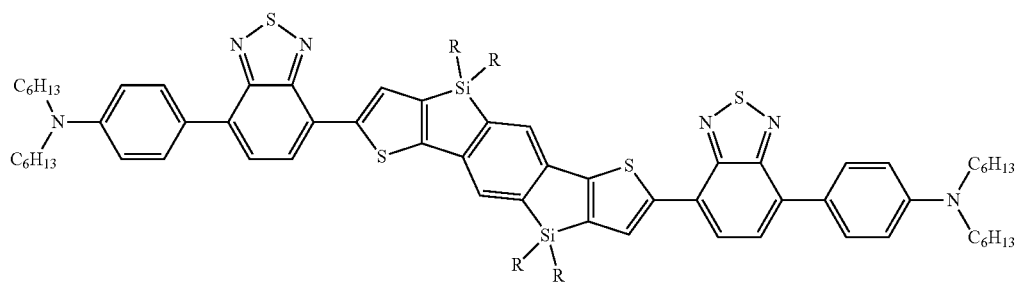
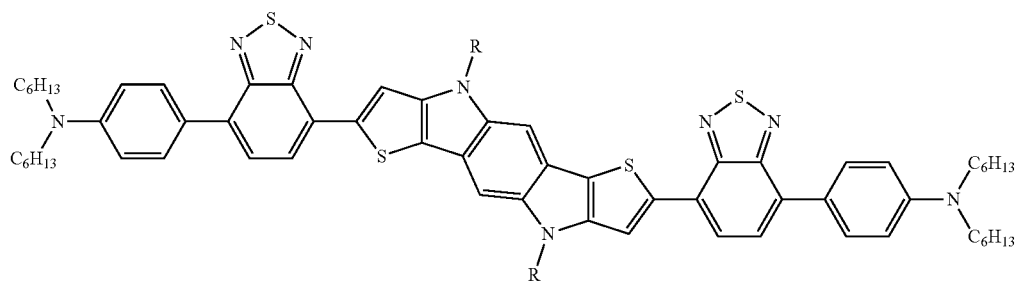

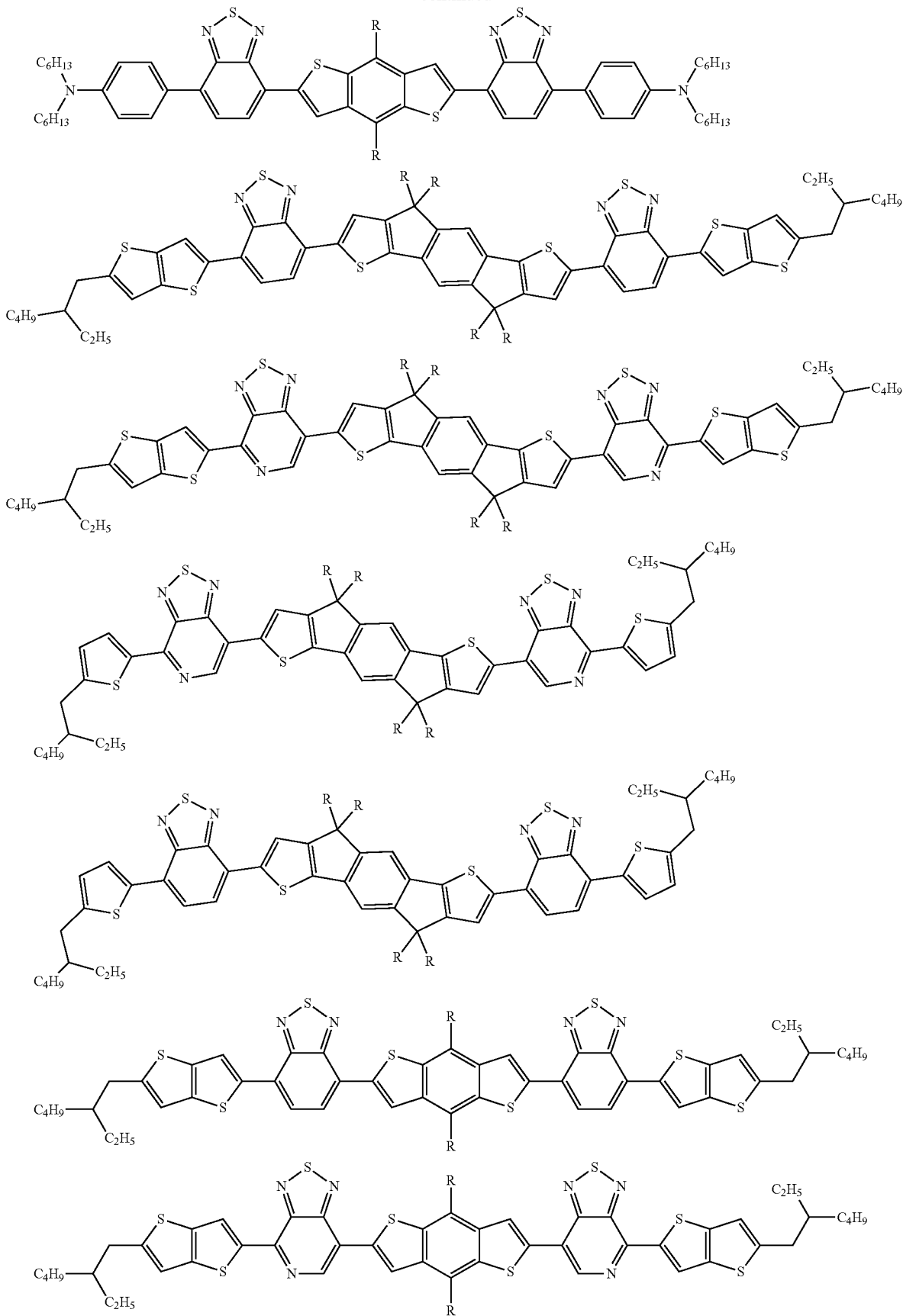

-continued

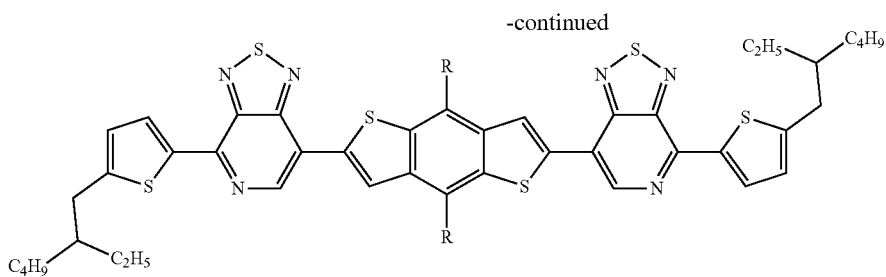

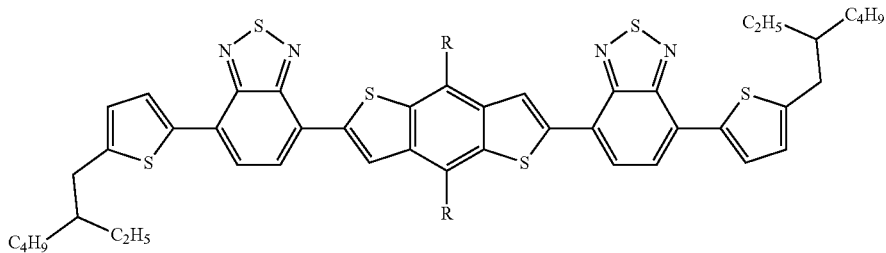

wherein R is 2-ethylhexyl

Use Examples

The dyes prepared are investigated with respect to their physical properties in order to establish their suitability for use in devices for regulating energy transmission.

All percentages provided for the following compositions and in the general description are % by weight.

Preparation of Liquid-Crystalline Dye Mixtures

The following nematic LC host mixtures are composed as follows:

| Mixture N-1: | | | |
|---|---|---|---|
| Composition Compound | | | |
| No. | Abbreviation | c [%] | Physical properties |
| 1 | CPG-3-F | 8 | T(N,I) [° C.] = 114 |
| 2 | CPG-5-F | 8 | Δn (20° C., 589.3 nm) = 0.130 |
| 3 | CPU-5-F | 14 | Δε (20° C., 1 kHz) = 10.0 |
| 4 | CPU-7-F | 11 | |
| 5 | CP-5-N | 18 | |
| 6 | CP-7-N | 13 | |
| 7 | CCGU-3-F | 7 | |
| 8 | CGPC-3-3 | 4 | |
| 9 | CGPC-5-3 | 4 | |
| 10 | CGPC-5-5 | 3 | |
| 11 | CCZPC-3-3 | 3 | |
| 12 | CCZPC-3-4 | 3 | |
| 13 | CCZPC-3-5 | 2 | |
| 14 | CC-3-O3 | 2 | |
| Σ | | 100 | |

| Mixture N-2: : | | | |
|---|---|---|---|
| Composition Compound | | | |
| No. | Abbreviation | c [%] | Physical properties |
| 1 | CC(CN)-3-4- | 14 | T(N,I) [° C.] = 114.6 |
| 2 | CC(CN)-5-5 | 14 | Δn (20° C., 589.3 nm) = 0.045 |
| 3 | CC(CN)-3-3 | 6 | Δε (20° C., 1 kHz) = −5.2 |
| 4 | CCZC-3-3 | 3 | |
| 5 | CCZC-3-5 | 3 | |
| 6 | CCZC-4-3 | 3 | |
| 7 | CCZC-4-5 | 3 | |
| 8 | CC-3-O1 | 11 | |
| 9 | CC-5-O1 | 4 | |
| 10 | CC-5-O2 | 4 | |
| 11 | CC(CN)C-3-5 | 10 | |
| 12 | CC(CN)C-5-5 | 12 | |
| 13 | CC(CN)C-5-3 | 10 | |
| 14 | CCZPC-3-3 | 3 | |
| Σ | | 100 | |

| Mixture N-3: | | | |
|---|---|---|---|
| Composition Compound | | | |
| No. | Abbreviation | c [%] | Physical properties |
| 1 | CY-3-O2 | 12.0 | T(N, I) [° C.] = 91.5 |
| 2 | CY-5-O2 | 12.0 | Δn (20° C., 589.3 nm) = 0.078 |
| 3 | CCY-3-O2 | 13.0 | Δε (20° C., 1 kHz) = −3.7 |
| 4 | CCY-5-O2 | 13.0 | LTS (−20° C.) [d] 27 |
| 5 | CCY-3-1 | 8.0 | |
| 6 | CCZC-3-3 | 4.0 | |
| 7 | CCZC-3-5 | 3.0 | |
| 8 | CCZC-4-3 | 3.0 | |
| 9 | CC-3-4 | 6.0 | |
| 10 | CC-3-5 | 6.0 | |
| 11 | CC-3-O3 | 8.0 | |
| 12 | CC-5-O1 | 4.0 | |
| 13 | CC-5-O2 | 4.0 | |
| 14 | CP-3-O2 | 4.0 | |
| Σ | | 100 | |

Mixture N-4:

| No. | Abbreviation | c [%] | Physical properties | | |
|---|---|---|---|---|---|
| 1 | CY-3-O2 | 12.0 | T(N, I) [° C.] | = | 79.5 |
| 2 | CY-5-O2 | 13.0 | Δn (20° C., 589.3 nm) | = | 0.100 |
| 3 | CCY-3-O2 | 11.0 | Δε (20° C., 1 kHz) | = | −3.1 |
| 4 | CCY-5-O2 | 10.0 | LTS (−20° C.) [d] | | >42 |
| 5 | CCY-2-1 | 9.0 | | | |
| 6 | CPP-3-2 | 6.0 | | | |
| 7 | CPP-5-2 | 4.0 | | | |
| 8 | CGP-3-2 | 6.0 | | | |
| 9 | CC-3-4 | 6.0 | | | |
| 10 | CC-3-5 | 6.0 | | | |
| 11 | CP-3-O2 | 17.0 | | | |
| Σ | | 100 | | | |

Mixture N-5:

| No. | Abbreviation | c [%] | Physical properties | | |
|---|---|---|---|---|---|
| 1 | CC(CN)-4-7 | 20.0 | T(N, I) [° C.] | = | 100.5 |
| 2 | CC(CN)-5-5 | 21.0 | Δn (20° C., 589.3 nm) | = | 0.044 |
| 3 | CC-3-O1 | 11.0 | Δε (20° C., 1 kHz) | = | −4.8 |
| 4 | CC-5-O1 | 5.0 | LTS (−20° C.) [d] | | >42 |
| 5 | CC-5-O2 | 5.0 | | | |
| 6 | CCZC-3-3 | 4.0 | | | |
| 7 | CCZC-3-5 | 4.0 | | | |
| 8 | CCZC-4-3 | 4.0 | | | |
| 9 | CCZC-4-5 | 4.0 | | | |
| 10 | CC(CN)C-5-5 | 22.0 | | | |
| Σ | | 100 | | | |

Mixture N-6:

| No. | Abbreviation | c [%] | Physical properties | | |
|---|---|---|---|---|---|
| 1 | CC(CN)-3-3 | 10.0 | T(N, I) [° C.] | = | 106.0 |
| 2 | CC(CN)-4-7 | 10.0 | Δn (20° C., 589.3 nm) | = | 0.118 |
| 3 | CC(CN)-5-7 | 10.0 | Δε (20° C., 1 kHz) | = | −6.0 |
| 4 | CY-3-O2 | 5.0 | LTS (−20° C.) [d] | | >73 |
| 5 | PPC(CN)-5-3 | 13.0 | | | |
| 6 | CCY-3-O2 | 5.0 | | | |
| 7 | CCY-3-O3 | 5.0 | | | |
| 8 | CCY-4-O2 | 6.0 | | | |
| 9 | CPY-2-O2 | 9.0 | | | |
| 10 | CPY-3-O2 | 8.0 | | | |
| 11 | PYP-2-3 | 7.0 | | | |
| 12 | PYP-2-4 | 6.0 | | | |
| 13 | CGPC-3-3 | 2.0 | | | |
| 14 | CGPC-5-3 | 2.0 | | | |
| 15 | CGPC-5-5 | 2.0 | | | |
| Σ | | 100 | | | |

Mixture N-7:

| No. | Abbreviation | c [%] | Physical properties | | |
|---|---|---|---|---|---|
| 1 | CC(CN)-3-3 | 8.0 | T(N, I) [° C.] | = | 113.5 |
| 2 | CC(CN)-4-7 | 8.0 | Δn (20° C., 589.3 nm) | = | 0.127 |
| 3 | CC(CN)-5-5 | 9.0 | Δε (20° C., 1 kHz) | = | −6.0 |
| 4 | CY-3-O2 | 5.0 | LTS (−20° C.) [d] | | >100 |
| 5 | PPC(CN)-5-3 | 12.0 | | | |
| 6 | CCY-3-O2 | 5.0 | | | |
| 7 | CCY-3-O3 | 5.0 | | | |
| 8 | CCY-4-O2 | 6.0 | | | |
| 9 | CPY-2-O2 | 9.0 | | | |
| 10 | CPY-3-O2 | 8.0 | | | |
| 11 | PYP-2-3 | 7.0 | | | |
| 12 | PYP-2-4 | 6.0 | | | |
| 13 | CGPC-3-3 | 2.0 | | | |
| 14 | CGPC-5-3 | 2.0 | | | |
| 15 | CGPC-5-5 | 2.0 | | | |
| 16 | CPP-3-2 | 3.0 | | | |
| 17 | CPP-5-2 | 3.0 | | | |
| Σ | | 100 | | | |

Mixture N-8:

| No. | Abbreviation | c [%] | Physical properties | | |
|---|---|---|---|---|---|
| 1 | CC(CN)-3-3 | 13.0 | T(N, I) [° C.] | = | 107.5 |
| 2 | CC(CN)-4-7 | 15.0 | Δn (20° C., 589.3 nm) | = | 0.103 |
| 3 | CC(CN)-5-5 | 12.0 | Δε (20° C., 1 kHz) | = | −4.9 |
| 4 | PPC(CN)-5-3 | 10.0 | LTS (−20° C.) [d] | | >83 |
| 5 | CPY-2-O2 | 5.0 | | | |
| 6 | CPY-3-O2 | 5.0 | | | |
| 7 | CCY-4-O2 | 5.0 | | | |
| 8 | PYP-2-3 | 10.0 | | | |
| 9 | CP-3-O1 | 8.0 | | | |
| 10 | CGPC-3-3 | 4.0 | | | |
| 11 | CGPC-5-3 | 3.0 | | | |
| 12 | CGPC-5-5 | 3.0 | | | |
| 13 | CCZPC-3-3 | 3.0 | | | |
| 14 | CCZPC-3-4 | 2.0 | | | |
| 15 | CCZPC-3-5 | 2.0 | | | |
| Σ | | 100 | | | |

Mixture N-9:

| No. | Abbreviation | c [%] | Physical properties | | |
|---|---|---|---|---|---|
| 1 | CC(CN)-4-7 | 10.0 | T(N, I) [° C.] | = | 111.5 |
| 2 | CC(CN)-5-5 | 10.0 | Δn (20° C., 589.3 nm) | = | 0.124 |
| 3 | CY-3-O2 | 6.0 | Δε (20° C., 1 kHz) | = | −4.7 |
| 4 | CP-3-O1 | 10.0 | LTS (−20° C.) [d] | | >73 |
| 5 | PPC(CN)-5-3 | 10.0 | | | |
| 6 | CPY-2-O2 | 7.0 | | | |
| 7 | CPY-3-O2 | 7.0 | | | |
| 8 | CCY-3-O2 | 6.0 | | | |
| 9 | CCY-5-O2 | 7.0 | | | |
| 10 | PYP-2-3 | 10.0 | | | |
| 11 | CGP-3-2 | 6.0 | | | |
| 12 | CGPC-3-3 | 3.0 | | | |
| 13 | CGPC-5-3 | 3.0 | | | |

Mixture N-9:

| No. | Abbreviation | c [%] | Physical properties |
|---|---|---|---|
| 14 | CGPC-5-5 | 2.0 | |
| 15 | CCZPC-3-3 | 3.0 | |
| Σ | | 100 | |

Mixture N-10:

| No. | Abbreviation | c [%] | Physical properties | | |
|---|---|---|---|---|---|
| 1 | CC(CN)-3-3 | 8.0 | T(N, I) [° C.] | = | 107.5 |
| 2 | CC(CN)-4-7 | 10.0 | Δn (20° C., 589.3 nm) | = | 0.129 |
| 3 | CC(CN)-5-5 | 10.0 | Δε (20° C., 1 kHz) | = | −5.5 |
| 4 | CY-3-O2 | 10.0 | LTS (−20° C.) [d] | | >73 |
| 5 | CPP(F,CN)-5-O2 | 10.0 | | | |
| 6 | CPY-2-O2 | 6.0 | | | |
| 7 | CPY-3-O2 | 9.0 | | | |
| 8 | CCY-4-O2 | 5.0 | | | |
| 9 | PYP-2-3 | 10.0 | | | |
| 10 | PYP-2-4 | 10.0 | | | |
| 11 | CGPC-3-3 | 3.0 | | | |
| 12 | CGPC-5-3 | 3.0 | | | |
| 13 | CGPC-5-5 | 3.0 | | | |
| 14 | CCZPC-3-3 | 3.0 | | | |
| Σ | | 100 | | | |

Mixture N-11:

| No. | Abbreviation | c [%] | Physical properties | | |
|---|---|---|---|---|---|
| 1 | CY-3-O2 | 9.0 | T(N, I) [° C.] | = | 110.5 |
| 2 | CY-3-O4 | 9.0 | Δn (20° C., 589.3 nm) | = | 0.132 |
| 3 | CY-5-O2 | 12.0 | Δε (20° C., 1 kHz) | = | −4.9 |
| 4 | CY-5-O4 | 8.0 | LTS (−20° C.) [d] | | >76 |
| 5 | CCY-3-O2 | 5.0 | | | |
| 6 | CCY-3-O3 | 5.0 | | | |
| 7 | CCY-4-O2 | 5.0 | | | |
| 8 | CPY-2-O2 | 7.0 | | | |
| 9 | CPY-3-O2 | 6.0 | | | |
| 10 | PYP-2-3 | 12.0 | | | |
| 11 | CCP-V-1 | 6.0 | | | |
| 12 | CCZPC-3-3 | 3.0 | | | |
| 13 | CCZPC-3-4 | 3.0 | | | |
| 14 | CGPC-3-3 | 5.0 | | | |
| 15 | CGPC-5-3 | 5.0 | | | |
| Σ | | 100 | | | |

Mixture N-12:

| No. | Abbreviation | c [%] | Physical properties | | |
|---|---|---|---|---|---|
| 1 | CC-3-V | 41.5 | T(N ,I) [° C.] | = | 74.0 |
| 2 | CCY-3-O1 | 5.0 | Δn (20° C., 589.3 nm) | = | 0.101 |
| 3 | CCY-3-O2 | 11.0 | Δε (20° C., 1 kHz) | = | −3.5 |
| 4 | CCY-4-O2 | 6.0 | LTS (−20° C.) [d] | | 13 |
| 5 | CPY-2-O2 | 5.0 | | | |
| 6 | CPY-3-O2 | 11.0 | | | |
| 7 | CY-3-O2 | 3.5 | | | |
| 8 | PY-3-O2 | 12.0 | | | |
| 9 | B-3-O2 | 5.0 | | | |
| Σ | | 100 | | | |

Mixture N-13:

| No. | Abbreviation | c [%] | Physical properties | | |
|---|---|---|---|---|---|
| 1 | CC-3-V | 40.5 | T(N, I) [° C.] | = | 74.0 |
| 2 | CCY-3-O1 | 5.0 | Δn (20° C., 589.3 nm) | = | 0.101 |
| 3 | CCY-3-O2 | 11.0 | Δε (20° C., 1 kHz) | = | −3.6 |
| 4 | CCY-4-O2 | 6.0 | LTS (−20° C.) [d] | | 15 |
| 5 | CPY-2-O2 | 5.5 | | | |
| 6 | CPY-3-O2 | 11.0 | | | |
| 7 | CY-3-O2 | 5.0 | | | |
| 8 | PY-3-O2 | 12.0 | | | |
| 9 | B-3-O2 | 4.0 | | | |
| Σ | | 100 | | | |

Mixture N-14:

| No. | Abbreviation | c [%] | Physical properties | | |
|---|---|---|---|---|---|
| 1 | CY-3-O2 | 12.5 | T(N, I) [° C.] | = | 110.5 |
| 2 | CCY-3-O1 | 9.0 | Δn (20° C., 589.3 nm) | = | 0.132 |
| 3 | CCY-3-O2 | 11.0 | Δε (20° C., 1 kHz) | = | −4.9 |
| 4 | CCY-4-O2 | 7.0 | LTS (−20° C.) [d] | | >76 |
| 5 | CPY-3-O2 | 3.0 | | | |
| 6 | CC-3-V | 31.0 | | | |
| 7 | B-2O-O5 | 4.0 | | | |
| 8 | PY-V2-O2 | 5.5 | | | |
| 9 | CPY-V-O2 | 6.0 | | | |
| 10 | CPY-V-O4 | 5.0 | | | |
| 11 | CCY-V-O2 | 6.0 | | | |
| Σ | | 100 | | | |

Mixture N-15:

| No. | Abbreviation | c [%] | Physical properties | | |
|---|---|---|---|---|---|
| 1 | CCGU-3-F | 6.0 | T(N, I) [° C.] | = | 109.5 |
| 2 | CCQU-3-F | 12.0 | Δn (20° C., 589.3 nm) | = | 0.0986 |
| 3 | CCQU-5-F | 10.0 | Δε (20° C., 1 kHz) | = | +9.0 |
| 4 | CCU-3-F | 10.0 | LTS (−20° C.) [d] | | >42 |
| 5 | CGPC-3-3 | 6.0 | | | |
| 6 | CP-3-O1 | 10.0 | | | |

-continued

Mixture N-15:

| No. | Abbreviation | c [%] | Physical properties | | |
|---|---|---|---|---|---|
| 7 | CCZU-3-F | 15.0 | | | |
| 8 | CCZU-5-F | 1.5 | | | |
| 9 | PGUQU-3-F | 2.5 | | | |
| 10 | CPGU-3-OT | 4.0 | | | |
| 11 | CPG-3-F | 4.0 | | | |
| 12 | CPP-3-2 | 5.0 | | | |
| 13 | CC-3-4 | 4.0 | | | |
| 14 | CC-3-5 | 5.0 | | | |
| 15 | CC-3-O1 | 5.0 | | | |
| Σ | | 100 | | | |

Mixture N-16:

| No. | Abbreviation | c [%] | Physical properties | | |
|---|---|---|---|---|---|
| 1 | CPU-3-F | 11.0 | T(N,I) [° C.] | = | 124.0 |
| 2 | CPU-5-F | 11.0 | Δn (20° C., 589.3 nm) | = | 0.1695 |
| 3 | CGU-2-F | 7.0 | Δε (20° C., 1 kHz) | = | +12.4 |
| 4 | CGU-3-F | 8.0 | LTS (−20° C.) [d] | | n/a |
| 5 | PGU-2-F | 9.0 | | | |
| 6 | PGU-3-F | 9.0 | | | |
| 7 | PGU-5-F | 7.0 | | | |
| 8 | CCGU-3-F | 8.0 | | | |
| 9 | CCP-V-1 | 6.0 | | | |
| 10 | CPPC-3-3 | 3.0 | | | |
| 11 | CGPC-3-3 | 5.0 | | | |
| 12 | CGPC-5-3 | 5.0 | | | |
| 13 | CGPC-5-5 | 5.0 | | | |
| 14 | PGIGI-3-F | 6.0 | | | |
| Σ | | 100 | | | |

Mixture N-17:

| No. | Abbreviation | c [%] | Physical properties | | |
|---|---|---|---|---|---|
| 1 | CC-3-O1 | 8.0 | T(N, I) [° C.] | = | 108.5 |
| 2 | CCP-3-1 | 4.0 | Δn (20° C., 589.3 nm) | = | 0.1082 |
| 3 | CCP-3-3 | 7.0 | Δε (20° C., 1 kHz) | = | +13.4 |
| 4 | CP-3-O1 | 8.0 | LTS (−20° C.) [d] | | >42 |
| 5 | CCP-3-OT | 9.0 | | | |
| 6 | CCP-5-OT | 5.0 | | | |
| 7 | CPU-3-F | 10.0 | | | |
| 8 | CCQU-3-F | 20.0 | | | |
| 9 | CCGU-3-F | 2.5 | | | |
| 10 | PUQU-3-F | 3.0 | | | |
| 11 | APUQU-2-F | 5.0 | | | |
| 12 | APUQU-3-F | 8.0 | | | |
| 13 | PGUQU-3-F | 5.0 | | | |
| 14 | CPGU-3-OT | 3.5 | | | |
| 15 | CPGP-4-3 | 2.0 | | | |
| Σ | | 100 | | | |

Mixture N-18:

| No. | Abbreviation | c [%] | Physical properties | | |
|---|---|---|---|---|---|
| 1 | CC-3-V1 | 10.0 | T(N, I) [° C.] | = | 114.3 |
| 2 | PGUQU-3-F | 4.0 | Δn (20° C., 589.3 nm) | = | 0.0861 |
| 3 | CCGU-3-F | 5.5 | Δε (20° C., 1 kHz) | = | +11.2 |
| 4 | CCG-3-OT | 9.0 | LTS (−20° C.) [d] | | >28 |
| 5 | CPU-3-F | 11.0 | | | |
| 6 | CPU-5-F | 4.0 | | | |
| 7 | CCQU-3-F | 10.0 | | | |
| 8 | CCQU-5-F | 7.5 | | | |
| 9 | CCZU-2-F | 4.0 | | | |
| 10 | CCZU-3-F | 12.0 | | | |
| 11 | CCZU-5-F | 4.0 | | | |
| 12 | CCEG-3-F | 12.0 | | | |
| 13 | CCEG-5-F | 7.0 | | | |
| Σ | | 100 | | | |

Mixture N-19:

| No. | Abbreviation | c [%] | Physical properties | | |
|---|---|---|---|---|---|
| 1 | CPG-3-F | 5.0 | T(N, I) [° C.] | = | 114.5 |
| 2 | CPG-5-F | 5.0 | Δn (20° C., 589.3 nm) | = | 0.1342 |
| 3 | CPU-3-F | 15.0 | Δε (20° C., 1 kHz) | = | 11.3 |
| 4 | CPU-5-F | 15.0 | LTS (−20° C.) [d] | | >1049 |
| 5 | CP-3-N | 16.0 | | | |
| 6 | CP-5-N | 16.0 | | | |
| 7 | CCGU-3-F | 7.0 | | | |
| 8 | CGPC-3-3 | 4.0 | | | |
| 9 | CGPC-5-3 | 4.0 | | | |
| 10 | CGPC-5-5 | 4.0 | | | |
| 11 | CCZPC-3-3 | 3.0 | | | |
| 12 | CCZPC-3-4 | 3.0 | | | |
| 13 | CCZPC-3-5 | 3.0 | | | |
| Σ | | 100 | | | |

Mixture N-20:

| No. | Abbreviation | c [%] | Physical properties | | |
|---|---|---|---|---|---|
| 1 | PZG-2-N | 0.936 | T(N, I) [° C.] | = | 108.5 |
| 2 | PZG-3-N | 0.936 | Δn (20° C., 589.3 nm) | = | 0.1082 |
| 3 | PZG-4-N | 2.184 | Δε (20° C., 1 kHz) | = | +13.4 |
| 4 | PZG-5-N | 2.184 | LTS (−20° C.) [d] | | n/a |
| 5 | CP-3-O1 | 7.488 | | | |
| 6 | CC-3-4 | 3.120 | | | |
| 7 | CPP-3-2 | 2.496 | | | |
| 8 | CCZGI-3-3 | 2.496 | | | |
| 9 | CCZGI-3-5 | 2.496 | | | |
| 10 | CCZPC-3-3 | 1.248 | | | |
| 11 | CCZPC-3-4 | 1.248 | | | |
| 12 | CCZPC-3-5 | 0.936 | | | |
| 13 | CPZG-3-N | 1.248 | | | |
| 14 | CGPC-5-3 | 1.248 | | | |
| 15 | CPPC-5-3 | 0.936 | | | |

Mixture N-20:

Composition Compound

| No. | Abbreviation | c [%] | Physical properties |
|---|---|---|---|
| 16 | CPU-3-F | 34.400 | |
| 17 | CPU-5-F | 34.400 | |
| Σ | | 100 | |

Mixture N-21:

Composition Compound

| No. | Abbreviation | c [%] | Physical properties | |
|---|---|---|---|---|
| 1 | CP-5-3 | 20.0 | T(N, I) [° C.] = | n/a |
| 2 | CC-3-5 | 10.0 | Δn (20° C., 589.3 nm) = | 0.0730 |

Mixture N-21:

Composition Compound

| No. | Abbreviation | c [%] | Physical properties | |
|---|---|---|---|---|
| 3 | CCU-2-F | 12.0 | Δε (20° C., 1 kHz) = | n/a |
| 4 | CCU-3-F | 10.0 | LTS (−20° C.) [d] | n/a |
| 5 | CCU-5-F | 8.0 | | |
| 6 | CCEG-3-F | 10.0 | | |
| 7 | CCEG-5-F | 10.0 | | |
| 8 | CCG-3-OT | 10.0 | | |
| 9 | CCG-5-OT | 10.0 | | |
| Σ | | 100 | | |

Device Examples

For the following device examples, the nematic host mixtures N-1 and N-2 are used and mixtures with the following dyes are prepared:

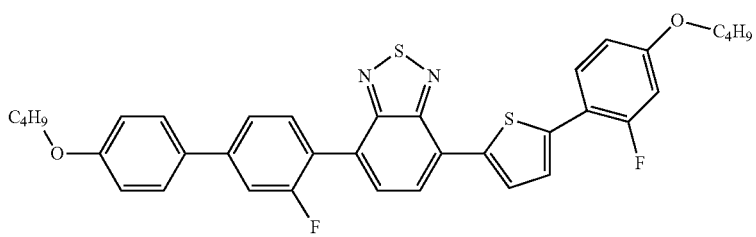

Ref-1

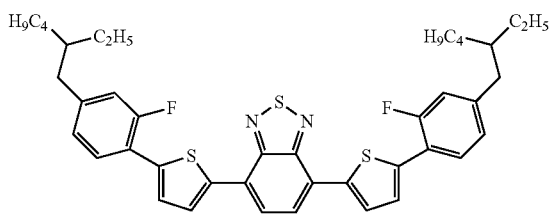

Ref-2

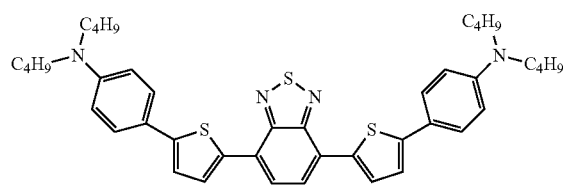

Ref-3

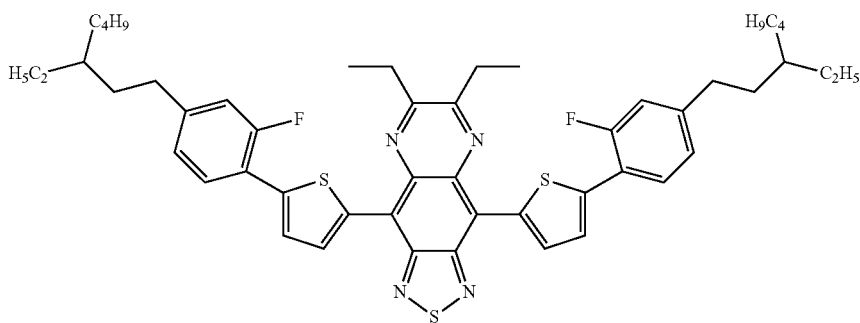

Ref-4

-continued
Ref-5
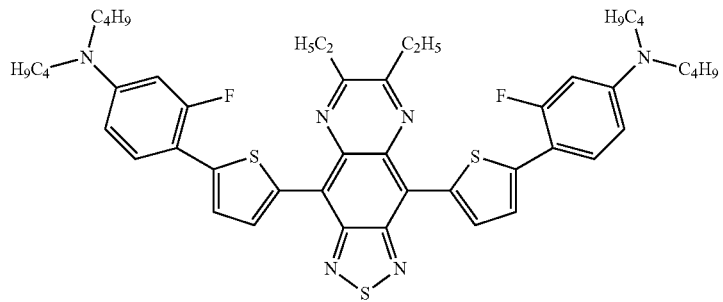
D-1
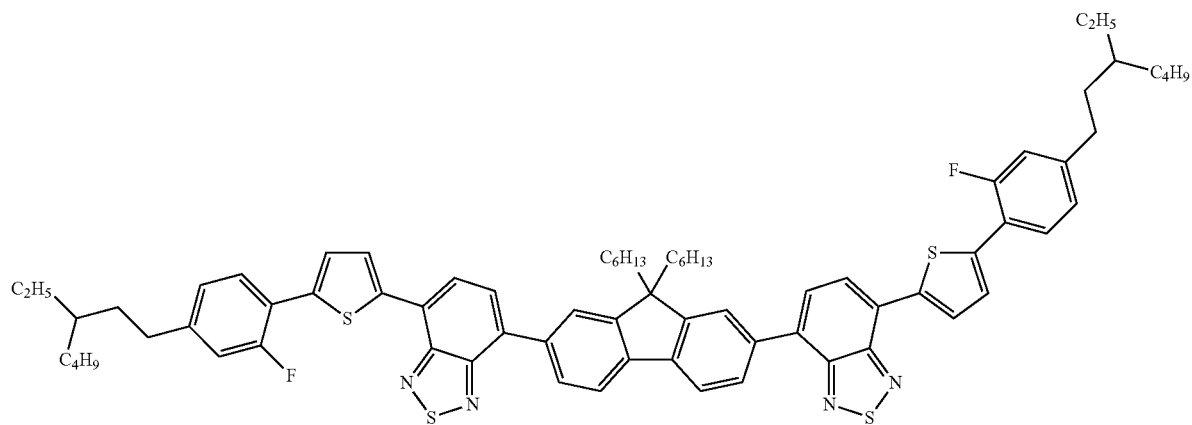
D-2
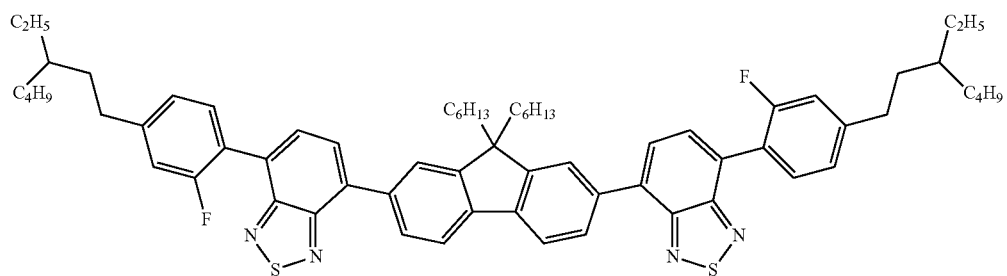
D-3
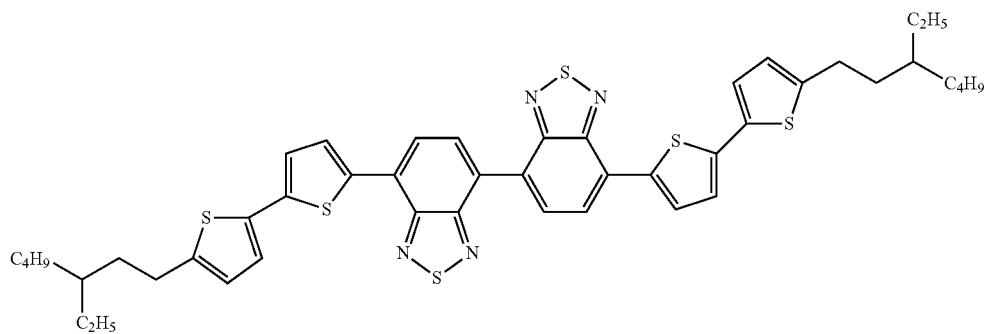

D-4
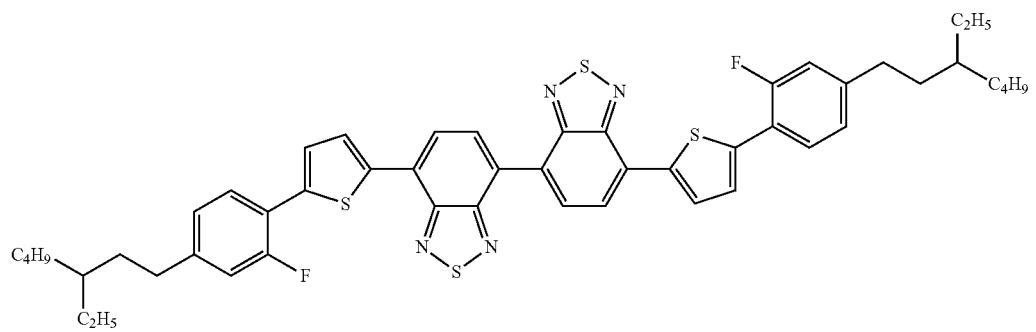
D-5
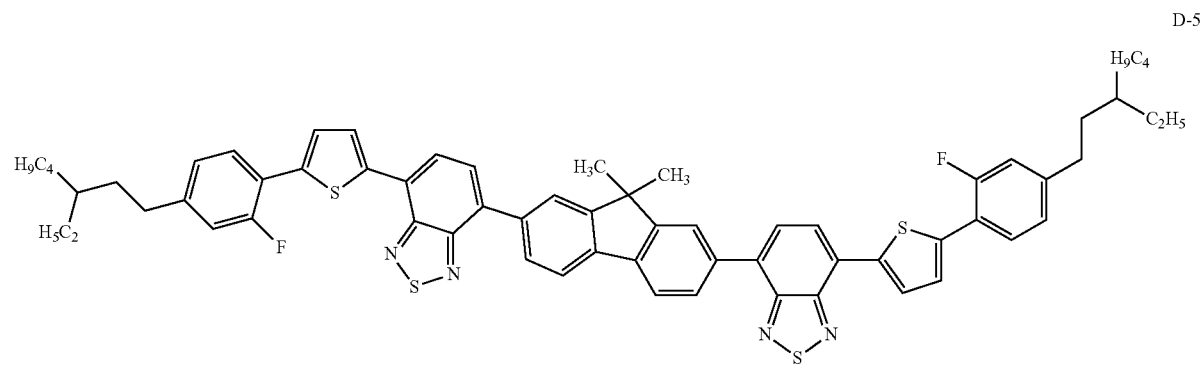
D-6
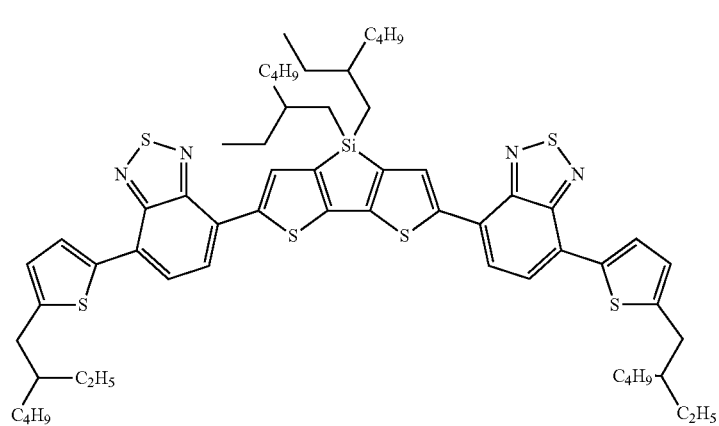
D-7
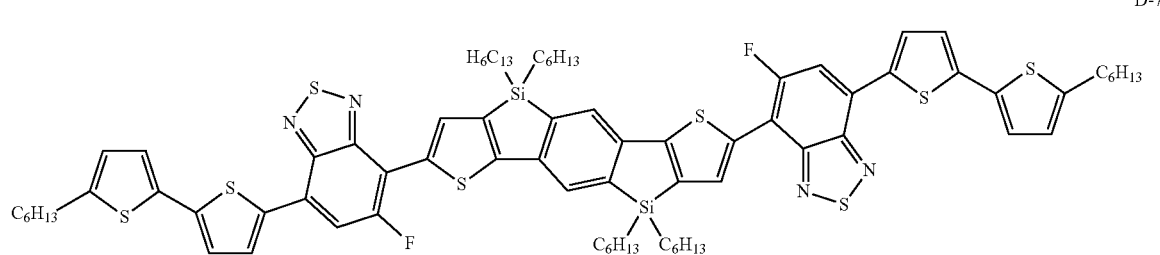

-continued
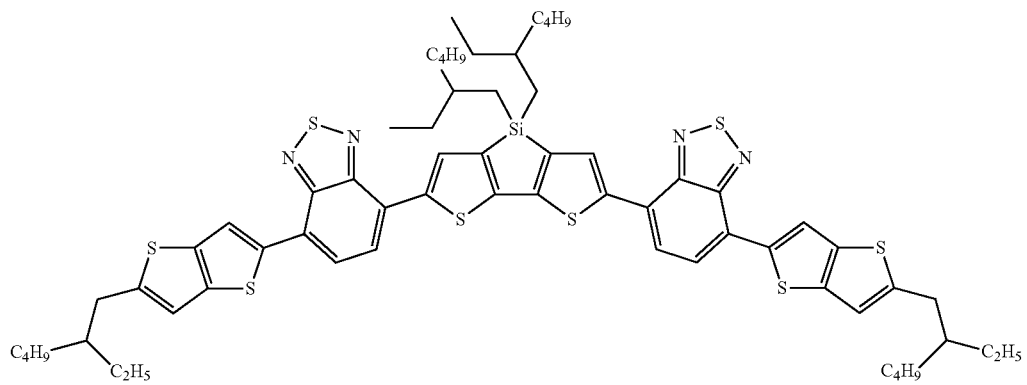
D-8
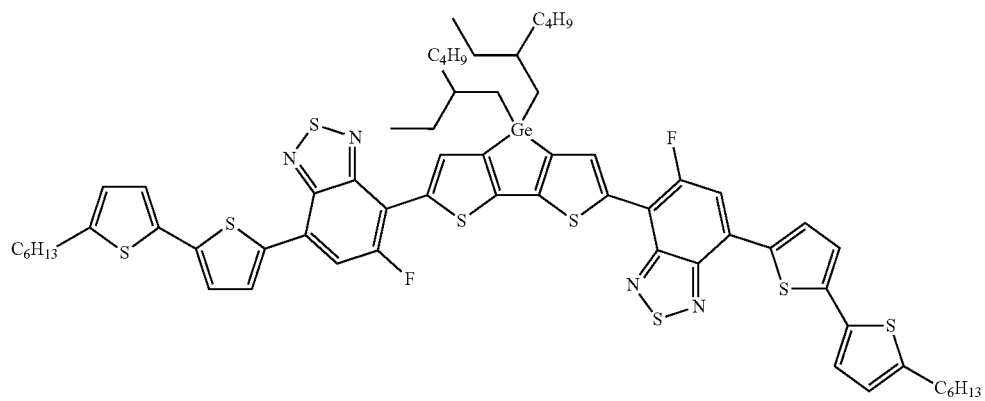
D-9
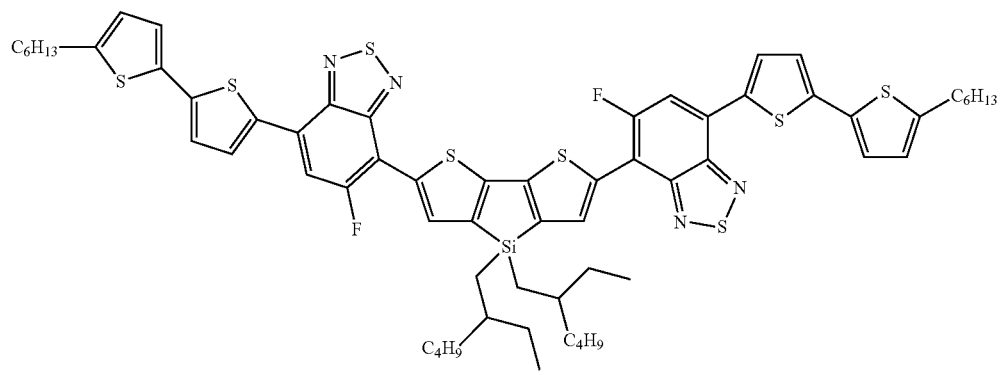
D-10
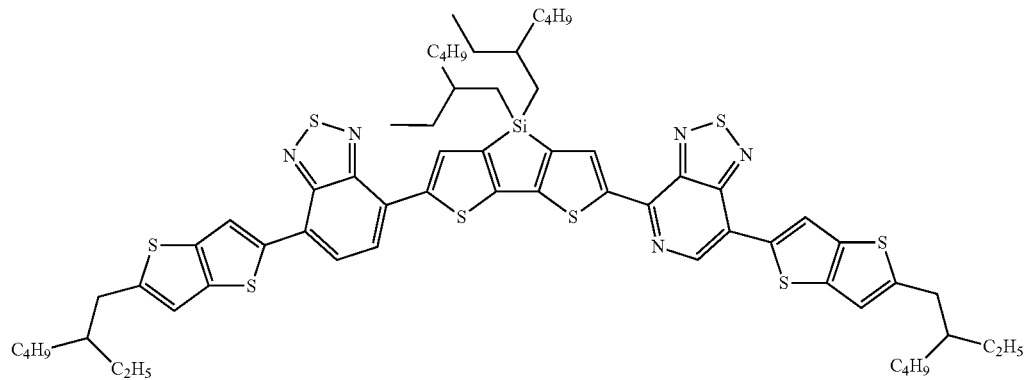
D-11

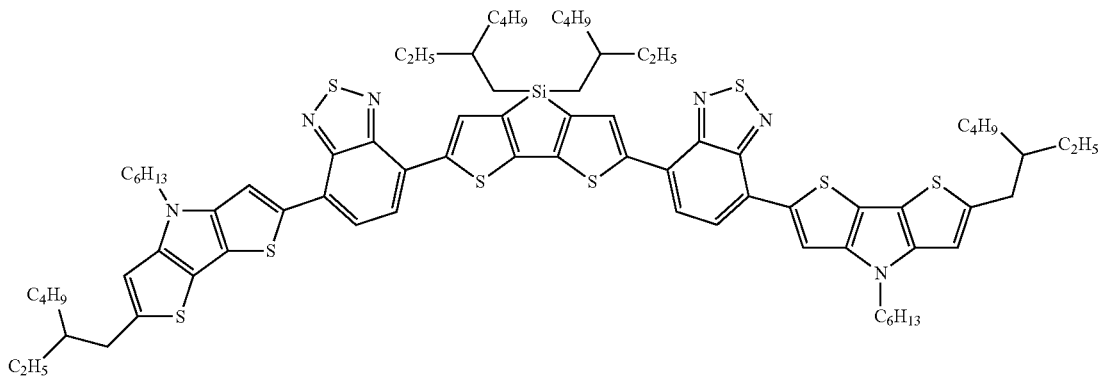

D-12

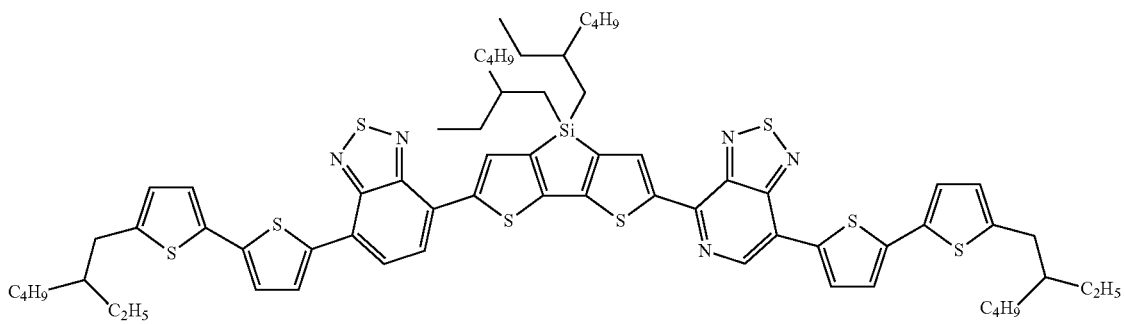

D-13

Single-Dye Mixture Examples for Evaluation

TABLE 1

For each dye the absorption maximum $\lambda_{max}$, the isotropic extinction coefficient and the degree of anisotropy R in the base mixture N-1 are provided. The concentration is about 0.1 mass %.

| Mixture example | Dye | $\lambda_{max}$ [nm] | isotropic extinction coefficient [1/(mass-%*cm)] | R |
|---|---|---|---|---|
| M-1 | Ref-1 | 459 | 375 | 0.78 |
| M-2 | Ref-2 | 505 | 395 | 0.71 |
| M-3 | Ref-3: | 585 | 465 | 0.73 |
| M-4 | Ref-4: | 670 | 275 | 0.68 |
| M-5 | Ref-5: | 779 | 345 | 0.66 |
| M-6 | D-1 | 486 | 432 | 0.76 |
| M-7 | D-2 | 426 | 371 | 0.68 |
| M-8 | D-3 | 530 | 454 | 0.74 |
| M-9 | D-4 | 507 | 454 | 0.75 |
| M-10 | D-5 | 487 | 550 | 0.78 |
| M-11 | D-6 | 585 | 465 | 0.70 |
| M-12 | D-7 | 590 | 560 | 0.78 |
| M-13 | D-8 | 605 | 511 | 0.76 |
| M-14 | D-9 | 617 | 520 | 0.78 |
| M-15 | D-10 | 633 | 505 | 0.70 |
| M-16 | D-11 | 656 | 540 | 0.74 |
| M-17 | D-12 | 590 | 560 | 0.73 |
| M-18 | D-13 | 668 | 555 | 0.71 |

The mixtures M-6 to M-18 are very well suitable for the use in devices for regulating the passage of energy from an outside space into an inside space, for example in windows. The mixtures have a suitable combination of high extinction, high degree of anisotropy (R) and good long term stability.

Multi-Dye Mixtures for Applications

The values shown in Table 1 as well as the corresponding values below are measured according to norm EN410.

The following mixtures are provided which are designed to have a neutral grey switching state:

Mixture Example E-1

The following mixture is prepared and investigated.

| Component | concentration c [%] |
|---|---|
| D-1 | 0.166 |
| D-2 | 0.261 |
| D-3 | 0.084 |
| D-9 | 0.288 |
| N-1 | Rest to 100 |

Mixture Example E-2

The following mixture is prepared and investigated.

| Component | concentration c [%] |
|---|---|
| D-1 | 0.220 |
| D-2 | 0.902 |
| D-3 | 0.221 |
| D-9 | 1.130 |
| N-2 | Rest to 100 |

Mixture Example E-3

The following mixture is prepared and investigated.

| Component | concentration c [%] |
|---|---|
| D-2 | 0.168 |
| D-3 | 0.118 |
| D-5 | 0.151 |
| D-11 | 0.294 |
| N-1 | Rest to 100 |

Mixture Example E-4

The following mixture is prepared and investigated.

| Component | concentration c [%] |
|---|---|
| D-2 | 0.884 |
| D-3 | 0.328 |
| D-5 | 0.428 |
| D-11 | 1.046 |
| N-2 | Rest to 100 |

Mixture Example E-5

The following mixture is prepared and investigated.

| Component | concentration c [%] |
|---|---|
| D-1 | 0.347 |
| D-9 | 0.253 |
| D-11 | 0.079 |
| N-1 | Rest to 100 |

Mixture Example E-6

The following mixture is prepared and investigated.

| Component | concentration c [%] |
|---|---|
| D-2 | 0.65 |
| D-7 | 0.43 |
| N-1 | Rest to 100 |

Mixture Example E-7

The following mixture is prepared and investigated.

| Component | concentration c [%] |
|---|---|
| D-2 | 1.379 |
| D-7 | 1.45 |
| N-2 | Rest to 100 |

Comparative Example C-1

The following comparative mixture C-1 is prepared and investigated.

| Component | concentration c [%] |
|---|---|
| Ref-1 | 0.930 |
| Ref-2 | 0.367 |
| Ref-3 | 0.987 |
| Ref-4 | 0.039 |
| N-2 | Rest to 100 |

The mixtures provided above are filled into test cells:

a) Double cell: Two parallel TN cells (twisted nematic, 90°) with 25 μm cell gap.

b) Single cell: VA cells (vertical alignment; rubbing direction 240°) with 15 μm cell gap.

TABLE 2

Total amounts of dye for a transmission $\tau_v$ in the bright state of the device of 59-62%, and the difference between on-state and off-state ($\Delta\tau_v$).

| Mixture | Type | Total amount dyes | $\tau_v$ bright state | $\tau_v$ dark state | $\Delta\tau_v$ difference |
|---|---|---|---|---|---|
| E-1 | double cell | 0.799% | 62.7% | 10.0% | 52.7% |
| E-2 | single cell | 2.473% | 61.7% | 18.0% | 43.7% |
| E-3 | double cell | 0.731% | 61.6% | 13.5% | 48.1% |
| E-4 | single cell | 2.686% | 61.4% | 21.3% | 40.1% |
| E-5 | double cell | 0.679% | 61.6% | 10.9% | 51.3% |
| E-6 | Double cell | 1.08% | 61.7% | 9.1% | 52.6% |
| E-7 | single cell | 2.829% | 61.7% | 16.8% | 44.9% |
| C-1 | single cell | 3.001% | 61.7% | 17.7% | 44% |

The mixtures E-1 to E-7 have a balanced grey or colorless appearance in one of the switching states.

The mixtures are very well suitable for the use in devices for regulating the passage of energy from an outside space into an inside space, for example in windows. The mixtures according to the invention have a suitably high difference between of the extinction in the on-state and off-state for the transmittance of white light, while at the same time the concentrations of dye are low.

A single cell with the conventional mixture C-1 requires a higher total amount of dyes (3.0%) in order to achieve a comparable extinction.

Stability in Sunlight Conditions

The relative extinction of samples is tested under daylight conditions (Suntest CPS by MTS Atlas; cut-off filter GG400 by Schott) at 20° C. base temperature. The surface temperature is 43° C.

The test is continued until the relative extinction drops to 80%.

As a standard 300 ppm of a stabilizer is added to the mixtures, which is of the following formula:

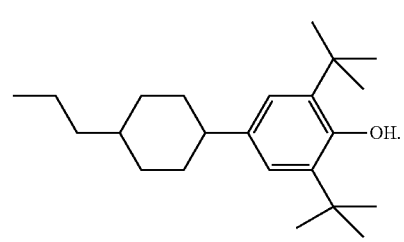 [SMILES: CCCC1CCC(c2cc(C(C)(C)C)c(O)c(C(C)(C)C)c2)CC1]

The lifetime of the mixtures according to the invention exceeds 4 weeks.

TABLE 3

Minimum lifetimes under suntest.

| Compound | Stability |
| --- | --- |
| D-6 | 74 weeks |
| D-7 | 66 weeks |
| D-8 | 76 weeks |
| D-9 | 68 weeks |
| D-10 | 70 weeks |
| D-11 | 58 weeks |
| D-12 | 68 weeks |
| D-13 | 62 weeks |

The invention claimed is:

1. A liquid crystalline medium comprising a dye component A) comprising one or more compounds of formula I,

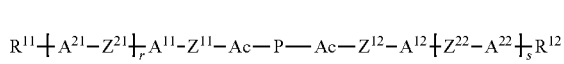

and
a liquid-crystalline component B) comprising one or more mesogenic compounds,
where in formula I
Ac independently of each other, denotes

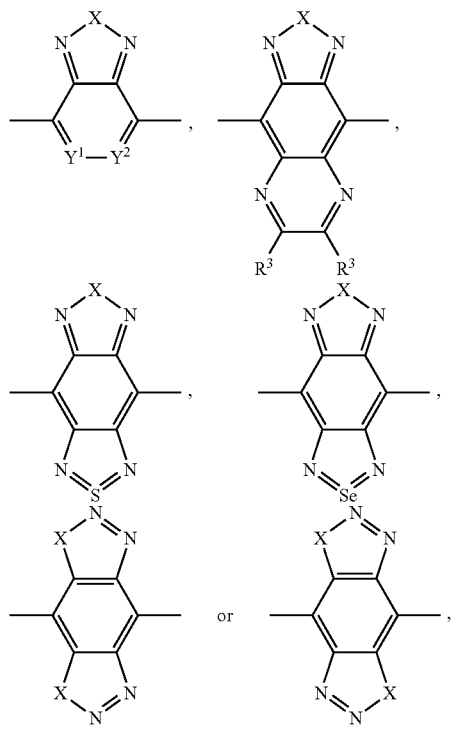

X independently is O, S, Se, $NR^2$ or Te,
$Y^1$, $Y^2$ independently are $CR^3$ or N,
$R^2$ independently is H, alkyl having 1 to 25 C atoms or aryl,
$R^3$ is H, F, Cl, CN, alkyl having 1 to 25 C atoms, alkoxy having 1 to 25 C atoms or aryl,
$R^{11}$, $R^{12}$ independently denote H, F, Cl, —CN, straight-chain alkyl having 1 to 25 C atoms or branched alkyl having 3 to 25 C atoms, in which one or more non-adjacent $CH_2$ groups may each be replaced, independently of one another, by —C($R^z$)=C($R^z$)—, —C≡C—, —N($R^z$)—, —O—, —S—, —CO—, —CO—O—, —O—CO— or —O—CO—O— in such a way that O and/or S atoms are not linked directly to one another, and in which one or more H atoms may be replaced by F, Cl, Br, I or CN,
$R^z$ on each occurrence, identically or differently, denotes H, halogen, straight-chain alkyl having 1 to 25 C atoms or branched or cyclic alkyl having 3 to 25 C atoms, in which one or more non-adjacent $CH_2$ groups may be replaced by —O—, —S—, —CO—, —CO—O—, —O—CO— or —O—CO—O— in such a way that O and/or S atoms are not linked directly to one another, and in which one or more H atoms may be replaced by F or Cl,
$A^{11}$, $A^{12}$ each, independently of one another, denote an aryl or heteroaryl group, which may be substituted by one or more groups L,
$A^{21}$, $A^{22}$ are each, independently of one another, denote an aryl or heteroaryl group, which may be substituted by one or ore groups L, or denote a cyclic alkyl group having 3 to 10 C atoms, in which one or more $CH_2$ groups may be replaced by O in such a way that no two O atoms are adjacent,
L on each occurrence, identically or differently, denotes OH, $CH_2OH$, F, Cl, Br, I, —CN, —$NO_2$, $SF_5$, —NCO, —NCS, —OCN, —SCN, —C(=O)N($R^z$)$_2$, —C(=O)$R^z$, —N($R^z$)$_2$, optionally substituted silyl, optionally substituted aryl having 6 to 20 C atoms, or straight-chain alkyl, alkoxy, alkylcarbonyl, alkoxycarbonyl, alkylcarbonyloxy or alkoxycarbonyloxy having 1 to 25 C atoms or branched alkyl, alkoxy, alkylcarbonyl, alkoxycarbonyl, alkylcarbonyloxy or alkoxycarbonyloxy having 3 to 25 C atoms, in which one or more H atoms may be replaced by F or Cl, an aryl or heteroaryl group, which may be substituted by one or more F, Cl, $C_1$-$C_6$ alkyl or alkoxy, and alternatively two adjacent groups L together denote a straight-chain alkylene group having 2 to 10 C atoms or branched alkylene group having 3 to 10 C atoms, in which one, several or all H atoms may be replaced by F and in which one or more —$CH_2CH_2$—groups can be replaced by —CH=CH—,
$Z^{11}$, $Z^{12}$ on each occurrence, identically or differently, denote a single bond, —$CR^{x1}$=$CR^{x2}$—, —C≡C— or —$NR^1$—,
$R^{x1}$, $R^{x2}$ independently of one another, denote H, F, Cl, CN or alkyl having 1-12 C atoms,
$R^1$ is H, F, alkyl having 1-12 C atoms or aryl,
$Z^{21}$, $Z^{22}$ are on each occurrence, identically or differently, denote a single bond, —$CR^{x1}$=$CR^{x2}$—, —C≡C— or —$NR^1$, or denote —O—, —S—, —$CR^{y1}R^{y2}$—, —$CF_2O$—, —$OCF_2$—, —C(O)—O—, —O—C(O)—, —O—C(O)—O—, —$OCH_2$—, —$CH_2O$—, —$SCH_2$—, —$CH_2S$—, —$CF_2S$—, —$SCF_2$—, —$(CH_2)_{n1}$—, —$CF_2CH_2$—, —$CH_2CF_2$—, —$(CF_2)_{n1}$—, —CH=CH—COO— or —OCO—CH=CH—,
n1 denotes 1, 2, 3 or 4,
$R^{y1}$, $R^{y2}$ each, independently of one another, denote H or alkyl having 1-12 C atoms,
r, s independently of one another, denote 0, 1, 2 or 3,
P denotes a single bond, —$(CH_2)_n$—, —O$(CH_2)_mO$—, —C≡C—, —NH—, —$NR^1$—, —O(CO)O—, —O—, —S— or one of the following groups:

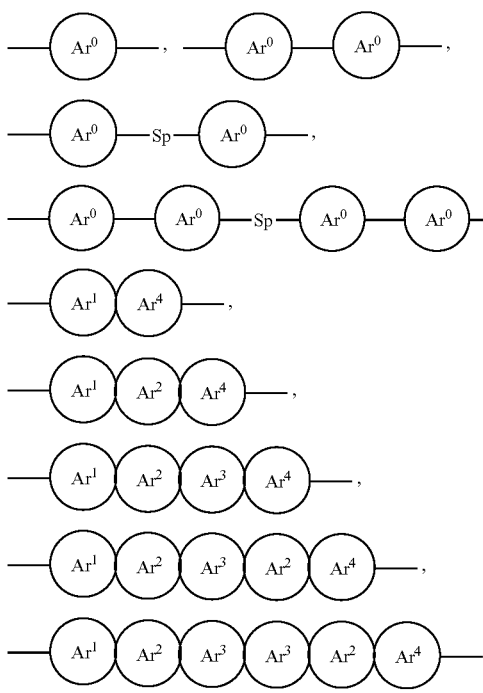

Ar⁰ is independently

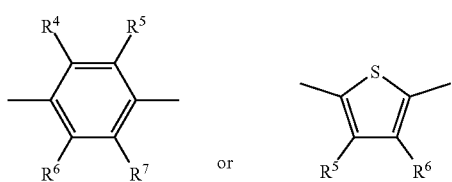

Ar¹ is independently selected from the following formulae

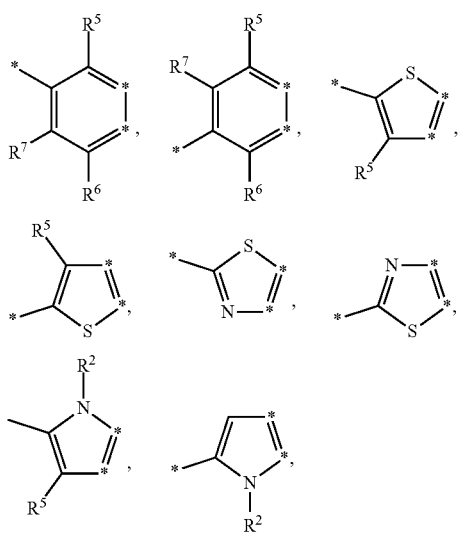

Ar⁴ is independently selected from the following formulae

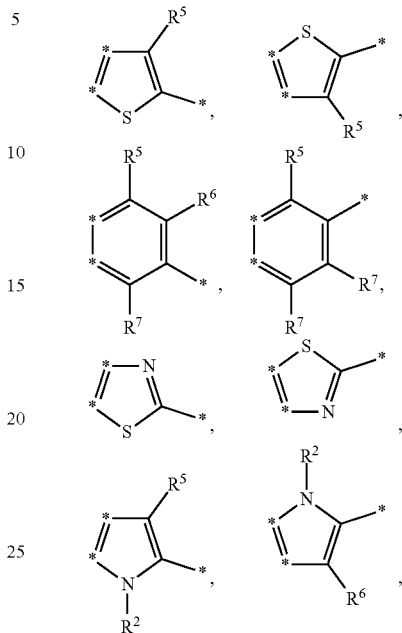

Ar², Ar³ are independently selected from the following formulae

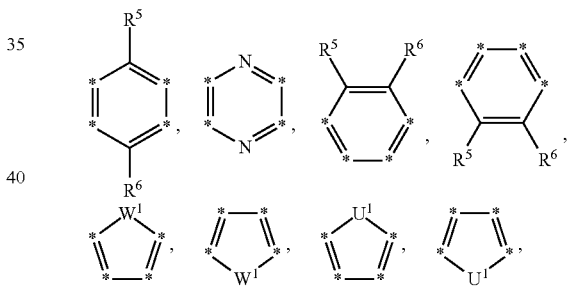

$W^1$ is S, O or Se,
$U^1$ is $CR^aR^b$, $GeR^aR^b$, $PR^2$ or $NR^2$, wherein $R^a$ and $R^b$ are independently defined as $R^4$,
$R^{4-7}$ independently are H, F, Cl, CN, or straight-chain alkyl with 1 to 30 C atoms or branched or cyclic alkyl with 3 to 30 C atoms, in which one or more $CH_2$ groups are optionally replaced by —O—, —S—, —C(=O)—, —C(=S)—, —C(=O)—O—, —O—C(=O)—, —NR⁰—, —SiR⁰R⁰⁰—, —CF₂—, —CR^{x1}=CR^{x2}— or —C≡C— in such a manner that O and/or S atoms are not linked directly to one another, and in which one or more H atoms are optionally replaced by F, Cl, Br, I or CN,
$R^0$, $R^{00}$ independently are H or straight-chain alkyl with 1 to 20 C atoms or branched alkyl with 3 to 20 C atoms that is optionally fluorinated,
Sp is a spacer group, and
each * is a point of attachment to an adjacent group, where each point of attachment is a shared carbon atom with the adjacent group.

2. The liquid crystalline medium according to claim 1, wherein one or more compounds of formula I are selected from the compounds of formulae IA to IC

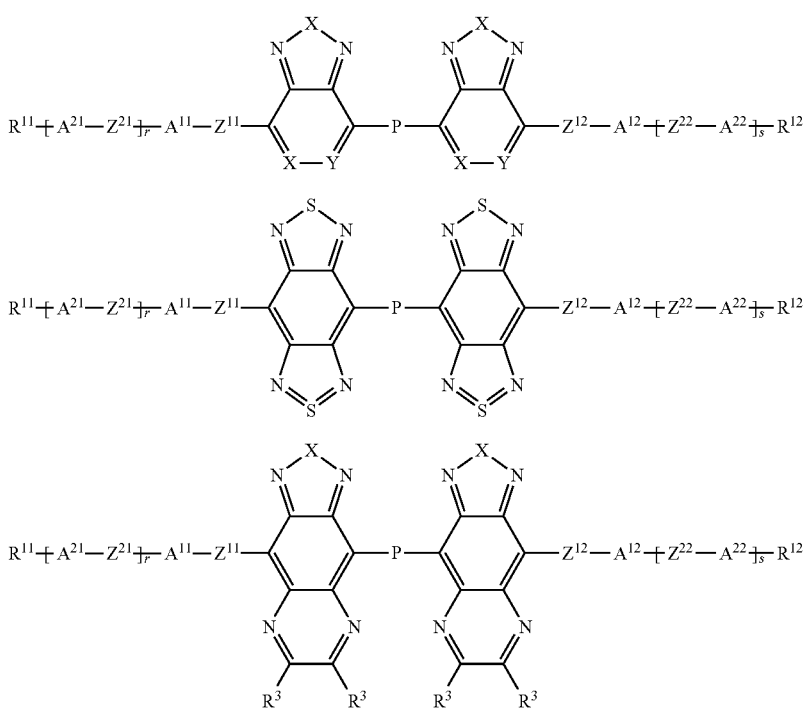

wherein

X independently is O, S, Se, NR$^2$ or Te,

R$^2$ independently is H, alkyl having 1 to 25 C atoms or aryl,

R$^3$ is H, F, Cl, CN, alkyl having 1 to 25 C atoms, alkoxy having 1 to 25 C atoms or aryl, R$^{11}$, R$^{12}$ independently denote H, F, Cl, —CN, straight-chain alkyl having 1 to 25 C atoms or branched alkyl having 3 to 25 C atoms, in which one or more non-adjacent CH$_2$ groups may each be replaced, independently of one another, by —C(R$^z$)=C(R$^z$)—, —C≡C—, —N(R$^z$)—, —O—, —S—, —CO—, —CO—O—, —O—CO— or —O—CO—O— in such a way that O and/or S atoms are not linked directly to one another, and in which one or more H atoms may be replaced by F, Cl, Br, I or CN, R$^z$ on each occurrence, identically or differently, denotes H, halogen, straight-chain alkyl having 1 to 25 C atoms or branched or cyclic alkyl having 3 to 25 C atoms, in which one or more non-adjacent CH$_2$ groups may be replaced by —O—, —S—, —CO—, —CO—O—, —O—CO— or —O—CO—O— in such a way that O and/or S atoms are not linked directly to one another, and in which, one or more H atoms may be replaced by F or Cl, A$^{11}$, A$^{12}$ each, independently of one another, denote an aryl or heteroaryl group, which may be substituted by one or more groups L, A$^{21}$, A$^{22}$ are each, independently of one another, denote an aryl or heteroaryl group, which may be substituted by one or more groups L or denote a cyclic alkyl group having 3 to 10 C atoms, in which one or more CH$_2$ groups may be replaced by O in such a way that no two O atoms are adjacent, L on each occurrence, identically or differently, denotes OH, CH$_2$OH, F, Cl, Br, I, —CN, —NO$_2$, SF$_5$, —NCO, —NCS, —OCN, —SCN, —C(=O)N(R$^z$)$_2$, —C(=O)R$^z$, —N(R$^z$)$_2$, optionally substituted silyl, optionally substituted aryl having 6 to 20 C atoms, or straight-chain alkyl, alkoxy, alkylcarbonyl, alkoxycarbonyl, alkylcarbonyloxy or alkoxycarbonyloxy having 1 to 25 C atoms or branched alkyl, alkoxy, alkylcarbonyl, alkoxycarbonyl, alkylcarbonyloxy or alkoxycarbonyloxy having 3 to 25 C atoms, in which one or more H atoms may be replaced by F or Cl, an aryl or heteroaryl group, which may be substituted by one or more F, Cl, C$_1$-C$_6$ alkyl or alkoxy, and alternatively two adjacent groups L together denote a straight-chain alkylene group having 2 to 10 C atoms or branched alkylene group having 3 to 10 C atoms, in which one, several or all H atoms may be replaced by F and in which one or more —CH$_2$CH$_2$— groups can be replaced by —CH=CH—, Z$^{11}$, Z$^{12}$ on each occurrence, identically or differently, denote a single bond, —CR$^{x1}$=CR$^{x2}$—, —C≡C— or —NR$^1$—, R$^{x1}$, R$^{x2}$ independently of one another, denote H, F, Cl, CN or alkyl having 1-12 C atoms, R$^1$ is H, F, alkyl having 1-12 C atoms or aryl, Z$^{21}$, Z$^{22}$ are on each occurrence, identically or differently, denote a single bond, —CR$^{x1}$=CR$^{x2}$, —C≡C— or —NR$^1$—, or denote —O—, —S—, —CR$^{y1}$R$^{y2}$—, —CF$_2$O—, —OCF$_2$—, —C(O)—O—, —O—C(O)—, —O—C(O)—O—, —OCH$_2$—, —CH$_2$O—, —SCH$_2$—, —CH$_2$S—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—COO or —OCO—CH=CH—, n1 denotes 1, 2, 3 or 4, R$^{y1}$, R$^{y2}$ each, independently of one another, denote H or alkyl having 1-12 C atoms, r, S independently of one another, denote 0, 1, 2 or 3, P denotes a single bond, —(CH$_2$)$_n$—, —O(CH$_2$)$_m$O—, —C≡C—, —NH—, —NR$^1$—, —O(CO)O—, —O—, —S— or one of the following groups:

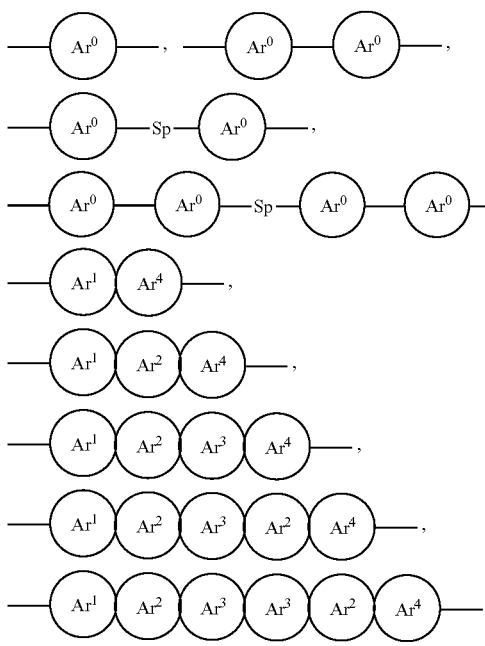

Ar$^0$ is independently

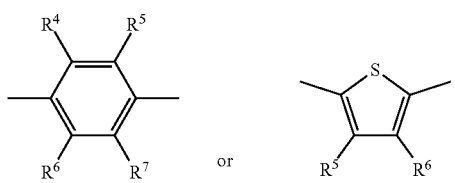

Ar$^1$ is independently selected from the following formulae

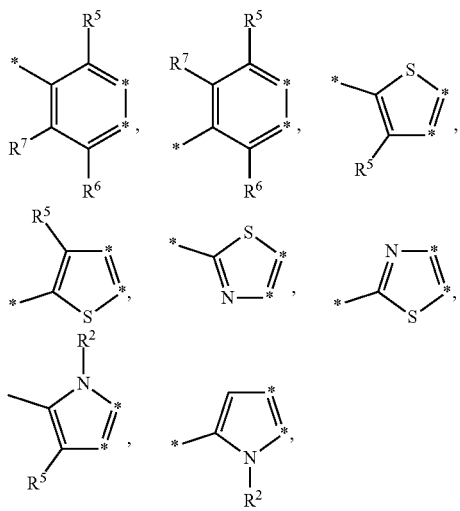

Ar$^4$ is independently selected from the following formulae

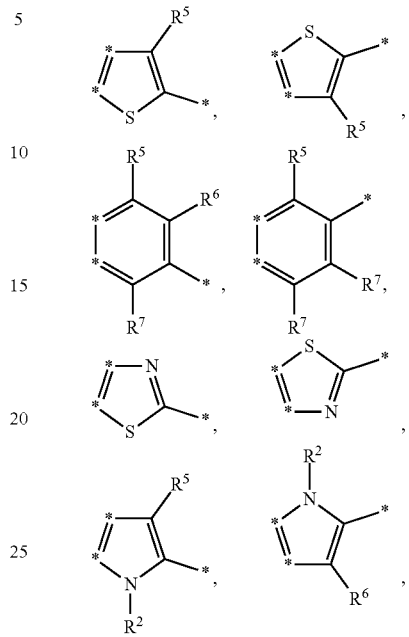

Ar$^2$, Ar$^3$ are independently selected from the following formulae

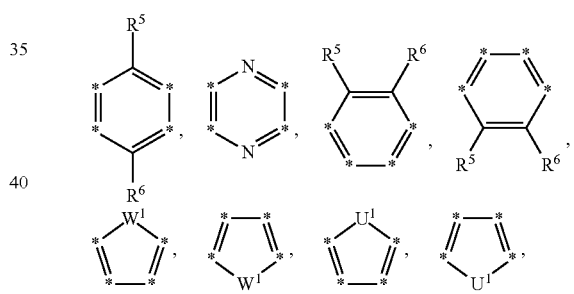

W$^1$ is S, O or Se,
U$^1$ is CR$^a$R$^b$, GeR$^a$R$^b$, PR$^2$ or NR$^2$,
R$^a$,R$^b$ are independently defined as R$^4$,
R$^{4-7}$ independently are H, F, Cl, CN, or straight-chain alkyl with 1 to 30 C atoms or branched or cyclic alkyl with 3 to 30 C atoms, in which one or more CH$_2$ groups are optionally replaced by —O—, —S—, —C(=O)—, —C(=S)—, —C(=O)—O—, —O—C(=O)—, —NR$^0$—, —SiR$^0$R$^{00}$—, —CF$_2$—, —CR$^{x1}$=CR$^{x2}$— or —C≡C— in such a manner that O and/or S atoms are not linked directly to one another, and in which one or more H atoms are optionally replaced by F, Cl, Br, I or CN,
R$^0$, R$^{00}$ independently are H or straight-chain alkyl with 1 to 20 C atoms or branched alkyl with 3 to 20 C atoms that is optionally fluorinated,
Sp is a spacer group, and
each * is a point of attachment to an adjacent g up, where each point of attachment is a shared carbon atom with the adjacent group.

3. The liquid crystalline medium according to claim 1, which comprises one or more compounds of the following formulae

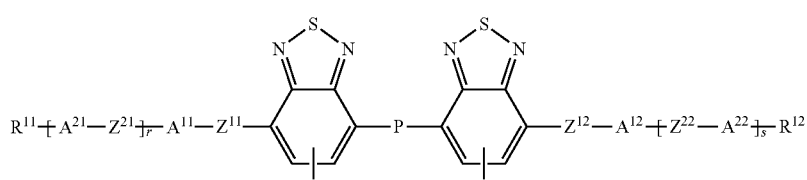

IA-1

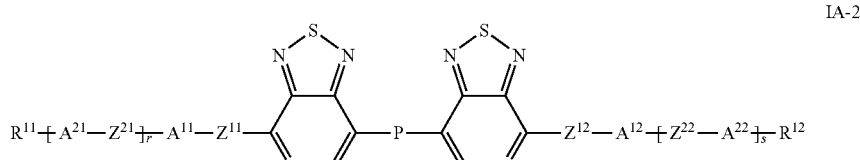

IA-2

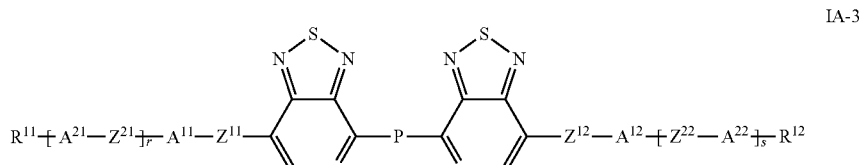

IA-3

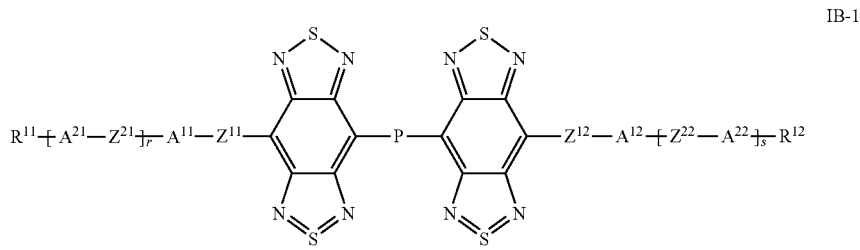

IB-1

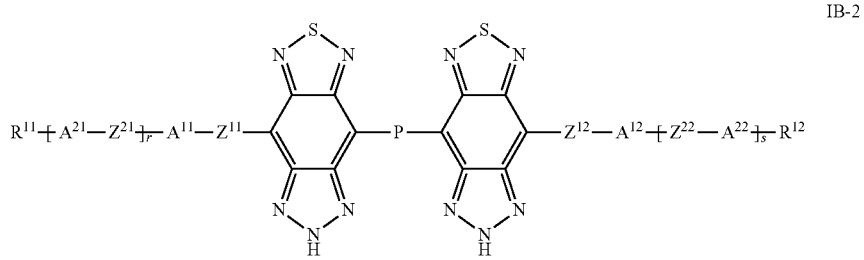

IB-2

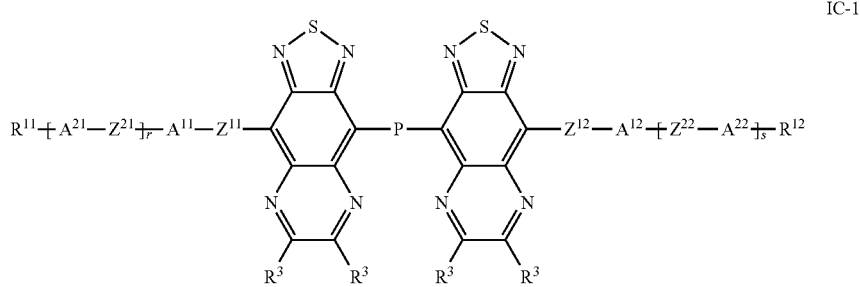

IC-1 where
- $Z^{21}$, $Z^{22}$ on each occurrence, identically or differently, preferably denote a single bond, —$CR^{x1}$=$CR^{x2}$—, —C≡C— or —C(O)—, and
- $R^3$ is H, F, Cl, CN, alkyl having 1 to 25 C atoms, alkoxy having 1 to 25 C atoms or aryl,
- $R^{11}$, $R^{12}$ independently denote H, F, Cl, —CN, straight-chain alkyl having 1 to 25 C atoms or branched alkyl having 3 to 25 C atoms, in which one or more non-adjacent CH$_2$ groups may each be replaced, independently of one another, by —C($R^z$)=C($R^z$)—, —C≡C—, —N($R^z$)—, —O—, —S—, —CO—, —CO—O—, —O—CO— or —O—CO—O— in such a way that O and/or S atoms are not linked directly to one another, and in which one or more H atoms may be replaced by F, Cl, Br, I or CN,
- $R^z$ on each occurrence, identically or differently, denotes H, halogen, straight-chain alkyl having 1 to 25 C atoms or branched or cyclic alkyl having 3 to 25 C atoms, in which one or more non-adjacent CH$_2$ groups may be replaced by —O—, —S—, —CO—, —CO—O—, —O—CO— or —O—CO—O— in such a way that O and/or S atoms are not linked directly to one another, and in which one or more H atoms may be replaced by F or Cl, $A^{11}$, $A^{12}$ each, independently of one another, denote an aryl or heteroaryl group, which may be substituted by one or more groups L, $A^{21}$, $A^{22}$ are each, independently of one another, denote an aryl or heteroaryl group, which may be substituted by one or more groups L or denote a cyclic alkyl group having 3 to 10 C atoms, in which one or more $CH_2$ groups may be replaced by O in such a way that no two O atoms are adjacent, L on each occurrence, identically or differently, denotes OH, $CH_2OH$, F, Cl, Br, I, —CN, $NO_2$, $SF_5$, —NCO, —NCS, —OCN, —SCN, —C(=O)N($R^z$)$_2$, —C(=O)$R^z$, —N($R^z$)$_2$, optionally substituted silyl, optionally substituted aryl having 6 to 20 C atoms, or straight-chain alkyl, alkoxy, alkylcarbonyl, alkoxycarbonyl, alkylcarbonyloxy or alkoxycarbonyloxy having 1 to 25 C atoms or branched alkyl, alkoxy, alkylcarbonyl alkoxycarbonyl, alkylcarbonyloxy or alkoxycarbonyloxy having 3 to 25 C atoms, in which one or more H atoms may be replaced by F or Cl, an aryl or heteroaryl group, which may be substituted by one or more F, Cl, $C_1$-$C_6$ alkyl or alkoxy, and alternatively two adjacent groups L together denote a straight-chain alkylene group having 2 to 10 C atoms or branched alkylene group having 3 to 10 C atoms, in which one, several or all H atoms may be replaced by F and in which one or more —$CH_2CH_2$— groups can be replaced by —CH=CH—, $Z^{11}$, $Z^{12}$ on each occurrence, identically or differently, denote a single bond, —$CR^{x1}$=$CR^{x2}$—, —C≡C— or —$NR^1$—, $R^{x1}$, $R^{x2}$ independently of one another, denote H, F, Cl, CN or alkyl having 1-12 C atoms, $R^1$ is H, F, alkyl having 1-12 C atoms or aryl, $Z^{21}$, $Z^{22}$ are on each occurrence, identically or differently, denote a single bond, —$CR^{x1}$=$CR^{x2}$—, —C≡C— or —$NR^1$—, or denote —O—, —S—, —$CR^{y1}R^{y2}$—, —$CF_2O$—, —$OCF_2$—, —C(O)—O—, —O—C(O)—, —O—C(O)—O—, —$OCH_2$—, —$CH_2O$—, —$SCH_2$—, —$CH_2S$—, —$CF_2S$—, —$SCF_2$—, —$(CH_2)_{n1}$—, —$CF_2CH_2$—, —$CH_2CF_2$—, —$(CF_2)_{n1}$—, —CH=CH—COO or —OCO—CH=CH—, n1 denotes 1, 2, 3 or 4, $R^{y1}$, $R^{y2}$ each, independently of one another, denote H or alkyl having 1-12 C atoms, r, S independently of one another, denote 0, 1, 2 or 3, P denotes a single bond, —$(CH_2)_n$—, —$O(CH_2)_mO$—, —C≡C—, —NH—, —$NR^1$—, —O(CO)O—, —O—, —S— or one of the following groups

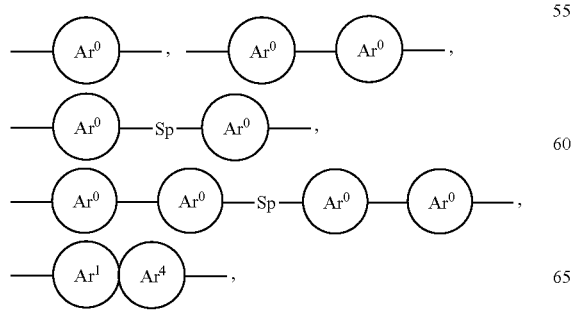

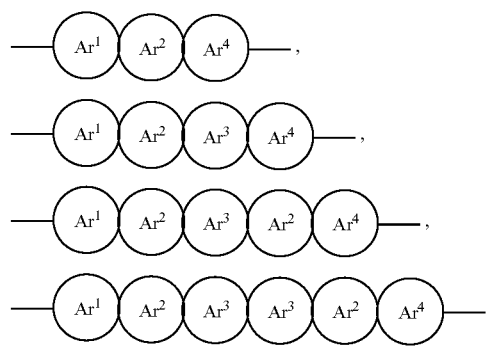

wherein $Ar^0$ is independently

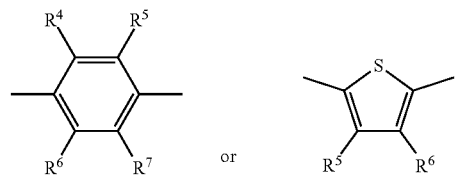

$Ar^1$ is independently selected from the following formulae

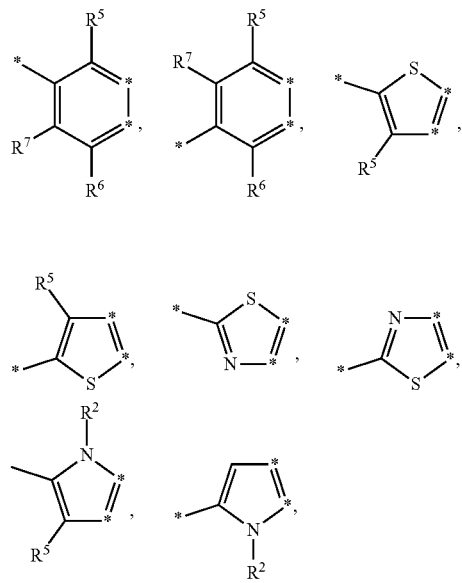

$Ar^4$ is independently selected from the following formulae

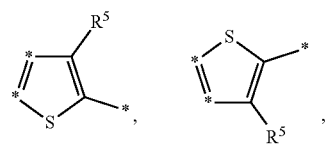

-continued

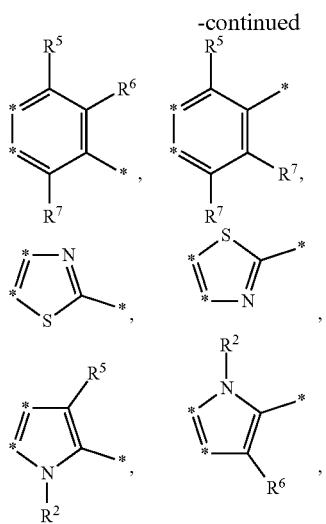

Ar², Ar³ are independently selected from the following formulae

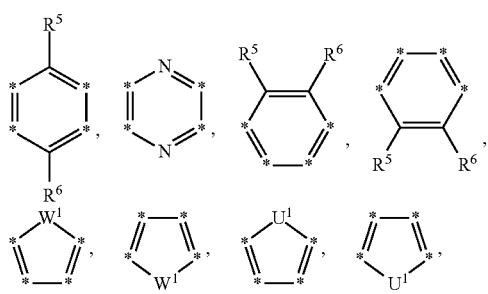

W¹ is S, O or Se,
U¹ is CR$^a$R$^b$, GeR$^a$R$^b$, PR² or NR²,
R$^a$, R$^b$ are independently defined as R⁴,
R$^{4-7}$ independently are H, F, Cl, CN, or straight-chain alkyl with 1 to 30 C atoms or branched or cyclic alkyl with 3 to 30 C atoms, in which one or more CH₂ groups are optionally replaced by —O—, —S—, —C(=O)—, —C(=S)—, —C(=O)—O—, —O—C(=O)—, —NR⁰—, —SiR⁰R⁰⁰—, —CF₂—, —CR$^{x1}$=CR$^{x2}$— or —C≡C— in such a manner that O and/or S atoms are not linked directly to one another, and in which one or more H atoms are optionally replaced by F, Cl, Br, I or CN,
R⁰, R⁰⁰ independently are H or straight-chain alkyl with 1 to 20 C atoms or branched alkyl with 3 to 20 C atoms that is optionally fluorinated,
Sp is a spacer group, and
each * is a point of attachment to an adjacent group, where each point of attachment is a shared carbon atom with the adjacent group.

4. The liquid crystalline medium according to claim 1, wherein A¹¹ and A¹² denote, independently of one another, 1,4-phenylene, 1,4-naphthylene, 2,6-naphthylene, thiazole-2,5-diyl, thiophene-2,5-diyl or thienothiophene-2,5-diyl, wherein one or more H atoms may be replaced by a group L.

5. The liquid crystalline medium according to claim 1, which comprises one or more compounds of formula I wherein Z²¹ and Z²² denote a single bond.

6. The liquid crystalline medium according to claim 1, which comprises one or more compounds of formula I wherein R¹¹ and R¹² denote a branched alkyl group having 3 to 25 C atoms, in which one or more H atoms can be replaced by F, one or more CH₂ groups can be replaced by O and/or NH and one or more CH groups can be replaced by N.

7. The liquid crystalline medium according to claim 1, which has negative dielectric anisotropy and comprises one or more compounds selected from the group of compounds of formulae CY, PY and AC CY
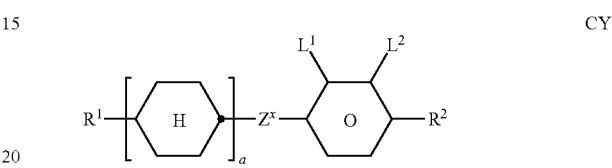

PY
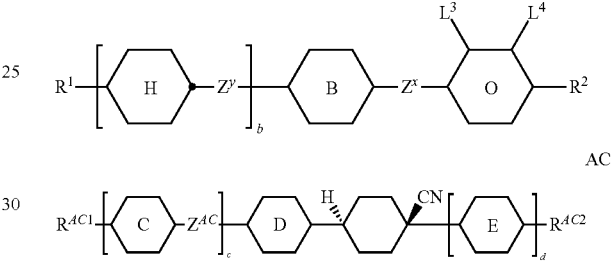

AC
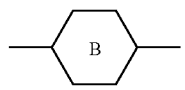

wherein

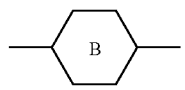

denotes

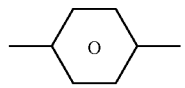

or

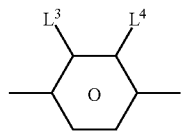 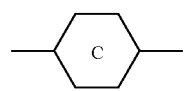

and

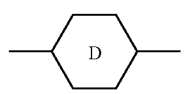

denote

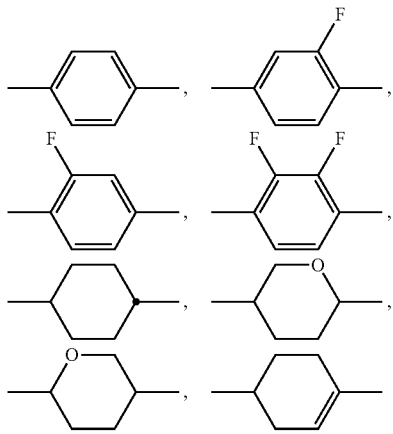

or

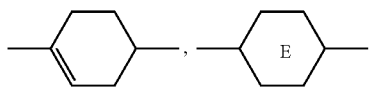

denotes one of the following groups

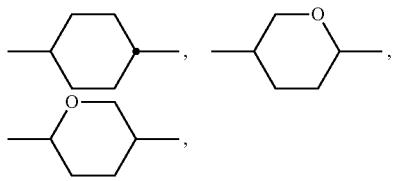

- R¹, R² each, independently of one another, denote alkyl having 1 to 12 C atoms, where one or two non-adjacent CH₂ groups may be replaced by —O—, —CH=CH—, —CO—, —OCO— or —COO— in such a way that O atoms are not linked directly to one another,
- $R^{AC1}$, $R^{AC2}$ each, independently of one another, denote alkyl having 1 to 12 C atoms, where one or two non-adjacent CH₂ groups may be replaced by —O—, —CH=CH—, —CO—, —OCO— or —COO— in such a way that O atoms are not linked directly to one another,
- $Z^x$, $Z^y$, $Z^{AC}$ each, independently of one another, denote —CH₂CH₂—, —CH=CH—, —CF₂O—, —OCF₂—, —CH₂O—, —OCH₂—, —CO—O—, —O—CO—, —C₂F₄—, —CF=CF—, —CH=CH—CH₂O— or a single bond,
- L¹ to L⁴ each, independently of one another, denote F, Cl, CN, OCF₃, CF₃, CH₃, CH₂F, CHF₂,
- a is 1 or 2,
- b is 0 or 1,
- c is 0, 1 or 2, and
- d is 0 or 1.

8. The liquid crystalline medium according to claim 1, which has positive dielectric anisotropy and comprises one or more compounds selected from the group of compounds of formulae II to VIII II
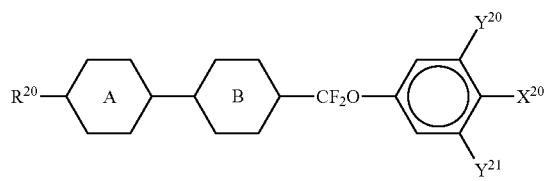

III
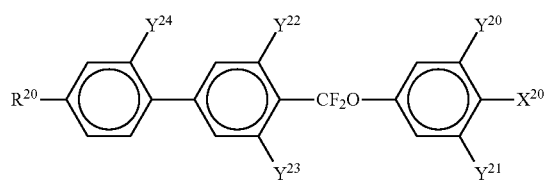

IV
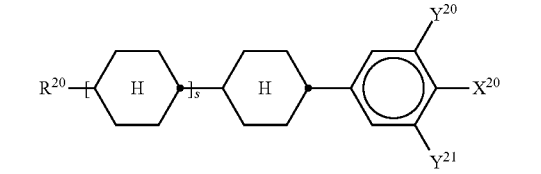

V
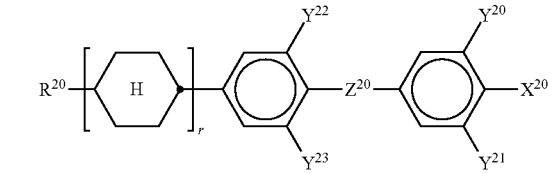

VI
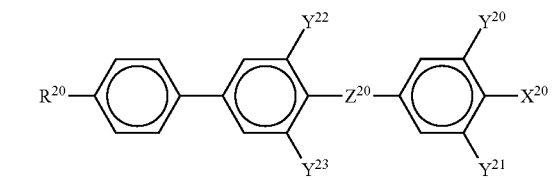

VII
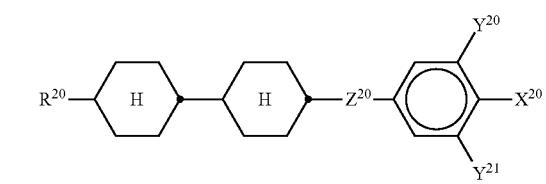

VIII
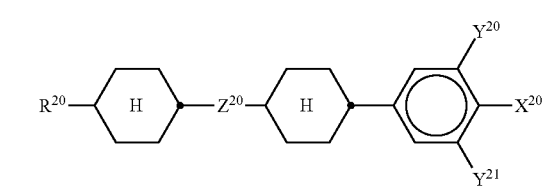

wherein

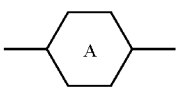

and

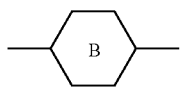

each independently of one another, denote

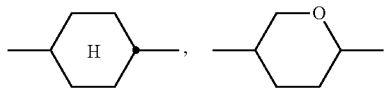

or

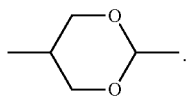

$R^{20}$ each, identically or differently, denote a halogenated or unsubstituted alkyl or alkoxy radical having 1 to 15 C atoms, where one or more $CH_2$ groups in these radicals may each be replaced, independently of one another, by —C≡C—, —$CF_2$O—, —CH=CH—,

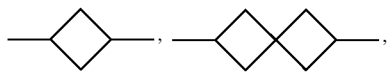

—O—, —CO—O— or —O—CO— in such a way that O atoms are not linked directly to one another, $X^{20}$ each, identically or differently, denote F, Cl, CN, $SF_5$, SCN, NCS, or a halogenated alkyl radical, or a halogenated alkoxy radical, each having 1 to 6 C atoms or a halogenated alkenyl radical or a halogenated alkenyloxy radical, each having 2 to 6 C atoms, and $Y^{20-24}$ each, identically or differently, denote H or F;

$Z^{20}$ denotes —$C_2H_4$—, —$(CH_2)_4$—, —CH=CH—, —CF=CF—, —$C_2F_4$—, —$CH_2CF_2$—, —$CF_2CH_2$—, —$CH_2$O—, —O$CH_2$—, —COO— or —O$CF_2$—, in formulae V and VI also a single bond, in formulae V and VIII also —$CF_2$O—, r denotes 0 or 1, and S denotes 0 or 1.

9. The liquid crystalline medium according to claim 1, which additionally comprises one or more compounds selected from the group of compounds of formulae DK and O

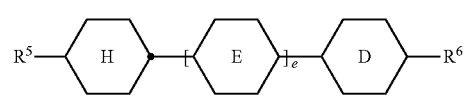 DK

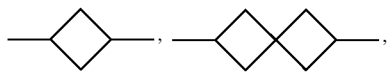 O wherein $R^5$, $R^6$, $R^{O1}$ and $R^{O2}$ each, independently of one another, denote alkyl having 1 to 12 C atoms, where one or two non-adjacent $CH_2$ groups may be replaced by —O—, —CH=CH—, —CO—, —OCO— or —COO— in such a way that O atoms are not linked directly to one another,

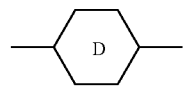

denotes

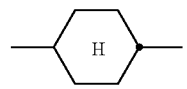

or

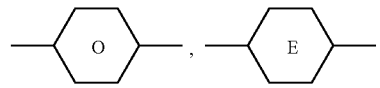

denotes

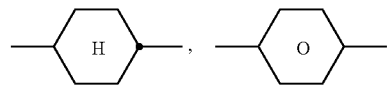

or

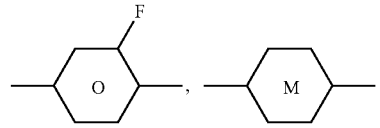

denotes

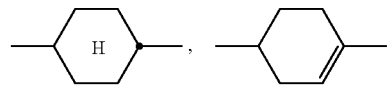

or

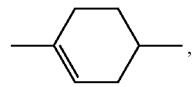

and

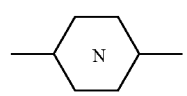

denotes

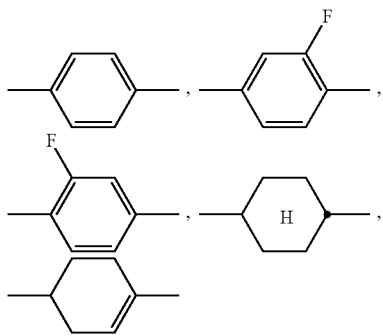

or

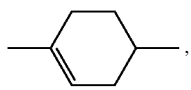

$Z^{O1}$ denotes —CH$_2$CH$_2$—, —CF$_2$CF$_2$—, —C≡C— or a single bond, $Z^{O2}$ denotes CH$_2$O, —C(O)O—, —CH$_2$CH$_2$—, —CF$_2$CF$_2$—, or a single bond, o is 1 or 2, and e is 1 or 2.

10. The liquid crystalline medium according to claim 9, which comprises one or more compounds of formula O3 to O5

O3

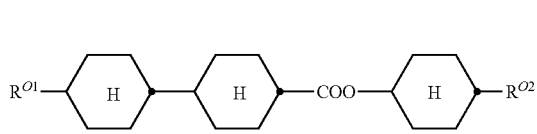

O4

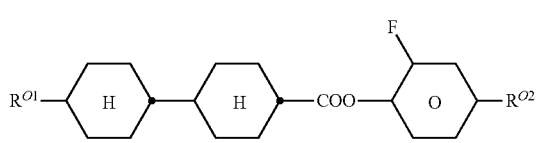

O5

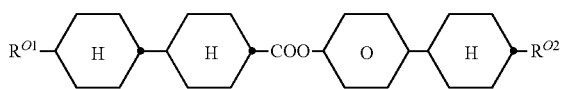

wherein $R^{O1}$ and $R^{O2}$, identically or differently, denote straight-chain alkyl having 1 to 6 C atoms or straight-chain alkenyl having 2 to 6 C atoms.

11. A method comprising incorporating the liquid crystalline media according to claim 1 in: electro-optical displays, devices for regulating the passage of energy from an outside space into an inside space, electrical semiconductors, organic field-effect transistors (OFETs), printed circuits, radio frequency identification elements (RFIDs), organic light-emitting diodes (OLEDs), lighting elements, photovoltaic devices, optical sensors, effect pigments, decorative elements or dyes for colouring polymers.

12. A device for regulating the passage of energy from an outside space into an inside space, where the device contains a switching layer comprising the liquid crystalline medium according to claim 1.

13. A window containing a device according to claim 12.

14. A compound of formula I

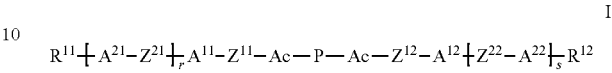

I wherein $A^{11}$, $A^{12}$ each, independently of one another, denote an aryl or heteroaryl group, which may be substituted by one or more groups L, $A^{21}$, $A^{22}$ are each, independently of one another, denote an aryl or heteroaryl group, which may be substituted by one or more groups L or denote a cyclic alkyl group having 3 to 10 C atoms, in which one or more CH$_2$ groups may be replaced by O in such a way that no two O atoms are adjacent, L on each occurrence, identically or differently, denotes OH, CH$_2$OH, F, Cl, Br, I, —CN, —NO$_2$ SF$_5$, —NCO, —NCS, —OCN, —SCN, —C(=O)N(R$^z$)$_2$, —C(=O)R$^z$, —N(R$^z$)$_2$, optionally substituted silyl, optionally substituted aryl having 6 to 20 C atoms, or straight-chain alkyl, alkoxy, alkylcarbonyl, alkoxycarbonyl, alkylcarbonyloxy or alkoxycarbonyloxy having 1 to 25 C atoms or branched alkyl, alkoxy, alkylcarbonyl, alkoxycarbonyl, alkylcarbonyloxy or alkoxycarbonyloxy having 3 to 25 C atoms, in which one or more H atoms may be replaced by F or Cl, an aryl or heteroaryl group, which may be substituted by one or more F, Cl, C$_1$-C$_6$ alkyl or alkoxy, and alternatively two adjacent groups L together denote a straight-chain alkylene group having 2 to 10 C atoms or branched alkylene group having 3 to 10 C atoms, in which one, several or all H atoms may be replaced by F and in which one or more —CH$_2$CH$_2$— groups can be replaced by CH=CH—, $Z^{11}$, $Z^{12}$ on each occurrence, identically or differently, denote a single bond, —CR$^{x1}$=CR$^{x2}$—, —C≡C— or —NR$^1$—, $R^{x1}$, $R^{x2}$ independently of one another, denote H, F, CL, CN or alkyl having 1-12 C atoms, $R^1$ is H, F, alkyl having 1-12 C atoms or aryl, $Z^{21}$, $Z^{22}$ are on each occurrence, identically or differently, denote a single bond, —CR$^{x1}$=CR$^{x2}$—, —C≡C— or —NR$^1$—, or denote —O—, —S—, —CR$^{y1}$R$^{y2}$—, —CF$_2$O—, —OCF$_2$—, —C(O)—O—, —O—C(O)—, —O—C(O)—O—, —OCH$_2$—, —CH$_2$O—, —SCH$_2$—, —CH$_2$S—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—COO or —OCO—CH=CH—, n1 denotes 1, 2, 3 or 4, $R^{y1}$, $R^{y2}$ each, independently of one another, denote H or alkyl having 1-12 C atoms, $R^{11}$, $R^{12}$ independently denote H, F, Cl, —CN, straight-chain alkyl having 1 to 25 C atoms or branched alkyl having 3 to 25 C atoms, in which one or more non-adjacent CH$_2$ groups may each be replaced, independently of one another, by —C(R$^z$)=C(R$^z$)—, —C≡C—, —N(R$^z$)—, —O—, —S—, —CO—, —CO—O—, —O—CO— or —O—CO—O—in such a way that O and/or S atoms are not linked directly to one another, and in which one or more H atoms may be replaced by F, Cl, Br, I or CN, r, S independently of one another, denote 0, 1, 2 or 3, P denotes

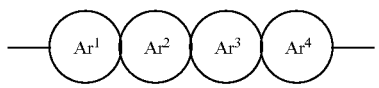

or

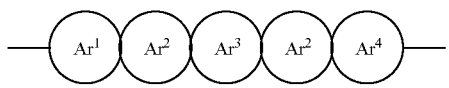

or

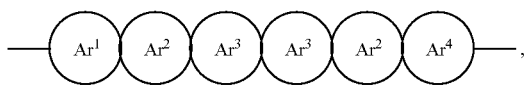

wherein

Ar$^1$ is independently selected from the following formulae

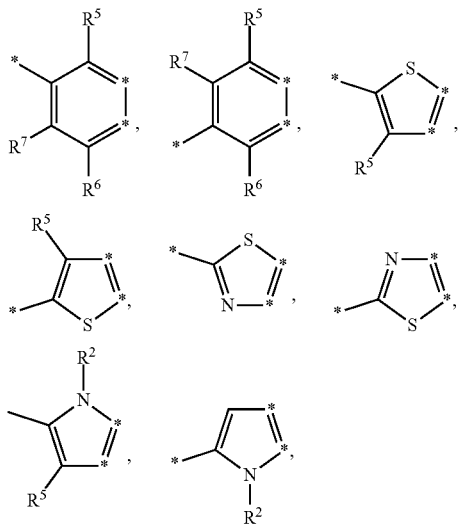

Ar$^4$ is independently selected from the following formulae

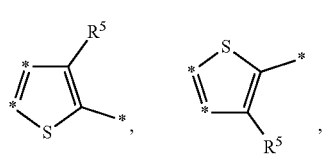

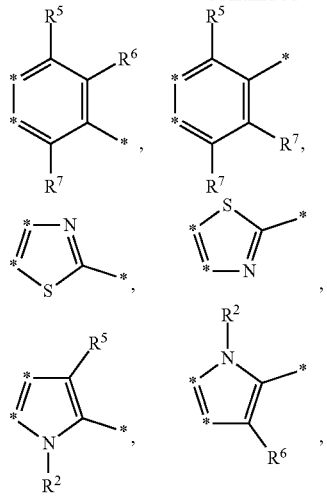

Ar$^2$, Ar$^3$ are independently selected from the following formulae

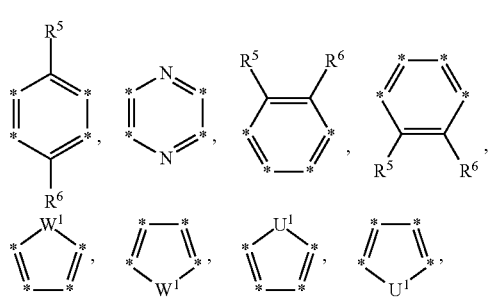

W$^1$ is S, O or Se,

U$^1$ is CR$^a$R$^b$, GeR$^a$R$^b$, PR$^2$ or NR$^2$,

R$^a$, R$^b$ are independently defined as R$^4$,

R$^{4-7}$ independently are H, F, Cl, CN, or straight-chain, alkyl with 1 to 30 C atoms or branched or cyclic alkyl with 3 to 30 C atoms, in which one or more CH$_2$ groups are optionally replaced by —O—, —S—, —C(=O)—, —C(=S)—, —C(=O)—O—, —O—C(=O)—, —NR$^0$—, —SiR$^0$R$^{00}$—, —CF$_2$—, —CR$^{x1}$=CR$^{x2}$— or —C≡C— in such a manner that O and/or S atoms are not linked directly to one another, and in which one or more H atoms are optionally replaced by F, Cl, Br, I or CN, R$^0$, R$^{00}$ independently are H or straight-chain o branched-alkyl with 1 to 20 C atoms or branched alkyl with 3 to 20 C atoms that is optionally fluorinated, Sp is a spacer group, and each * is a point of attachment to an adjacent group, where each point of attachment is a shared carbon atom with the adjacent group.

15. The compound according to claim 14, wherein P is

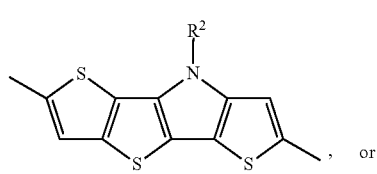, or

-continued

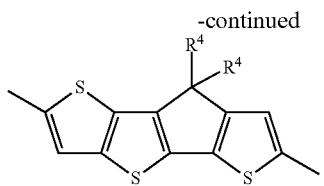

wherein
R² is H, alkyl having 1 to 25 C atoms or aryl,
each R⁴ is independently H, F, Cl, CN, or straight-chain alkyl with 1 to 30 C atoms or branched or cyclic alkyl with 3 to 30 C atoms, in which one or more CH₂ groups are optionally replaced by —O—, —S—, —C(=O)—, —C(=S)—, —C(=O)—O—, —O—C(=O)—, —NR⁰—, —SiR⁰R⁰⁰ —CF₂—, —CR$^{x1}$=CR$^{x2}$—or —C≡C—in such a manner that O and/or S atoms are not linked directly to one another, and in which one or more H atoms are optionally replaced by F, Cl, Br, I or CN,
R$^{x1}$, R$^{x2}$ independently of one another, denote H, F, Cl, CN or alkyl having 1-12 C atoms, and
R⁰, R⁰⁰ independently are H or straight-chain alkyl with 1 to 20 C atoms that is optionally fluorinated or branched alkyl with 3 to 20 C atoms that is optionally fluorinated.

16. The liquid crystalline medium according to claim 1, wherein, in the compound of formula I,
Sp is —O(CH₂)$_m$O—, —(CH₂)$_n$—, —NH— or —NR¹—,
m is 2 to 18, and
n is 1 to 18.

17. The compound according to claim 14, wherein
Sp is —O(CH₂)$_m$O—, —(CH₂)$_n$—, —NH— or —NR¹—,
m is 2 to 18, and
n is 1 to 18.

18. The liquid crystalline medium according to claim 1, wherein, in the compound of formula I,
P denotes a single bond, —(CH₂)$_n$—, —O(CH₂)$_m$O—, —C≡C—, —NH—, —NR¹—, —O(CO)O—, —O— or —S—.

19. A liquid crystalline medium comprising a dye component A) comprising one or more compounds of formula I,

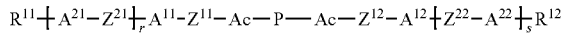

I and
a liquid-crystalline component B) comprising one or more mesogenic compounds,
where in formula I
Ac independently of each other, denotes

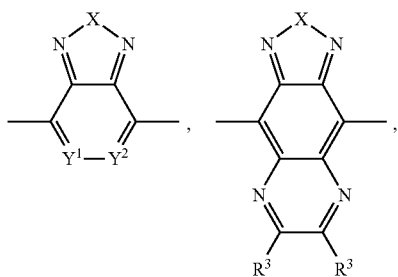

-continued

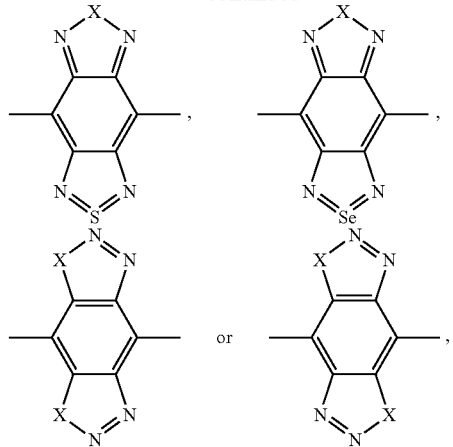

X independently is O, S, Se, NR² or Te,
Y¹, Y² independently are CR³ or N,
R² independently is H, alkyl having 1 to 25 C atoms or aryl,
R³ is H, F, Cl, CN, alkyl having 1 to 25 C atoms, alkoxy having 1 to 25 C atoms or aryl,
R¹¹, R¹² independently denote H, F, Cl, —CN, straight-chain alkyl having 1 to 25 C atoms or branched alkyl having 3 to 25 C atoms, in which one or more non-adjacent CH₂ groups may each be replaced, independently of one another, by —C(R$^z$)=C(R$^z$)—, —C≡C—, —N(R$^z$)—, —O—, —S—, —CO—, —CO—O—, —O—CO— or —O—CO—O— in such a way that O and/or S atoms are not linked directly to one another, and in which one or more H atoms may be replaced by F, Cl, Br, I or CN,
R$^z$ on each occurrence, identically or differently, denotes H, halogen, straight-chain alkyl having 1 to 25 C atoms or branched or cyclic alkyl having 3 to 25 C atoms, in which one or more non-adjacent CH₂ groups may be replaced by —O—, —S—, —CO—, —CO—O—, —O—CO— or —O—CO—O— in such a way that O and/or S atoms are not linked directly to one another, and in which one or more H atoms may be replaced by F or Cl,
A¹¹, A¹² each, independently of one another, denote an aryl or heteroaryl group, which may be substituted by one or more groups L,
A²¹, A²² are each, independently of one another, denote an aryl or heteroaryl group, which may be substituted by one or more groups L, or denote a cyclic alkyl group having 3 to 10 C atoms, in which one or more CH₂ groups may be replaced by O in such a way that no two O atoms are adjacent,
L on each occurrence, identically or differently, denotes OH, CH₂OH, F, Cl, Br, I, —CN, —NO₂, SF₅, —NCO, —NCS, —OCN, —SCN, —C(=O)N(R$^z$)₂, —C(=O) R$^z$, —N(R$^z$)₂, optionally substituted silyl, optionally substituted aryl having 6 to 20 C atoms, or straight-chain alkyl, alkoxy, alkylcarbonyl, alkoxycarbonyl, alkylcarbonyloxy or alkoxycarbonyloxy having 1 to 25 C atoms or branched alkyl, alkoxy, alkylcarbonyl, alkoxycarbonyl, alkylcarbonyloxy or alkoxycarbonyloxy having 3 to 25 C atoms, in which one or more H atoms may be replaced by F or Cl, an aryl or heteroaryl group, which may be substituted by one or more F, Cl, C₁-C₆ alkyl or alkoxy, and alternatively two adjacent groups L together denote a straight-chain alkylene group having 2 to 10 C atoms or branched alkylene group having 3 to 10 C atoms, in which one, several or all H atoms may be replaced by F and in which one or more —CH$_2$CH$_2$— groups can be replaced by —CH=CH—, $Z^{11}$, $Z^{12}$ on each occurrence, identically or differently, denote a single bond, —CR$^{x1}$=CR$^{x2}$—, —C≡C— or —NR$^1$—, $R^{x1}$, $R^{x2}$ independently of one another, denote H, F, Cl, CN or alkyl having 1-12 C atoms, $R^1$ is H, F, alkyl having 1-12 C atoms or aryl, $Z^{21}$, $Z^{22}$ are on each occurrence, identically or differently, denote a single bond, —CR$^{x1}$=CR$^{x2}$—, —C≡C— or —NR$^1$—, or denote —O—, —S—, —CR$^{y1}$R$^{y2}$—, —CF$_2$O—, —OCF$_2$—, —C(O)—O—, —O—C(O)—, —O—C(O)—O—, —OCH$_2$—, —CH$_2$O—, —SCH$_2$—, —CH$_2$S—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—COO or —OCO—CH=CH—, n1 denotes 1, 2, 3 or 4, $R^{y1}$, $R^{y2}$ each, independently of one another, denote H or alkyl having 1-12 C atoms, r, S independently of one another, denote 0, 1, 2 or 3, P denotes a single bond, —(CH$_2$)$_n$—, —O(CH$_2$)$_m$O—, —C≡C—, —NH—, —NR$^1$—, —O(CO)O—, —O—, —S— or one of the following groups:

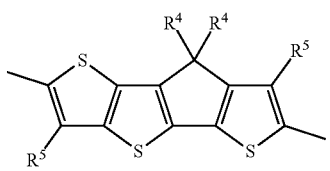

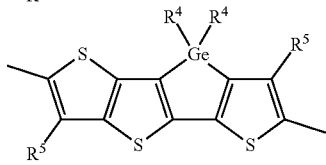

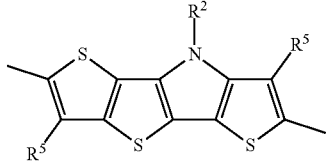

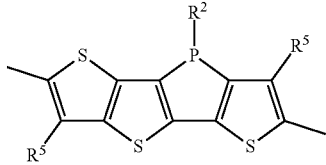

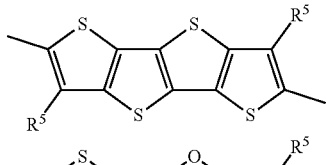

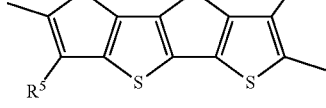

-continued

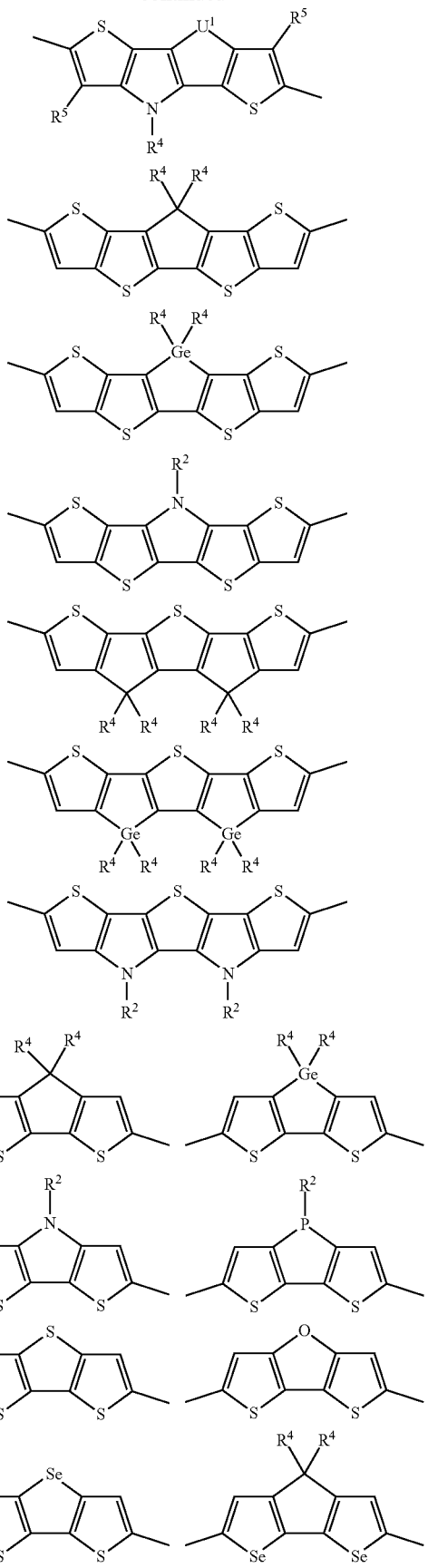

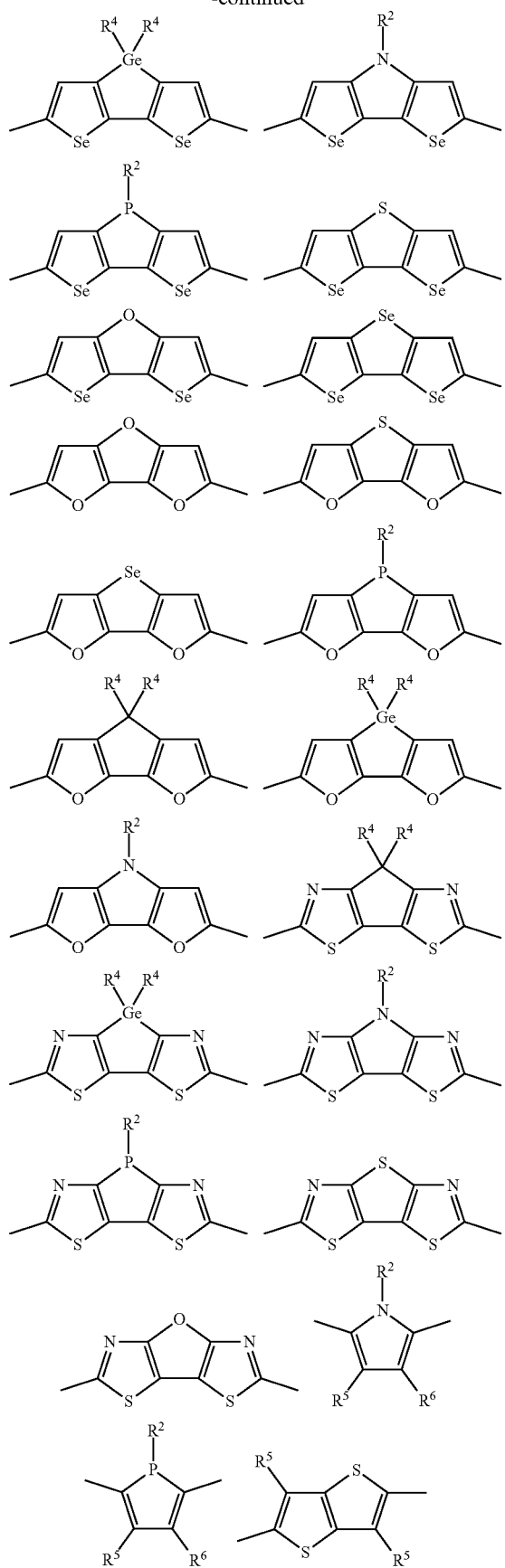
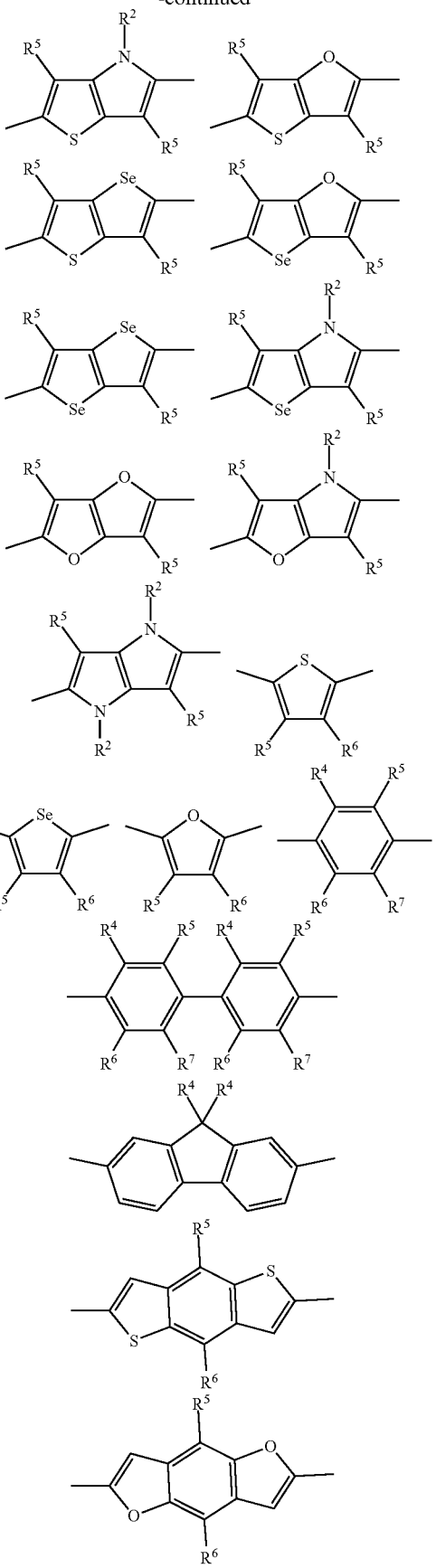

-continued

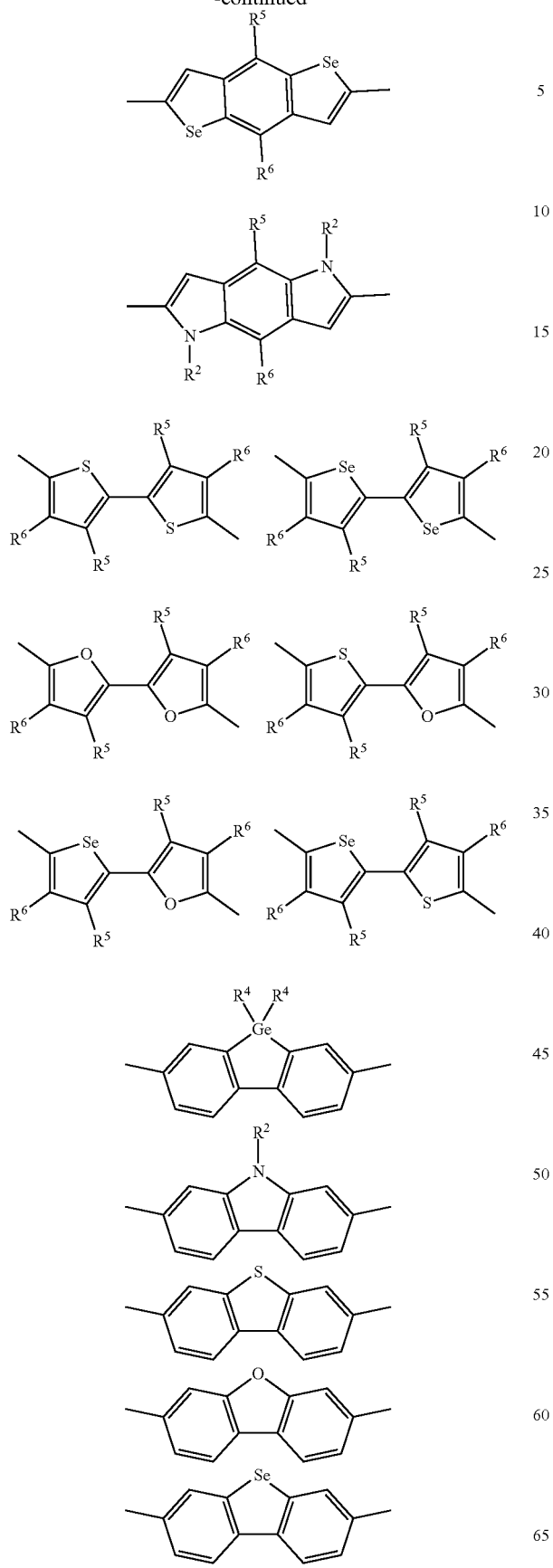

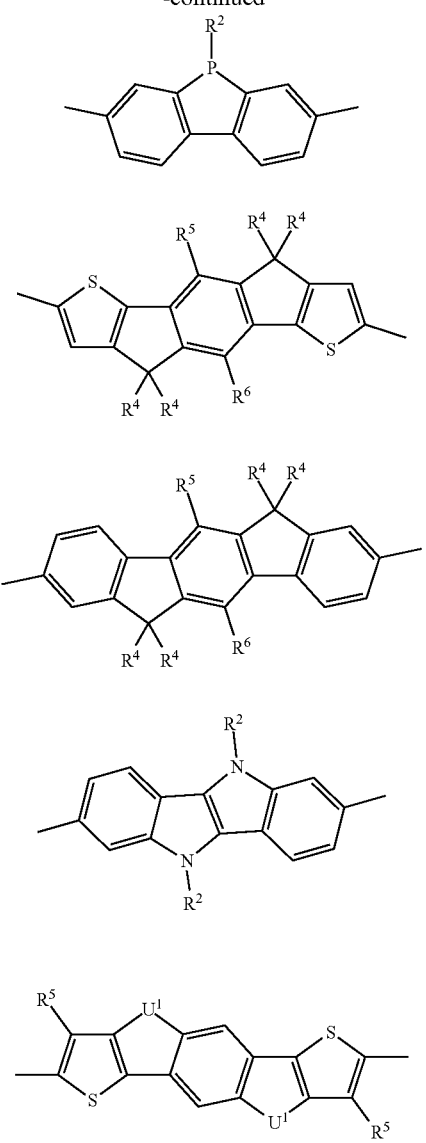

U¹ is $CR^aR^b$, $GeR^aR^b$, $PR^2$ or $NR^2$, $R^a$, $R^b$ are independently defined as $R^4$, $R^{4-6}$ independently are H, F, Cl, CN, or straight-chain alkyl with 1 to 30 C atoms or branched or cyclic alkyl with 3 to 30 C atoms, in which one or more $CH_2$ groups are optionally replaced by —O—, —S—, —C(=O)—, —C(=S)—, —C(=O)—O—, —O—C(=O)—, —NR⁰—, —SiR⁰R⁰⁰—, —CF₂—, —CR^{x1}=CR^{x2}— or —C≡C— in such a manner that O and/or S atoms are not linked directly to one another, and in which one or more H atoms are optionally replaced by F, Cl, Br, I or CN, $R^0$, $R^{00}$ independently are H or straight-chain alkyl with 1 to 20 C atoms or branched alkyl with 3 to 20 C atoms that is optionally fluorinated, and $R^{x1}$, $R^{x2}$ independently of one another, denote H, F, Cl, CN or alkyl having 1-12 C atoms.

20. The liquid crystalline medium according to claim 1, which contains one of the following compounds

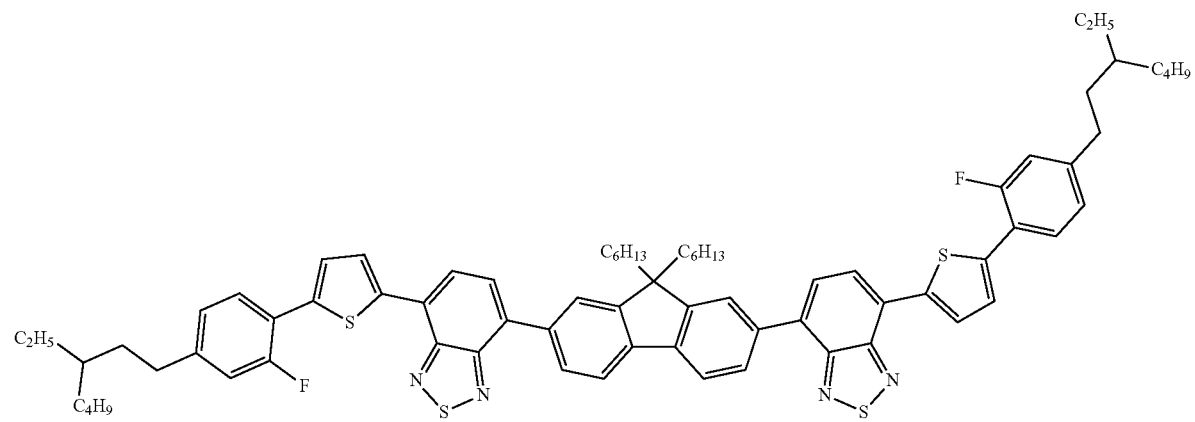
D-1
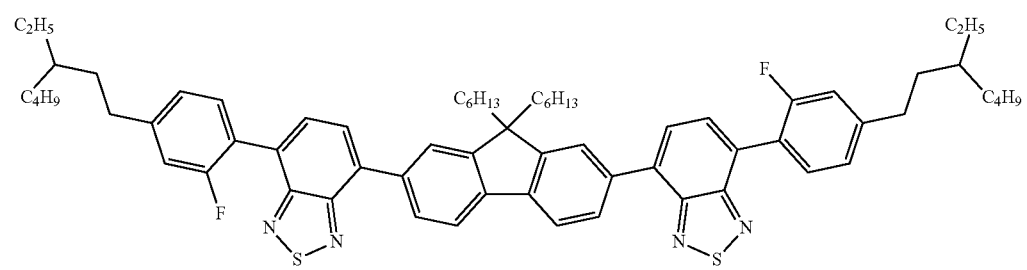
D-2
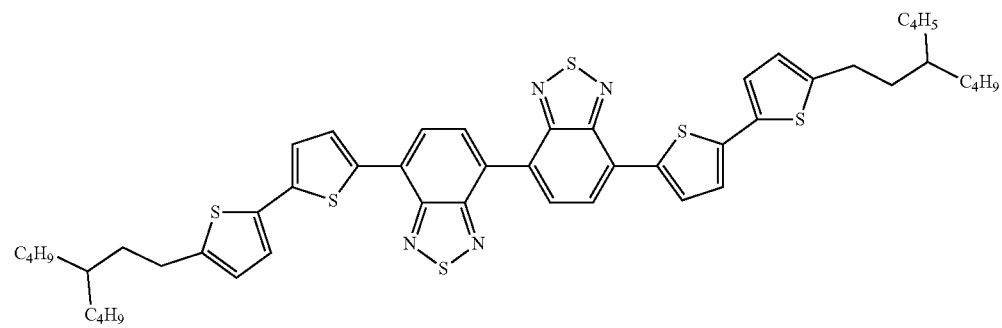
D-3
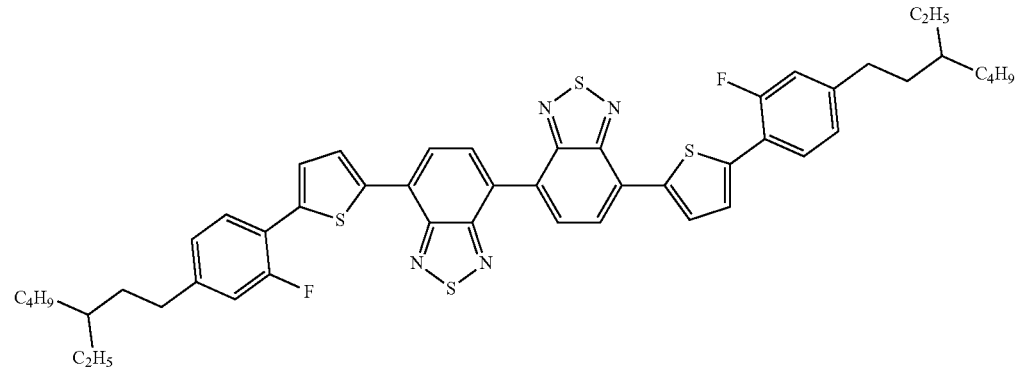
D-4

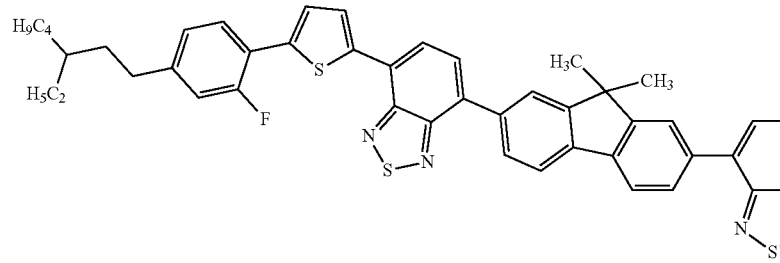
D-5
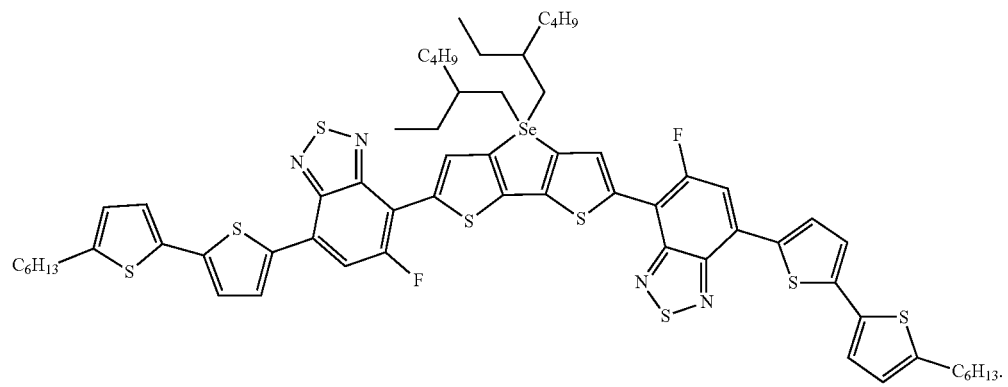
D-9
\* \* \* \* \*